US009604996B2

(12) United States Patent
Härter et al.

(10) Patent No.: US 9,604,996 B2
(45) Date of Patent: Mar. 28, 2017

(54) CYCLIC THIENOURACIL-CARBOXAMIDES AND USE THEREOF

(71) Applicant: Bayer Pharma Aktiengesellschaft, Berlin (DE)

(72) Inventors: Michael Härter, Leverkusen (DE); Martina Delbeck, Heiligenhaus (DE); Bernd Kalthof, Wuppertal (DE); Klemens Lustig, Wuppertal (DE); Niels Lindner, Wuppertal (DE); Raimund Kast, Wuppertal (DE); Pierre Wasnaire, Düsseldorf (DE); Frank Süßmeier, Munich (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/027,519

(22) PCT Filed: Oct. 2, 2014

(86) PCT No.: PCT/EP2014/071113
§ 371 (c)(1),
(2) Date: Apr. 6, 2016

(87) PCT Pub. No.: WO2015/052065
PCT Pub. Date: Apr. 16, 2015

(65) Prior Publication Data
US 2016/0244461 A1    Aug. 25, 2016

(30) Foreign Application Priority Data

Oct. 7, 2013 (EP) .................................... 13187487
Jan. 24, 2014 (EP) .................................... 14152518

(51) Int. Cl.
C07D 495/04 (2006.01)
A61K 31/519 (2006.01)
A61K 45/06 (2006.01)
C07D 519/00 (2006.01)

(52) U.S. Cl.
CPC .......... *C07D 495/04* (2013.01); *A61K 31/519* (2013.01); *A61K 45/06* (2013.01); *C07D 519/00* (2013.01)

(58) Field of Classification Search
CPC .... C07D 495/04; C07D 519/00; A61K 45/06; A61K 31/519
See application file for complete search history.

(56) References Cited

U.S. PATENT DOCUMENTS 6,180,635 B1 * 1/2001 Cheshire .............. C07D 495/04
514/260.1
7,928,111 B2    4/2011 Tachdjian et al.
7,947,692 B2    5/2011 Brinkman et al.
2007/0208040 A1    9/2007 Elzein et al.
2007/0244133 A1 * 10/2007 Bower ................. A61K 31/519
514/260.1

FOREIGN PATENT DOCUMENTS

| EP | 1847541 | 10/2007 |
| WO | 98/54190 | 12/1998 |
| WO | 00/12514 | 3/2000 |
| WO | 2004/014916 | 2/2004 |
| WO | 2005/117890 | 12/2005 |
| WO | 2007/103776 | 9/2007 |
| WO | 02/064598 | 8/2008 |
| WO | 2008/115912 | 9/2008 |
| WO | 2009037468 A1 | 3/2009 |
| WO | 2013/071169 | 5/2013 |

OTHER PUBLICATIONS

European Patent Office, International Search Report (with English translation) for International Patent Application No. PCT/EP2014/071113, Dec. 12, 2014, 5 pages.
European Patent Office, Written Opinion for International Patent Application No. PCT/EP2014/071113, Apr. 16, 2015, 6 pages.
Anderson, et al., "Nanomolar Potency and Metabolically Stable Inhibitors of Kidney Urea Transporter UT-B", Journal of Medicinal Chemistry, 55, 2012, pp. 5942-5950.
Barnes, "Chronic Obstructive Pulmonary Disease", N. Engl. J. Med., vol. 343, No. 4, 2000, pp. 269-280.
Behr, et al., "Pulmonary hypertension in interstitial lung disease", Eur. Respir. J., 31, 2008, pp. 1357-1367.
Blanco, et al., "Hemodynamic and Gas Exchange Effects of Sildenafil in Patients with Chronic Obstructive Pulmonary Disease and Pulmonary Hypertension", Am. J. Respir. Crit. Care Med., vol. 181, 2010, pp. 270-278.
Cavarra, et al., "Early response to bleomycin is characterized by different cytokine and cytokine receptor profiles in lungs", Am. Journal Physiol. Lung Cell Mol. Physiol, 287, 2004, pp. L1186-L1192.
Esteene, et al., "Bronchiolitis Obliterans after Human Lung Transplantation", Am. J. Respir. Crit. Care Med., vol. 166, 2005, pp. 440-444.
Ghofrani, et al., "Neue Therapieoptionen in der Behandlung der pulmonalarteriellen Hypertonie", Herz 30, No. 4, 2005, pp. 296-302.
Giaid, et al., "Response to Endothelin-1 in Pulmonary Hypertension", The New England Journal of Medicine, vol. 329, No. 26, 1993, pp. 1967-1968.
Hirota, et al., "Synthesis of 6-Substituted Thieno[2,3-d]pyrimidine-2,4(1H,3H)-diones", J. Heterocycl. Chem., 27(3), 1990, pp. 717-721.
Hoeper, et al., "Diagnosis, Assessment, and Treatment of Non-Pulmonary Arterial Hypertension Pulmonary Hypertension", Journal of the American College of Cardiology, vol. 54, No. 1, Suppl. S, 2009, pp. S85-S96.

(Continued)

*Primary Examiner* — Sudhakar Katakam
(74) *Attorney, Agent, or Firm* — Aseem Mehta

(57) ABSTRACT

The present application relates to novel 2,4-dioxo-1,2,3,4-tetrahydrothieno[2,3-d]pyrimidine-6-carboxamide derivatives ("thienouracil"-carboxamides), to processes for their preparation, to their use alone or in combinations for the treatment and/or prevention of diseases and to their use for the preparation of medicaments for the treatment and/or prevention of diseases, in particular for the treatment and/or prevention of pulmonary and cardiovascular disorders.

11 Claims, No Drawings

(56) References Cited

OTHER PUBLICATIONS

Hughes, "Progress in the Mitsunobu Reaction. A Review", Organic Preparations and Procedures International: The New Journal for Organic Synthesis, 28(2), 1996, pp. 127-164.

Hughes, "The Mitsunobu Reaction", Chapter 2, Organic Reactions, 42, 1992, pp. 335-656.

Humbert, et al., "Cellular and Molecular Pathobiology of Pulmonary Arterial Hypertension", Journal of the American College of Cardiology, vol. 43, No. 12, Suppl. S, 2004, pp. 13S-24S.

Ito, et al., "Current Drug Targets and Future Therapy of Pulmonary Arterial Hypertension", Current Medicinal Chemistry, 14, 2007, pp. 719-733.

Karmouty-Quintana, et al., "Adenosine A2B Receptor and Hyaluronan Modulate Pulmonary Hypertension Associated with Chronic Obstructive Pulmonary Disease", Am. J. Respir. Cell Mol. Biol., vol. 49, Issue 6, Dec. 2013, pp. 1038-1047.

Karmouty-Quintana, et al., "The A2B adenosine receptor modulates pulmonary hypertension associated with interstitial lung disease", The FASEB Journal, 26, 2012, pp. 2546-2557.

Kiankarimi, et al., "Diphenyl 2-pyridylphosphine and di-tert-butylazodicarboxylate: Convenient reagents for the Mitsunobu reaction", Tetrahedron Letters, vol. 40, Issue 24, Jun. 11, 1999, pp. 4497-4500.

Lettieri, et al., "Prevalence and Outcomes of Pulmonary Arterial Hypertension in Advanced Idiopathic Pulmonary Fibrosis", Chest, 129, 2006, pp. 746-752.

Levine, "Thiophene-fused Borepins as Directly Functionalizable Boron-Containing π-Electron Systems", Journal of the American Chemical Society, 136(19), 2014, pp. 7132-7139.

Ley, et al., "Clinical Course and Prediction of Survival in Idiopathic Pulmonary Fibrosis", Am. J. Respir. Crit. Care Med., vol. 183, 2011, pp. 431-440.

McKibben, et al., "Practical Synthesis of Tetrasubstituted Thiophenes for Use in Compound Libraries", Tetrahedron Letters, 40, 1999, pp. 5471-5474.

Montani, et al., "Updated clinical classification of pulmonary hypertension", Pulmonary Circulation, Diseases and their treatment, 3rd edition, Hodder Arnold Publ., 2011, pp. 197-206.

Naeije, "Pulmonary vascular function", Pulmonary Circulation, Diseases and their treatment, 3rd edition, Hodder Arnold Publ., 2011, 3 pages.

Rosenzweig, "Emerging treatments for pulmonary arterial hypertension", Expert Opinion on Emerging Drugs, 2006, pp. 609-619.

Selman, "Accelerated Variant of Idiopathic Pulmonary Fibrosis: Clinical Behavior and Gene Expression Pattern", PLoS ONE, Issue 5, May 2007, 11 pages.

Steiner, et al., "Interleukin-6 Overexpression Induces Pulmonary Hypertension", Circulation Research, 104, 2009, pp. 236-244.

Stolz, et al., "A randomised, controlled trial of bosentan in severe COPD", Eur. Respir. J., 32, 2008, pp. 619-628.

Strieter, et al., "New Mechanisms of Pulmonary Fibrosis", Chest, 136, 2009, pp. 1364-1370.

Sun, et al., "Role of A2B adenosine receptor signaling in adenosine-dependent pulmonary inflammation and injury", The Journal of Clinical Investigation, vol. 116, No. 8, Aug. 2006, pp. 2173-2182.

Tanaka, et al., "Synthesis of Chiral 5-Deazaflavin Derivatives and Their Use in Asymmetric Reduction of Ethyl Benzoylformate", Chem. Pharm. Bull., 35(4), 1987, pp. 1397-1404.

Toldo, et al., "GS-6201, a Selective Blocker of the A2B Adenosine Receptor, Attenuates Cardiac Remodeling after Acute Myocardial Infarction in the Mouse", The Journal of Pharmacology and Experimental Therapeutics, vol. 343, No. 3, 2012, pp. 587-595.

Von Der Beck, "Die therapie der idiopathischen pulmonalen Fibrose", Pneumologe, 10, 2013, pp. 105-111.

Yokoe, et al., "Facile Synthesis of 3-Substituted Chromones from an Enaminoketone", Chem. Pharm. Bull., 42(8), 1994, pp. 1697-1699.

Zhong, et al., "Synergy between A2B Adenosine Receptors and Hypoxia in Activating Human Lung Fibroblasts", Am. J. Respir. Cell. Mol. Biol., vol. 32, 2005, pp. 2-8.

Zhou, et al., "Alterations in Adenosine Metabolism and Signaling in Patients with Chronic Obstructive Pulmonary Disease and Idiopathic Pulmonary Fibrosis", PLoS ONE, 5(2), Feb. 16, 2010, 15 pages.

\* cited by examiner

CYCLIC THIENOURACIL-CARBOXAMIDES AND USE THEREOF

CROSS-REFERENCE TO RELATED APPLICATIONS

This application is a U.S. national phase application of International Patent Application No. PCT/EP2014/071113, filed Oct. 2, 2014 and titled CYCLIC THIENOURACIL-CARBOXAMIDES AND USE THEREOF, which claims priority to both European Patent Application No. 13187487.7, filed Oct. 7, 2013 and titled CYCLIC THIENOURACIL-CARBOXAMIDES AND USE THEREOF, and European Patent Application No. 14152518.8, filed Jan. 24, 2014 and titled CYCLIC THIENOURACIL-CARBOXAMIDES AND USE THEREOF, the contents of each of which are incorporated herein by reference in their entirety.

The present application relates to novel 2,4-dioxo-1,2,3,4-tetrahydrothieno[2,3-d]pyrimidine-6-carboxamide derivatives ("thienouracil"-carboxamides), to processes for their preparation, to their use alone or in combinations for the treatment and/or prevention of diseases and to their use for the preparation of medicaments for the treatment and/or prevention of diseases, in particular for the treatment and/or prevention of pulmonary and cardiovascular disorders.

The endogenous purine nucleoside adenosine is formed ubiquitously and modulates, as important signal molecule, a large number of physiological and pathophysiological processes. Most of it is formed during the intra- and extracellular degradation of adenine nucleotides, and a smaller amount is formed during the intracellular hydrolysis of S-adenosyl homocysteine. Under physiological conditions, extracellular adenosine can be re-phosphorylated by adenosine kinase to adenosine monophosphate (AMP) or rearranged by adenosine deaminase to inosine. The extracellular concentration is between 30 and 300 nM. As a result of tissue damage caused, for example, by hypoxia, in inflammation reaction and during oxidative stress, there is an increased formation and accumulation of adenosine, such that the extracellular concentration may increase to up to 15 μM.

The biological actions of adenosine are mediated via G-protein-coupled receptors located at the plasma membrane. Currently, four adenosine receptor subtypes have been demonstrated: A1 adenosine receptor (A1R), A2a adenosine receptor (A2aR), A2b adenosine receptor (A2bR) and A3 adenosine receptor (A3R). From among the adenosine receptors mentioned above, the A2b receptor has the weakest affinity for adenosine. For this reason, in contrast to the other adenosine receptors, it is not activated under normal physiological conditions. A1 and A3 receptors are coupled to Gi proteins which inhibit adenylate cyclase, whereas A2a and A2b receptors, via Gs proteins, stimulate adenylate cyclase, thus causing an intracellular increase of cAMP. Via Gq proteins, both the A1, the A3 and the A2b receptor activate phospholipase C which cleaves membrane-bound phosphatidylinositol-4,5-bisphosphate into inositol-1,4,5-triphosphate and diacylglycerol. This in turn leads to an increase of the intracellular calcium concentration and activation of further target proteins such as protein kinase C and the MAP kinases.

A2b receptors are expressed on pulmonary epithelial and smooth muscle cells, vascular endothelial and smooth muscle cells, fibroblasts and also inflammatory cells. Expression of the A2b receptor at the cell surface is a dynamic process and is greatly enhanced, for example, by hypoxia, inflammatory factors and free radicals. The adenosine-activated A2b receptors lead to formation and release of pro-inflammatory and pro-fibrotic cytokines such as, for example, IL-6, IL-4 and IL-8. Studies have shown that the A2b receptor plays an important role at the chronic stage of pulmonary disorders during tissue remodelling and promotes inter alia differentiation of fibroblasts in myofibroblasts, resulting in enhanced synthesis and deposition of collagen.

In pulmonary tissue samples of patients suffering from idiopathic pulmonary fibrosis, COPD and pulmonary hypertension associated with COPD [Zhou et al., *PLoS One* 5, e9224 (2010); Selmann et al., *PLoS One* 2, e482 (2007)] and various animal models of fibro-proliferative pulmonary disorders [Karmouty-Quintana et al., *Am. J. Respir. Cell. [mol%] Biol.*, publ. online, 15 July 2013; Karmouty-Quintana et al., *Faseb J.* 26, 2546-2557 (2012); Sun et al., *J. Clin. Invest.* 116, 2173-2182 (2006)], it was possible to detect an increased expression of the A2b receptor. In the animal model of bleomycin-induced pulmonary fibrosis and pulmonary hypertension in the mouse, a genetic knock-out of the A2b receptor resulted both in inhibition of the progression of pulmonary fibrosis and pulmonary vascular remodeling and the resulting pulmonary hypertension [Karmouty-Quintana et al., *Faseb J.* 26, 2546-2557 (2012)]. It is assumed that the release of inter alia endothelin-1 (ET-1) and interleukin-6 (IL-6) from vascular cells, which is modulated by the A2b receptor, plays a role during the development of pulmonary hypertension associated with pulmonary fibrosis. Stimulation of human pulmonary arterial endothelial and smooth muscle cells with 5'-(N-ethylcarboxamido)adenosine (NECA), an adenosine analog, results in the release of ET-1 and IL-6, which can be prevented by A2b receptor inhibition [Karmouty-Quintana et al., *Faseb J.* 26, 2546-2557 (2012)]. Elevated endothelin-1- and IL-6 concentrations were found in lung tissue and serum of patients suffering from pulmonary hypertension [Giaid et al., *N. Engl. J. Med.* 329, 1967-1968 (1993); Steiner et al., *Circ. Res.* 104, 236-244 (2009)]. Furthermore, it is assumed that the A2b receptor-mediated release of inter alia IL-6 and other profibrotic mediators and stimulation of the differentiation of fibroblasts in myofibroblasts in the lung leads to induction of fibrosis. Stimulation of human fibroblasts with NECA leads to the release of IL-6 which is increased by hypoxia and can be prevented by inhibiting the A2b receptor. It was possible to demonstrate an increased IL-6 expression in patients suffering from idiopathic pulmonary fibrosis and in animal models of pulmonary fibrosis [Zhong et al., *Am. J. Respir. Cell. [mol%] Biol.* 32, 2-8 (2005); Cavarra et al., *Am. J. Physiol. Lung Cell. [mol%] Physiol.* 287, L1186-L1192 (2004)].

The A2b receptor also plays an important role in tissue remodelling after myocardial infarction. In the animal model of the permanent ligature of the coronary artery in the mouse, inhibition of the A2b receptor resulted in a reduction of caspase-1 activity and the invasion of inflammatory cells in heart tissue and the cytokines and adhesion molecules in plasma and in an improvement of systolic and diastolic heart function [Toldo et al., *J. Pharmacol. Exp. Ther.* 343, 587-595 (2012)].

It is therefore assumed that the A2b receptor plays an important role in many disorders, injuries and pathological changes whose aetiology and/or progression is associated with inflammatory events and/or proliferative and fibro-proliferative tissue and vessel remodelling. These can be in particular disorders of and/or damage to the lung, the cardiovascular system or the kidney, or it can be a blood disorder, a neoplastic disease or other inflammatory disorders.

Disorders of and damage to the lung which may be mentioned in this context are in particular idiopathic pulmonary fibrosis, pulmonary hypertension, the bronchiolitis obliterans syndrome (BOS), chronic-obstructive pulmonary disease (COPD), asthma and cystic fibrosis. Disorders of and damage to the cardiovascular system in which the A2b receptor is involved are, for example, tissue changes following myocardial infarction and associated with heart failure. Renal disorders are, for example, renal insufficiency and kidney failure. A blood disorder is, for example, sickle cell anaemia. Examples of tissue degradation and remodelling during neoplastic processes are the invasion of cancer cells into healthy tissue (formation of metastases) and neovascularization (neoangiogenesis). Another inflammatory disease where the A2b receptor is involved is, for example, multiple sclerosis.

Idiopathic fibrosis of the lung or idiopathic pulmonary fibrosis (IPF) is a progressive lung disease which, left untreated, results in death on average within 2.5 to 3.5 years after diagnosis. At the time of diagnosis, the patients are in most cases more than 60 years old, men being slightly more frequently affected than women. Onset of IPF is insidious and characterized by increasing shortness of breath and dry tickly cough. IPF belongs to the group of idiopathic interstitial pneumonias (IIP), a heterogeneous group of pulmonary disorders characterized by fibrosis and inflammation of varying severity which can be distinguished using clinical, imaging and fine tissue criteria. Within this group, the idiopathic pulmonary fibrosis is of particular significance owing to its frequency and aggressive progression [Ley et al., *Am. J. Respir. Crit. Care Med.* 183, 431-440 (2011)]. IPF may either occur sporadically or be hereditary. As yet, the causes are unknown. However, in recent years there have been numerous indications that chronic damage of the alveolar epithelium leads to the release of profibrotic cytokines/mediators followed by increased fibroblast proliferation and increased collagen fibre formation, resulting in a patchy fibrosis and the typical honeycomb structure of the lung [Strieter et al., *Chest* 136, 1364-1370 (2009)]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonal hypertension [Beck et al., *Pneumologe* 10, 105-111 (2013)]. The prevalence of pulmonary hypertension in interstitial pulmonary disorders is 10-40% [Lettieri et al., *Chest* 129, 746-752 (2006); Behr et al., *Eur. Respir. J.* 31, 1357-1367 (2008)]. Currently, there is no curative treatment for IPF—except for lung transplantation.

Pulmonary hypertension (PH) is a progressive lung disease which, left untreated, leads to death on average within 2.8 years after diagnosis. By definition, the mean pulmonary aterial pressure (mPAP) in case of chronic pulmonary hypertension is >25 mmHg at rest or >30 mmHg during exertion (normal value <20 mmHg). The pathophysiology of pulmonary hypertension is characterized by vasoconstriction and remodelling of the pulmonary vessels. In chronic PH there is neomuscularization primarily of unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), *Pulmonary Circulation. Diseases and their treatment*, 3$^{rd}$ edition, Hodder Arnold Publ., 2011, p. 3]. Since 2008, pulmonary hypertension is classified in accordance with the Dana Point classification into various sub-groups according to the respective aetiology [D. Montana and G. Simonneau, in: A. J. Peacock et al. (Eds.), *Pulmonary Circulation. Diseases and their treatment*, 3$^{rd}$ edition, Hodder Arnold Publ., 2011, pp. 197-206].

Despite all the advances in the therapy of PH there is as yet no prospect of cure of this serious disorder. Standard therapies available on the market (for example prostacyclin analogues, endothelin receptor antagonists, phosphodiesterase inhibitors) are able to improve the quality of life, the exercise tolerance and the prognosis of the patients. These are therapeutic principles which are administered systemically and act primarily heamodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilatation, they lead to a reduction (desaturation) of the arterial oxygen content in the patients. The probable reason for this is an unfavourable effect on the ventilation-perfusion adaptation in the lung in heterogeneous lung disorders owing to the systemic administration of non-selective vasodilatators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective aetiology [D. Montana and G. Simonneau, in: A. J. Peacock et al. (Eds.), *Pulmonary Circulation. Diseases and their treatment*, 3$^{rd}$ edition, Hodder Arnold Publ., 2011, pp. 197-206; Hoeper et al., *J. Am. Coll. Cardiol.*, 2009, 54 (1), Suppl. S, p85-p96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite supressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

The bronchiolitis obliterans syndrome (BOS) is a chronic rejection reaction after a lung transplantation. Within the first five years after a lung transplantation, about 50-60% of all patients, within the first nine years more than 90% of the patients are affected [Estenne et al., *Am. J. Respir. Crit. Care Med.* 166, 440-444 (2003)]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages.

Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements during more intensive immunosuppression, patients not showing any response experience persistent worsening such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade in life. In the subsequent years of life, the shortness of breath frequently worsens and cough becomes manifest, associated with plentiful and in some cases purulent expectoration and stenosis breathing up to breathlessness (dyspnoea). COPD is primarily a disease of smokers: Smoking is the cause of 90% of all cases of COPD and of 80-90% of all COPD-related deaths. COPD is a big medicinal problem and constitutes the sixth most frequent cause of death world-wide. Of people over the age of 45, about 4-6% are affected. Although the obstruction of the respiratory flow may only be partial and temporal, COPD can not be cured. Accordingly, the aim of the treatment is to improve the quality of life, to alleviate the symptoms, to prevent an acute worsening and to slow the progressive impairment of lung function. Existing pharmacotherapies, which have hardly changed over the last two or three decades, are the use of bronchodilators to open blocked respiratory passages, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodelling of the bronchi.

It is therefore an object of the present invention to provide novel substances which act as potent and selective antagonists of the adenosine A2b receptor and are suitable as such for treatment and/or prevention in particular of pulmonary and cardiovascular disorders.

WO 98/54190-A1 and WO 00/12514-A1 disclose thieno [2,3-d]pyrimidinediones (thienouracils) having immunosuppressive activity. WO 02/064598-A1 and WO 2004/014916-A1 describe bicyclic pyrimidine derivatives as inhibitors of matrix metalloproteinases (MMPs), in particular of MMP-13. Further bicyclic pyrimidine derivatives are disclosed in WO 2005/117890-A2 as CCR2 antagonists in particular for the treatment of inflammatory disorders, and EP 1 847 541-A1 claims bicyclic pyrimidine derivatives as GnRH antagonists for the treatment of hormone-dependent disorders. U.S. Pat. No. 7,928,111-B2 describes thienopyrimidinone derivatives having taste-enhancing properties. WO 2007/103776-A2 discloses thieno[2,3-d]pyrimidinediones as antagonists of the adenosine A2a receptor which are suitable in particular for the treatment of CNS disorders and addictions. WO 2013/071169-A1 claims thieno[2,3-d]pyrimidinediones as ACC inhibitors for the treatment of infections and metabolic disorders.

The present invention provides compounds of the general formula (I)

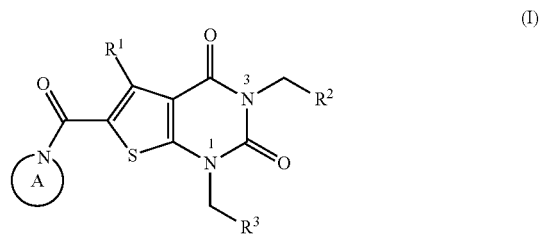

in which
R¹ represents hydrogen, methyl or ethyl, where methyl and ethyl may be substituted up to three times by fluorine,
R² represents methyl, ethyl, n-propyl, isopropyl, cyclopropyl, cyclopropylmethyl, 2,2-difluorovinyl, 3,3-difluoroallyl or propargyl or represents a group of the formula

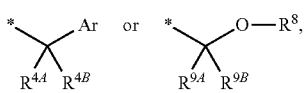

in which * denotes the point of attachment to the CH$_2$ group,

Ar represents phenyl or 5- or 6-membered heteroaryl having up to two ring nitrogen atoms,
  where phenyl and heteroaryl may be mono- or disubstituted by identical or different radicals selected from the group consisting of fluorine, chlorine, methyl, trifluoromethyl, methoxy and trifluoromethoxy, $R^{4A}$ represents hydrogen, fluorine or methyl, $R^{4B}$ represents hydrogen, fluorine, methyl, trifluoromethyl, hydroxy or methoxy, or $R^{4A}$ and $R^{4B}$ are attached to one another and together with the carbon atom to which they are attached form a cyclopropyl or cyclobutyl ring, $R^8$ represents methyl or trifluoromethyl and $R^{9A}$ and $R^{9B}$ independently of one another represent hydrogen, methyl or trifluoromethyl, $R^3$ represents $(C_1-C_6)$-alkyl, $(C_2-C_6)$-alkenyl, $(C_3-C_7)$-cycloalkyl or $[(C_3-C_7)$-cycloalkyl]methyl,
  where alkyl and alkenyl may be substituted up to three times and cycloalkyl may be substituted up to two times by fluorine
  and
  where in alkyl and cycloalkyl up to two CH$_2$ groups may be replaced by —O— or —S—, with the proviso that there are at least two carbon atoms between such heteroatoms including the uracil N$^1$-atom, and the ring A represents a mono- or bicyclic aza heterocycle of the formula

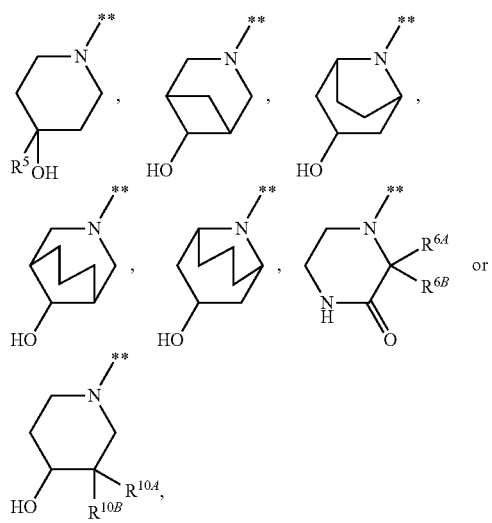

in which ** denotes the point of attachment to the carbonyl group, $R^5$ represents hydrogen, methyl, trifluoromethyl, hydroxymethyl or ethyl, $R^{6A}$ and $R^{6B}$ each independently of one another represent hydrogen, methyl or ethyl, $R^{10A}$ represents methyl, ethyl, hydroxy or methoxy, and $R^{10B}$ represents hydrogen, methyl or ethyl, and their salts, solvates and solvates of the salts.

Compounds according to the invention are the compounds of the formula (I) and their salts, solvates and solvates of the salts, the compounds encompassed by formula (I) of the formulae mentioned below and their salts, solvates and solvates of the salts and the compounds encompassed by formula (I) and mentioned below as working examples, and their salts, solvates and solvates of the salts, if the compounds encompassed by formula (I) and mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{34}C$ isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the compounds according to the invention may therefore in some cases also constitute a preferred embodiment of the present invention. Isotopic variants of the compounds according to the invention can be prepared by generally customary processes known to those skilled in the art, for example by the methods described below and the procedures reported in the working examples, by using corresponding isotopic modifications of the particular reagents and/or starting compounds therein.

In addition, the present invention also encompasses prodrugs of the compounds according to the invention. The term "prodrugs" refers here to compounds which may themselves be biologically active or inactive, but are converted while present in the body, for example by a metabolic or hydrolytic route, to compounds according to the invention.

In the context of the present invention, unless specified otherwise, the substituents and radicals are defined as follows:

$(C_1-C_6)$-Alkyl and $(C_2-C_4)$-alkyl in the context of the invention represent a straight-chain or branched alkyl radical having 1 to 6 and 2 to 4 carbon atoms, respectively. A straight-chain or branched alkyl radical having 2 to 4 carbon atoms is preferred. Preferred examples include: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

$(C_2-C_6)$-Alkenyl and $(C_2-C_4)$-alkenyl in the context of the invention represent a straight-chain or branched alkenyl radical having a double bond and 2 to 6 and 2 to 4 carbon atoms, respectively. A straight-chain or branched alkenyl radical having 2 to 4 carbon atoms is preferred. Preferred examples include: vinyl, prop-1-en-1-yl, prop-2-en-1-yl (allyl), prop-1-en-2-yl (isopropenyl), 2-methylprop-2-en-1-yl, but-1-en-1-yl, but-1-en-2-yl, but-2-en-1-yl, but-2-en-2-yl, but-3-en-1-yl, pent-2-en-1-yl, pent-3-en-1-yl, pent-4-en-1-yl, 3-methylbut-2-en-1-yl and 4-methylpent-3-en-1-yl.

$(C_3-C_7)$-Cycloalkyl and $(C_3-C_6)$-cycloalkyl in the context of the invention represent a monocyclic saturated cycloalkyl group having 3 to 7 and 3 to 6 carbon atoms, respectively. A cycloalkyl radical having 3 to 6 carbon atoms is preferred. Preferred examples include: cyclopropyl, cyclobutyl, cyclopentyl, cyclohexyl and cycloheptyl.

5-membered heteroaryl in the definition of the group Ar represents an aromatic heterocycle (heteroaromatic radical) having a total of 5 ring atoms which contains one or two ring nitrogen atoms and is attached via a ring carbon atom or a ring nitrogen atom. Examples include: pyrrolyl, pyrazolyl and imidazolyl. Preference is given to imidazolyl.

6-membered heteroaryl in the definition of the group Ar represents an aromatic heterocycle (heteroaromatic radical) having a total of 6 ring atoms which contains one or two ring nitrogen atoms and is attached via a ring carbon atom. Examples include: pyridyl, pyrimidinyl, pyridazinyl and pyrazinyl. Preference is given to pyridyl.

In the context of the present invention, it is the case that for all radicals which occur more than once, their meaning is independent of the others. When radicals in the compounds according to the invention are substituted, the radicals may be mono- or polysubstituted, unless specified otherwise. Substitution by one or two identical or different substituents is preferred. Particular preference is given to substitution by one substituent.

In a particular embodiment, the present invention encompasses compounds of the formula (I) in which $R^1$ represents hydrogen, methyl, difluoromethyl, trifluoromethyl or ethyl, $R^2$ represents methyl, ethyl, n-propyl, isopropyl, cyclopropyl, cyclopropylmethyl or propargyl or represents a group of the formula

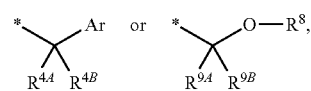

in which * denotes the point of attachment to the $CH_2$ group,

Ar represents phenyl or 5- or 6-membered heteroaryl having up to two ring nitrogen atoms,
where phenyl and heteroaryl may be mono- or disubstituted by identical or different radicals selected from the group consisting of fluorine, chlorine, methyl, trifluoromethyl, methoxy and trifluoromethoxy, $R^{4A}$ represents hydrogen, fluorine or methyl, $R^{4B}$ represents hydrogen, fluorine, methyl, trifluoromethyl, hydroxy or methoxy, or $R^{4A}$ and $R^{4B}$ are attached to one another and together with the carbon atom to which they are attached form a cyclopropyl or cyclobutyl ring, $R^8$ represents methyl or trifluoromethyl and $R^{9A}$ and $R^{9B}$ independently of one another represent hydrogen, methyl or trifluoromethyl, $R^3$ represents $(C_1-C_6)$-alkyl, $(C_2-C_6)$-alkenyl, $(C_3-C_7)$-cycloalkyl or $[(C_3-C_7)$-cycloalkyl]methyl,
where alkyl and alkenyl may be substituted up to three times and cycloalkyl may be substituted up to two times by fluorine
and
where in alkyl and cycloalkyl up to two $CH_2$ groups may be replaced by —O— or —S—, with the proviso that there are at least two carbon atoms between such heteroatoms including the uracil $N^1$-atom, and the ring A represents a mono- or bicyclic aza heterocycle of the formula

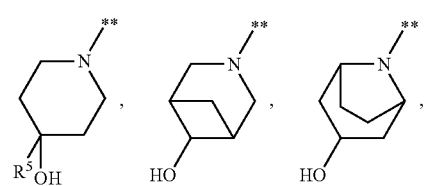

-continued

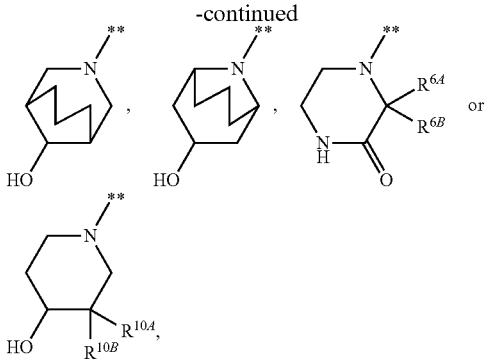

in which ** denotes the point of attachment to the carbonyl group, $R^5$ represents hydrogen, methyl, trifluoromethyl, hydroxymethyl or ethyl, $R^{6A}$ and $R^{6B}$ each independently of one another represent hydrogen, methyl or ethyl, $R^{10A}$ represents methyl or ethyl, and $R^{10B}$ represents hydrogen, methyl or ethyl, and their salts, solvates and solvates of the salts.

In a further embodiment, the present invention encompasses compounds of the formula (I) in which $R^1$ represents hydrogen, methyl, difluoromethyl or trifluoromethyl, $R^2$ represents methyl, ethyl, n-propyl or isopropyl or represents a group of the formula

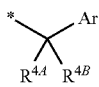

in which * denotes the point of attachment to the $CH_2$ group,

Ar represents phenyl or 6-membered heteroaryl having up to two ring nitrogen atoms, where phenyl and heteroaryl may be mono- or disubstituted by identical or different radicals selected from the group consisting of fluorine, chlorine, methyl, trifluoromethyl, methoxy and trifluoromethoxy, $R^{4A}$ represents hydrogen, fluorine or methyl, $R^{4B}$ represents hydrogen, fluorine, methyl or methoxy, or $R^{4A}$ and $R^{4B}$ are attached to one another and together with the carbon atom to which they are attached form a cyclopropyl or cyclobutyl ring, $R^3$ represents $(C_1\text{-}C_6)$-alkyl, $(C_2\text{-}C_6)$-alkenyl, $(C_3\text{-}C_7)$-cycloalkyl or $[(C_3\text{-}C_7)$-cycloalkyl]methyl, where alkyl and alkenyl may be substituted up to three times and cycloalkyl may be substituted up to two times by fluorine and where in alkyl and cycloalkyl up to two $CH_2$ groups may be replaced by —O— or —S—, with the proviso that there are at least two carbon atoms between such heteroatoms including the uracil $N^1$-atom, and the ring A represents a mono- or bicyclic aza heterocycle of the formula

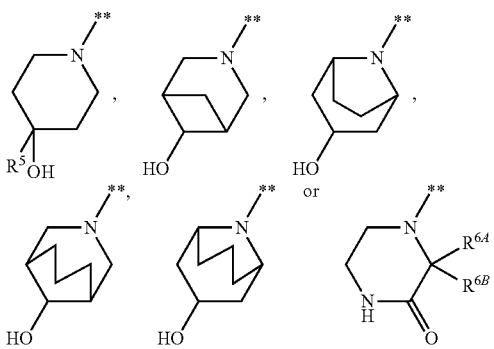

in which ** denotes the point of attachment to the carbonyl group, $R^5$ represents hydrogen, methyl, trifluoromethyl or hydroxymethyl, and $R^{6A}$ and $R^{6B}$ each independently of one another represent hydrogen, methyl or ethyl, and their salts, solvates and solvates of the salts.

Preference is given in the context of the present invention to compounds of the formula (I) in which $R^1$ represents methyl, difluoromethyl, trifluoromethyl, ethyl or 1-fluoroethyl, $R^2$ represents methyl, ethyl, n-propyl, isopropyl, 3,3-difluoroallyl or propargyl or represents a group of the formula

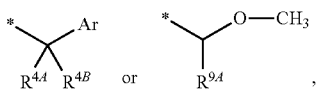

in which * denotes the point of attachment to the $CH_2$ group,

Ar represents phenyl or pyridyl, where phenyl and pyridyl may be substituted by fluorine, chlorine, methyl or methoxy, $R^{4A}$ represents hydrogen, fluorine or methyl, $R^{4B}$ represents hydrogen, fluorine, methyl, hydroxy or methoxy, or $R^{4A}$ and $R^{4B}$ are attached to one another and together with the carbon atom to which they are attached form a cyclopropyl ring, and $R^{9A}$ represents hydrogen, methyl or trifluoromethyl, $R^3$ represents $(C_2\text{-}C_4)$-alkyl, $(C_2\text{-}C_4)$-alkenyl, $(C_3\text{-}C_6)$-cycloalkyl or $[(C_3\text{-}C_6)$-cycloalkyl]methyl, where alkyl and alkenyl may be substituted up to three times and cycloalkyl may be substituted up to two times by fluorine and where in alkyl and cycloalkyl one $CH_2$ group may be replaced by —O— or —S—, with the proviso that there are at least two carbon atoms between such a heteroatom and the uracil $N^1$-atom, and
the ring A represents an aza heterocycle of the formula

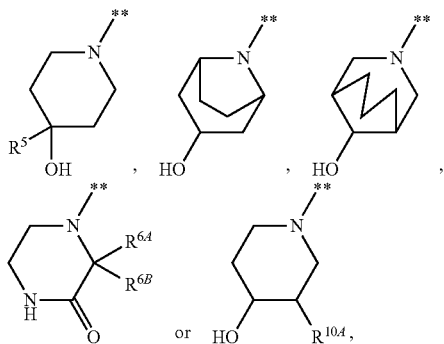

in which ** denotes the point of attachment to the carbonyl group,
$R^5$ represents hydrogen, methyl, trifluoromethyl, hydroxymethyl or ethyl,
$R^{6A}$ and $R^{6B}$ independently of one another represent hydrogen, methyl or ethyl,
and
$R^{10A}$ represents methyl or ethyl,
and their salts, solvates and solvates of the salts.

In a further preferred embodiment, the present invention encompasses compounds of the formula (I) in which
$R^1$ represents methyl, difluoromethyl, trifluoromethyl or ethyl,
$R^2$ represents methyl, ethyl, n-propyl, isopropyl or propargyl or represents a group of the formula

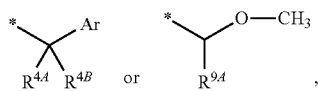

in which * denotes the point of attachment to the $CH_2$ group,
Ar represents phenyl or pyridyl,
 where phenyl and pyridyl may be substituted by fluorine, chlorine, methyl or methoxy,
$R^{4A}$ represents hydrogen, fluorine or methyl,
$R^{4B}$ represents hydrogen, fluorine, methyl, hydroxy or methoxy,
or
$R^{4A}$ and $R^{4B}$ are attached to one another and together with the carbon atom to which they are attached form a cyclopropyl ring,
and
$R^{9A}$ represents hydrogen, methyl or trifluoromethyl,
$R^3$ represents $(C_2-C_4)$-alkyl, $(C_2-C_4)$-alkenyl, $(C_3-C_6)$-cycloalkyl or $[(C_3-C_6)$-cycloalkyl]methyl,
 where alkyl and alkenyl may be substituted up to three times and cycloalkyl may be substituted up to two times by fluorine
and
 where in alkyl and cycloalkyl one $CH_2$ group may be replaced by —O— or —S—, with the proviso that there are at least two carbon atoms between such a heteroatom and the uracil $N^1$-atom, and
the ring A represents an aza heterocycle of the formula

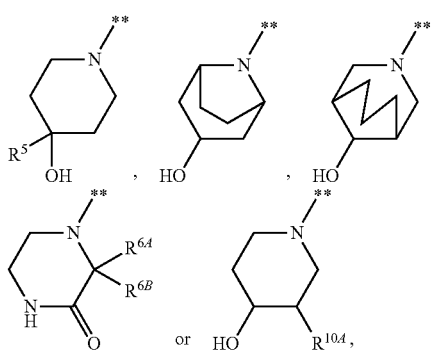

in which ** denotes the point of attachment to the carbonyl group,
$R^5$ represents hydrogen, methyl, trifluoromethyl, hydroxymethyl or ethyl,
$R^{6A}$ and $R^{6B}$ independently of one another represent hydrogen, methyl or ethyl,
and
$R^{10A}$ represents methyl or ethyl,
and their salts, solvates and solvates of the salts.

In a further preferred embodiment, the present invention encompasses compounds of the formula (I) in which
$R^1$ represents methyl or trifluoromethyl,
$R^2$ represents methyl, ethyl, n-propyl or isopropyl or represents a group of the formula

in which * denotes the point of attachment to the $CH_2$ group,
Ar represents phenyl or pyridyl,
 where phenyl and pyridyl may be substituted by fluorine, chlorine, methyl or methoxy,
$R^{4A}$ represents hydrogen, fluorine or methyl,
$R^{4B}$ represents hydrogen, fluorine, methyl or methoxy,
or
$R^{4A}$ and $R^{4B}$ are attached to one another and together with the carbon atom to which they are attached form a cyclopropyl ring,
$R^3$ represents $(C_2-C_4)$-alkyl, $(C_2-C_4)$-alkenyl, $(C_3-C_6)$-cycloalkyl or $[(C_3-C_6)$-cycloalkyl]methyl,
 where alkyl and alkenyl may be substituted up to three times and cycloalkyl may be substituted up to two times by fluorine
and
 where in alkyl and cycloalkyl one $CH_2$ group may be replaced by —O— or —S—, with the proviso that there are at least two carbon atoms between such a heteroatom and the uracil $N^1$-atom, and
the ring A represents an aza heterocycle of the formula

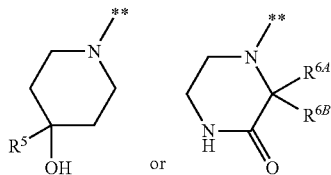

in which ** denotes the point of attachment to the carbonyl group,
$R^5$ represents hydrogen, methyl, trifluoromethyl or hydroxymethyl,
and
$R^{6A}$ and $R^{6B}$ each independently of one another represent hydrogen, methyl or ethyl,
and their salts, solvates and solvates of the salts.

A particular embodiment of the present invention relates to compounds of the formula (I) in which
$R^1$ represents methyl or ethyl,
and their salts, solvates and solvates of the salts.

A further particular embodiment of the present invention relates to compounds of the formula (I) in which
$R^1$ represents difluoromethyl or trifluoromethyl
and their salts, solvates and solvates of the salts.

A further particular embodiment of the present invention relates to compounds of the formula (I) in which
$R^2$ represents methyl, ethyl or isopropyl,
and their salts, solvates and solvates of the salts.

A further particular embodiment of the present invention relates to compounds of the formula (I) in which
$R^2$ represents propargyl,
and their salts, solvates and solvates of the salts.

A further particular embodiment of the present invention relates to compounds of the formula (I) in which
$R^2$ represents a group of the formula

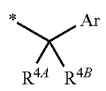

in which * denotes the point of attachment to the $CH_2$ group,
Ar represents phenyl which may be substituted by fluorine, chlorine, methyl or methoxy,
$R^{4A}$ represents hydrogen
and
$R^{4B}$ represents hydrogen, fluorine, methyl or methoxy,
and their salts, solvates and solvates of the salts.

A further particular embodiment of the present invention relates to compounds of the formula (I) in which
$R^2$ represents a group of the formula

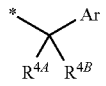

in which * denotes the point of attachment to the $CH_2$ group,
Ar represents phenyl which may be substituted by fluorine, chlorine, methyl or methoxy,
$R^{4A}$ represents hydrogen or methyl,
and
$R^{4B}$ represents hydroxy,
and their salts, solvates and solvates of the salts.

A further particular embodiment of the present invention relates to compounds of the formula (I) in which
$R^2$ represents a group of the formula

in which * denotes the point of attachment to the $CH_2$ group,
Ar represents phenyl which may be substituted by fluorine, chlorine, methyl or methoxy,
and
$R^{4A}$ and $R^{4B}$ each represent fluorine or are attached to one another and together with the carbon atom to which they are attached form a cyclopropyl ring,
and their salts, solvates and solvates of the salts.

A further particular embodiment of the present invention relates to compounds of the formula (I) in which
$R^2$ represents a group of the formula

in which * denotes the point of attachment to the $CH_2$ group,
Ar represents pyridyl
and
$R^{4A}$ and $R^{4B}$ both represent hydrogen,
and their salts, solvates and solvates of the salts.

A further particular embodiment of the present invention relates to compounds of the formula (I) in which
$R^2$ represents a group of the formula

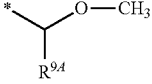

in which * denotes the point of attachment to the $CH_2$ group
and
$R^{9A}$ represents hydrogen, methyl or trifluoromethyl,
and their salts, solvates and solvates of the salts.

A further particular embodiment of the present invention relates to compounds of the formula (I) in which
$R^3$ represents $(C_2-C_4)$-alkyl, $(C_2-C_4)$-alkenyl or $(C_3-C_6)$-cycloalkyl,
where alkyl and alkenyl may be substituted up to three times by fluorine
and
where in alkyl and cycloalkyl one $CH_2$ group may be replaced by —O— or —S—, with the proviso that there are at least two carbon atoms between such a heteroatom and the uracil $N^1$-atom,
and their salts, solvates and solvates of the salts.

A further particular embodiment of the present invention relates to compounds of the formula (I) in which $R^3$ represents 2,2,2-trifluoroethyl or (trifluoromethoxy)methyl,
and their salts, solvates and solvates of the salts.

A further particular embodiment of the present invention relates to compounds of the formula (I) in which
the ring A represents an aza heterocycle of the formula

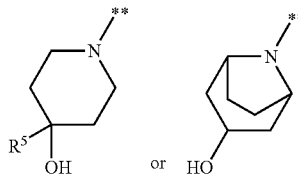

in which ** denotes the point of attachment to the carbonyl group,
and
$R^5$ represents hydrogen, methyl, trifluoromethyl, hydroxymethyl or ethyl,
and their salts, solvates and solvates of the salts.

A further particular embodiment of the present invention relates to compounds of the formula (I) in which
the ring A represents an aza heterocycle of the formula

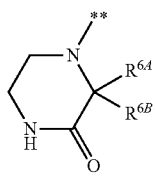

in which ** denotes the point of attachment to the carbonyl group,
and
$R^{6A}$ and $R^{6B}$ each independently of one another represent hydrogen, methyl or ethyl,
and their salts, solvates and solvates of the salts.

In the context of the present invention, particular preference is given to compounds of the formula (I) in which
$R^1$ represents methyl, difluoromethyl, trifluoromethyl or ethyl,
$R^2$ represents methyl, ethyl, isopropyl or propargyl or represents a group of the formula

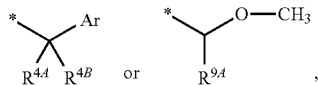

in which * denotes the point of attachment to the CH$_2$ group,
Ar represents phenyl, 3-pyridyl or 4-pyridyl,
where phenyl may be substituted in the meta- or para-position by fluorine or in the ortho-position by fluorine, chlorine or methyl,
$R^{4A}$ represents hydrogen, fluorine or methyl,
$R^{4B}$ represents hydrogen, fluorine, methyl, hydroxy or methoxy,
or
$R^{4A}$ and $R^{4B}$ are attached to one another and together with the carbon atom to which they are attached form a cyclopropyl ring, and
$R^{9A}$ represents methyl or trifluoromethyl,
$R^3$ represents 2,2,2-trifluoroethyl, 3,3-difluoroprop-2-en-1-yl, methoxymethyl, (trifluoromethoxy)methyl or [(trifluoromethyl)sulphanyl]methyl,
and
the ring A represents an aza heterocycle of the formula

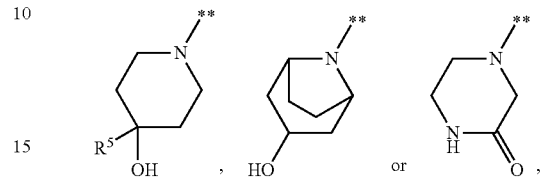

in which ** denotes the point of attachment to the carbonyl group
and
$R^5$ represents hydrogen, methyl, trifluoromethyl, hydroxymethyl or ethyl,
and their salts, solvates and solvates of the salts.

In a further particularly preferred embodiment, the present invention encompasses compounds of the formula (I) in which
$R^1$ represents methyl, difluoromethyl, trifluoromethyl or ethyl,
$R^2$ represents methyl, ethyl, isopropyl or propargyl or represents a group of the formula

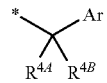

in which * denotes the point of attachment to the CH$_2$ group,
Ar represents phenyl, 3-pyridyl or 4-pyridyl,
where phenyl may be substituted in the meta- or para-position by fluorine or in the ortho-position by fluorine, chlorine or methyl,
$R^{4A}$ represents hydrogen or fluorine,
$R^{4B}$ represents hydrogen, fluorine, methyl, hydroxy or methoxy,
or
$R^{4A}$ and $R^{4B}$ are attached to one another and together with the carbon atom to which they are attached form a cyclopropyl ring,
$R^3$ represents 2,2,2-trifluoroethyl, 3,3-difluoroprop-2-en-1-yl, methoxymethyl, (trifluoromethoxy)methyl or [(trifluoromethyl)sulphanyl]methyl, and
the ring A represents an aza heterocycle of the formula

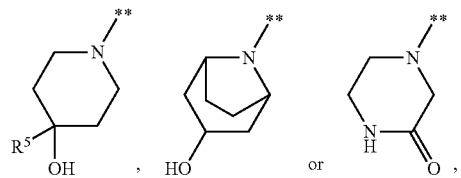

in which ** denotes the point of attachment to the carbonyl group and

R⁵ represents hydrogen, methyl, trifluoromethyl, hydroxymethyl or ethyl, and their salts, solvates and solvates of the salts.

In a further particularly preferred embodiment, the present invention encompasses compounds of the formula (I) in which R¹ represents methyl, R² represents methyl, ethyl or isopropyl or represents a group of the formula

in which * denotes the point of attachment to the CH₂ group,

Ar represents phenyl or 3-pyridyl,
where phenyl may be substituted in the ortho-position by fluorine, chlorine or methyl, R⁴ᴬ represents hydrogen
and R⁴ᴮ represents hydrogen, methyl or methoxy, R³ represents 2,2,2-trifluoroethyl, 3,3-difluoroprop-2-en-1-yl, methoxymethyl or (trifluoromethoxy)methyl, and the ring A represents an aza heterocycle of the formula

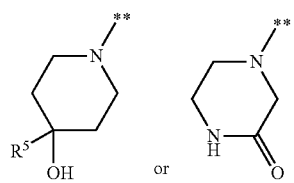

in which ** denotes the point of attachment to the carbonyl group
and

R⁵ represents hydrogen, methyl or hydroxymethyl, and their salts, solvates and solvates of the salts.

The individual radical definitions specified in the particular combinations or preferred combinations of radicals are, independently of the particular combinations of the radicals specified, also replaced as desired by radical definitions of other combinations.

Very particular preference is given to combinations of two or more of the abovementioned preferred ranges.

The invention further provides a process for preparing the compounds according to the invention of the formula (I), characterized in that either

[A-1] a compound of the formula (II)

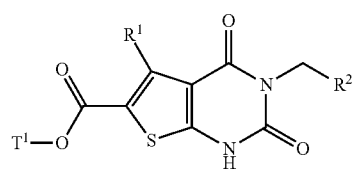

in which R¹ and R² have the meanings given above and

T¹ represents (C₁-C₄)-alkyl or benzyl, is alkylated in the presence of a base with a compound of the formula (III)

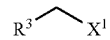

in which R³ has the meaning given above
and

X¹ represents a leaving group, for example chlorine, bromine, iodine, mesylate, triflate or tosylate, to give a compound of the formula (IV)

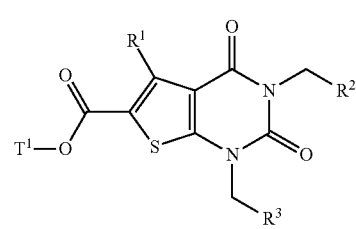

in which R¹, R², R³ and T¹ have the meanings given above, then the ester radical T¹ is cleaved off and the carboxylic acid of the formula (V) obtained in this manner

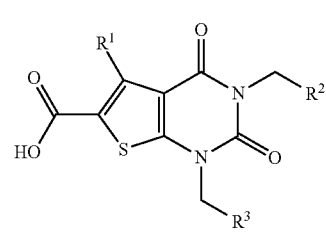

in which R¹, R² and R³ have the meanings given above is then coupled with activation of the carboxyl function with an amine of the formula (VI)

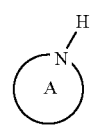

in which the ring A has the meaning given above
or—in a changed order of the above reaction steps—
[A-2] the compound of the formula (II)

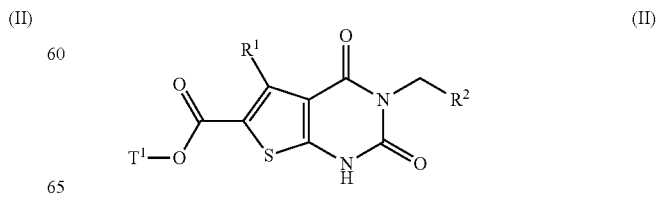

in which R¹, R² and T¹ have the meanings given above is initially converted by cleavage of the ester radical T¹ into the carboxylic acid of the formula (VII)

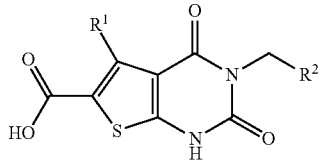
(VII)

in which R¹ and R² have the meanings given above,
then coupled with activation of the carboxyl function with an amine of the formula (VI)

(VI)

in which the ring A has the meaning given above
to give a compound of the formula (VIII)

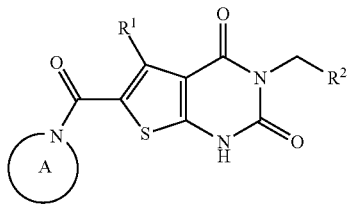
(VIII)

in which R¹, R² and the ring A have the meanings given above
and this is then alkylated in the presence of a base with a compound of the formula (III)

(III)

in which R³ and X¹ have the meaning given above
or
[B] initially an N³ protected compound of the formula (IX)

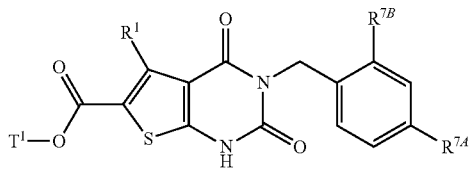
(IX)

in which R¹ and T¹ have the meanings given above
and
R⁷ᴬ and R⁷ᴮ independently of one another represent hydrogen or methoxy is alkylated in the presence of a base with a compound of the formula (III)

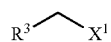
(III)

in which R³ and X¹ have the meanings given above
to give a compound of the formula (X)

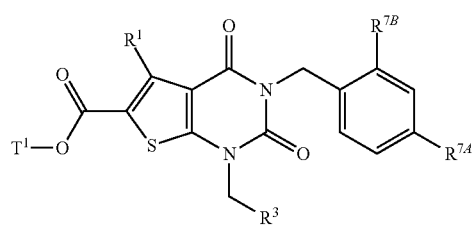
(X)

in which R¹, R³, R⁷ᴬ, R⁷ᴮ and T¹ have the meanings given above,
the N³-benzyl group and the ester radical T¹ are then cleaved off simultaneously by treatment with a strong Lewis acid such as aluminium trichloride, the carboxylic acid of the formula (XI) obtained in this manner

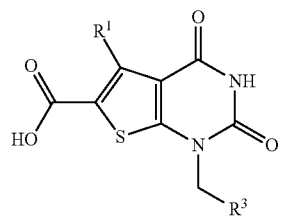
(XI)

in which R¹ and R³ have the meanings given above,
is then coupled with activation of the carboxyl function with an amine of the formula (VI)

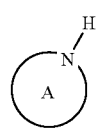
(VI)

in which the ring A has the meaning given above
to give a compound of the formula (XII)

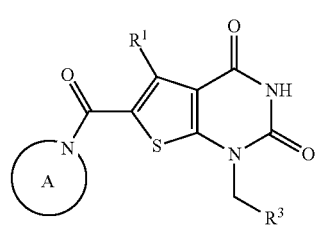
(XII)

in which $R^1$, $R^3$ and the ring A have the meanings given above and the latter is then either reacted (a) in the presence of a base with a compound of the formula (XIII)

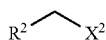
(XIII)

in which $R^2$ has the meaning given above
and
$X^2$ represents a leaving group, for example chlorine, bromine, iodine, mesylate, triflate or tosylate,
or (b) in the presence of a suitable phosphine and an azodicarboxylate with a compound of the formula (XIV)

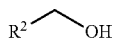
(XIV)

in which $R^2$ has the meaning given above,
and the compounds of the formula (I) prepared in this manner are optionally converted with the appropriate (i) solvents and/or (ii) acids into their solvates, salts and/or solvates of the salts.

In the processes described above, it may optionally be required or advantageous to protect temporarily a hydroxyl group present in the amine compound of the formula (VI) during the coupling of this amine [reactions (V)+(VI)→(I), (VII)+(VI)→(VIII) and (XI)+(VI)→(X)] and/or during the subsequent alkylation reactions [(VIII)+(III)→(I) and (XII)+(XIII) or (XIV)→(I)] and only to deprotect again at the end of the reaction sequence. Suitable for this purpose are customary hydroxyl-protective groups such as acetyl, pivaloyl, benzoyl, tert-butyl, 2-(trimethylsilyl)ethyl, benzyl, triphenylmethyl, methoxymethyl, 2-(trimethylsilyl)ethoxymethyl, tetrahydropyran-2-yl, trimethylsilyl, triisopropylsilyl or tert-butyldimethylsilyl. The hydroxyl-protective group used is preferably acetyl.

It may also be expedient to block temporarily an amidic NH group present in the compound (VI) to avoid selectivity problems in subsequent alkylation reactions in the uracil moiety of the molecule [see reactions (VIII)+(III)→(I) and (XII)+(XIII) or (XIV)→(I)]. Suitable for this purpose are known amide protective groups such as allyl, 2-(trimethylsilyl)ethyl, 4-methoxybenzyl, 2,4-dimethoxybenzyl, methoxymethyl or benzyloxymethyl.

Introduction and removal of the protective groups mentioned are carried out by generally customary methods [see, for example, T. W. Greene and P. G. M. Wuts, *Protective Groups in Organic Synthesis*, Wiley, New York, 1999].

Suitable inert solvents for the alkylation reactions (II)+(III)→(IV), (VIII)+(III)→(I), (IX)+(III)→(X) and (XII)+(XIII)→(I) are in particular ethers such as diethyl ether, diisopropyl ether, methyl tert-butyl ether, tetrahydrofuran, 1,4-dioxane, 1,2-dimethoxyethane or bis(2-methoxyethyl) ether, or polar aprotic solvents such as acetonitrile, butyronitrile, acetone, methyl ethyl ketone, ethyl acetate, N,N-dimethylformamide (DMF), N,N-dimethylacetamide (DMA), dimethyl sulphoxide (DMSO), N,N'-dimethylpropyleneurea (DMPU) or N-methylpyrrolidinone (NMP). It is also possible to use mixtures of these solvents. Preference is given to using N,N-dimethylformamide.

Suitable bases for these alkylation reactions are in particular customary inorganic bases. These include alkali metal hydroxides such as lithium hydroxide, sodium hydroxide or potassium hydroxide, alkali metal bicarbonates such as sodium bicarbonate or potassium bicarbonate, alkali metal carbonates such as lithium carbonate, sodium carbonate, potassium carbonate or caesium carbonate, or alkali metal hydrides such as sodium hydride or potassium hydride. Preference is given to using caesium carbonate.

The reactions mentioned are generally carried out in a temperature range of from +20° C. to +100° C.

Cleavage of the ester group $T^1$ in the process steps (IV)→(V) and (II)→(VII) is carried out by customary methods by treating the ester in an inert solvent with an acid or a base, where in the latter variant the salt, initially formed, of the carboxylic acid is converted by subsequent treatment with acid into the free carboxylic acid. In the case of the tert-butyl esters, ester cleavage is preferably carried out using an acid. Methyl and ethyl ester are preferably cleaved using a base. Alternatively, benzyl ester can also be cleaved by hydrogenation (hydrogenolysis) in the presence of a suitable catalyst such as, for example, palladium on activated carbon.

Suitable inert solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulphoxide. It is equally possible to use mixtures of these solvents. In the case of a basic ester hydrolysis, preference is given to using mixtures of water with tetrahydrofuran, 1,4-dioxane, methanol and/or ethanol. In the case of the reaction with trifluoroacetic acid, preference is given to using dichloromethane, and in the case of the reaction with hydrogen chloride 1,4-dioxane, in each case under anhydrous conditions.

Suitable bases for a hydrolysis reaction are the customary inorganic bases. These include in particular alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using lithium hydroxide.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to using hydrogen chloride or trifluoroacetic acid.

The ester cleavage is effected generally within a temperature range of from −20° C. to +100° C., preferably at from 0° C. to +50° C.

The coupling reactions (V)+(VI)→(I), (VII)+(VI)→(VIII) and (XI)+(VI)→(XII) [amide formation] can be carried out with the aid of a condensing or activating agent, or via the intermediate stage of the corresponding carboxylic acid chlorides.

Suitable such condensing or activating agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, (1-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl) phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as base alkali metal carbonates, for example sodium carbonate or potassium carbonate, or tertiary amine bases such as triethylamine, N-methylmorpholine (NMM), N-methylpiperidine (NMP), N,N-diisopropylethylamine, pyridine or 4-N,N-dimethylaminopyridine (DMAP). Preference is given to using O-(7-azabenzotriazol-1-yl)-N,N,N',N'-tetramethyluronium hexafluorophosphate (HATU) in combination with N,N-diisopropylethylamine, or N-(3-dimethylaminopropyl)-N'-ethylcarbodiimide hydrochloride (EDC) in combination with 1-hydroxybenzotriazole (HOBt) and triethylamine.

In the case in which the reaction is carried out in two steps via the corresponding carboxylic acid chlorides, coupling with the amine component (VI) is carried out in the presence of a customary auxiliary base such as sodium carbonate, potassium carbonate, triethylamine, N-methylmorpholine (NMM), N-methylpiperidine (NMP), N,N-diisopropylethylamine, pyridine, 2,6-dimethylpyridine, 4-N,N-dimethylaminopyridine (DMAP), 1,8-diazabicyclo[5.4.0]undec-7-ene (DBU) or 1,5-diazabicyclo[4.3.0]non-5-ene (DBN); preference is given to using N,N-diisopropylethylamine. For their part, the carboxylic acid chlorides are prepared in a customary manner by treating the carboxylic acid (V), (VII) or (XI) with thionyl chloride or oxalyl chloride in an inert solvent such as dichloromethane.

Inert solvents for the coupling reactions mentioned are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halogenated hydrocarbons such as dichloromethane, trichloromethane, carbon tetrachloride, 1,2-dichloroethane, trichloroethylene or chlorobenzene, or polar aprotic solvents such as acetone, methyl ethyl ketone, acetonitrile, butyronitrile, ethyl acetate, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of such solvents. Preference is given to using dichloromethane, tetrahydrofuran, N,N-dimethylformamide or mixtures of these solvents.

The couplings are generally carried out within a temperature range of from −20° C. to +60° C., preferably at from 0° C. to +40° C.

Simultaneous removal of the $N^3$-benzyl protective group and the ester radical $T^1$ in process step (X)→(XI) is expediently carried out by treating (X) with a strong Lewis acid such as, in particular, excess aluminium trichloride, in an inert solvent such as toluene, xylene or chlorobenzene in a temperature range of from +20° C. to +120° C., preferably in a temperature range of from +40° C. to +70° C.

The reaction (XII)+(XIV)→(I) is carried out under the customary conditions of a Mitsunobu reaction in the presence of triphenylphosphine and an azodicarboxylate such as diethyl azodicarboxylate (DEAD) or diisopropyl azodicarboxylate (DIAD) [see, for example, D. L. Hughes, *Org. Reactions* 42, 335 (1992); D. L. Hughes, *Org. Prep. Proced. Int.* 28 (2), 127 (1996)]. The preferred inert solvent used for this reaction is tetrahydrofuran.

The process steps described above can be carried out at atmospheric, elevated or reduced pressure (for example in the range from 0.5 to 5 bar); in general, the reactions are each carried out at atmospheric pressure.

Compounds of the formula (II) in which $R^1$ represents methyl or ethyl can be prepared by reacting a compound of the formula (XV)

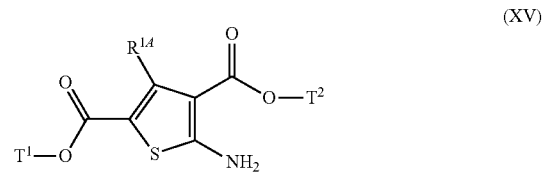

(XV)

in which $T^1$ has the meaning given above,
$R^{1A}$ represents methyl or ethyl
and
$T^2$ represents methyl or ethyl
in the presence of a base either (α) initially with a phosgene equivalent such as N,N'-carbonyldiimidazole and then with an amine of the formula (XVI)

(XVI)

in which $R^2$ has the meaning given above,
or (b) with an isocyanate of the formula (XVII)

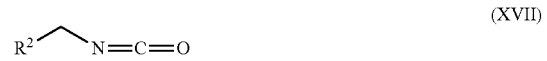

(XVII)

in which $R^2$ has the meaning given above,
to give a compound of the formula (XVIII)

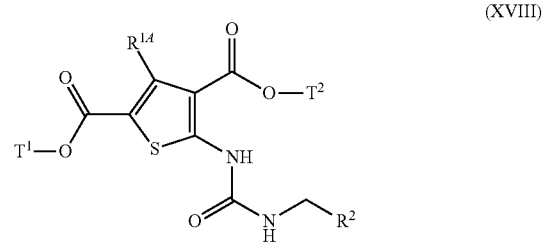

(XVIII)

in which $R^{1A}$, $R^2$, $T^1$ and $T^2$ have the meanings given above and then cyclizing this by treatment with a base to give the compound of the formula (II-A)

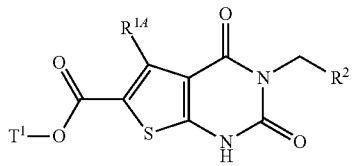

(II-A)

in which $R^{14}$, $R^2$ and $T^1$ have the meanings given above.

Inert solvents for the conversion of the aminothiophene (XV) into the urea derivative (XVIII) with the aid of N,N'-carbonyldiimidazole and the amine (XVI) or using the isocyanate (XVII) are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halogenated hydrocarbons such as dichloromethane, trichloromethane, carbon tetrachloride, 1,2-dichloroethane, trichloroethylene or chlorobenzene, or polar aprotic solvents such as acetone, methyl ethyl ketone, acetonitrile, butyronitrile, ethyl acetate, pyridine, dimethyl sulphoxide (DMSO), N,N-dimethylformamide (DMF), N,N-dimethylacetamide (DMA), N,N'-dimethylpropyleneurea (DMPU) or N-methylpyrrolidinone (NMP). It is also possible to use mixtures of these solvents. Preference is given to using dichloromethane or tetrahydrofuran.

Preferred auxiliary bases used for these reactions are tertiary amine bases such as triethylamine, N-methylmorpholine (NMM), N-methylpiperidine (NMP), N,N-diisopropylethylamine, pyridine or 4-N,N-dimethylaminopyridine (DMAP); preference is given to triethylamine.

As alternative phosgene equivalents, in addition to N,N'-carbonyldiimidazole, trichloromethyl chloroformate ("diphosgene"), bis(trichloromethyl) carbonate ("triphosgene") or similar reagents may be considered.

The reactions are generally carried out in a temperature range from 0° C. to +100° C., preferably at from +20° C. to +60° C.

The base-induced cyclization reaction (XVIII)→(II-A) is preferably carried out with the aid of an alkali metal alkoxide such as sodium methoxide or potassium methoxide, sodium ethoxide or potassium ethoxide or sodium tert-butoxide or potassium tert-butoxide in the alcohol in question as solvent or with the aid of an alkali metal hydride such as sodium hydride or potassium hydride in tetrahydrofuran or N,N-dimethylformamide as inert solvent; preference is given to using sodium ethoxide in ethanol. The reaction is generally carried out in a temperature range of from 0° C. to +100° C., preferably at from +20° C. to +60° C. [for the synthesis sequence (XV)→(XVIII)→(II-A) generally cf., for example, also the processes described in EP 1 847 541-A1 for preparing other thienouracil derivatives].

For their part, the compounds of the formula (XV) can be obtained by a route known from the literature via the 3-component reaction of an acetoacetic acid or β-ketovaleric acid ester (for $R^{14}$=methyl or ethyl) using a α-cyanoacetic ester and elemental sulphur [Gewald reaction; see, for example, B. P. McKibben et al., *Tetrahedron Lett.* 40, 5471-5474 (1999) and the literature cited therein].

Compounds of the formula (II) in which $R^1$ represents hydrogen can be prepared by converting a compound of the formula (XIX)

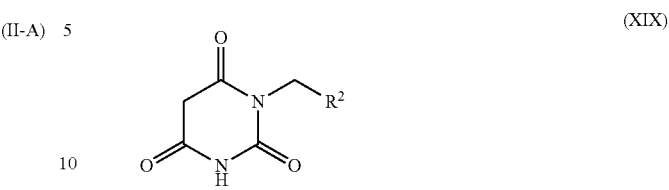

(XIX)

in which $R^2$ has the meaning given above, with a mixture of phosphorus oxychloride and N,N-dimethylformamide into a compound of the formula (XX)

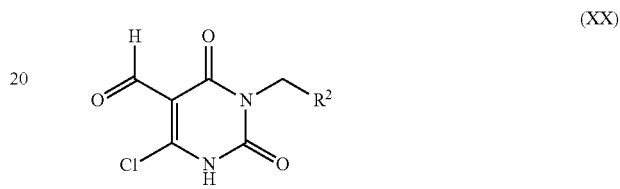

(XX)

in which $R^2$ has the meaning given above, and then condensing this in the presence of a base with an α-mercaptoacetic ester of the formula (XXI)

(XXI)

in which $T^1$ has the meaning given above to give the compound of the formula (II-B)

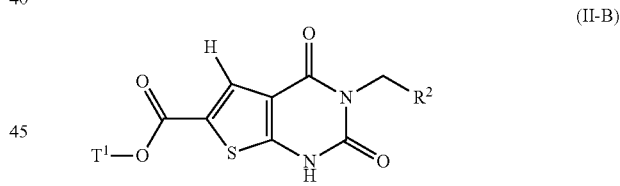

(II-B)

in which $R^2$ and $T^1$ have the meanings given above.

The conversion of the barbituric acid derivative (XIX) into the 6-chloro-5-formylpyrimidinedione (XX) is carried out via a regioselective Vilsmaier-Haack reaction by treating (XIX) with a pre-formed mixture of phosphorus oxychloride and N,N-dimethylformamide which is used in a large excess and simultaneously also serves as solvent [cf., for example, K. Tanaka et al., *Chem. Pharm. Bull.* 35 (4), 1397-1404 (1987)]. The reaction is carried out in a temperature range of from +20° C. to +120° C.

Bases suitable for the subsequent condensation reaction (XX)+(XXI)→(II-B) are in particular alkali metal carbonates such as lithium carbonate, sodium carbonate, potassium carbonate or caesium carbonate, alkali metal alkoxides such as sodium methoxide or potassium methoxide, sodium ethoxide or potassium ethoxide or sodium tert-butoxide or potassium tert-butoxide, or alkali metal hydrides such as sodium hydride or potassium hydride; sodium carbonate or potassium carbonate are preferably used [cf. also K. Hirota et al., *J. Heterocycl. Chem.* 27 (3), 717-721 (1990)].

The reaction is preferably carried out in an alcoholic solvent such as methanol, ethanol, isopropanol or tert-butanol, or in an inert polar-aprotic solvent such as N,N-dimethylformamide (DMF), N,N'-dimethylpropyleneurea (DMPU) or N-methylpyrrolidinone (NMP), in a temperature range of from +20° C. to +150° C., and it has been found to be advantageous to carry out the reaction under microwave irradiation. The solvent used is preferably ethanol.

For their part, the compounds of the formula (XIX) can be prepared by a customary process by base-induced condensation of a malonic ester of the formula (XXII)

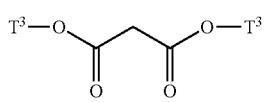
(XXII)

in which
$T^3$ represents methyl or ethyl
with a urea derivative of the formula (XXIII)

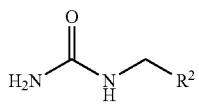
(XXIII)

in which $R^2$ has the meaning given above.

The condensation (XXII)+(XXIII)→(XIX) is usually carried out with the aid of an alkali metal alkoxide such as sodium methoxide or potassium methoxide, sodium ethoxide or potassium ethoxide or sodium tert-butoxide or potassium tert-butoxide in the alcohol in question as solvent or with the aid of an alkali metal hydride such as sodium hydride or potassium hydride in tetrahydrofuran or N,N-dimethylformamide as inert solvent; preference is given to using sodium ethoxide in ethanol. The reaction is generally carried out in a temperature range of from +20° C. to +100° C.

Using the process described above (for $R^1$=methyl, ethyl or hydrogen), it is not possible to obtain compounds of the formula (II) in which $R^1$ represents difluoromethyl or trifluoromethyl, or only in low yields (<10%). Accordingly, the present invention furthermore provides a novel process for preparing compounds of the formula (II-C)

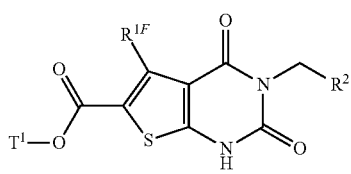
(II-C)

in which $R^2$ has the meaning given above,
$R^{1F}$ represents difluoromethyl or trifluoromethyl
and
$T^1$ represents ($C_1$-$C_4$)-alkyl or benzyl, characterized in that a compound of the formula (XIX)

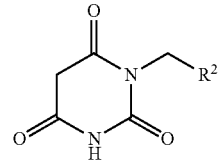
(XIX)

in which $R^2$ has the meaning given above,
is converted with phosphorus oxychloride into a compound of the formula (XXIV)

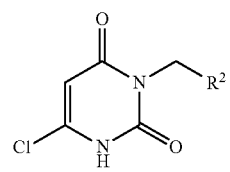
(XXIV)

in which $R^2$ has the meaning given above,
then in the presence of excess pyridine is reacted with an anhydride of the formula (XXV)

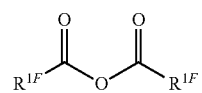
(XXV)

in which $R^{1F}$ has the meaning given above
to give a betaine compound of the formula (XXVI)

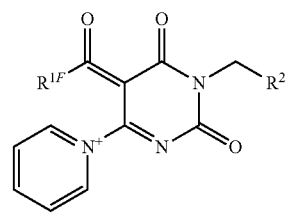
(XXVI)

in which $R^{1F}$ and $R^2$ have the meanings given above
and these are then condensed in the presence of a base with an α-mercaptoacetic ester of the formula (XXI)

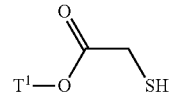
(XXI)

in which $T^1$ has the meaning given above
to give the compound (II-C).

The conversion of the barbituric acid derivative (XIX) into the 6-chloropyrimidinedione (XXIV) is carried out with the aid of excess phosphorus oxychloride in an aqueous alcohol such as methanol or ethanol as solvent in a temperature range of from 0° C. to +100° C.

Subsequent conversion into the pyridinium enolate betaine (XXVI) is carried out analogously to a method described in the literature for the synthesis of 3-substituted chromone derivatives [I. Yokoe et al., *Chem. Pharm. Bull.* 42 (8), 1697-1699 (1994)] by treating the 6-chloropyrimidinedione (XXIV) in the presence of a relatively large excess of pyridine (about ten-fold) with the anhydride (XXV). The reaction is generally carried out in a temperature range of from 0° C. to +40° C., and the inert solvent used is preferably acetonitrile.

Finally, the condensation of the betaine (XXVI) with the mercaptoacetic ester (XXI) to give the target compound (II-C) is carried out in a manner analogous to that described above for the reaction (XX)+(XXI)→(II-B), and here, too, it is advantageous to carry out the reaction under microwave irradiation.

The intermediates of the formula (IX) from process [B], which are protected temporarily at the uracil $N^3$ atom, can be obtained in an analogous manner with the aid of the reaction sequences described above by employing, instead of the compounds (XVI), (XVII) or (XXIII), the corresponding benzyl derivatives, for example compounds of the formula (XXVII) or (XXVIII)

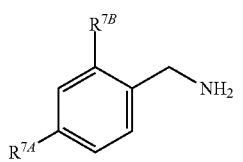
(XXVII)

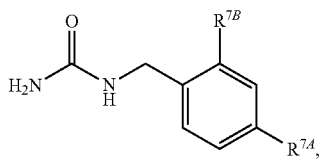
(XXVIII)

in which $R^{7A}$ and $R^{7B}$ have the meanings given above.

Compounds of the formula (IV) in which $R^1$ represents difluoromethyl can also be obtained by initially preparing, starting with a compound of the formula (IV-A)

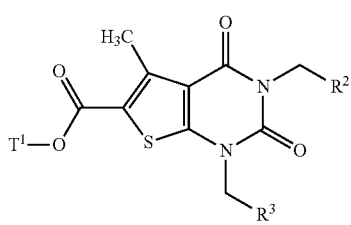
(IV-A)

in which $R^2$, $R^3$ and $T^1$ have the meanings given above, by treatment with N-bromosuccinimide (NBS) in the presence of catalytic 2,2'-azobis(2-methylpropionitrile) (AIBN), the bromomethyl compound (XXIX)

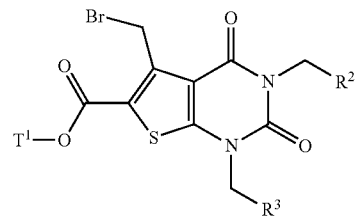
(XXIX)

in which $R^2$, $R^3$ and $T^1$ have the meanings given above, then oxidizing this by known methods to the formyl compound (XXX)

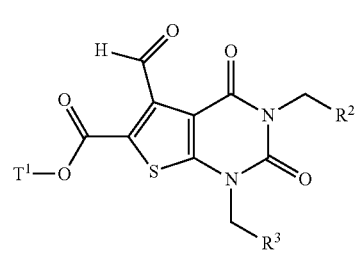
(XXX)

in which $R^2$, $R^3$ and $T^1$ have the meanings given above, and then fluorinating to give the difluoromethyl compound (IV-B)

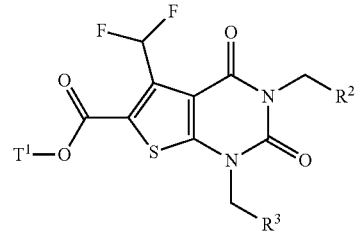
(IV-B)

in which $R^2$, $R^3$ and $T^1$ have the meanings given above.

The oxidation in reaction step (XXIX)→(XXX) is preferably carried out with the aid of N-methylmorpholine N-oxide (NMO) in the presence of molecular sieve [cf., for example, D. R. Levine et al., *J. Am. Chem. Soc.* 2014, 136 (19), 7132-7139]. The reaction is generally carried out in a temperature range of from −20° C. to +25° C. in an inert solvent such as, for example, acetonitrile.

Suitable for the deoxyfluorination in process step (XXX)→(IV-B) are known agents such as diethylaminosulphur trifluoride (DAST), morpholinosulphur trifluoride (Morpho-DAST) or bis(2-methoxyethyl)aminosulphur trifluoride)(Deoxo-Fluor®). The reaction is usually carried out in a temperature range of from −10° C. to +25° C. in an inert solvent such as, for example, dichloromethane or tetrahydrofuran.

Compounds of the formula (IV) in which $R^1$ represents fluoromethyl, i.e. compounds of the formula (IV-C)

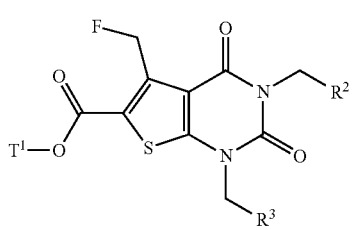

(IV-C)

in which $R^2$, $R^3$ and $T^1$ have the meanings given above, can be prepared in a simple manner by a substitution reaction of the bromomethyl compound (XXIX) described above with a fluoride such as, for example potassium fluoride, caesium fluoride or tetra-n-butylammonium fluoride (TBAF). The reaction is generally carried out in a temperature range of from 0° C. to +60° C. in an inert solvent such as acetone, acetonitrile, N,N-dimethylformamide (DMF) or tetrahydrofuran or mixtures thereof.

Compounds of the formula (IV) in which $R^1$ represents 1-fluoromethyl, i.e. compounds of the formula (IV-D)

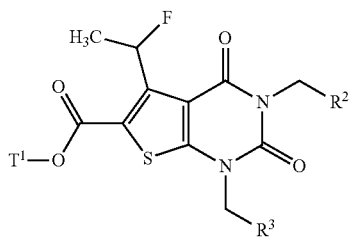

(IV-D)

in which $R^2$, $R^3$ and $T^1$ have the meanings given above can be obtained by converting the formyl compound (XXX) described above with methylmagnesium bromide under customary conditions at about 0° C. into the 1-hydroxyethyl compound (XXXI)

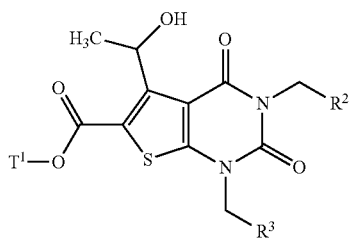

(XXXI)

in which $R^2$, $R^3$ and $T^1$ have the meanings given above and then treating this in a manner analogous to that described above for the transformation (XXX)→(IV-B) with a fluorinating agent such as diethylaminosulphur trifluoride (DAST) or bis(2-methoxyethyl)aminosulphur trifluoride (Deoxo-Fluor®).

The intermediates of the formulae (IV-B), (IV-C) and (IV-D) which can be obtained in this manner are then converted further according to the reaction sequence (IV)→(V) and (V)+(VI)→(I) described above under [A-1] into the corresponding compounds of the formula (I) according to the invention.

An alternative process for the preparation of compounds of the formula (V-A)

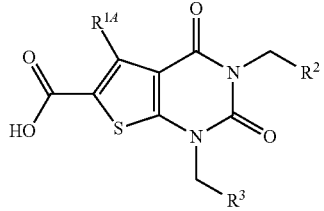

(V-A)

in which $R^2$ and $R^3$ have the meanings given above and $R^{1A}$ represents methyl or ethyl
consists in initially converting a compound of the formula (XXXII)

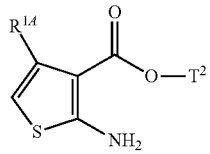

(XXXII)

in which $R^{1A}$ has the meaning given above and
$T^2$ represents methyl or ethyl
analogously to the reaction sequence (XV)→(XVIII)→(II-A) and (II)→(IV) described above into a compound of the formula (XXXIII)

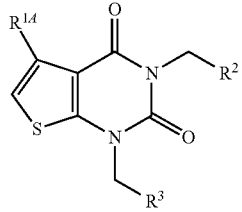

(XXXIII)

in which $R^{1A}$, $R^2$ and $R^3$ have the meanings given above, then formylating these with a mixture of N,N-dimethylformamide and phosphorus oxychloride to give a compound of the formula (XXXIV)

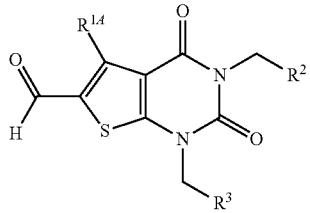

(XXXIV)

in which $R^{1A}$, $R^2$ and $R^3$ have the meanings given above, and finally oxidizing to the carboxyl compound of the formula (V-A).

The transformation (XXXIII)→(XXXIV) is carried out under the customary conditions of a Vilsmaier-Haack reaction using a mixture of N,N-dimethylformamide and phosphorus oxychloride which is employed in a large excess and simultaneously also serves as solvent. The reaction is generally carried out in a temperature range of from 0° C. to +120° C.

The oxidizing agent used for the transformation (XXXIV)→(V-A) is preferably sodium chlorite in the presence of hydrogenphosphate-buffered sulfaminic acid [cf., for example, WO 2008/115912-A1, Example 2; M. O. Anderson et al., *J. Med. Chem.* 2012, 55 (12), 5942-5950]. The reaction is usually carried out in a temperature range of from −10° C. to +20° C. in a mixture of water with acetone or 1,4-dioxane as inert solvent.

The compounds of the formulae (III), (VI), (XIII), (XIV), (XVI), (XVII), (XXI), (XXII), (XXIII), (XXV), (XXVII), (XXVIII) and (XXXII) are either commercially available or described as such in the literature, or they can be prepared from other commercially available compounds by methods familiar to the person skilled in the art and known from the literature. Numerous detailed procedures and further literature references can also be found in the Experimental Part, in the section on the preparation of the starting compounds and intermediates.

The preparation of the compounds according to the invention can be illustrated by the following reaction schemes:

Scheme 1

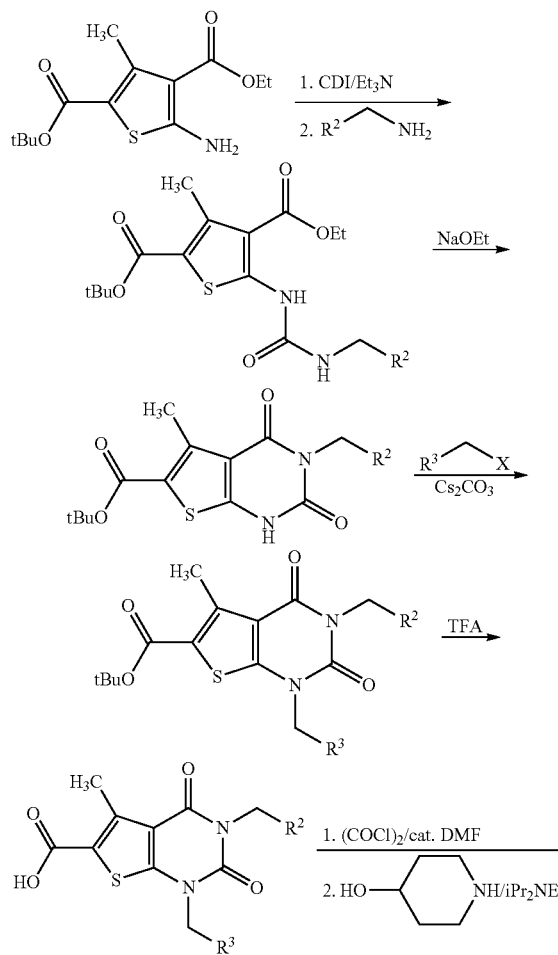

Scheme 2

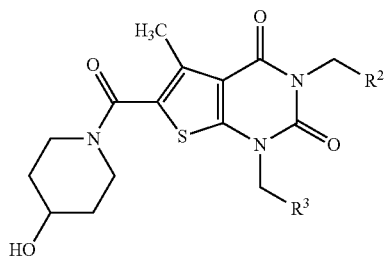

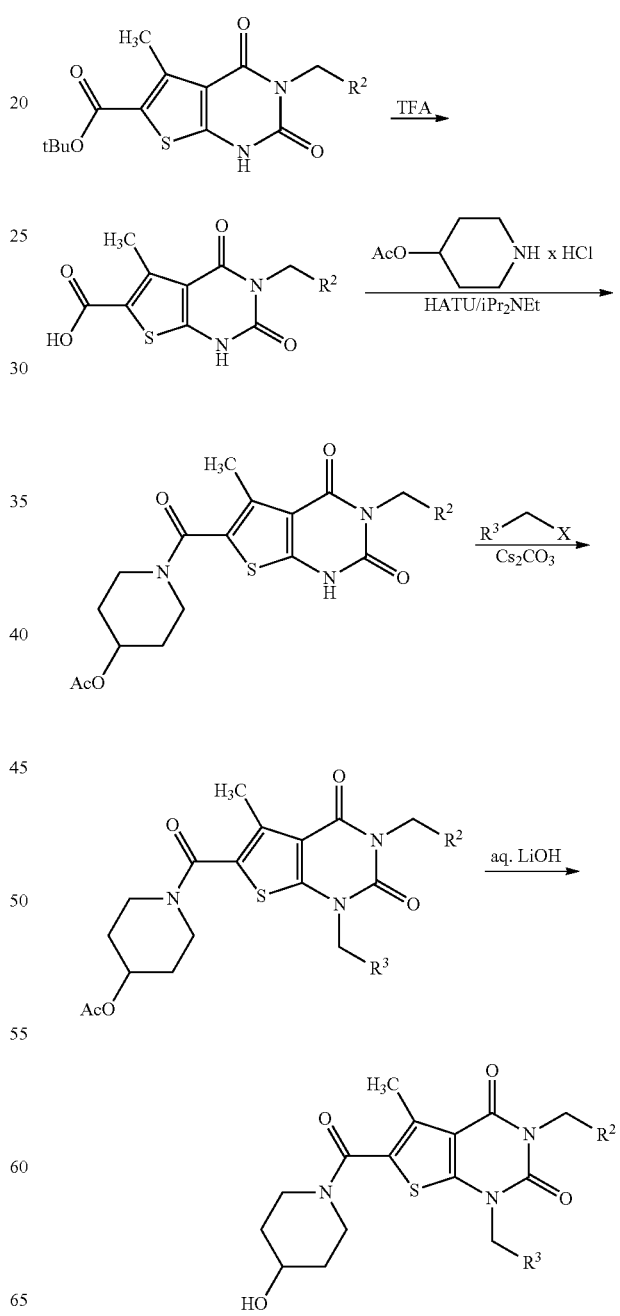

Scheme 3
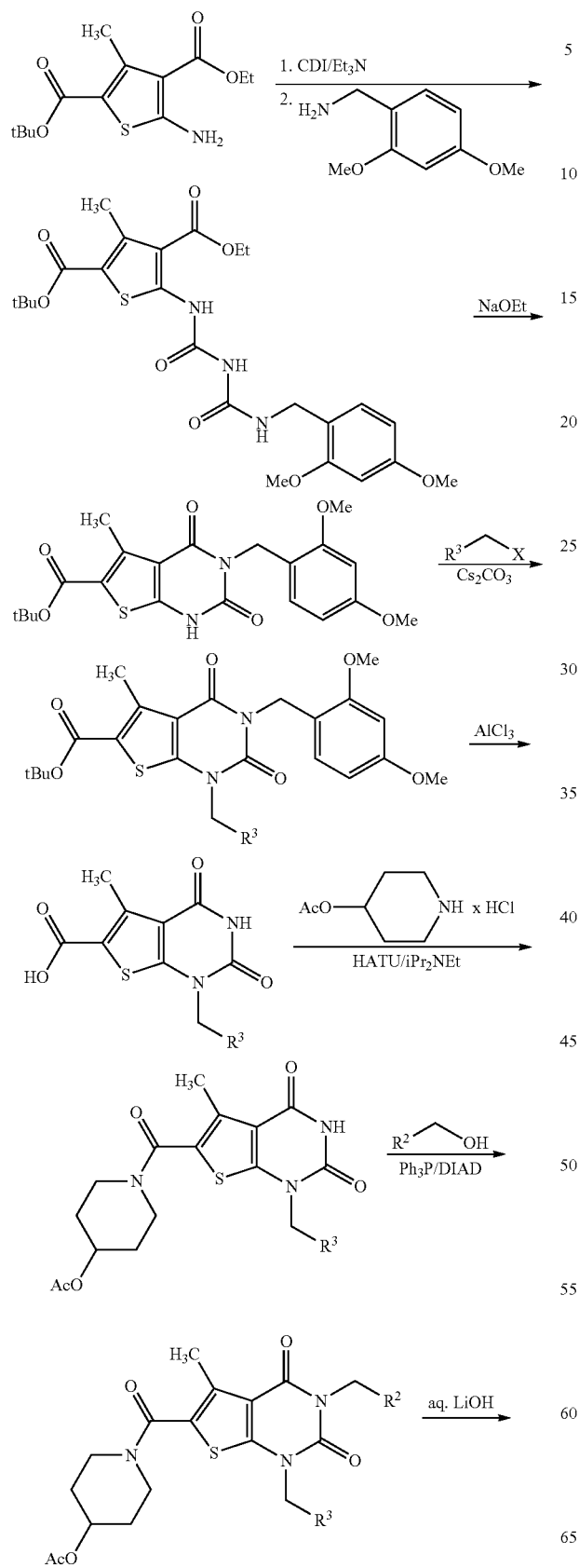
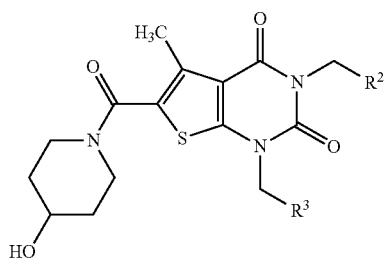
Scheme 4
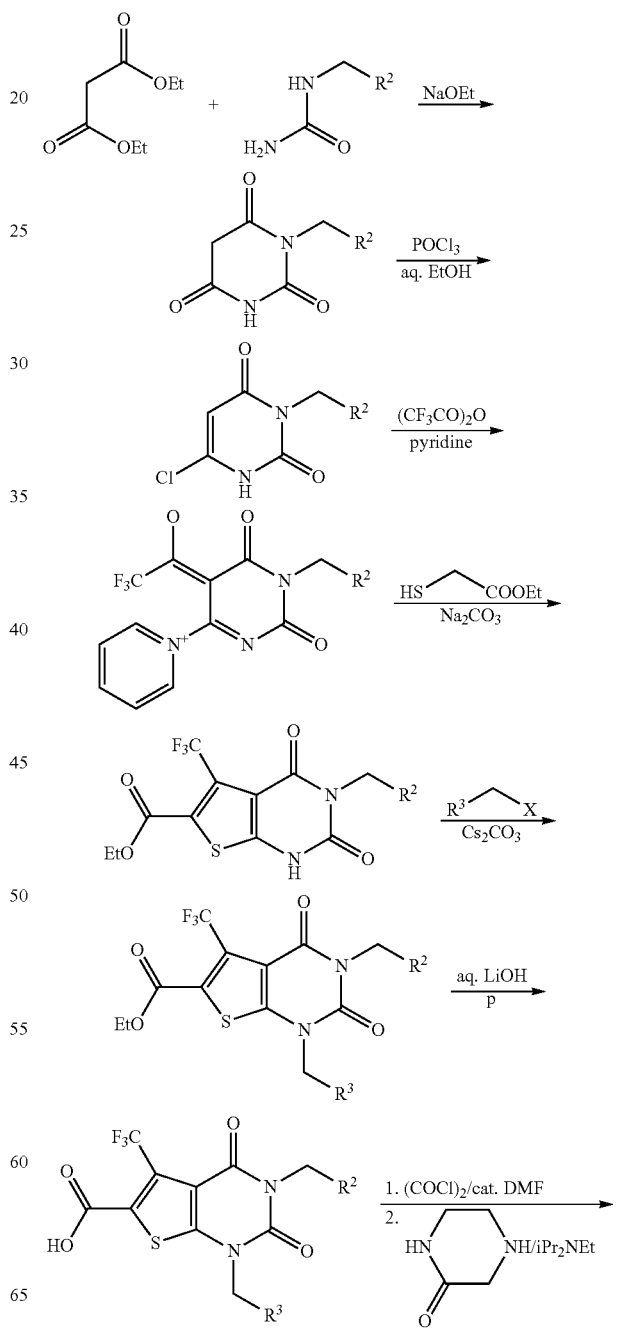

Scheme 5
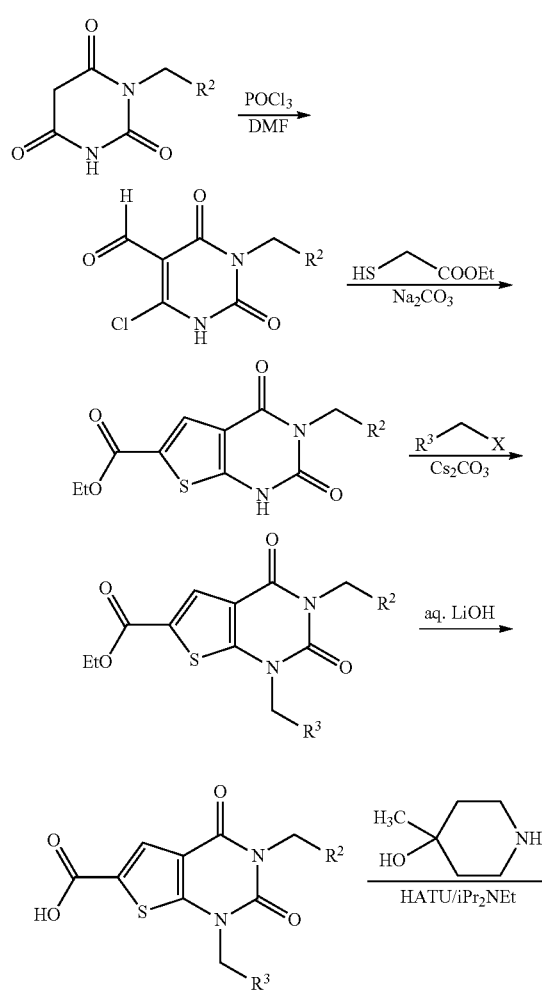
[X = Br or I].
Scheme 6
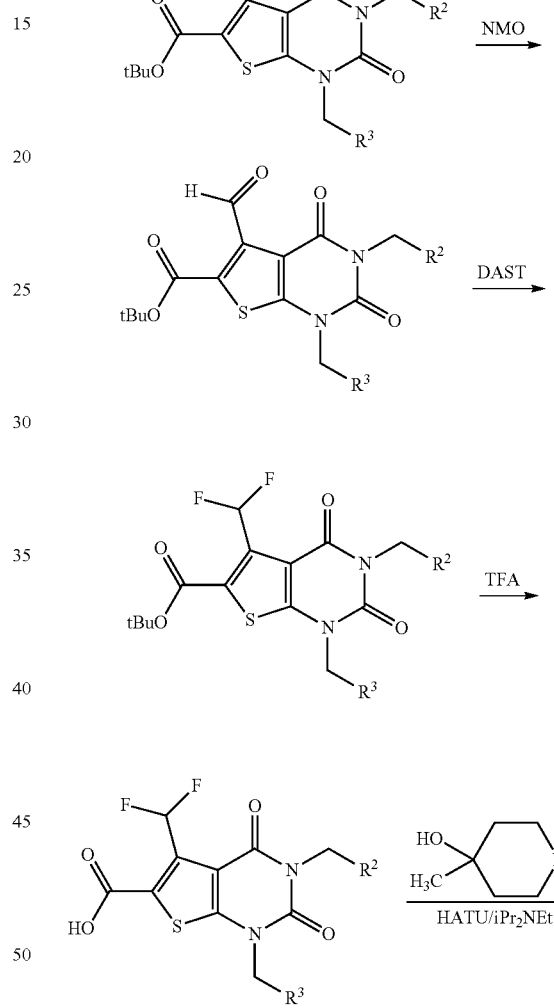

Scheme 7
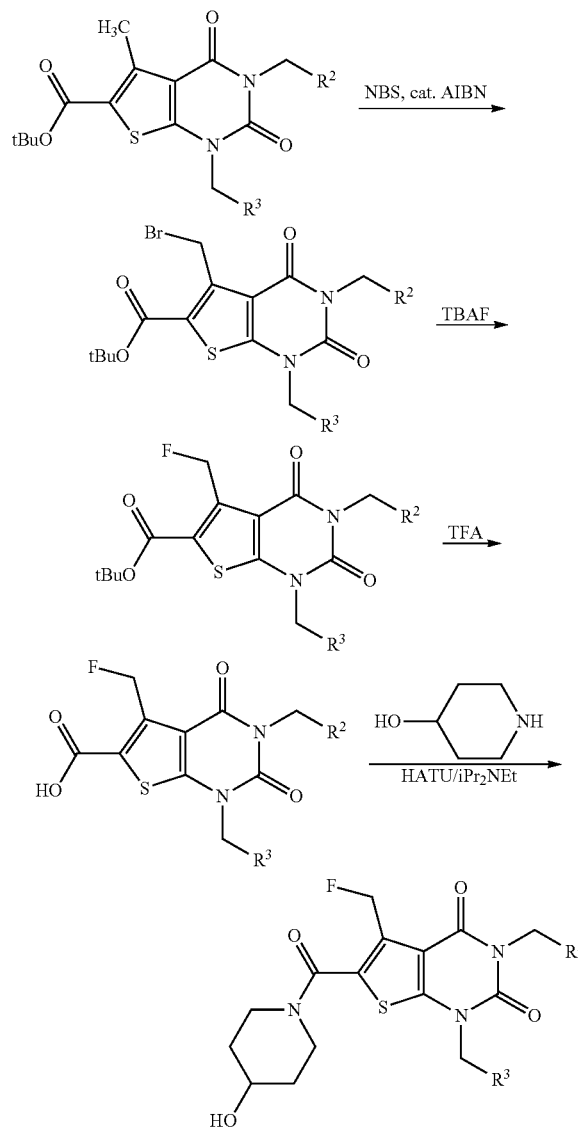
-continued
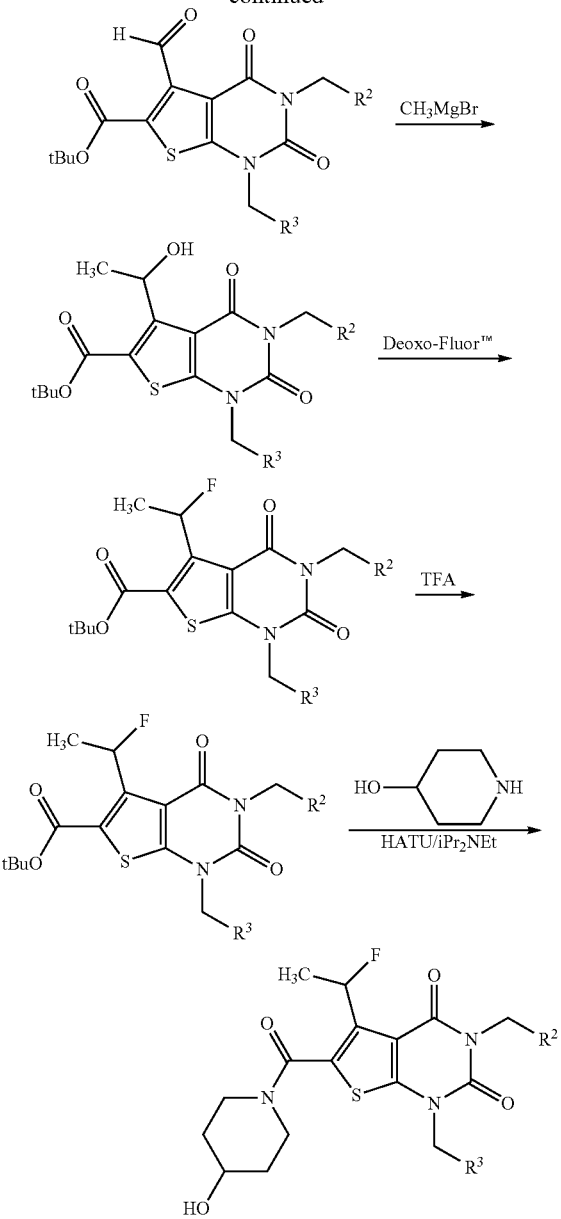
Scheme 8
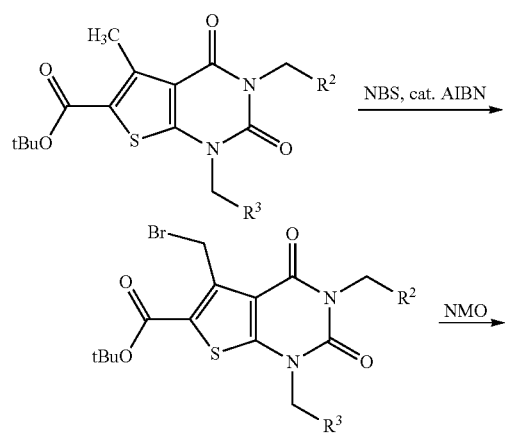
Scheme 9a
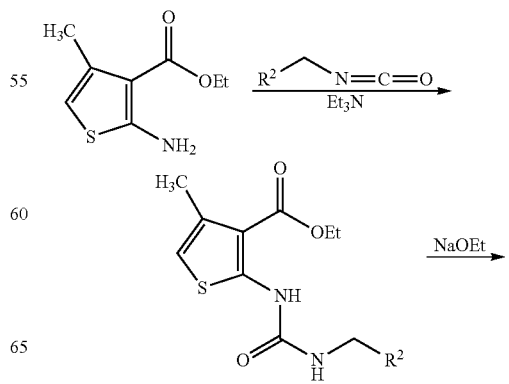

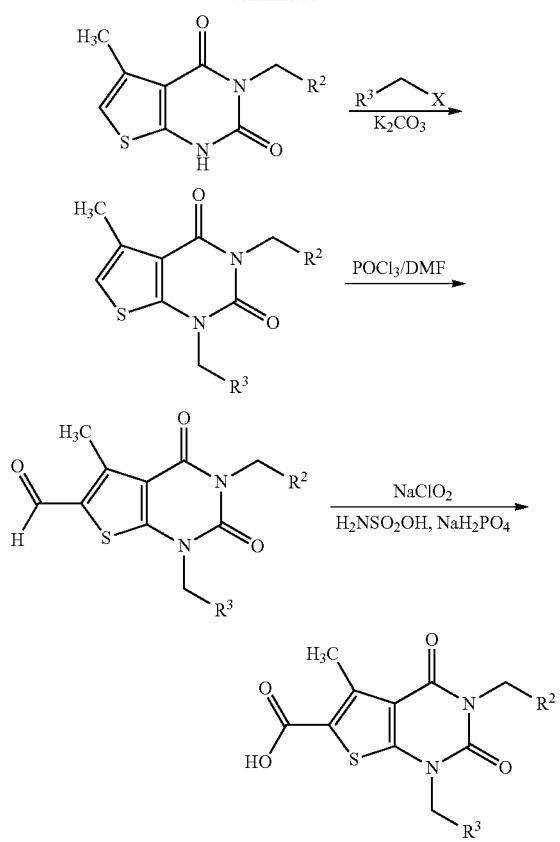

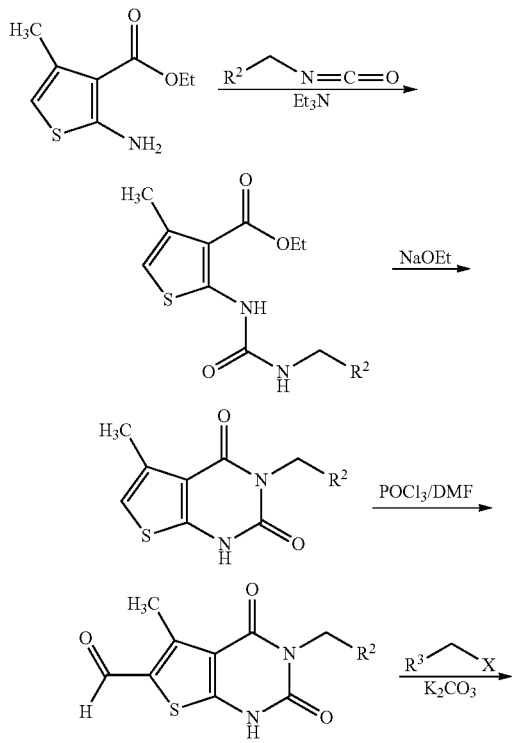

Scheme 9b

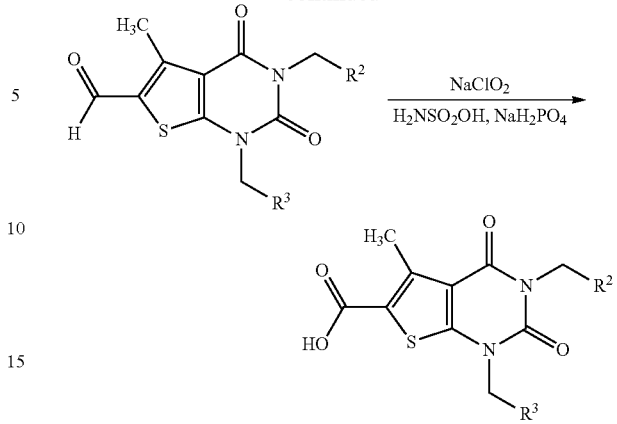

The compounds according to the invention have valuable pharmacological properties and can be used for prevention and treatment of diseases in humans and animals.

The compounds according to the invention are potent and selective antagonists of the adenosine A2b receptor and are therefore suitable in particular for the treatment and/or prevention of disorders and pathological processes, especially those where the A2b receptor is involved in the course of an inflammatory event and/or tissue or vessel reconstruction.

In the context of the present invention, these include in particular disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, furthermore granulomatous interstitial lung diseases, interstitial lung diseases of known aetiology and other interstitial lung diseases of unknown aetiology, pulmonary arterial hypertension (PAH) and other forms of pulmonary hypertension (PH), bronchiolitis obliterans syndrome (BOS), chronic-obstructive pulmonary disease (COPD), acute respiratory distress syndrome (ARDS), acute lung injury (ALI), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anaemia and inflammatory and fibrotic eye disorders.

The compounds according to the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

In addition, the compounds according to the invention can be used for the treatment and/or prevention of cardiovascular disorders such as, for example, high blood pressure (hypertension), heart failure, coronary heart disease, stable and unstable angina pectoris, renal hypertension, peripheral and cardiac vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, sick sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds according to the invention are also suitable for the treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also comprises the use of the compounds according to the invention for the treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds according to the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB) and (IC), incontinence such as, for example, mixed urinary incontinence, urge urinary incontinence, stress urinary incontinence or overflow urinary incontinence (MUI, UUI, SUI, OUI), pelvic pain, and also erectile dysfunction and female sexual dysfunction.

In addition, the compounds according to the invention have antiinflammatory action and can therefore be used as antiinflammatory agents for treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epididymitis, oophoritis, salpingitis, vulvovaginitis, rheumatoid disorders, inflammatory disorders of the central nervous system, multiple sclerosis, inflammatory skin disorders and inflammatory eye disorders.

Furthermore, the compounds according to the invention are suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphoea, keloids, hypertrophic scarring, naevi, diabetic retinopathy, proliferative vitroretinopathy and disorders of the connective tissue (for example sarcoidosis). The compounds according to the invention can also be used for promoting wound healing, for controlling postoperative scarring, for example as a result of glaucoma operations and cosmetically for ageing or keratinized skin.

The compounds according to the invention can also be employed for the treatment and/or prevention of anaemias such as haemolytic anaemias, in particular haemoglobinopathies such as sickle cell anaemia and thalassaemias, megaloblastic anaemias, iron deficiency anaemias, anaemias owing to acute blood loss, displacement anaemias and aplastic anaemias.

Moreover, the compounds according to the invention are suitable for the treatment of cancers such as, for example, skin cancer, brain tumours, breast cancer, bone marrow tumours, leukaemias, liposarcomas, carcinomas of the gastrointestinal tract, of the liver, the pancreas, the lung, the kidney, the ureter, the prostate and the genital tract and also of malignant tumours of the lymphoproliferative system, for example Hodgkin- and Non-Hodgkin-lymphoma.

In addition, the compounds according to the invention can be used for the treatment and/or prevention of arteriosclerosis, impaired lipid metabolism and dyslipidaemias (hypolipoproteinaemia, hypertriglyceridaemias, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinaemia, insulin resistance, glucose intolerance and diabetic sequelae, such as retinopathy, nephropathy and neuropathy), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathies, such as, for example, arthropathia deformans, arthropathia neuropathica, arthropathia ovaripriva, arthropathia psoriatica and arthropathia tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Günther syndrome and the Münchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

Owing to their property profile, the compounds according to the invention are particularly suitable for the treatment and/or prevention of interstitial lung diseases, especially idiopathic pulmonary fibrosis (IPF), and also of pulmonary hypertension (PH), bronchiolitis obliterans syndrome (BOS), chronic obstructive pulmonary disease (COPD), asthma, cystic fibrosis (CF), myocardial infarction, heart failure and haemoglobinopathies, in particular sickle cell anemia.

The above-mentioned, well-characterized diseases in humans can also occur with a comparable aetiology in other mammals and can likewise be treated there with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds according to the invention for the treatment and/or prevention of disorders, in particular the disorders mentioned above.

The present invention further provides for the use of the compounds according to the invention for producing a medicament for the treatment and/or prevention of disorders, in particular the disorders mentioned above.

The present invention further provides a medicament comprising at least one of the compounds according to the invention, for the treatment and/or prevention of disorders, in particular the disorders mentioned above.

The present invention furthermore provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with one or more other pharmacologically active substances, provided that this combination does not lead to undesirable and unacceptable side effects. The present invention furthermore therefore provides medicaments containing at least one of the compounds according to the invention and one or more further active compounds, in particular for treatment and/or prevention of the abovementioned disorders. Preferred examples of active compounds suitable for combinations include:

- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
- NO- and haem-independent activators of soluble guanylate cyclase (sGC), such as in particular the compounds described in WO 01/19355, WO 01/19776, WO 01/19778, WO 01/19780, WO 02/070462 and WO 02/070510;
- NO-independent but haem-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;
- prostacyclin analogues and IP receptor agonists, by way of example and with preference iloprost, beraprost, treprostinil, epoprostenol or NS-304;
- edothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
- compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
- compounds which block the binding of serotonin to its receptor, by way of example and with preference antagonists of the 5-$HT_{2B}$ receptor such as PRX-08066;
- antagonists of growth factors, cytokines and chemokines, by way of example and with preference antagonists of TGF-$\beta$, CTGF, IL-1, IL-4, IL-5, IL-6, IL-8, IL-13 and integrins;
- Rho kinase-inhibiting compounds, by way of example and with preference fasudil, Y-27632, SLx-2119, BF-66851, BF-66852, BF-66853, KI-23095 or BA-1049;
- compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;
- compounds which influence the energy metabolism of the heart, by way of example and with preference etomoxir, dichloroacetate, ranolazine or trimetazidine;
- anti-obstructive agents as used, for example, for the therapy of chronic obstructive pulmonary disease (COPD) or bronchial asthma, by way of example and with preference from the group of the inhalatively or systemically administered agonists of the beta-adrenergic receptor (beta-mimetics) and the inhalatively administered anti-muscarinergic substances;
- antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, IFN-$\gamma$, pirfenidone or etanercept;
- antifibrotic agents, by way of example and with preference lysophosphatidic acid receptor 1 (LPA-1) antagonists, lysyl oxidase (LOX) inhibitors, lysyl oxidase-like-2 inhibitors, vasoactive intestinal peptide (VIP), VIP analogues, $\alpha_v\beta_6$-integrin antagonists, cholchicine, IFN-$\beta$, D-penicillamine, inhibitors of the WNT signal path or CCR2 antagonists;
- antithrombotic agents, by way of example and with preference from the group of platelet aggregation inhibitors, the anticoagulants and the profibrinolytic substances;
- hypotensive active compounds, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics;
- lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists; and/or
- chemotherapeutics like those employed, for example, for the therapy of neoplasms in the lung or other organs.

In a preferred embodiment of the invention, the compounds according to the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds according to the invention are administered in combination with an antimuscarinergic substance, by way of example and with preference ipratropium bromide, tiotropium bromide or oxitropium bromide.

In a preferred embodiment of the invention, the compounds according to the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, melagatran, dabigatran, bivalirudin or clexane.

In a preferred embodiment of the invention, the compounds according to the invention are administered in combination with a GPIIb/IIIa antagonist such as, by way of example and with preference tirofiban or abciximab.

In a preferred embodiment of the invention, the compounds according to the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a diuretic, by way of example and with preference furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), JJT-705 or CETP vaccine (Avant).

In a preferred embodiment of the invention, the compounds according to the invention are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

Particular preference is given to combinations of the compounds according to the invention with one or more further active compounds selected from the group of the PDE 5 inhibitors, sGC activators, sGC stimulators, prostacyclin analogs, endothelin antagonists, of the antifibrotic agents, the antiinflammatory, immunomodulating, immunosuppressive and/or cytotoxic agents and/or the signal transduction cascade-inhibiting compounds.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary where appropriate to deviate from the stated amounts, specifically as a function of the body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms
abs. absolute
Ac acetyl
AIBN 2,2'-azobis(2-methylpropionitrile)
aq. aqueous, aqueous solution
br. broad (in NMR signal)

Ex. Example
Bu butyl
c concentration
cat. catalytic
CDI N,N'-carbonyldiimidazole
CI chemical ionization (in MS)
d doublet (in NMR)
d day(s)
DAST N,N-diethylaminosulphur trifluoride
TLC thin-layer chromatography
DCI direct chemical ionization (in MS)
dd doublet of doublets (in NMR)
Deoxo-Fluor®/™ bis(2-methoxyethyl)aminosulphur trifluoride
DIAD diisopropyl azodicarboxylate
DME 1,2-dimethoxyethane
DMF N,N-dimethylformamide
DMSO dimethyl sulphoxide
dq doublet of quartets (in NMR)
dt doublet of triplets (in NMR)
EDC N'-(3-dimethylaminopropyl)-N-ethylcarbodiimide hydrochloride
ee enantiomeric excess
EI electron impact ionization (in MS)
eq. equivalent(s)
ESI electrospray ionization (in MS)
Et ethyl
GC gas chromatography
GC/MS gas chromatography-coupled mass spectrometry
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure high-performance liquid chromatography
iPr isopropyl
conc. concentrated (in case of a solution)
LC liquid chromatography
LC/MS liquid chromatography-coupled mass spectrometry
lit. literature (reference)
m multiplet (in NMR)
Me methyl
min minute(s)
MPLC medium-pressure liquid chromatography (on silica gel; also referred to as flash chromatography)
MS mass spectrometry
NBS N-bromosuccinimide
NMM N-methylmorpholine
NMO N-methylmorpholine N-oxide
NMP N-methyl-2-pyrrolidinone
NMR nuclear magnetic resonance spectrometry
Pd/C palladium on activated carbon
PEG polyethylene glycol
Ph phenyl
Pr propyl
quant. quantitative (in chemical yield)
quart quartet (in NMR)
quint quintet (in NMR)
$R_f$ retention index (in TLC)
RP reversed phase (in HPLC)
RT room temperature
$R_t$ retention time (in HPLC, LC/MS)
s singlet (in NMR)
sept septet (in NMR)
SFC supercritical fluid chromatography
t triplet (in NMR)
TBAF tetra-n-butylammonium fluoride
TBME tert-butyl methyl ether
TBTU N-[(1H-benzotriazol-1-yloxy)(dimethylamino)methylene]-N-methylmethanaminium tetrafluoroborate
tBu tert-butyl
TFA trifluoroacetic acid
THF tetrahydrofuran
TMS tetramethylsilane
UV ultraviolet spectrometry
v/v ratio by volume (of a solution)
tog. together
HPLC, LC/MS and GC/MS Methods:
Method 1 (LC/MS):
  Instrument: Waters ACQUITY SQD UPLC System; column: Waters Acquity UPLC HSS T3 1.8 µm, 50 mm×1 mm; mobile phase A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; temperature: 50° C.; flow rate: 0.40 ml/min; UV detection: 210-400 nm.
Method 2 (LC/MS):
  Instrument: Micromass Quattro Premier with Waters UPLC Acquity; column: Thermo Hypersil GOLD 1.9 µm, 50 mm×1 mm; mobile phase A: 1 l of water+0.5 ml of 50% strength formic acid, mobile phase B: 1 l of acetonitrile+0.5 ml of 50% formic acid; gradient: 0.0 min 97% A→0.5 min 97% A→3.2 min 5% A→4.0 min 5% A; temperature: 50° C.; flow rate: 0.30 ml/min; UV detection: 210 nm.
Method 3 (LC/MS):
  Instrument: Waters SQD with Waters UPLC; column: Zorbax SB-Aq (Agilent) 1.8 µm, 50 mm×2.1 mm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; temperature: 40° C.; flow rate: 0.60 ml/min; UV detection: DAD, 210 nm.
Method 4 (GC/MS):
  Instrument: Thermo DFS, Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintained for 3.33 min).
Method 5 (Preparative HPLC):
  column: Chromatorex C18, 10 µm, 125 mm×30 mm; mobile phase: acetonitrile/water with 0.1% of formic acid; gradient: 20:80→95:5 over 20 min.
Method 6 (Preparative HPLC):
  column: Chromatorex C18, 10 µm, 125 mm×30 mm; mobile phase: acetonitrile/water with 0.1% of formic acid; gradient: 30:70→95:5 over 20 min.
Method 7 (Preparative HPLC):
  column: Chromatorex C18, 10 µm, 125 mm×30 mm; mobile phase: methanol/water with 0.1% of formic acid; gradient: 20:80→95:5 over 20 min.
Method 8 (Preparative HPLC with Mass Detection):
  Instrument: Waters; column: Phenomenex Luna 5 µm C18(2) 100A, AXIA Tech., 50 mm×21.2 mm; mobile phase A: water+0.05% formic acid, mobile phase B: acetonitrile+0.05% formic acid; gradient: 0.0 min 95% A→0.15 min 95% A→8.0 min 5% A→9.0 min 5% A; flow rate: 40 ml/min; UV detection: DAD, 210-400 nm.
Method 9 (LC/MS):
  Instrument: Agilent MS Quad 6150 with HPLC Agilent 1290; column: Waters Acquity UPLC HSS T3 1.8 µm, 50 mm×2.1 mm; mobile phase A: 1 l of water+0.25 ml of 99% formic acid, eluent B: 1 l of acetonitrile+0.25 ml of 99% formic acid; gradient: 0.0 min 90% A→0.3 min 90% A→1.7 min 5% A→3.0 min 5% A; flow rate: 1.20 ml/min, temperature: 50° C.; UV detection: 205-305 nm.

Method 10 (LC/MS):
Instrument: Waters Synapt G2S with UPLC Waters Acquity I-CLASS; column: Waters HSS T3 C18 1.8 µm, 50 mm×2.1 mm; mobile phase A: 1 l of water+0.01% formic acid, mobile phase B: 1 l of acetonitrile+0.01% formic acid; gradient: 0.0 min 10% B→0.3 min 10% B→1.7 min 95% B→2.5 min 95% B; flow rate: 1.20 ml/min, temperature: 50° C.; UV detection: 210 nm.
Method 11 (Preparative HPLC):
    column: Chromatorex C18, 10 µm, 125 mm×30 mm; mobile phase: methanol/water with 0.1% of formic acid; gradient: 30:70→95:5 over 20 min.
Method 12 (Preparative HPLC):
    column: Chromatorex C18, 10 µm, 125 mm×30 mm; mobile phase A: water+0.05% trifluoroacetic acid, mobile phase B: acetonitrile+0.05% trifluoroacetic acid; gradient 0.0 min 75% A→5.0 min 75% A→8.5 min 53% A→15 min 53% A.
Method 13 (Preparative HPLC):
    column: Chromatorex C18, 10 µm, 125 mm×30 mm; mobile phase A: water+0.05% trifluoroacetic acid, mobile phase B: acetonitrile+0.05% trifluoroacetic acid; gradient 0.0 min 75% A→5.0 min 75% A→7.0 min 60% A→16 min 45% A→18 min 45% A.
Method 14 (Preparative HPLC):
    column: Chromatorex C18, 10 µm, 125 mm×30 mm; mobile phase A: water+0.05% trifluoroacetic acid, mobile phase B: acetonitrile+0.05% trifluoroacetic acid; gradient 0.0 min 80% A→5.0 min 80% A→8.0 min 55% A→15 min 55% A.
Method 15 (Preparative HPLC):
    column: Chromatorex C18, 10 µm, 125 mm×30 mm; mobile phase: acetonitrile/water with 0.1% of formic acid; gradient: 40:60→95:5 over 20 min.
Method 16 (Preparative HPLC):
    column: Chromatorex C18, 10 µm, 125 mm×30 mm; mobile phase: acetonitrile/water with 0.1% of formic acid; gradient: 15:85→95:5 over 20 min.
Method 17 (LC/MS):
    Instrument: Waters Acquity SQD UPLC System; column: Waters Acquity UPLC HSS T3 1.8 µm, 50 mm×1 mm; mobile phase A: 1 l of water+0.25 ml of 99% formic acid, eluent B: 1 l of acetonitrile+0.25 ml of 99% formic acid; gradient: 0.0 min 95% A→6.0 min 5% A→7.5 min 5% A; oven: 50° C.; flow rate: 0.35 ml/min; UV detection: 210-400 nm.
Method 18 (Preparative HPLC):
    column: Reprosil-Pur C18, 10 µm, 125 mm×30 mm; mobile phase: acetonitrile/water with 0.05% of trifluoroacetic acid; gradient: 50:50→100:0 over 12 min.
Method 19 (Preparative HPLC):
    column: Reprosil-Pur C18, 10 µm, 125 mm×30 mm; mobile phase: acetonitrile/water with 0.05% of trifluoroacetic acid; gradient: 10:90→100:0 over 12 min.
Further Details:
The descriptions of the coupling patterns of $^1$H NMR signals below refer to the optical appearance of the signals in question and do not necessarily correspond to a strict, physically correct interpretation. In general, the stated chemical shift refers to the centre of the signal in question; in the case of broad multiplets, an interval is generally given.
Melting points and melting points ranges, if stated, are uncorrected.
In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates

Example 1A 2-tert-Butyl 4-ethyl 5-amino-3-methylthiophene-2,4-dicarboxylate

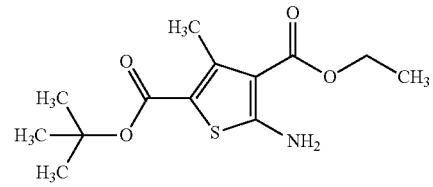 [SMILES: CCOC(=O)c1c(N)sc(C(=O)OC(C)(C)C)c1C]

10.0 g (63.2 mmol) of tert-butyl acetoacetate, 7.15 g (63.2 mmol) of ethyl cyanoacetate and 2.23 g (69.5 mmol) of sulphur were initially charged in 15 ml of ethanol and warmed to 45° C. 7.5 ml (72.7 mmol) of diethylamine were added dropwise to this mixture. The reaction mixture was then stirred at 65° C. for 8 h. All the volatile constituents were then removed on a rotary evaporator. About 500 ml of water were added to the residue that remained, and the mixture was extracted three times with in each case about 200 ml of ethyl acetate. The combined organic extracts were washed with about 200 ml of saturated sodium chloride solution and dried over anhydrous magnesium sulphate. After filtration, the mixture was evaporated to dryness. The crude product obtained was purified by MPLC (about 300 g of silica gel, cyclohexane/ethyl acetate 10:1). This gave, after combination of the product fractions, evaporation and drying of the residue under high vacuum, 9.72 g (52% of theory) of the title compound.

$^1$H-NMR (400 MHz, CDCl$_3$, δ/ppm): 6.44 (br. s, 2H), 4.31 (quart, 2H), 2.66 (s, 3H), 1.54 (s, 9H), 1.37 (t, 3H).
LC/MS (Method 1, ESIpos): R$_t$=1.20 min, m/z=286 [M+H]$^+$.

Example 2A 2-tert-Butyl 4-ethyl 3-methyl-5-{[(2-phenylethyl)carbamoyl]amino}thiophene-2,4-dicarboxylate

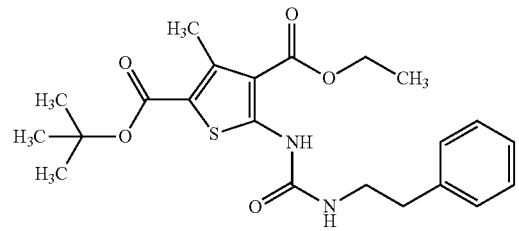 [SMILES: CCOC(=O)c1c(NC(=O)NCCc2ccccc2)sc(C(=O)OC(C)(C)C)c1C]

10.0 g (35.0 mmol) of 2-tert-butyl 4-ethyl 5-amino-3-methylthiophene-2,4-dicarboxylate (Example 1A) were dissolved in 500 ml of dichloromethane and 11.4 g (70.1 mmol) of N,N'-carbonyldiimidazole (CDI) and 19.6 ml (140 mmol) of triethylamine were added. The reaction mixture was stirred at RT for 2 days, after which 8.8 ml (70.1 mmol) of 2-phenethylamine were added. After a further 2 h of stirring at RT, the mixture was evaporated to dryness on a rotary evaporator. The residue that remained was purified by MPLC (silica gel, cyclohexane/ethyl acetate 20:1→10:1). This gave, after evaporation of the product fractions and drying of the residue under high vacuum, 14.4 g (95% of theory) of the title compound.

$^1$H-NMR (400 MHz, DMSO-$d_6$, δ/ppm): 10.54 (s, 1H), 8.17 (t, 1H), 7.33-7.29 (m, 2H), 7.26-7.19 (m, 3H), 4.30 (quart, 2H), 3.36 (quart, 2H), 2.77 (t, 2H), 2.62 (s, 3H), 1.50 (s, 9H), 1.32 (t, 3H).

LC/MS (Method 1, ESIpos): $R_t$=1.43 min, m/z=433 [M+H]$^+$.

Example 3A 2-tert-Butyl 4-ethyl 5-({[2-(2-fluorophenyl)ethyl]carbamoyl}amino)-3-methylthiophene-2,4-dicarboxylate

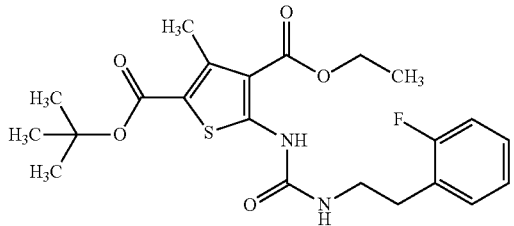 [SMILES: CCOC(=O)c1c(NC(=O)NCCc2ccccc2F)sc(C(=O)OC(C)(C)C)c1C]

Analogously to the process described in Ex. 2A, 2.0 g (7.01 mmol) of 2-tert-butyl 4-ethyl 5-amino-3-methylthiophene-2,4-dicarboxylate (Example 1A), 2.27 g (14.0 mmol) of CDI, 3.9 ml (28.0 mmol) of triethylamine and 3.5 ml (14.0 mmol) of 2-(2-fluorophenyl)ethylamine gave 1.82 g (55% of theory, purity 95%) of the title compound. In deviation, MPLC purification was carried out using the mobile phase cyclohexane/ethyl acetate 10:1.

$^1$H-NMR (400 MHz, CDCl$_3$, δ/ppm): 10.90 (br. s, 1H), 7.24-7.19 (m, 2H), 7.10-7.01 (m, 2H), 5.18 (t, 1H), 4.32 (quart, 2H), 3.58 (quart, 2H), 2.94 (t, 2H), 2.71 (s, 3H), 1.55 (s, 9H), 1.39 (t, 3H).

LC/MS (Method 1, ESIpos): $R_t$=1.38 min, m/z=451 [M+H]$^+$.

Example 4A 2-tert-Butyl 4-ethyl 5-({[2-(2-chlorophenyl)ethyl]carbamoyl}amino)-3-methylthiophene-2,4-dicarboxylate

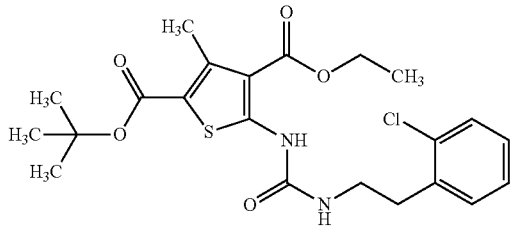 [SMILES: CCOC(=O)c1c(NC(=O)NCCc2ccccc2Cl)sc(C(=O)OC(C)(C)C)c1C]

Analogously to the process described in Ex. 2A, 2.0 g (7.01 mmol) of 2-tert-butyl 4-ethyl 5-amino-3-methylthiophene-2,4-dicarboxylate (Example 1A), 2.27 g (14.0 mmol) of CDI, 3.9 ml (28.0 mmol) of triethylamine and 2.18 g (14.0 mmol) of 2-(2-chlorophenyl)ethylamine gave 2.49 g (72% of theory, purity 95%) of the title compound. In deviation, MPLC purification was carried out here using the mobile phase cyclohexane/ethyl acetate 10:1.

$^1$H-NMR (400 MHz, CDCl$_3$, δ/ppm): 10.91 (br. s, 1H), 7.38-7.35 (m, 1H), 7.26-7.16 (m, 3H), 5.14 (t, 1H), 4.33 (quart, 2H), 3.60 (quart, 2H), 3.04 (t, 2H), 2.71 (s, 3H), 1.55 (s, 9H), 1.39 (t, 3H).

LC/MS (Method 1, ESIpos): $R_t$=1.42 min, m/z=467/469 [M+H]$^+$.

Example 5A 2-tert-Butyl 4-ethyl 3-methyl-5-({[2-(pyridin-3-yl)ethyl]carbamoyl}amino)thiophene-2,4-dicarboxylate

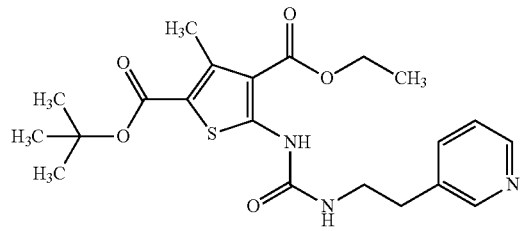 [SMILES: CCOC(=O)c1c(NC(=O)NCCc2cccnc2)sc(C(=O)OC(C)(C)C)c1C]

Analogously to the process described in Ex. 2A, 2.0 g (7.01 mmol) of 2-tert-butyl 4-ethyl 5-amino-3-methylthiophene-2,4-dicarboxylate (Example 1A), 2.27 g (14.0 mmol) of CDI, 3.9 ml (28.0 mmol) of triethylamine and 1.71 g (14.0 mmol) of 2-(pyridin-3-yl)ethanamine gave 2.46 g (75% of theory, purity 93%) of the title compound. In deviation, MPLC purification was carried out here using the mobile phase cyclohexane/ethyl acetate 1:2.

$^1$H-NMR (400 MHz, CDCl$_3$, δ/ppm): 10.94 (br. s, 1H), 8.50 (m, 1H), 8.46 (m, 1H), 7.56 (m, 1H), 7.24 (m, 1H), 5.42 (br. s, 1H), 4.31 (quart, 2H), 3.59 (quart, 2H), 2.92 (t, 2H), 2.70 (s, 3H), 1.55 (s, 9H), 1.39 (t, 3H).

LC/MS (Method 1, ESIpos): $R_t$=0.99 min, m/z=434 [M+H]$^+$.

Example 6A 2-tert-Butyl 4-ethyl 5-[(ethylcarbamoyl)amino]-3-methylthiophene-2,4-dicarboxylate

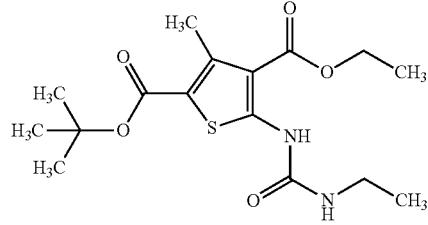 [SMILES: CCNC(=O)Nc1sc(C(=O)OC(C)(C)C)c(C)c1C(=O)OCC]

6.0 g (21.0 mmol) of 2-tert-butyl 4-ethyl 5-amino-3-methylthiophene-2,4-dicarboxylate (Example 1A) were dissolved in 300 ml of dichloromethane and 6.82 g (42.1 mmol)

of CDI and 11.7 ml (84.1 mmol) of triethylamine were added. The reaction mixture was stirred at RT for 2 days, after which 42 ml (84.1 mmol) of a 2 M solution of ethylamine in THF were added. After a further 2 h of stirring at RT, the mixture was evaporated to dryness on a rotary evaporator. The residue that remained was purified by MPLC (Biotage cartridge with 340 g of silica gel, cyclohexane/ethyl acetate 10:1→5:1). This gave, after evaporation of the product fractions and drying of the residue under high vacuum, 6.98 g (93% of theory) of the title compound.

$^1$H-NMR (400 MHz, DMSO-d$_6$, δ/ppm): 10.52 (br. s, 1H), 8.06 (br. t, 1H), 4.31 (quart, 2H), 3.13 (dq, 2H), 2.77 (t, 2H), 2.62 (s, 3H), 1.50 (s, 9H), 1.32 (t, 3H), 1.07 (t, 3H).

LC/MS (Method 1, ESIpos): R$_t$=1.26 min, m/z=357 [M+H]$^+$.

Example 7A 2-tert-Butyl 4-ethyl 5-{[(2,4-dimethoxybenzyl)carbamoyl]amino}-methylthiophene-2,4-dicarboxylate

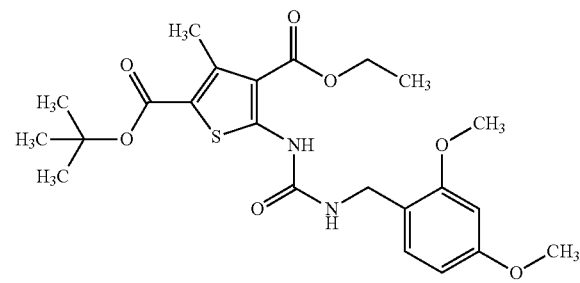 [SMILES: CCOC(=O)c1c(NC(=O)NCc2ccc(OC)cc2OC)sc(C(=O)OC(C)(C)C)c1C]

8.78 g (30.8 mmol) of 2-tert-butyl 4-ethyl 5-amino-3-methylthiophene-2,4-dicarboxylate (Example 1A) were dissolved in 300 ml of dichloromethane and 9.98 g (61.5 mmol) of CDI and 17.2 ml (123 mmol) of triethylamine were added. The reaction mixture was stirred at RT for 2 days, after which 9.3 ml (61.5 mmol) of 2,4-dimethoxybenzylamine were added. After a further 2 h of stirring at RT, the mixture was diluted with 200 ml of dichloromethane and washed successively with in each case about 200 ml of water and saturated sodium chloride solution. After drying over anhydrous magnesium sulphate, the mixture was filtered and the filtrate was evaporated. The residue that remained was taken up in dichloromethane, insolubles being removed by filtration. The filtrate was applied to silica gel and chromatographed on silica gel using the mobile phase cyclohexane/ethyl acetate 2:1→1:1. This gave, after combination of the product fractions, evaporation and drying of the residue under high vacuum, 12.8 g (87% of theory) of the title compound.

$^1$H-NMR (400 MHz, DMSO-d$_6$, δ/ppm): 10.56 (s, 1H), 8.32 (t, 1H), 7.13 (d, 1H), 6.57 (d, 1H), 6.49 (dd, 1H), 4.30 (quart, 2H), 4.19 (d, 2H), 3.80 (s, 3H), 3.75 (s, 3H), 2.62 (s, 3H), 1.50 (s, 9H), 1.32 (t, 3H).

LC/MS (Method 1, ESIpos): R$_t$=1.40 min, m/z=479 [M+H]$^+$.

Example 8A tert-Butyl 5-methyl-2,4-dioxo-3-(2-phenylethyl)-1,2,3,4-tetrahydrothieno[2,3-d]pyrimidine-6-carboxylate

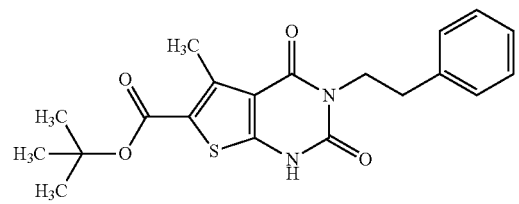

7.34 g (17.0 mmol) of the compound from Ex. 2A were dissolved in 145 ml of ethanol, and 9.5 ml (25.4 mmol) of a 20% solution of sodium ethoxide in ethanol were added. The reaction mixture was stirred at RT for 2 h. The mixture was then poured into about 400 ml of water and adjusted to a pH of about 5 using 5 M acetic acid. In the course of this, the product precipitated out. The product was filtered off with suction, washed neutral with water and dried under a high vacuum. 5.89 g (91% of theory) of the title compound were obtained.

$^1$H-NMR (400 MHz, DMSO-d$_6$, δ/ppm): 12.44 (s, 1H), 7.33-7.29 (m, 2H), 7.25-7.20 (m, 3H), 4.01 (m, 2H), 2.83 (m, 2H), 2.72 (s, 3H), 1.52 (s, 9H).

LC/MS (Method 1, ESIpos): R$_t$=1.28 min, m/z=387 [M+H]$^+$.

Example 9A tert-Butyl 3-[2-(2-fluorophenyl)ethyl]-5-methyl-2,4-dioxo-1,2,3,4-tetrahydrothieno[2,3-d]pyrimidine-6-carboxylate

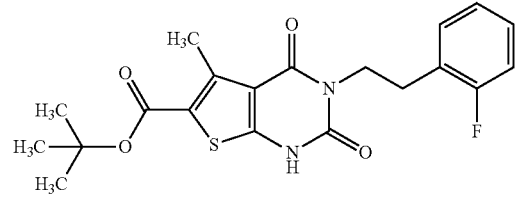 [SMILES: Cc1c(C(=O)OC(C)(C)C)sc2[nH]c(=O)n(CCc3ccccc3F)c(=O)c12]

Analogously to the process described under Ex. 8A, 1.76 g (3.90 mmol) of the compound from Ex.

3A gave 1.55 g (98% of theory) of the title compound. Here, in deviation to the process described above, the precipitated product was, after filtration with suction, dissolved in ethyl acetate and once more washed with water. The organic phase was then dried over anhydrous magnesium sulphate, filtered and concentrated, and the residue was finally dried under high vacuum.

$^1$H-NMR (400 MHz, CDCl$_3$, δ/ppm): 7.28-7.24 (m, 1H, partially obscured by the CHCl$_3$ signal), 7.22-7.17 (m, 1H), 7.08-6.99 (m, 2H), 4.25 (t, 2H), 3.03 (t, 2H), 2.82 (s, 3H), 1.58 (s, 9H).

LC/MS (Method 1, ESIpos): R$_t$=1.25 min, m/z=405 [M+H]$^+$.

Example 10A tert-Butyl 3-[2-(2-chlorophenyl)ethyl]-5-methyl-2,4-dioxo-1,2,3,4-tetrahydrothieno[2,3-d]pyrimidine-6-carboxylate

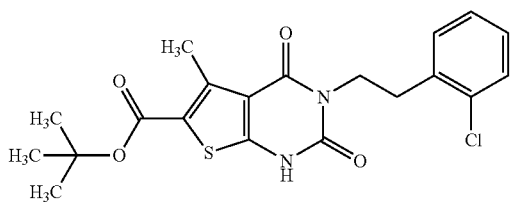

Analogously to the process described under Ex. 8A, 2.42 g (5.17 mmol) of the compound from Ex. 4A gave 1.71 g (76% of theory, purity 97%) of the title compound. Here, in deviation to the process described above, the precipitated product was, after filtration with suction, dissolved in ethyl acetate and once more washed with water. The organic phase was then dried over anhydrous magnesium sulphate, filtered and concentrated, and the residue was finally dried under high vacuum.

$^1$H-NMR (400 MHz, CDCl$_3$, δ/ppm): 7.35 (dd, 1H), 7.30 (dd, 1H), 7.20-7.14 (m, 2H), 4.26 (t, 2H), 3.13 (t, 2H), 2.83 (s, 3H), 1.58 (s, 9H).

LC/MS (Method 1, ESIpos): R$_t$=1.30 min, m/z=421/422 [M+H]$^+$.

Example 11A tert-Butyl 5-methyl-2,4-dioxo-3[2-(pyridin-3-yl)ethyl]-1,2,3,4-tetrahydrothieno[2,3-d]pyrimidine-6-carboxylate

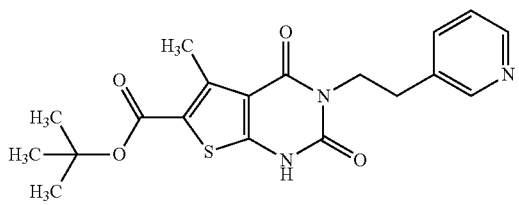 [SMILES: Cc1c(C(=O)OC(C)(C)C)sc2[nH]c(=O)n(CCc3cccnc3)c(=O)c12]

Analogously to the process described under Ex. 8A, 2.41 g (5.56 mmol) of the compound from Ex. 5A gave 1.89 g (87% of theory) of the title compound. Here, in deviation to the process described above, the precipitated product was, after filtration with suction, dissolved in ethyl acetate and once more washed with water and saturated sodium hydrogencarbonate solution. The organic phase was then dried over anhydrous magnesium sulphate, filtered and concentrated, and the residue was finally dried under high vacuum.

$^1$H-NMR (400 MHz, DMSO-d$_6$, δ/ppm): 8.42-8.40 (m, 2H), 7.64 (dt, 1H), 7.31 (dd, 1H), 4.01 (t, 2H), 2.81 (t, 2H), 2.67 (s, 3H), 1.49 (s, 9H).

LC/MS (Method 1, ESIpos): R$_t$=0.82 min, m/z=388 [M+H]$^+$.

Example 12A tert-Butyl 3-ethyl-5-methyl-2,4-dioxo-1,2,3,4-tetrahydrothieno[2,3-d]pyrimidine-6-carboxylate

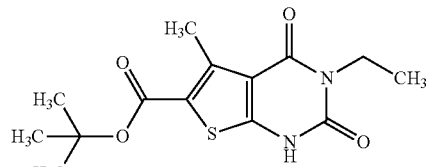

6.98 g (19.6 mmol) of the compound from Ex. 6A were dissolved in 130 ml of ethanol, and 11 ml (29.4 mmol) of a 20% solution of sodium ethoxide in ethanol were added. The reaction mixture was stirred at RT for 2 h. The mixture was then poured into about 400 ml of water and adjusted to a pH of about 5 using 5 M acetic acid. In the course of this, the product precipitated out. The product was filtered off with suction, washed neutral with water and dried under a high vacuum. 5.89 g (97% of theory) of the title compound were obtained.

$^1$H-NMR (400 MHz, DMSO-d$_6$, δ/ppm): 12.39 (s, 1H), 3.85 (quart, 2H), 2.71 (s, 3H), 1.51 (s, 9H), 1.11 (t, 3H).

LC/MS (Method 1, ESIpos): R$_t$=1.06 min, m/z=311 [M+H]$^+$.

Example 13A tert-Butyl 3-(2,4-dimethoxybenzyl)-5-methyl-2,4-dioxo-1,2,3,4-tetrahydrothieno [2,3-d]pyrimidine-6-carboxylate

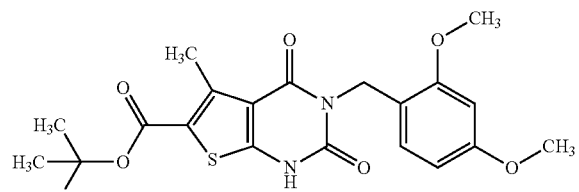

12.8 g (26.8 mmol) of the compound from Ex. 7A were dissolved in 250 ml of ethanol, and 15 ml (40.2 mmol) of a 20% solution of sodium ethoxide in ethanol were added. The reaction mixture was stirred at RT for about 16 h. The mixture was then poured into about 1.5 l of water and adjusted to a pH of about 5 using acetic acid. In the course of this, the product precipitated out. The product was filtered off with suction, washed neutral with water and dried under a high vacuum. 11.3 g (97% of theory) of the title compound were obtained.

$^1$H-NMR (400 MHz, DMSO-d$_6$, δ/ppm): 12.50 (s, 1H), 6.72 (d, 1H), 6.56 (d, 1H), 6.39 (dd, 1H), 4.89 (s, 2H), 3.82 (s, 3H), 3.72 (s, 3H), 2.69 (s, 3H), 1.52 (s, 9H).

LC/MS (Method 1, ESIpos): R$_t$=1.20 min, m/z=433 [M+H]$^+$.

Example 14A 1-(2-Phenylethyl)pyrimidine-2,4,6(1H,3H,5H)-trione

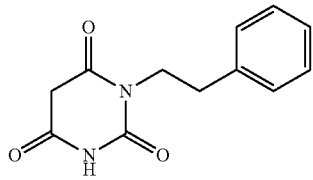 [SMILES: O=C1CC(=O)N(CCc2ccccc2)C(=O)N1]

20.0 g (122 mmol) of 2-phenethylurea [commercially available; lit. e.g.: L. De Luca, A. Porcheddu, G. Giacomelli, I. Murgia, *Synlett* 2010 (16), 2439-2442] and 18.5 ml (122 mmol) of diethyl malonate were dissolved in 70 ml of ethanol, and 45.5 ml (122 mmol) of a 20% strength solution of sodium ethoxide in ethanol were added. The mixture was heated under reflux for 16 h. Most of the solvent was then removed on a rotary evaporator, and about 100 ml of water were added to the residue that remained Insolubles were filtered off and the filtrate was acidified with concentrated hydrochloric acid to pH 3-4. This resulted in the precipitation of the product, which was filtered off with suction and washed initially with water and then with hexane/diethyl ether 1:1. Drying under high vacuum gave 20.9 g (72% of theory) of the title compound.

$^1$H-NMR (400 MHz, DMSO-d$_6$, δ/ppm): 11.36 (s, 1H), 7.33-7.29 (m, 2H), 7.25-7.20 (m, 3H), 3.86 (dd, 2H), 3.62 (s, 2H), 2.77 (dd, 2H).

LC/MS (Method 1, ESIpos): R$_t$=0.76 min, m/z=233 [M+H]$^+$.

Example 15A

1-Ethylpyrimidine-2,4,6(1H,3H,5H)-trione

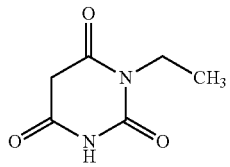

25.0 g (284 mmol) of ethylurea and 43 ml (284 mmol) of diethyl malonate were dissolved in 150 ml of ethanol, and 106 ml (284 mmol) of a 20% solution of sodium ethoxide in ethanol were added. The mixture was heated under reflux for 1 h, resulting in the formation of a precipitate. After cooling to RT, the precipitate was separated off and the filtrate was freed from most of the solvent on a rotary evaporator. About 500 ml of water were added to the residue that remained, and the mixture was acidified with 5 M hydrochloric acid to pH 3-4. The aqueous solution was then extracted three times with about 100 ml of ethyl acetate each time. Drying over anhydrous magnesium sulphate, filtration and evaporation of the combined organic extracts gave a first fraction of the title compound (14.1 g, 31% of theory). The aqueous phase left earlier was concentrated to a volume of about 250 ml and adjusted to pH 1 with 5 M hydrochloric acid, and solid sodium chloride was added to saturation. The mixture was once more extracted with ethyl acetate and the organic phase was dried over magnesium sulphate, filtered and concentrated. At RT, the product obtained in this manner was stirred with 200 ml of diethyl ether. The mixture was then filtered and the residue was dried under high vacuum. This gave a second fraction of the title compound (6.0 g, 13% of theory). A total of 20.1 g (45% of theory) of the title compound were thus obtained.

$^1$H-NMR (400 MHz, DMSO-d$_6$, δ/ppm): 11.30 (s, 1H), 3.70 (quart, 2H), 3.59 (s, 2H), 1.06 (t, 3H).

GC/MS (method 4, ESIpos): R$_t$=4.28 min, m/z=156 [M]$^+$.

Example 16A

6-Chloro-3-(2-phenylethyl)pyrimidine-2,4(1H,3H)-dione

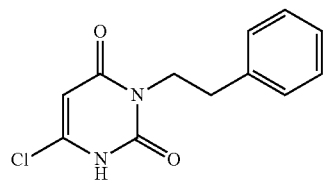 [SMILES: O=c1cc(Cl)[nH]c(=O)n1CCc1ccccc1]

At a temperature of 0° C., 36.5 ml (392 mmol) of phosphorus oxychloride were added carefully to 8.2 ml of 50% strength aqueous ethanol. Then, likewise at 0° C., 10.2 g (43.9 mmol) of the compound from Ex. 14A were added a little at a time. After the addition had ended, the reaction mixture was heated first for 30 min at 50° C. and then for 90 min at 100° C. After the mixture had cooled to RT, it was poured into about 100 ml of ice-water and stirred for 1 h. The precipitated solid was filtered off with suction and washed initially with water and then with hexane. The solid was then stirred with a little dichloromethane at RT, once more filtered off with suction and finally dried under high vacuum. This gave 3.16 g (26% of theory, 93% pure) of the title compound.

$^1$H-NMR (400 MHz, DMSO-d$_6$, δ/ppm): 12.38 (s, 1H), 7.32-7.28 (m, 2H), 7.23-7.19 (m, 3H), 5.91 (s, about 1H), 3.93 (dd, 2H), 2.80 (dd, 2H).

LC/MS (Method 1, ESIpos): R$_t$=0.79 min, m/z=251/253 [M+H]$^+$.

Example 17A

6-Chloro-3-ethylpyrimidine-2,4(1H,3H)-dione

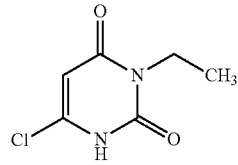

At a temperature of 0° C., 28.8 ml (309 mmol) of phosphorus oxychloride were added carefully to 6.6 ml of 50% strength aqueous ethanol. Then, likewise at 0° C., 5.4 g (34.6 mmol) of the compound from Ex. 15A were added a little at a time. After the addition had ended, the reaction mixture was heated first for 30 min at 50° C. and then for 2 h at 100° C. After the mixture had cooled to RT, it was poured into about 100 ml of ice-water. The precipitated solid was filtered off with suction and washed with water. Drying under high vacuum gave 2.78 g (46% of theory) of the title compound.

$^1$H-NMR (400 MHz, DMSO-$d_6$, δ/ppm): 12.34 (s, 1H), 5.89 (s, about 1H), 3.76 (quart, 2H), 1.07 (t, 3H).

LC/MS (Method 1, ESIpos): $R_t$=0.42 min, m/z=175/177 [M+H]$^+$.

Example 18A

1-[2,6-Dioxo-1-(2-phenylethyl)-4-(pyridinium-1-yl)-1,6-dihydropyrimidin-5(2H)-ylidene]-2,2,2-trifluoroethanolate

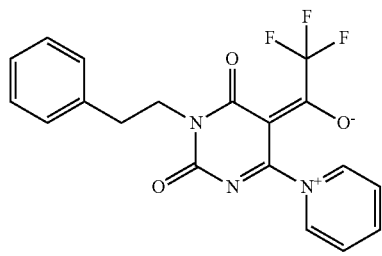 [SMILES: O=C1N=C([n+]2ccccc2)/C(=C(\[O-])C(F)(F)F)C(=O)N1CCc1ccccc1]

At RT, 3.2 ml (39.9 mmol) of pyridine were added to a suspension of 1.0 g (3.99 mmol) of the compound from Ex. 16A in 10 ml of acetonitrile. 2.3 ml (16.0 mmol) of trifluoroacetic anhydride were then slowly added dropwise. After the addition had ended, stirring of the mixture was continued at RT for 1 h. About 100 ml of water were then added, and the mixture was extracted with about 100 ml of ethyl acetate. The organic extract was washed with saturated aqueous sodium chloride solution. The solid, which was finely suspended in the extract, was then filtered off with suction and washed with a little ethyl acetate. The residue was dried under high vacuum, thus giving a first fraction of the title compound (659 mg, 42% of theory). The resulting filtrate was dried over anhydrous magnesium sulphate, filtered and evaporated to dryness. The solid that remained was stirred in a mixture of 25 ml of diisopropyl ether and 11 ml of ethyl acetate at 40° C. for 30 min. After cooling to RT, the solid present was filtered off with suction and washed with a little diethyl ether. This gave, after drying under high vacuum, a second fraction of the title compound (499 mg, 32% of theory). A total of 1.16 g (74% of theory) of the title compound were obtained in this manner.

$^1$H-NMR (400 MHz, DMSO-$d_6$, δ/ppm): 9.28 (d, 2H), 8.81 (t, 1H), 8.28 (t, 2H), 7.36-7.28 (m, 4H), 7.25-7.21 (m, 1H), 4.03 (dd, 2H), 2.83 (dd, 2H).

LC/MS (Method 1, ESIpos): $R_t$=0.85 min, m/z=390 [M+H]$^+$.

Example 19A

1-[1-Ethyl-2,6-dioxo-4-(pyridinium-1-yl)-1,6-dihydropyrimidin-5(2H)-ylidene]-2,2,2-trifluoroethanolate

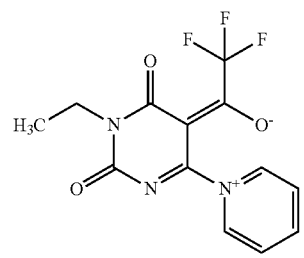 [SMILES: CCN1C(=O)N=C([n+]2ccccc2)/C(=C(\[O-])C(F)(F)F)C1=O]

At RT, 4.6 ml (57.3 mmol) of pyridine were added to a suspension of 1.0 g (5.73 mmol) of the compound from Ex. 17A in 15 ml of acetonitrile. 3.2 ml (22.9 mmol) of trifluoroacetic anhydride were then slowly added dropwise. After the addition had ended, stirring of the mixture was continued at RT for 1 h. About 100 ml of water were then added, and the mixture was extracted twice with about 100 ml of ethyl acetate each time. The organic extract was washed with saturated aqueous sodium chloride solution and then evaporated to dryness. The solid that remained was stirred in a mixture of 25 ml of diisopropyl ether and 5 ml of ethyl acetate at 40° C. for 30 min. After cooling to RT, the solid present was filtered off with suction and washed with a little pentane. Drying under high vacuum gave 1.54 g (86% of theory) of the title compound.

$^1$H-NMR (400 MHz, DMSO-$d_6$, δ/ppm): 9.28 (d, 2H), 8.80 (t, 1H), 8.26 (t, 2H), 3.87 (quart, 2H), 1.13 (t, 3H).

LC/MS (Method 1, ESIpos): $R_t$=0.56 min, m/z=314 [M+H]$^+$.

Example 20A

Ethyl 2,4-dioxo-3-(2-phenylethyl)-5-(trifluoromethyl)-1,2,3,4-tetrahydrothieno[2,3-d]pyrimidine-6-carboxylate

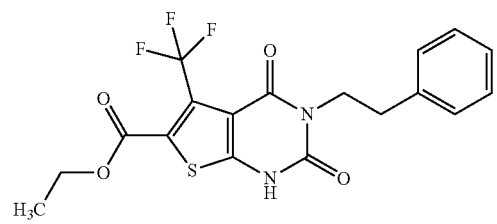 [SMILES: CCOC(=O)c1sc2[nH]c(=O)n(CCc3ccccc3)c(=O)c2c1C(F)(F)F]

In a microwave oven (Biotage Initiator with dynamic control of irradiation power), a mixture of 950 mg (2.44 mmol) of the compound from Ex. 18A, 569 mg (5.37 mmol) of sodium carbonate and 535 µl (4.88 mmol) of ethyl mercaptoacetate in 26 ml of ethanol was heated at 120° C. for 1 h. Then the mixture was evaporated to dryness on a rotary evaporator. The residue that remained was taken up in about 700 ml of ethyl acetate and the mixture was washed successively with about 300 ml each of semisaturated aqueous sodium chloride solution, water and saturated sodium chloride solution. After drying over anhydrous magnesium sulphate, the mixture was filtered and the filtrate was evaporated. The crude product was purified by preparative HPLC (Method 5). This gave, after combination and evaporation of the product fractions and drying of the residue under high vacuum, 728 mg (72% of theory) of the title compound.

$^1$H-NMR (400 MHz, DMSO-$d_6$, δ/ppm): 12.61 (s, 1H), 7.33-7.29 (m, 2H), 7.26-7.20 (m, 3H), 4.33 (quart, 2H), 4.02 (m, 2H), 2.83 (m, 2H), 1.29 (t, 3H).

LC/MS (Method 1, ESIpos): $R_t$=1.13 min, m/z=413 [M+H]$^+$.

Example 21A

Ethyl 3-ethyl-2,4-dioxo-5-(trifluoromethyl)-1,2,3,4-tetrahydrothieno[2,3-d]pyrimidine-6-carboxylate

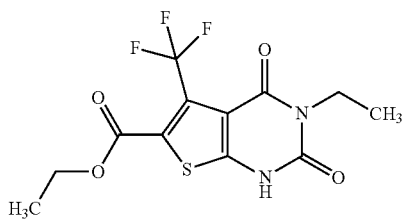 [SMILES: CCOC(=O)c1sc2[nH]c(=O)n(CC)c(=O)c2c1C(F)(F)F]

In a microwave oven (Biotage Initiator with dynamic control of irradiation power), a mixture of 4.75 g (15.2 mmol) of the compound from Ex. 19A, 3.54 g (33.4 mmol) of sodium carbonate and 3.3 ml (30.3 mmol) of ethyl mercaptoacetate in 39 ml of ethanol was heated at 120° C. for 1 h. Then the mixture was evaporated to dryness on a rotary evaporator. About 200 ml of water were added to the residue that remained, and the mixture was acidified slightly with acetic acid (about pH 4). The mixture was extracted three times with about 100 ml of dichloromethane each time. The combined organic phases were washed with saturated sodium chloride solution and dried over anhydrous magnesium sulphate and then filtered and evaporated. The crude product was purified by MPLC (Puriflash cartridge with 25 g of silica gel, cyclohexane/ethyl acetate 3:1→1:1). This gave, after combination and evaporation of the product fractions and drying of the residue under high vacuum, 2.78 g (54% of theory) of the title compound.

$^1$H-NMR (400 MHz, CDCl$_3$, δ/ppm): 11.38 (s, 1H), 4.40 (quart, 2H), 4.10 (quart, 2H), 1.39 (t, 3H), 1.29 (t, 3H).

LC/MS (Method 2, ESIpos): $R_t$=2.06 min, m/z=337 [M+H]$^+$.

Example 22A

1-[2,6-Dioxo-1-(2-phenylethyl)-4-(pyridinium-1-yl)-1,6-dihydropyrimidin-5(2H)-ylidene]-2,2-difluoroethanolate

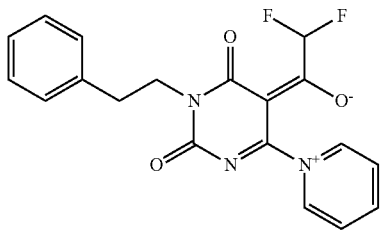 [SMILES: O=C1N=C([n+]2ccccc2)/C(=C(\[O-])C(F)F)C(=O)N1CCc1ccccc1]

At RT, 16.1 ml (199 mmol) of pyridine were added to a suspension of 5.0 g (19.9 mmol) of the compound from Ex. 16A in 50 ml of acetonitrile. 9.9 ml (79.8 mmol) of difluoroacetic anhydride were then slowly added dropwise. After the addition had ended, stirring was continued at RT for 1 h. About 500 ml of water were then added, and the mixture was extracted twice with about 500 ml of ethyl acetate each time. The organic extract was washed with saturated aqueous sodium chloride solution. The solid, which was finely suspended in the extract, was then filtered off with suction and washed with a little ethyl acetate. The solid was dried under high vacuum, thus giving a first fraction of the title compound (2.8 g, 37% of theory). The filtrate was dried over anhydrous magnesium sulphate, filtered and concentrated to dryness. The residue that remained was initially stirred in a mixture of 20 ml of diisopropyl ether and 8 ml of ethyl acetate at RT. Since the solid obtained after filtration with suction was still slightly contaminated, the product was for a second time stirred with a mixture of 30 ml of diethyl ether and 10 ml of ethyl acetate. This gave, after another filtration with suction and drying under high vacuum, a second fraction of the title compound (2.3 g, 31% of theory). In total, 5.1 g (68% of theory) of the title compound were obtained in this manner.

$^1$H-NMR (400 MHz, DMSO-$d_6$, δ/ppm): 9.22 (d, 2H), 8.81 (t, 1H), 8.27 (t, 2H), 7.36-7.28 (m, 4H), 7.26-7.22 (m, 1H), 6.97 (t, 1H), 4.04 (m, 2H), 2.84 (m, 2H).

LC/MS (Method 1, ESIpos): $R_t$=0.82 min, m/z=372 [M+H]$^+$.

Example 23A

Ethyl 2,4-dioxo-3-(2-phenylethyl)-5-(difluoromethyl)-1,2,3,4-tetrahydrothieno[2,3-d]pyrimidine-6-carboxylate

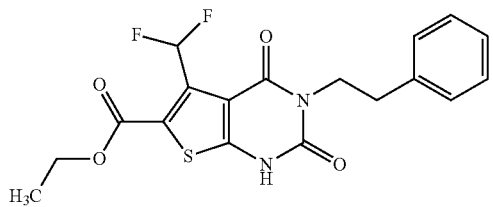 [SMILES: CCOC(=O)c1sc2[nH]c(=O)n(CCc3ccccc3)c(=O)c2c1C(F)F]

In a microwave oven (Biotage Initiator with dynamic control of irradiation power), a mixture of 4.0 g (10.8 mmol) of the compound from Ex. 22A, 2.51 g (23.7 mmol) of sodium carbonate and 2.36 ml (21.5 mmol) of ethyl mercaptoacetate in 22.4 ml of ethanol was heated at 120° C. for 2 h. The reaction mixture was then evaporated to dryness on a rotary evaporator. The residue that remained was taken up in about 400 ml of water, acidified slightly by addition of acetic acid and extracted three times with about 400 ml of dichloromethane each. The solid, which was finely suspended in the combined organic extracts, was filtered off with suction and stirred at RT with a mixture of 25 ml of pentane and 25 ml of dichloromethane for 30 min. This gave, after another filtration with suction and drying under high vacuum, a first fraction of the title compound (1.76 g, 41% of theory). The filtrate from the filtration of the combined organic extracts was washed with saturated aqueous sodium chloride solution, dried over anhydrous magnesium sulphate, filtered and concentrated. At RT, the solid that remained was stirred in a mixture of 20 ml of pentane and 20 ml of dichloromethane for 30 min. This gave, after filtration with suction and drying under high vacuum, a second fraction of the title compound (1.14 g, 26% of theory). In total, 2.9 g (68% of theory) of the title compound were obtained in this manner.

$^1$H-NMR (400 MHz, DMSO-$d_6$, δ/ppm): 12.67 (s, 1H), 7.72 (t, 1H), 7.34-7.29 (m, 2H), 7.26-7.20 (m, 3H), 4.33 (quart, 2H), 4.02 (m, 2H), 2.84 (m, 2H), 1.31 (t, 3H).

LC/MS (Method 1, ESIpos): $R_t$=1.06 min, m/z=395 [M+H]$^+$.

Example 24A

6-Chloro-2,4-dioxo-3-(2-phenylethyl)-1,2,3,4-tetra-hydropyrimidine-5-carbaldehyde

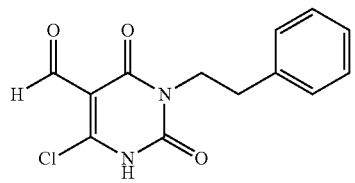 [SMILES: O=Cc1c(Cl)[nH]c(=O)n(CCc2ccccc2)c1=O]

At a temperature of 0° C., 31.7 ml (340 mmol) of phosphorus oxychloride were added dropwise to 7.9 ml of DMF. After the addition had ended, the cooling bath was removed and 3.95 g (17.0 mmol) of the compound from Ex. 14A were added a little at a time at RT. The mixture was then heated under reflux for 2 h. After cooling, excess phosphorus oxychloride was removed on a rotary evaporator. The residue that remained was, with vigorous stirring, carefully poured into ice-water. The resulting precipitate was filtered off with suction and then dissolved in ethyl acetate. The mixture was extracted successively with water and saturated sodium chloride solution. The combined aqueous wash phases were re-extracted with dichloromethane, and the dichloromethane phase was combined with the ethyl acetate phase. After concentration of the combined organic phases, the crude product was suspended in about 70 ml of ethyl acetate and stirred at RT for 30 min. This gave, after the solid had been filtered off with suction and dried under high vacuum, a first fraction of the title compound (1.08 g, purity 91%, 20% of theory). The filtrate was concentrated and then subjected to coarse purification by filtration with suction through silica gel using the mobile phase ethyl acetate. After re-evaporation, the solid that remained was stirred at RT in a mixture of 10 ml of ethyl acetate and 3 ml of pentane for 3 h. This gave, after filtration with suction and drying under high vacuum, a second fraction of the title compound (0.91 g, purity 63%, 12% of theory). Both fractions could be employed for further reactions without further purification. This gave a total of 1.99 g (78% purity, 33% of theory) of the title compound.

$^1$H-NMR (500 MHz, CDCl$_3$, δ/ppm): 10.14 (s, 1H), 9.91 (br. s, 1H), 7.33-7.29 (m, 2H), 7.28-7.22 (m, 3H), 4.19 (m, 2H), 2.96 (m, 2H).

LC/MS (Method 1, ESIpos): $R_t$=0.72 min, m/z=279/281 [M+H]$^+$.

Example 25A

Ethyl 2,4-dioxo-3-(2-phenylethyl)-1,2,3,4-tetrahy-drothieno[2,3-d]pyrimidine-6-carboxylate

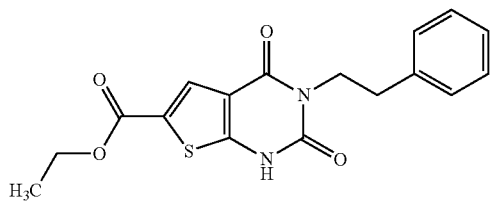 [SMILES: CCOC(=O)c1cc2c(=O)n(CCc3ccccc3)c(=O)[nH]c2s1]

In a microwave oven (Biotage Initiator with dynamic control of irradiation power), a mixture of 1.08 g (3.88 mmol) of the compound from Ex. 24A, 411 mg (3.88 mmol) of sodium carbonate and 425 μl (3.88 mmol) of ethyl mercaptoacetate in 15 ml of ethanol was heated at 120° C. for 90 min. The reaction mixture was then evaporated to dryness on a rotary evaporator. The residue that remained was taken up in ethyl acetate and washed twice with water and once with saturated aqueous sodium chloride solution. After drying over anhydrous magnesium sulphate, the mixture was filtered and concentrated. The residue that remained with dissolved in a little dichloromethane, a few drops of ethanol were added and the material was then purified on a Biotage cartridge (50 g of silica gel, mobile phase gradient: 5:1→1:2 cyclohexane/ethyl acetate). This gave, after evaporation of the product fractions and drying of the residue under high vacuum, 901 mg (67% of theory) of the title compound.

$^1$H-NMR (400 MHz, DMSO-$d_6$, δ/ppm): 12.54 (s, 1H), 7.77 (s, 1H), 7.33-7.28 (m, 2H), 7.24-7.20 (m, 3H), 4.29 (quart, 2H), 4.03 (m, 2H), 2.84 (m, 2H), 1.30 (t, 3H).

LC/MS (Method 1, ESIpos): $R_t$=1.00 min, m/z=345 [M+H]$^+$.

Example 26A tert-Butyl 5-methyl-2,4-dioxo-3-(2-phenylethyl)-1-(3,3,3-trifluoropropyl)-1,2,3,4-tetrahydrothieno[2,3-d]pyrimidine-6-carboxylate

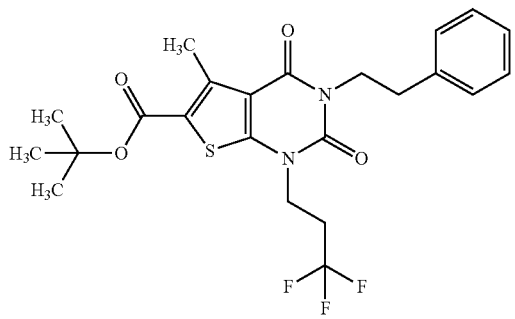 [SMILES: Cc1c(C(=O)OC(C)(C)C)sc2c1c(=O)n(CCc1ccccc1)c(=O)n2CCC(F)(F)F]

5.55 g (17.0 mmol) of caesium carbonate were added to a solution of 5.98 g (15.5 mmol) of the compound from Ex. 8A in 150 ml of DMF, and the mixture was stirred at RT for 15 min. 4.16 g (18.6 mmol) of 3,3,3-trifluoro-1-iodopropane were then added, and the mixture was heated at 100° C. for 3 h. The mixture was then evaporated to dryness on a rotary evaporator. The residue that remained was taken up in ethyl acetate and washed successively with water and saturated sodium chloride solution. After drying over anhydrous magnesium sulphate, the mixture was filtered and the filtrate was evaporated. The crude product was purified by MPLC (Biotage cartridge with 340 g of silica gel, cyclohexane/ethyl acetate 10:1). The product fractions were combined and concentrated. The residue was then stirred in 50 ml of pentane/dichloromethane (100:5) at RT. This gave, after another filtration, evaporation and drying under high vacuum, 5.33 g (71% of theory) of the title compound.

$^1$H-NMR (400 MHz, DMSO-$d_6$, δ/ppm): 7.33-7.28 (m, 2H), 7.25-7.20 (m, 3H), 4.14 (t, 2H), 4.06 (m, 2H), 2.84 (m, 2H), 2.79-2.72 (m, 2H), 2.76 (s, 3H), 1.54 (s, 9H).

LC/MS (Method 1, ESIpos): $R_t$=1.49 min, m/z=483 [M+H]$^+$.

Example 27A tert-Butyl 1-(4,4-difluorobut-3-en-1-yl)-5-methyl-2,4-dioxo-3-(2-phenylethyl)-1,2,3,4-tetrahydrothieno[2,3-d]pyrimidine-6-carboxylate

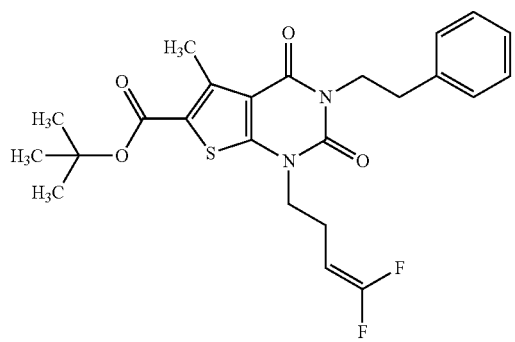 [SMILES: Cc1c(C(=O)OC(C)(C)C)sc2c1c(=O)n(CCc1ccccc1)c(=O)n2CCC=C(F)F]

Analogously to the process described in Ex. 26A, 1.0 g (2.59 mmol) of the compound from Ex. 8A, 1.27 g (3.88 mmol) of caesium carbonate and 664 mg (3.88 mmol) of 4-bromo-1,1-difluorobut-1-ene gave 468 mg (37% of theory) of the title compound. In deviation from the process described above, here, MPLC purification could be dispensed with. The crude product was purified by stirring at RT with a mixture of 20 ml of pentane and 0.5 ml of dichloromethane.

$^1$H-NMR (400 MHz, CDCl$_3$, δ/ppm): 7.32-7.29 (m, 4H), 7.26-7.20 (m, 1H), 4.28-4.24 (m, 1H), 4.24-4.18 (m, 2H), 3.97 (t, 2H), 2.96-2.92 (m, 2H), 2.86 (s, 3H), 2.47 (quart, 2H), 1.59 (s, 9H).

LC/MS (Method 1, ESIpos): $R_t$=1.52 min, m/z=477 [M+H]$^+$.

Example 28A tert-Butyl 1-(2-methoxyethyl)-5-methyl-2,4-dioxo-3-(2-phenylethyl)-1,2,3,4-tetrahydrothieno[2,3-d]pyrimidine-6-carboxylate

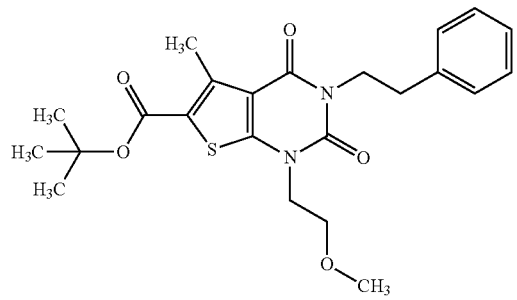 [SMILES: COCCn1c(=O)n(CCc2ccccc2)c(=O)c2c(C)c(C(=O)OC(C)(C)C)sc21]

1.85 g (5.69 mmol) of caesium carbonate were added to a solution of 2.0 g (5.18 mmol) of the compound from Ex. 8A in 60 ml of DMF, and the mixture was stirred at RT for 10 min. 863 mg (6.21 mmol) of 2-bromomethyl methyl ether were then added, and the mixture was heated at 100° C. for 30 min. The mixture was then evaporated to dryness on a rotary evaporator. The residue that remained was taken up in ethyl acetate and washed successively with water and saturated sodium chloride solution. After drying over anhydrous magnesium sulphate, the mixture was filtered and the filtrate was evaporated. The crude product was purified by MPLC (Puriflash column with 80 g of silica gel, cyclohexane/ethyl acetate 10:1). Filtration, evaporation and drying of the residue under high vacuum gave 2.22 g (96% of theory) of the title compound.

$^1$H-NMR (400 MHz, DMSO-$d_6$, δ/ppm): 7.32-7.28 (m, 2H), 7.24-7.20 (m, 3H), 4.09-4.04 (m, 4H), 3.61 (t, 2H), 3.24 (s, 3H), 2.84 (dd, 2H), 2.74 (s, 3H), 1.53 (s, 9H).

LC/MS (Method 1, ESIpos): $R_t$=1.40 min, m/z=445 [M+H]$^+$.

Example 29A tert-Butyl 3-[2-(2-fluorophenyl)ethyl]-5-methyl-2,4-dioxo-1-(3,3,3-trifluoropropyl)-1,2,3,4-tetrahydrothieno[2,3-d]pyrimidine-6-carboxylate

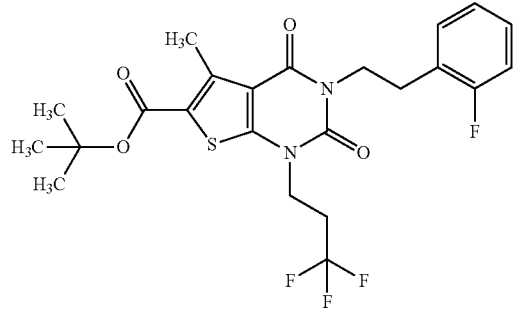

665 mg (2.04 mmol) of caesium carbonate were added to a solution of 750 mg (1.85 mmol) of the compound from Ex. 9A in 20 ml of DMF, and the mixture was stirred at RT for 15 min. 498 mg (2.23 mmol) of 3,3,3-trifluoro-1-iodopropane were then added. The mixture was heated at 100° C. for a total of 17 h, with another 498 mg (2.23 mmol) of 3,3,3-trifluoro-1-iodopropane being added after a reaction time of 5 h and a further 249 mg (1.12 mmol) of 3,3,3-trifluoro-1-iodopropane being added after a reaction time of 8 h. After the reaction had ended, the mixture was evaporated to dryness on a rotary evaporator. The residue that remained was taken up in ethyl acetate and washed successively with water and saturated sodium chloride solution. After drying over anhydrous magnesium sulphate, the mixture was filtered and the filtrate was evaporated. The crude product was purified by MPLC (Puriflash column with 200 g of silica gel, cyclohexane/ethyl acetate 5:1). The product fractions were combined and concentrated. Finally, the residue was stirred at RT in a mixture of 30 ml of pentane and 1 ml of dichloromethane. This gave, after another filtration, evaporation and drying under high vacuum, 430 mg (44% of theory, purity 95%) of the title compound.

$^1$H-NMR (400 MHz, DMSO-$d_6$, δ/ppm): 7.29-7.24 (m, 2H), 7.15-7.09 (m, 2H), 4.12 (t, 2H), 4.10 (t, 2H), 2.91 (t, 2H), 2.73 (s, 3H), 2.71 (t, 2H), 1.53 (s, 9H).

LC/MS (Method 1, ESIpos): $R_t$=1.42 min, m/z=501 [M+H]$^+$.

Example 30A tert-Butyl 1-(4,4-difluorobut-3-en-1-yl)-3-[2-(2-fluorophenyl)ethyl]-5-methyl-2,4-dioxo-1,2,3,4-tetrahydrothieno[2,3-d]pyrimidine-6-carboxylate

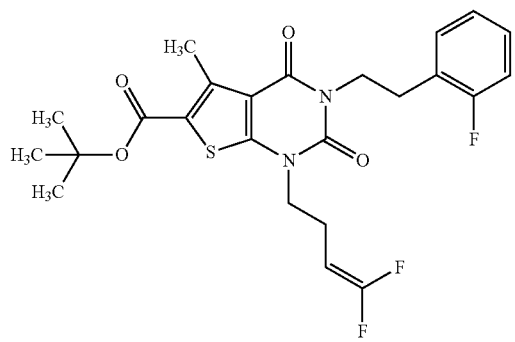 [SMILES: Cc1c(C(=O)OC(C)(C)C)sc2c1c(=O)n(CCc1ccccc1F)c(=O)n2CCC=C(F)F]

Analogously to the process described in Ex. 29A, 750 mg (1.85 mmol) of the compound from Ex. 9A, 906 mg (2.78 mmol) of caesium carbonate and 476 mg (2.78 mmol) of 4-bromo-1,1-difluorobut-1-ene gave 480 mg (52% of theory) of the title compound. In deviation from the process described above, here the reaction time was only 60 min, and during this time there was no further addition of alkylating agent. Moreover, MPLC purification could be dispensed with. The crude product was purified by stirring in 20 ml of pentane at RT.

$^1$H-NMR (400 MHz, DMSO-$d_6$, δ/ppm): 7.29-7.23 (m, 2H), 7.15-7.09 (m, 2H), 4.60 (d of t of d, 1H), 4.10 (t, 2H), 3.94 (t, 2H), 2.90 (t, 2H), 2.72 (s, 3H), 2.38-2.32 (m, 2H), 1.53 (s, 9H).

LC/MS (Method 1, ESIpos): $R_t$=1.46 min, m/z=495 [M+H]$^+$.

Example 31A tert-Butyl 3-[2-(2-chlorophenyl)ethyl]-5-methyl-2,4-dioxo-1-(3,3,3-trifluoropropyl)-1,2,3,4-tetrahydrothieno[2,3-d]pyrimidine-6-carboxylate

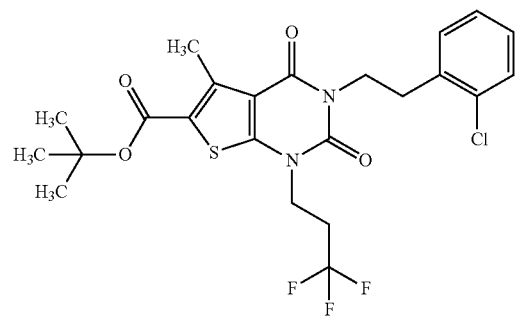 [SMILES: Cc1c(C(=O)OC(C)(C)C)sc2c1c(=O)n(CCc1ccccc1Cl)c(=O)n2CCC(F)(F)F]

Analogously to the process described in Ex. 29A, 750 mg (1.78 mmol) of the compound from Ex. 10A, 639 mg (1.69 mmol) of caesium carbonate and initially 479 mg (2.14 mmol) of 3,3,3-trifluoro-1-iodopropane gave 440 mg (48% of theory) of the title compound. In deviation from the process described above, here the reaction time was 3 days in total, and the addition of further alkylating agent was carried out after 6 h and 16 h (in each case 240 mg, 1.07 mmol).

$^1$H-NMR (400 MHz, CDCl$_3$, δ/ppm): 7.36-7.33 (m, 1H), 7.27-7.23 (m, 1H, partially obscured by the CHCl$_3$ signal), 7.19-7.14 (m, 2H), 4.28 (t, 2H), 4.13 (t, 2H), 3.11 (t, 2H), 2.84 (s, 3H), 2.59-2.47 (m, 2H), 1.59 (s, 9H).

LC/MS (Method 1, ESIpos): $R_t$=1.46 min, m/z=517/519 [M+H]$^+$.

Example 32A tert-Butyl 3-[2-(2-chlorophenyl)ethyl]-1-(4,4-difluorobut-3-en-1-yl)-5-methyl-2,4-dioxo-1,2,3,4-tetrahydrothieno[2,3-d]pyrimidine-6-carboxylate

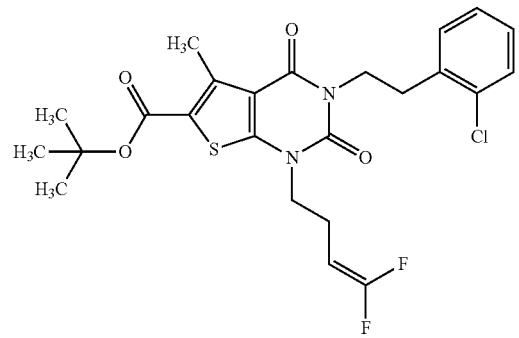 [SMILES: Cc1c(C(=O)OC(C)(C)C)sc2c1c(=O)n(CCc1ccccc1Cl)c(=O)n2CCC=C(F)F]

Analogously to the process described in Ex. 29A, 750 mg (1.85 mmol) of the compound from Ex.

10A, 871 mg (2.67 mmol) of caesium carbonate and 457 mg (2.67 mmol) of 4-bromo-1,1-difluorobut-1-ene gave 543 mg (57% of theory) of the title compound. In deviation from the process described above, here the reaction time was only 60 min, and during this time there was no further addition of alkylating agent. Moreover, MPLC purification could be dispensed with. The crude product was purified by stirring in 20 ml of pentane at RT.

¹H-NMR (400 MHz, DMSO-$d_6$, δ/ppm): 7.42-7.38 (m, 1H), 7.30-7.22 (m, 3H), 4.60 (d of t of d, 1H), 4.12 (t, 2H), 3.93 (t, 2H), 2.99 (t, 2H), 2.72 (s, 3H), 2.37-2.31 (m, 2H), 1.53 (s, 9H).

LC/MS (Method 1, ESIpos): $R_t$=1.50 min, m/z=511/513 [M+H]⁺.

Example 33A tert-Butyl 5-methyl-2,4-dioxo-3-[2-(pyridin-3-yl) ethyl]-1-(3,3,3-trifluoropropyl)-1,2,3,4-tetrahydrothieno[2,3-d]pyrimidine-6-carboxylate

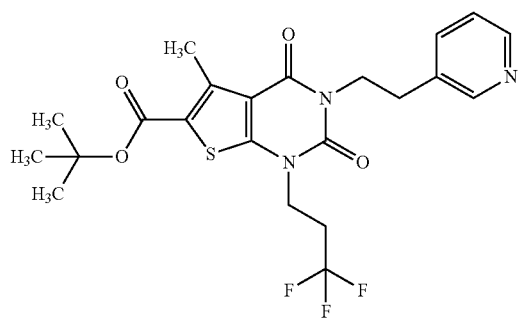 [SMILES: Cc1c(C(=O)OC(C)(C)C)sc2c1c(=O)n(CCc1cccnc1)c(=O)n2CCC(F)(F)F]

1.14 g (3.48 mmol) of caesium carbonate were added to a solution of 900 mg (2.32 mmol) of the compound from Ex. 11A in 25 ml of DMF, and the mixture was stirred at RT for 15 min. 780 mg (3.48 mmol) of 3,3,3-trifluoro-1-iodopropane were then added, and the mixture was heated at 90° C. for 6 h. The mixture was then evaporated to dryness on a rotary evaporator. The residue that remained was taken up in ethyl acetate and washed successively with water and saturated sodium chloride solution. After drying over anhydrous magnesium sulphate, the mixture was filtered and the filtrate was evaporated. The crude product was purified by MPLC (Biotage cartridge with 50 g of silica gel, cyclohexane/ethyl acetate 5:1→1:1). The product fractions were combined and concentrated. At RT, the residue was then stirred in a mixture of 20 ml of cyclohexane and 1 ml of dichloromethane for 2 h. This gave, after another filtration, evaporation and drying under high vacuum, a first fraction of the title compound (117 mg, 10% of theory). After evaporation, the filtrate was purified further by preparative HPLC (Method 5). This gave, after combination and evaporation of the product fractions, a second fraction of the title compound (381 mg, 33% of theory). A total of 498 mg (44% of theory) of the title compound were thus obtained.

¹H-NMR (400 MHz, DMSO-$d_6$, δ/ppm): 8.43-8.41 (m, 2H), 7.67-7.63 (m, 1H), 7.31 (dd, 1H), 4.13 (t, 2H), 4.10 (t, 2H), 2.89 (t, 2H), 2.80-2.69 (m, 2H), 2.73 (s, 3H), 1.53 (s, 9H).

LC/MS (Method 1, ESIpos): $R_t$=1.07 min, m/z=484 [M+H]⁺.

Example 34A tert-Butyl 1-(4,4-difluorobut-3-en-1-yl)-5-methyl-2, 4-dioxo-3-[2-(pyridin-3-yl)ethyl]-1,2,3,4-tetrahydrothieno[2,3-d]pyrimidine-6-carboxylate

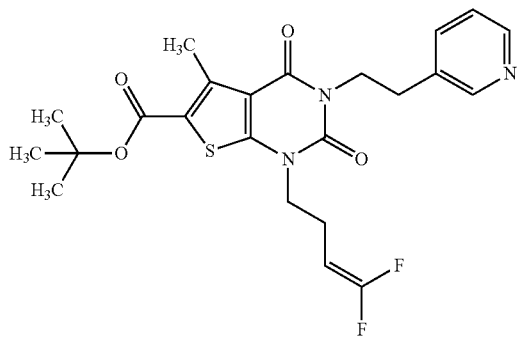 [SMILES: Cc1c(C(=O)OC(C)(C)C)sc2c1c(=O)n(CCc1cccnc1)c(=O)n2CCC=C(F)F]

Analogously to the process described in Ex. 33A, 900 mg (2.32 mmol) of the compound from Ex. 11A, 1.14 g (3.48 mmol) of caesium carbonate and 596 mg (3.48 mmol) of 4-bromo-1,1-difluorobut-1-ene gave a total of 610 mg (55% of theory) of the title compound.

¹H-NMR (400 MHz, DMSO-$d_6$, δ/ppm): 8.43-8.40 (m, 2H), 7.67-7.64 (m, 1H), 7.31 (dd, 1H), 4.61 (d of t of d, 1H), 4.10 (t, 2H), 3.94 (t, 2H), 2.88 (t, 2H), 2.73 (s, 3H), 2.39-2.33 (m, 2H), 1.53 (s, 9H).

LC/MS (Method 1, ESIpos): $R_t$=1.10 min, m/z=478 [M+H]⁺.

Example 35A tert-Butyl 3-ethyl-5-methyl-2,4-dioxo-1-(3,3,3-trifluoropropyl)-1,2,3,4-tetrahydrothieno[2,3-d]pyrimidine-6-carboxylate

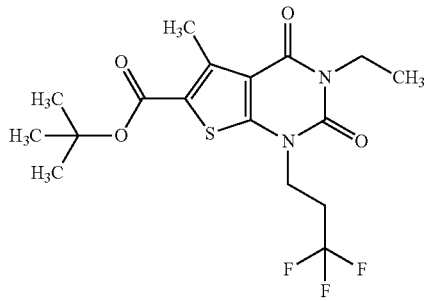 [SMILES: CCn1c(=O)c2c(C)c(C(=O)OC(C)(C)C)sc2n(CCC(F)(F)F)c1=O]

4.72 g (14.5 mmol) of caesium carbonate were added to a solution of 3.0 g (9.67 mmol) of the compound from Ex. 12A in 100 ml of DMF, and the mixture was stirred at RT for 20 min. 2.57 g (14.5 mmol) of 3,3,3-trifluoro-1-iodopropane were then added, and the mixture was heated at 100° C. for 5 h. The mixture was then evaporated to dryness on a rotary evaporator. The residue that remained was taken up in ethyl acetate and washed successively with water and saturated sodium chloride solution. After drying over anhydrous magnesium sulphate, the mixture was filtered and the filtrate was evaporated. The crude product was purified by MPLC (Puriflash column with 120 g of silica gel, cyclohexane/ethyl acetate 10:1). The product fractions were combined and concentrated, and the residue was dried under high vacuum. This gave 3.24 g (76% of theory, 93% pure) of the title compound.

$^1$H-NMR (400 MHz, DMSO-d$_6$, δ/ppm): 4.15 (t, 2H), 3.90 (quart, 2H), 2.84-2.74 (m, 2H), 2.76 (s, 3H), 1.53 (s, 9H), 1.13 (t, 3H).

LC/MS (Method 1, ESIpos): R$_t$=1.36 min, m/z=407 [M+H]$^+$.

Example 36A tert-Butyl 1-(4,4-difluorobut-3-en-1-yl)-3-ethyl-5-methyl-2,4-dioxo-1,2,3,4-tetrahydrothieno[2,3-d]pyrimidine-6-carboxylate

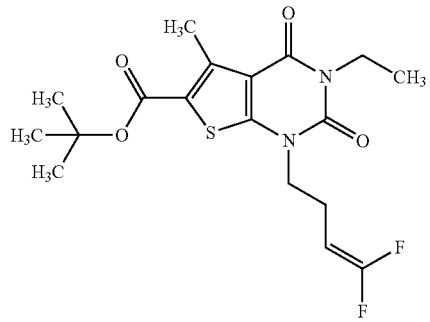 [SMILES: CCn1c(=O)c2c(C)c(C(=O)OC(C)(C)C)sc2n(CCC=C(F)F)c1=O]

Analogously to the process described in Ex. 35A, 800 mg (2.58 mmol) of the compound from Ex. 12A, 1.26 g (3.87 mmol) of caesium carbonate and 661 mg (3.87 mmol) of 4-bromo-1,1-difluorobut-1-ene gave 778 mg (76% of theory) of the title compound. In deviation to the process described above, here the reaction time was only 1 h. Also in deviation, a Puriflash cartridge containing 40 g of silica gel was used for MPLC purification, and the product was then purified by stirring in pentane/dichloromethane (30:1).

$^1$H-NMR (400 MHz, CDCl$_3$, δ/ppm): 4.25 (d of t of d, 1H), 4.06 (quart, 2H), 3.98 (t, 2H), 2.85 (s, 3H), 2.51 (pseudo-quart, 2H), 1.59 (s, 9H), 1.25 (t, 3H).

LC/MS (Method 1, ESIpos): R$_t$=1.39 min, m/z=401 [M+H]$^+$.

Example 37A tert-Butyl 3-ethyl-1-(2-methoxyethyl)-5-methyl-2,4-dioxo-1,2,3,4-tetrahydrothieno[2,3-d]pyrimidine-6-carboxylate

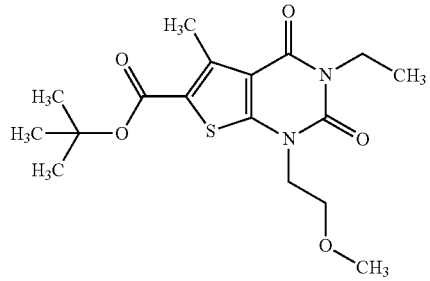 [SMILES: CCn1c(=O)c2c(C)c(C(=O)OC(C)(C)C)sc2n(CCOC)c1=O]

Analogously to the process described in Ex. 35A, 800 mg (2.58 mmol) of the compound from Ex. 12A, 1.26 g (3.87 mmol) of caesium carbonate and 537 mg (3.87 mmol) of 2-bromoethyl methyl ether gave 680 mg (71% of theory) of the title compound. In deviation to the process described above, here a Biotage cartridge containing 50 g of silica gel was used for MPLC purification, and the product was then purified by stirring in 31 ml of pentane/dichloromethane (30:1).

$^1$H-NMR (400 MHz, CDCl$_3$, δ/ppm): 4.13 (t, 2H), 4.07 (quart, 2H), 3.74 (t, 2H), 3.36 (s, 3H), 2.84 (s, 3H), 1.58 (s, 9H), 1.26 (t, 3H).

LC/MS (Method 1, ESIpos): R$_t$=1.24 min, m/z=369 [M+H]$^+$.

Example 38A

Ethyl 2,4-dioxo-3-(2-phenylethyl)-5-(trifluoromethyl)-1-(3,3,3-trifluoropropyl)-1,2,3,4-tetrahydrothieno[2,3-d]pyrimidine-6-carboxylate

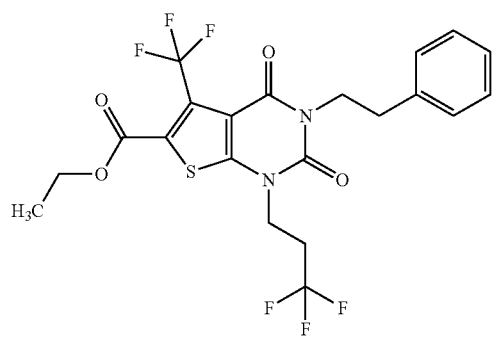 [SMILES: CCOC(=O)c1sc2c(c1C(F)(F)F)c(=O)n(CCc1ccccc1)c(=O)n2CCC(F)(F)F]

719 mg (2.21 mmol) of caesium carbonate were added to a solution of 700 mg (1.70 mmol) of the compound from Ex. 20A in 20 ml of DMF, and the mixture was stirred at RT for 15 min. 570 mg (2.55 mmol) of 3,3,3-trifluoro-1-iodopropane were then added, and the mixture was heated at 100° C. for 60 min. 400 ml of water were then added, and the mixture was extracted three times with about 100 ml of diethyl ether each time. The combined organic extracts were washed with saturated sodium chloride solution. After drying over anhydrous magnesium sulphate, the mixture was filtered and the filtrate was evaporated. At RT, the crude product was triturated in a mixture of 25 ml of pentane and 0.5 ml of diethyl ether for 1 h. The mixture was filtered and the residue was dried under high vacuum. This gave a first fraction of the title compound (497 mg, 57% of theory). A second fraction was isolated by preparative HPLC (Method 6) from the mother liquor obtained after stirring (138 mg, 16% of theory). A total of 635 mg (73% of theory) of the title compound were thus obtained.

$^1$H-NMR (400 MHz, CDCl$_3$, δ/ppm): 7.32-7.20 (m, 5H, partially obscured by the CHCl$_3$ signal), 4.42 (quart, 2H), 4.26-4.22 (m, 2H), 4.16 (t, 2H), 2.98-2.94 (m, 2H), 2.64-2.53 (m, 2H), 1.41 (t, 3H).

LC/MS (Method 1, ESIpos): R$_t$=1.30 min, m/z=509 [M+H]$^+$.

Example 39A

Ethyl 3-ethyl-2,4-dioxo-5-(trifluoromethyl)-1-(3,3,3-trifluoro9propyl)-1,2,3,4-tetrahydrothieno[2,3-d]pyrimidine-6-carboxylate

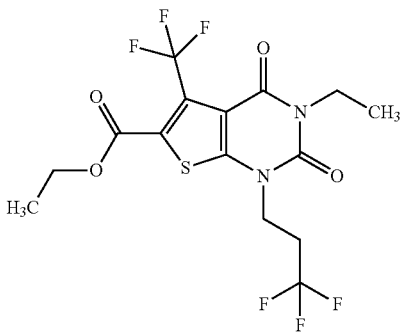 [SMILES: CCOC(=O)c1sc2c(c1C(F)(F)F)c(=O)n(CC)c(=O)n2CCC(F)(F)F]

1.39 g (13.1 mmol) of caesium carbonate were added to a solution of 2.0 g (5.95 mmol) of the compound from Ex. 21A in 40 ml of DMF, and the mixture was stirred at RT for 15 min. 2.66 g (11.9 mmol) of 3,3,3-trifluoro-1-iodopropane were then added, and the mixture was heated at 60° C. After 1 h, a further 2.66 g (11.9 mmol) of 3,3,3-trifluoro-1-iodopropane were added. Stirring at 60° C. was continued for 16 h. After cooling to RT, about 160 ml of water were added and the mixture was extracted three times with about 80 ml of diethyl ether each time. The combined organic extracts were washed with saturated sodium chloride solution. After drying over anhydrous magnesium sulphate, the mixture was filtered and the filtrate was evaporated. The crude product was purified by MPLC on a Puriflash cartridge (100 g of silica gel, cyclohexane/ethyl acetate 7:1→1:1). The product fractions were combined and concentrated, and the residue was dried under high vacuum. This gave 1.86 g (72% of theory) of the title compound.

$^1$H-NMR (400 MHz, CDCl$_3$, δ/ppm): 4.41 (quart, 2H), 4.20 (t, 2H), 4.08 (quart, 2H), 2.73-2.61 (m, 2H), 1.40 (t, 3H), 1.26 (t, 3H).

LC/MS (Method 1, ESIpos): R$_t$=1.15 min, m/z=433 [M+H]$^+$.

Example 40A

Ethyl 5-(difluoromethyl)-2,4-dioxo-3-(2-phenylethyl)-1-(3,3,3-trifluoropropyl)-1,2,3,4-tetrahydrothieno[2,3-d]pyrimidine-6-carboxylate

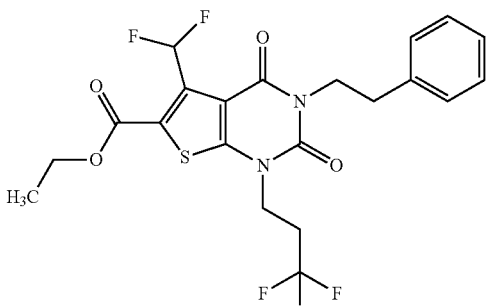

Analogously to the process described in Ex. 38A, 2.90 g (7.35 mmol) of the compound from Ex. 23A and 1.72 ml (14.7 mmol) of 3,3,3-trifluoro-1-iodopropane gave 2.22 g (61% of theory) of the title compound. Here, for purification the crude product was, at RT, stirred successively with the following solvent mixtures: In the first and second instance in each case with 100 ml of pentane and 5 ml of diethyl ether, in the third instance with 50 ml of pentane and 5 ml of diethyl ether.

$^1$H-NMR (400 MHz, DMSO-d$_6$, δ/ppm): 7.74 (t, 1H), 7.33-7.29 (m, 2H), 7.26-7.21 (m, 3H), 4.36 (quart, 2H), 4.20 (t, 2H), 4.08 (m, 2H), 2.87-2.75 (m, 4H), 1.32 (t, 3H).

LC/MS (Method 1, ESIpos): R$_t$=1.27 min, m/z=491 [M+H]$^+$.

Example 41A

Ethyl 2,4-dioxo-3-(2-phenylethyl)-1-(3,3,3-trifluoropropyl)-1,2,3,4-tetrahydrothieno [2,3-d]pyrimidine-6-carboxylate

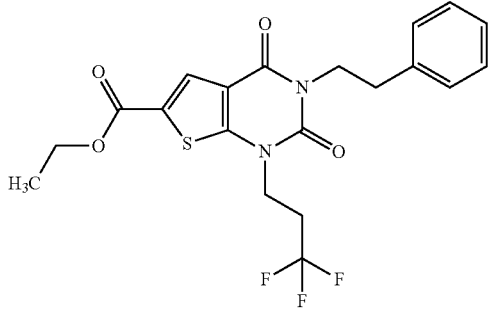 [SMILES: CCOC(=O)c1cc2c(=O)n(CCc3ccccc3)c(=O)n(CCC(F)(F)F)c2s1]

1.28 g (3.92 mmol) 01 caesium carbonate were added to a solution of 900 mg (2.61 mmol) of the compound from Ex. 25A in 10 ml of DMF, and the mixture was stirred at RT for 20 min. 878 mg (3.92 mmol) of 3,3,3-trifluoro-1-iodopropane were then added, and the mixture was stirred in a microwave oven (Biotage Initiator with dynamic control of irradiation power) at 100° C. for 2 h 45 min. After cooling to RT, about 60 ml of water were added and the mixture was extracted with ethyl acetate. The organic extract was washed with water and saturated sodium chloride solution. After drying over anhydrous magnesium sulphate, the mixture was filtered and concentrated. At RT, the solid obtained was stirred in a mixture of 20 ml of pentane and 1 ml of diethyl ether for about 16 h. This gave, after filtration with suction and drying under high vacuum, 895 mg (77% of theory) of the title compound.

$^1$H-NMR (400 MHz, DMSO-d$_6$, δ/ppm): 7.87 (s, 1H), 7.32-7.28 (m, 2H), 7.24-7.19 (m, 3H), 4.32 (quart, 2H), 4.17 (t, 2H), 4.09 (m, 2H), 2.89-2.73 (m, 4H), 1.31 (t, 3H).

LC/MS (Method 1, ESIpos): R$_t$=1.24 min, m/z=441 [M+H]$^+$.

Example 42A tert-Butyl 3-(2,4-dimethoxybenzyl)-5-methyl-2,4-dioxo-1-(3,3,3-trifluoropropyl)-1,2,3,4-tetrahydrothieno[2,3-d]pyrimidine-6-carboxylate

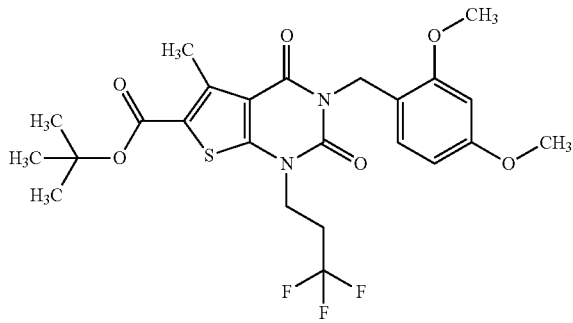 [SMILES: COc1ccc(Cn2c(=O)c3c(C)c(C(=O)OC(C)(C)C)sc3n(CCC(F)(F)F)c2=O)c(OC)c1]

6.10 g (57.6 mmol) of caesium carbonate were added to a solution of 11.3 g (26.2 mmol) of the compound from Ex. 13A in 250 ml of DMF, and the mixture was stirred at RT for 15 min. 11.7 g (52.3 mmol) of 3,3,3-trifluoro-1-iodopropane were then added, and the mixture was heated at 70° C. After 6 h, a further 11.7 g (52.3 mmol) of 3,3,3-trifluoro-1-iodopropane were added. Stirring at 70° C. was continued for 7 h. After cooling to RT, most of the volatile components (including DMF) were removed on a rotary evaporator. About 400 ml of ethyl acetate were added to the residue, and the mixture was washed successively with water and saturated sodium chloride solution. After drying of the organic phase over anhydrous magnesium sulphate, the mixture was filtered and evaporated. The crude product was purified by MPLC on a Biotage cartridge (340 g of silica gel, cyclohexane/ethyl acetate 5:1). The product fractions were combined and concentrated. Stirring of the residue with pentane/dichloromethane (25:1), another filtration and drying under high vacuum gave 8.78 g (63% of theory) of the title compound.

$^1$H-NMR (400 MHz, DMSO-$d_6$, δ/ppm): 6.75 (d, 1H), 6.57 (d, 1H), 6.39 (dd, 1H), 4.95 (s, 2H), 4.17 (t, 2H), 3.81 (s, 3H), 3.72 (s, 3H), 2.87-2.74 (m, 2H), 2.74 (s, 3H), 1.54 (s, 9H).

LC/MS (Method 1, ESIpos): $R_t$=1.38 min, m/z=529 [M+H]$^+$.

Example 43A

5-Methyl-2,4-dioxo-3-(2-phenylethyl)-1-(3,3,3-trifluoropropyl)-1,2,3,4-tetrahydrothieno[2,3-d]pyrimidine-6-carboxylic acid

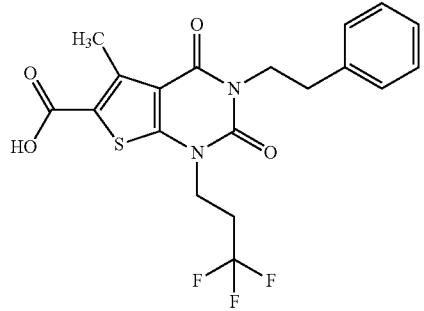 [SMILES: Cc1c(C(=O)O)sc2c1c(=O)n(CCc1ccccc1)c(=O)n2CCC(F)(F)F]

80 ml of trifluoroacetic acid were added to a solution of 5.69 g (11.8 mmol) of the compound from Ex. 26A in 240 ml of dichloromethane, and the mixture was stirred at RT for 2 h. The reaction mixture was then evaporated to dryness on a rotary evaporator. The residue that remained was stirred in diethyl ether and filtered off with suction, and the solid was dried under high vacuum. This gave 4.89 g (97% of theory) of the title compound.

$^1$H-NMR (400 MHz, DMSO-$d_6$, δ/ppm): 13.47 (br. s, 1H), 7.33-7.28 (m, 2H), 7.26-7.20 (m, 3H), 4.14 (t, 2H), 4.07 (m, 2H), 2.84 (m, 2H), 2.80-2.70 (m, 2H), 2.77 (s, 3H).

LC/MS (Method 1, ESIpos): $R_t$=1.11 min, m/z=427 [M+H]$^+$.

Example 44A 1-(4,4-Difluorobut-3-en-1-yl)-5-methyl-2,4-dioxo-3-(2-phenylethyl)-1,2,3,4-tetrahydrothieno[2,3-d]pyrimidine-6-carboxylic acid

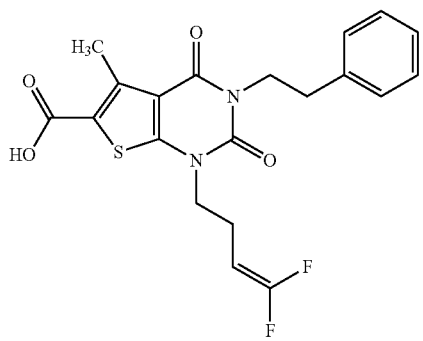 [SMILES: Cc1c(C(=O)O)sc2c1c(=O)n(CCc1ccccc1)c(=O)n2CCC=C(F)F]

Analogously to the process described in Ex. 43A, 520 mg (1.09 mmol) of the compound from Ex. 27A and 5 ml of trifluoroacetic acid in 10 ml of dichloromethane gave 328 mg (71% of theory) of the title compound.

$^1$H-NMR (400 MHz, DMSO-$d_6$, δ/ppm): 13.42 (br. s, 1H), 7.33-7.28 (m, 2H), 7.25-7.20 (m, 3H), 4.63 (d of t of d, 1H), 4.07 (m, 2H), 3.96 (t, 2H), 2.83 (m, 2H), 2.76 (s, 3H), 2.38 (m, 2H).

LC/MS (Method 1, ESIpos): $R_t$=1.15 min, m/z=421 [M+H]$^+$.

Example 45A 1-(2-Methoxyethyl)-5-methyl-2,4-dioxo-3-(2-phenylethyl)-1,2,3,4-tetrahydrothieno[2,3-d]pyrimidine-6-carboxylic acid

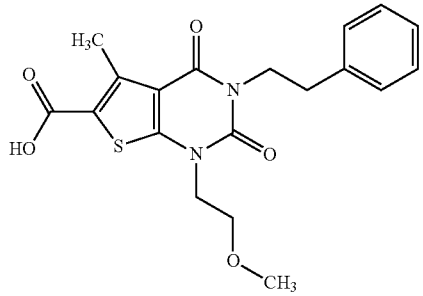 [SMILES: COCCn1c(=O)n(CCc2ccccc2)c(=O)c2c(C)c(C(=O)O)sc21]

75 ml of trifluoroacetic acid were added to a solution of 5.0 g (11.2 mmol) of the compound from Ex. 28A in 225 ml of dichloromethane, and the mixture was stirred at RT for 2 h. The reaction mixture was then evaporated to dryness on a rotary evaporator. The residue that remained was stirred in diethyl ether and filtered off with suction, and the solid was dried under high vacuum. 4.1 g (92% of theory) of the title compound were obtained.

$^1$H-NMR (400 MHz, DMSO-$d_6$, δ/ppm): 13.37 (br. s, 1H), 7.33-7.29 (m, 2H), 7.25-7.20 (m, 3H), 4.09-4.04 (m, 4H), 3.62 (t, 2H), 3.25 (s, 3H), 2.84 (dd, 2H), 2.75 (s, 3H).

LC/MS (Method 1, ESIpos): $R_t$=1.03 min, m/z=389 [M+H]$^+$.

Example 46A

3-[2-(2-Fluorophenyl)ethyl]-5-methyl-2,4-dioxo-1-(3,3,3-trifluoropropyl)-1,2,3,4-tetrahydrothieno[2,3-d]pyrimidine-6-carboxylic acid

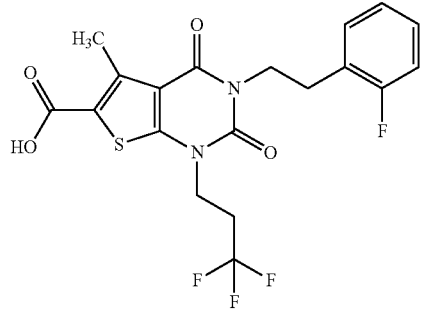 [SMILES: Cc1c(C(=O)O)sc2c1c(=O)n(CCc1ccccc1F)c(=O)n2CCC(F)(F)F]

10 ml of trifluoroacetic acid were added to a solution of 420 mg (0.84 mmol) of the compound from Ex. 29A in 20 ml of dichloromethane, and the mixture was stirred at RT for 1 h. The reaction mixture was then evaporated to dryness on a rotary evaporator and the residue was subsequently dried under high vacuum. 300 mg (79% of theory) of the title compound were obtained.

$^1$H-NMR (400 MHz, DMSO-$d_6$, δ/ppm): 13.47 (br. s, 1H), 7.29-7.24 (m, 2H), 7.16-7.09 (m, 2H), 4.12 (t, 2H), 4.10 (t, 2H), 2.91 (t, 2H), 2.74 (s, 3H), 2.70 (t, 2H).

LC/MS (Method 1, ESIpos): $R_t$=1.11 min, m/z=445 [M+H]$^+$.

Example 47A 1-(4,4-Difluorobut-3-en-1-yl)-3-[2-(2-fluorophenyl)ethyl]-5-methyl-2,4-dioxo-1,2,3,4-tetrahydrothieno[2,3-d]pyrimidine-6-carboxylic acid

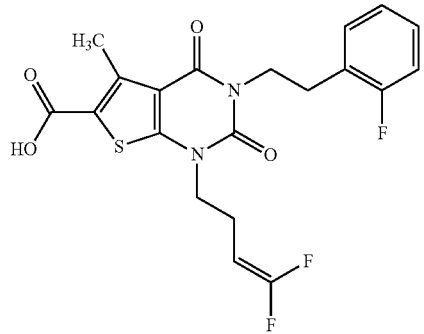 [SMILES: Cc1c(C(=O)O)sc2c1c(=O)n(CCc1ccccc1F)c(=O)n2CCC=C(F)F]

15 ml of trifluoroacetic acid were added to a solution of 750 mg (1.52 mmol) of the compound from Ex. 30A in 30 ml of dichloromethane, and the mixture was stirred at RT for 1 h. The reaction mixture was then evaporated to dryness on a rotary evaporator. The residue that remained was stirred in diethyl ether and filtered off with suction, and the solid was dried under high vacuum. 320 mg (47% of theory) of the title compound were thus obtained. Since, except for the target compound, the mother liquor did not contain any further impurities, it was evaporated completely, and the residue that remained was likewise dried under high vacuum (290 mg, 42% of theory). A total of 610 mg (90% of theory) of the title compound were obtained in this manner.

$^1$H-NMR (400 MHz, DMSO-$d_6$, δ/ppm): 13.42 (br. s, 1H), 7.30-7.24 (m, 2H), 7.16-7.10 (m, 2H), 4.61 (d of t of d, 1H), 4.10 (t, 2H), 3.93 (t, 2H), 2.90 (t, 2H), 2.73 (s, 3H), 2.38-2.32 (m, 2H).

LC/MS (Method 1, ESIpos): $R_t$=1.15 min, m/z=439 [M+H]$^+$.

Example 48A

3-[2-(2-Chlorophenyl)ethyl]-5-methyl-2,4-dioxo-1-(3,3,3-trifluoropropyl)-1,2,3,4-tetrahydrothieno[2,3-d]pyrimidine-6-carboxylic acid

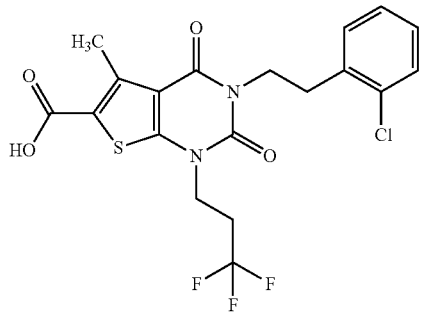 [SMILES: Cc1c(C(=O)O)sc2c1c(=O)n(CCc1ccccc1Cl)c(=O)n2CCC(F)(F)F]

7 ml of trifluoroacetic acid were added to a solution of 420 mg (0.81 mmol) of the compound from Ex. 31A in 15 ml of dichloromethane, and the mixture was stirred at RT for 2 h. The reaction mixture was then evaporated to dryness on a rotary evaporator. The residue that remained was stirred in diethyl ether and filtered off with suction, and the solid was dried under high vacuum. 295 mg (79% of theory) of the title compound were obtained.

$^1$H-NMR (400 MHz, DMSO-$d_6$, δ/ppm): 13.46 (br. s, 1H), 7.43-7.39 (m, 1H), 7.31-7.24 (m, 3H), 4.15-4.10 (m, 4H), 3.00 (t, 2H), 2.76-2.67 (m, 2H), 2.74 (s, 3H).

LC/MS (Method 1, ESIpos): $R_t$=1.17 min, m/z=461/463 [M+H]$^+$.

Example 49A

3-[2-(2-Chlorophenyl)ethyl]-1-(4,4-difluorobut-3-en-1-yl)-5-methyl-2,4-dioxo-1,2,3,4-tetrahydrothieno[2,3-d]pyrimidine-6-carboxylic acid

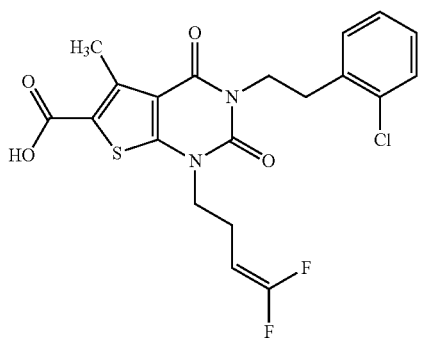 [SMILES: Cc1c(C(=O)O)sc2c1c(=O)n(CCc1ccccc1Cl)c(=O)n2CCC=C(F)F]

Analogously to the process described in Ex. 48A, 525 mg (1.03 mmol) of the compound from Ex. 32A and 7 ml of trifluoroacetic acid in 15 ml of dichloromethane gave 345 mg (73% of theory) of the title compound.

$^1$H-NMR (400 MHz, DMSO-d$_6$, δ/ppm): 13.41 (br. s, 1H), 7.42-7.39 (m, 1H), 7.31-7.24 (m, 3H), 4.61 (d of t of d, 1H), 4.12 (t, 2H), 3.93 (t, 2H), 2.99 (t, 2H), 2.73 (s, 3H), 2.37-2.31 (m, 2H).

LC/MS (Method 1, ESIpos): R$_t$=1.19 min, m/z=455/457 [M+H]$^+$.

Example 50A

5-Methyl-2,4-dioxo-3-[2-(pyridin-3-yl)ethyl]-1-(3,3,3-trifluoropropyl)-1,2,3,4-tetrahydrothieno[2,3-d]pyrimidine-6-carboxylic acid hydrochloride

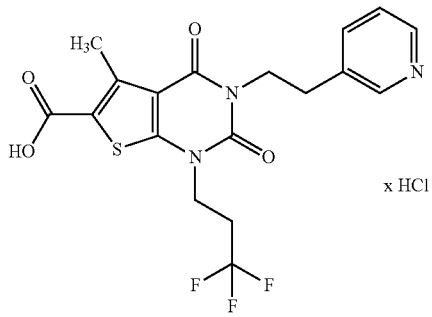 [SMILES: Cc1c(C(=O)O)sc2c1c(=O)n(CCc1cccnc1)c(=O)n2CCC(F)(F)F]

9.3 ml of a 4 M solution of hydrogen chloride in dioxane were added to 450 mg (0.93 mmol) of the compound from Ex. 33A, and the mixture was stirred at RT for about 16 h. The reaction mixture was then evaporated to dryness on a rotary evaporator. The residue that remained was stirred in 10 ml of diethyl ether at RT for 30 min and filtered off with suction, and the solid was dried under high vacuum. 463 mg (91% of theory) of the title compound were obtained.

$^1$H-NMR (400 MHz, DMSO-d$_6$, δ/ppm): 13.50 (br. s, 1H), 8.82 (s, 1H), 8.74 (d, 1H), 8.36 (d, 1H), 7.88 (t, 1H), 4.19 (t, 2H), 4.12 (t, 2H), 3.09 (t, 2H), 2.80-2.68 (m, 2H), 2.72 (s, 3H).

LC/MS (Method 1, ESIpos): R$_t$=0.67 min, m/z=428 [M+H]$^+$.

Example 51A 1-(4,4-Difluorobut-3-en-1-yl)-5-methyl-2,4-dioxo-3-[2-(pyridin-3-yl)ethyl]-1,2,3,4-tetrahydrothieno[2,3-d]pyrimidine-6-carboxylic acid hydrochloride

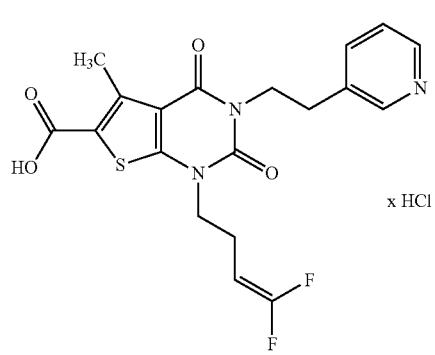 [SMILES: Cc1c(C(=O)O)sc2c1c(=O)n(CCc1cccnc1)c(=O)n2CCC=C(F)F]

Analogously to the process described under Ex. 50A, 450 mg (0.94 mmol) of the compound from Ex. 34A gave 365 mg (82% of theory) of the title compound.

$^1$H-NMR (400 MHz, DMSO-d$_6$, δ/ppm): 13.45 (br. s, 1H), 8.82 (s, 1H), 8.73 (d, 1H), 8.35 (d, 1H), 7.87 (t, 1H), 4.61 (d of t of d, 1H), 4.19 (t, 2H), 3.92 (t, 2H), 3.08 (t, 2H), 2.72 (s, 3H), 2.37-2.30 (m, 2H).

LC/MS (Method 1, ESIpos): R$_t$=0.70 min, m/z=422 [M+H]$^+$.

Example 52A

3-Ethyl-5-methyl-2,4-dioxo-1-(3,3,3-trifluoropropyl)-1,2,3,4-tetrahydrothieno[2,3-d]pyrimidine-6-carboxylic acid

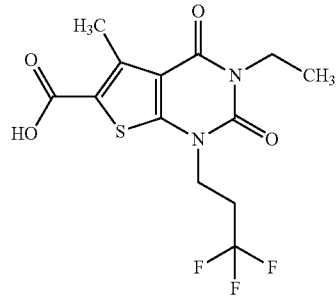 [SMILES: CCn1c(=O)c2c(C)c(C(=O)O)sc2n(CCC(F)(F)F)c1=O]

Method A:

80 ml of trifluoroacetic acid were added to a solution of 6.89 g (16.9 mmol) of the compound from Ex. 35A in 240 ml of dichloromethane, and the mixture was stirred at RT for 2 h. The reaction mixture was then evaporated to dryness on a rotary evaporator. The residue that remained was stirred in diethyl ether and filtered off with suction, and the solid was dried under high vacuum. 5.13 g (86% of theory) of the title compound were obtained.

$^1$H-NMR (400 MHz, DMSO-d$_6$, δ/ppm): 13.46 (br. s, 1H), 4.15 (t, 2H), 3.91 (quart, 2H), 2.85-2.73 (m, 2H), 2.76 (s, 3H), 1.13 (t, 3H).

LC/MS (Method 1, ESIpos): $R_t$=0.94 min, m/z=351 [M+H]⁺.

Method B:

At about 2° C., 926 mg (9.54 mmol) of sulphaminic acid and 1.56 g (13.0 mmol) of sodium dihydrogenphosphate were added to a solution of 2.9 g (8.67 mmol) of the compound from Ex. 167A in a mixture of 22 ml of acetone and 10 ml of water. A solution of 1.03 g (9.11 mmol, content 80%) of sodium chlorite in 4 ml of water was then slowly added dropwise such that the temperature of the reaction mixture did not rise above 6° C. After 30 min, the cooling bath was removed and stirring of the mixture was continued overnight. The mixture was then diluted with 100 ml of water and extracted twice with 150 ml of ethyl acetate each time. The organic extract was dried over anhydrous sodium sulphate and then filtered, and the filtrate was concentrated to dryness. The crude product was purified by chromatography (40 g of silica gel, mobile phase: dichloromethane/methanol 100:0→90:10). This gave, after concentration of the product fractions and drying of the residue, 2.60 g (85% of theory) of the title compound.

Example 53A 1-(4,4-Difluorobut-3-en-1-yl)-3-ethyl-5-methyl-2,4-dioxo-1,2,3,4-tetrahydrothieno[2,3-d]pyrimidine-6-carboxylic acid

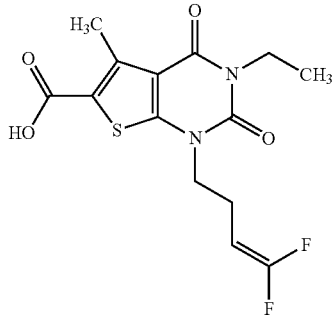 [SMILES: CCn1c(=O)c2c(C)c(C(=O)O)sc2n(CCC=C(F)F)c1=O]

Analogously to the process described under Ex. 52A, 750 mg (1.87 mmol) of the compound from Ex. 36A gave 528 mg (81% of theory) of the title compound.

¹H-NMR (400 MHz, DMSO-d₆, δ/ppm): 13.40 (br. s, 1H), 4.64 (d of t of d, 1H), 3.96 (t, 2H), 3.90 (quart, 2H), 2.76 (s, 3H), 2.40 (pseudo-quart, 2H), 1.12 (t, 3H).

LC/MS (Method 1, ESIpos): $R_t$=0.94 min, m/z=345 [M+H]⁺.

Example 54A

3-Ethyl-1-(2-methoxyethyl)-5-methyl-2,4-dioxo-1,2,3,4-tetrahydrothieno[2,3-d]pyrimidine-6-carboxylic acid

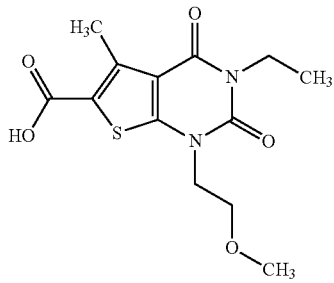 [SMILES: CCn1c(=O)c2c(C)c(C(=O)O)sc2n(CCOC)c1=O]

Analogously to the process described under Ex. 52A, 650 mg (1.76 mmol) of the compound from Ex. 37A gave 469 mg (85% of theory) of the title compound.

¹H-NMR (400 MHz, DMSO-d₆, δ/ppm): 13.36 (br. s, 1H), 4.07 (t, 2H), 3.90 (quart, 2H), 3.65 (t, 2H), 3.25 (s, 3H), 2.75 (s, 3H), 1.13 (t, 3H).

LC/MS (Method 1, ESIpos): $R_t$=0.78 min, m/z=313 [M+H]⁺.

Example 55A 2,4-Dioxo-3-(2-phenylethyl)-5-(trifluoromethyl)-1-(3,3,3-trifluoropropyl)-1,2,3,4-tetrahydrothieno[2,3-d]pyrimidine-6-carboxylic acid

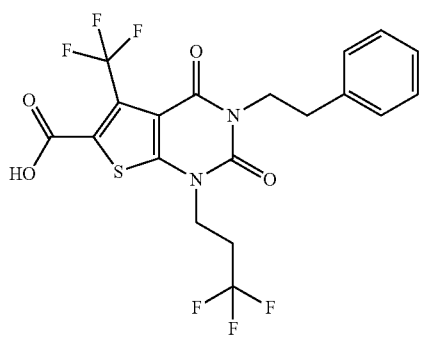 [SMILES: O=C(O)c1sc2c(c1C(F)(F)F)c(=O)n(CCc1ccccc1)c(=O)n2CCC(F)(F)F]

A solution of 35 mg (1.46 mmol) of lithium hydroxide in 10 ml of water was added to a solution of 495 mg (0.970 mmol) of the compound from Ex. 38A in 20 ml of ethanol, and the mixture was stirred at RT for about 16 h. All the volatile constituents were then removed on a rotary evaporator. The residue that remained was taken up in water and acidified with 2 ml of 1 M hydrochloric acid. The product precipitated out and was filtered off with suction, washed with water and dried under high vacuum. 460 mg (95% of theory) of the title compound were obtained.

¹H-NMR (400 MHz, DMSO-d₆, δ/ppm): 14.50 (br. s, 1H), 7.33-7.28 (m, 2H), 7.26-7.20 (m, 3H), 4.18 (t, 2H), 4.07 (m, 2H), 2.74-2.68 (m, 4H).

LC/MS (Method 2, ESIpos): $R_t$=2.34 min, m/z=481 [M+H]⁺.

Example 56A

3-Ethyl-2,4-dioxo-5-(trifluoromethyl)-1-(3,3,3-trifluoropropyl)-1,2,3,4-tetrahydrothieno[2,3-d]pyrimidine-6-carboxylic acid

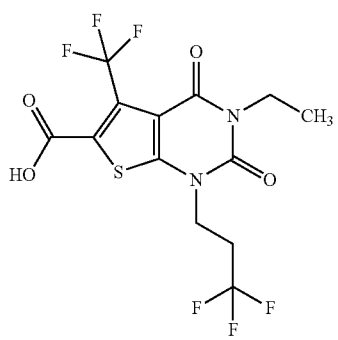 [SMILES: CCn1c(=O)c2c(C(F)(F)F)c(C(=O)O)sc2n(CCC(F)(F)F)c1=O]

Analogously to the process described under Ex. 55A, 231 mg (0.540 mmol) of the compound from Ex. 39A gave 178 mg (82% of theory) of the title compound.

$^1$H-NMR (400 MHz, DMSO-d$_6$, δ/ppm): 14.51 (br. s, 1H), 4.18 (t, 2H), 3.91 (quart, 2H), 2.87-2.75 (m, 2H), 1.13 (t, 3H).

LC/MS (Method 1, ESIpos): R$_t$=0.76 min, m/z=405 [M+H]$^+$.

Example 57A 5-(Difluoromethyl)-2,4-dioxo-3-(2-phenylethyl)-1-(3,3,3-trifluoropropyl)-1,2,3,4-tetrahydrothieno[2,3-d]pyrimidine-6-carboxylic acid

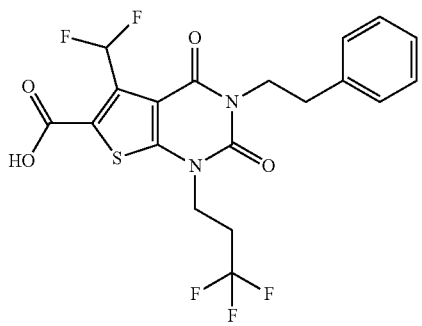 [SMILES: O=C(O)c1sc2c(c1C(F)F)c(=O)n(CCc1ccccc1)c(=O)n2CCC(F)(F)F]

A solution of 59 mg (2.45 mmol) of lithium hydroxide in 17 ml of water was added to a solution of 800 mg (1.63 mmol) of the compound from Ex. 40A in 33 ml of ethanol, and the mixture was stirred at RT for 3 h. All the volatile constituents were then removed on a rotary evaporator. The residue that remained was taken up in water and acidified with 2 ml of 1 M hydrochloric acid. The mixture was extracted three times with about 100 ml of dichloromethane each time. The combined organic extracts were washed once with saturated sodium chloride solution, dried over anhydrous magnesium sulphate, filtered and concentrated. At RT, the solid that remained was stirred in a mixture of 30 ml of pentane and 3 ml of diethyl ether. This gave, after filtration with suction and drying under high vacuum, 482 mg (63% of theory) of the title compound.

$^1$H-NMR (400 MHz, DMSO-d$_6$, δ/ppm): 7.79 (t, 1H), 7.34-7.29 (m, 2H), 7.26-7.20 (m, 3H), 4.19 (t, 2H), 4.07 (m, 2H), 2.87-2.73 (m, 4H).

LC/MS (Method 1, ESIpos): R$_t$=1.01 min, m/z=463 [M+H]$^+$.

Example 58A 2,4-Dioxo-3-(2-phenylethyl)-1-(3,3,3-trifluoropropyl)-1,2,3,4-tetrahydrothieno[2,3-d]pyrimidine-6-carboxylic acid

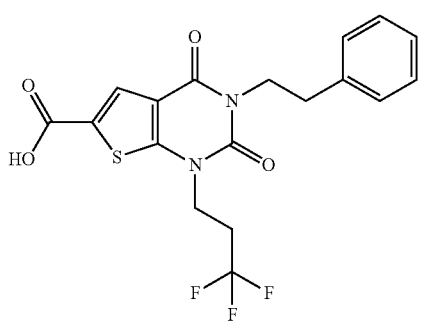 [SMILES: O=C(O)c1cc2c(=O)n(CCc3ccccc3)c(=O)n(CCC(F)(F)F)c2s1]

A solution of 65 mg (2.73 mmol) of lithium hydroxide in 8 ml of water was added to a solution of 800 mg (1.82 mmol) of the compound from Ex. 41A in 24 ml of ethanol 2 ml of THF were then added. The reaction mixture was stirred at RT for 3 h. All the volatile constituents were then removed on a rotary evaporator. The residue that remained was taken up in about 200 ml of water and acidified with 3 ml of 1 M hydrochloric acid. The product precipitated out and was filtered off with suction, washed with water until neutral and dried under high vacuum. This gave 639 mg (83% of theory, 97% pure) of the title compound.

$^1$H-NMR (400 MHz, DMSO-d$_6$, δ/ppm): 13.63 (br. s, 1H), 7.79 (s, 1H), 7.32-7.28 (m, 2H), 7.24-7.20 (m, 3H), 4.16 (t, 2H), 4.08 (m, 2H), 2.85 (m, 2H), 2.78 (m, 2H).

LC/MS (Method 1, ESIpos): R$_t$=1.04 min, m/z=413 [M+H]$^+$.

Example 59A

5-Methyl-2,4-dioxo-1-(3,3,3-trifluoropropyl)-1,2,3,4-tetrahydrothieno[2,3-d]pyrimidine-6-carboxylic acid

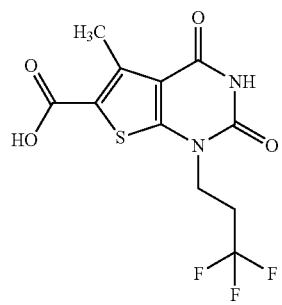 [SMILES: Cc1c(C(=O)O)sc2c1c(=O)[nH]c(=O)n2CCC(F)(F)F]

3.32 g (6.27 mmol) of the compound from Ex. 42A were dissolved in 130 ml of toluene, and 5.02 g (37.6 mmol) of solid aluminium trichloride were added at RT. The reaction mixture was then stirred at 50° C. for 90 min. After cooling to RT, 70 ml of water and 300 ml of ethyl acetate were added. After phase separation, the organic phase was washed successively with water and saturated sodium chloride solution. After drying over anhydrous magnesium sulphate, the mixture was filtered and the filtrate was evaporated. The crude product was stirred with 50 ml of pentane/dichloromethane (20:1) at RT. Filtration with suction and drying of the solid under high vacuum gave 1.93 g (87% of theory, about 92% pure) of the title compound.

$^1$H-NMR (400 MHz, DMSO-d$_6$, δ/ppm): 13.40 (broad, 1H), 11.63 (s, 1H), 4.09 (t, 2H), 2.83-2.69 (m, 2H), 2.72 (s, 3H).

LC/MS (Method 1, ESIpos): R$_t$=0.65 min, m/z=323 [M+H]$^+$.

Example 60A

1-{[5-Methyl-2,4-dioxo-1-(3,3,3-trifluoropropyl)-1,2,3,4-tetrahydrothieno[2,3-d]pyrimidin-6-yl]carbonyl}piperidin-4-yl acetate

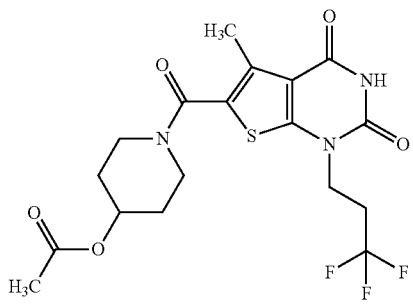 [SMILES: CC(=O)OC1CCN(C(=O)c2sc3c(c2C)c(=O)[nH]c(=O)n3CCC(F)(F)F)CC1]

1.93 g (6.0 mmol) of the compound from Ex. 59A were dissolved in 40 ml of DMF, and 2.74 g (7.20 mmol) of HATU, 1.29 g (7.20 mmol) of piperidin-4-yl acetate hydrochloride [lit.: T. Kikuchi et al., *J. Med. Chem.* 2005, 48 (7), 2577-2583] and 3.1 ml (18.0 mmol) of N,N-diisopropylethylamine were successively added. After the reaction mixture had been stirred at RT for about 16 h, the mixture was poured onto water, resulting in the precipitation of the product. The product was filtered off with suction, washed with a little water and dried under a high vacuum. Stirring with diethyl ether gave 2.35 g (80% of theory, purity about 92%) of the title compound.

$^1$H-NMR (400 MHz, CDCl$_3$, δ/ppm): 8.38 (s, 1H), 5.04 (m, 1H), 4.15 (t, 2H), 3.88-3.80 (m, 2H), 3.55-3.48 (m, 2H), 2.71-2.59 (m, 2H), 2.49 (s, 3H), 2.09 (s, 3H), 1.98-1.91 (m, 2H), 1.77-1.69 (m, 2H).

LC/MS (Method 1, ESIpos): R$_t$=0.81 min, m/z=448 [M+H]$^+$.

Example 61A

3-Ethyl-5-methyl-2,4-dioxo-1,2,3,4-tetrahydrothieno[2,3-d]pyrimidine-6-carboxylic acid

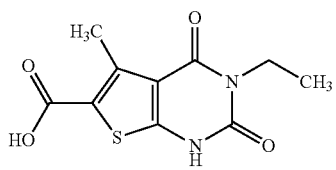 [SMILES: CCn1c(=O)[nH]c2sc(C(=O)O)c(C)c2c1=O]

149 ml of trifluoroacetic acid were added to a solution of 30.0 g (96.7 mmol) of the compound from Ex. 12A in 300 ml of dichloromethane, and the mixture was stirred at RT for 12 h. The reaction mixture was then evaporated to dryness on a rotary evaporator. The residue that remained was stirred in diisopropyl ether and filtered off with suction, and the solid was dried under high vacuum. 22.80 g (92% of theory) of the title compound were obtained.

LC/MS (Method 1, ESIpos): R$_t$=0.61 min, m/z=255 [M+H]$^+$.

Example 62A

1-[(3-Ethyl-5-methyl-2,4-dioxo-1,2,3,4-tetrahydrothieno[2,3-d]pyrimidin-6-yl)carbonyl]piperidin-4-yl acetate

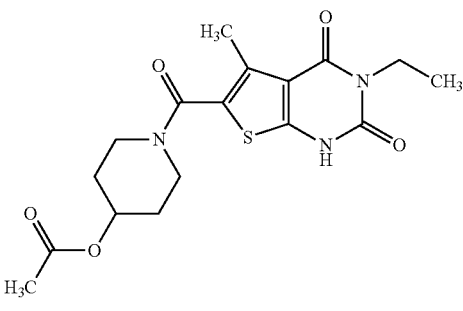 [SMILES: CCn1c(=O)[nH]c2sc(C(=O)N3CCC(OC(C)=O)CC3)c(C)c2c1=O]

19.50 g (76.7 mmol) of the compound of Ex. 61A and 15.16 g (84.4 mmol) of piperidin-4-yl acetate hydrochloride [lit.: T. Kikuchi et al., *J. Med. Chem.* 2005, 48 (7), 2577-2583] were dissolved in 390 ml of DMF, and 43.7 g (115 mmol) of HATU and 47 ml (268 mmol) of N,N-diisopropylethylamine were added successively at 0° C. After the reaction mixture had been stirred at RT for about 16 h, it was diluted with about 400 ml of ethyl acetate and washed successively with water, 1 M hydrochloric acid, water and saturated aqueous sodium chloride solution. After drying over anhydrous magnesium sulphate, the mixture was filtered and evaporated to dryness. The residue obtained was purified by filtration with suction through silica gel using a cyclohexane/ethyl acetate gradient. This gave, after evaporation of the product fraction and drying of the residue under high vacuum, 8.80 g (30% of theory) of the title compound.

$^1$H-NMR (400 MHz, DMSO-d$_6$, δ/ppm): 12.23 (s, 1H), 4.90 (m, 1H), 3.86 (quart, 2H), 3.77-3.69 (m, 2H), 3.41-3.33 (m, 2H, partially obscured by the water signal), 2.35 (s, 3H), 2.02 (s, 3H), 1.90-1.83 (m, 2H), 1.58-1.49 (m, 2H), 1.11 (t, 3H).

LC/MS (Method 1, ESIpos): R$_t$=0.72 min, m/z=380 [M+H]$^+$.

Example 63A 1-({5-Methyl-3-[2-(2-methylphenyl)ethyl]-2,4-dioxo-1-(3,3,3-trifluoropropyl)-1,2,3,4-tetrahydrothieno[2,3-d]pyrimidin-6-yl}carbonyl)piperidin-4-yl acetate

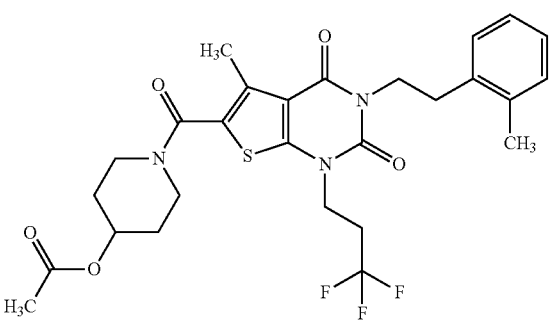 [SMILES: CC(=O)OC1CCN(C(=O)c2sc3c(c2C)c(=O)n(CCc2ccccc2C)c(=O)n3CCC(F)(F)F)CC1]

70 mg (0.156 mmol) of the compound from Ex. 60A and 31.5 μl (0.235 mmol) of 2-(2-methylphenyl)ethyl alcohol were dissolved in 2 ml of anhydrous THF, and 62 mg (0.235 mmol) of triphenylphosphine and 46.5 μl (0.235 mmol) of diisopropyl azodicarboxylate (DIAD) were added successively. After about 16 h of stirring at RT, the reaction mixture, in two portions, was separated by preparative HPLC into its components (Method 5). The product fractions were combined and concentrated, and the residue was dried under high vacuum. 66 mg (72% of theory) of the title compound were obtained.

$^1$H-NMR (400 MHz, CDCl$_3$, δ/ppm): 7.22-7.11 (m, 4H), 5.04 (m, 1H), 4.18-4.13 (m, 4H), 3.89-3.81 (m, 2H), 3.55-3.48 (m, 2H), 2.95 (m, 2H), 2.64-2.55 (m, 2H), 2.53 (s, 3H), 2.47 (s, 3H), 2.09 (s, 3H), 1.99-1.91 (m, 2H), 1.78-1.69 (m, 2H).

LC/MS (Method 1, ESIpos): R$_t$=1.24 min, m/z=566 [M+H]$^+$.

Example 64A 1-({3-[2-(3-Fluorophenyl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

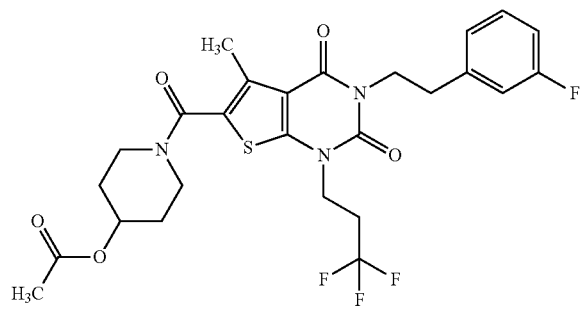 [SMILES: CC(=O)OC1CCN(C(=O)c2sc3c(c2C)c(=O)n(CCc2cccc(F)c2)c(=O)n3CCC(F)(F)F)CC1]

Analogously to the process described in Ex. 63A, 70 mg (0.156 mmol) of the compound from Ex. 60A and 29.3 μl (0.235 mmol) of 2-(3-fluorophenyl)ethyl alcohol gave 65 mg (73% of theory) of the title compound.

$^1$H-NMR (400 MHz, CDCl$_3$, δ/ppm): 7.07 (d, 1H), 7.00 (d, 1H), 6.92 (dt, 1H), 5.04 (m, 1H), 4.23-4.13 (m, 4H), 3.89-3.81 (m, 2H), 3.56-3.48 (m, 2H), 2.94 (m, 2H), 2.66-2.55 (m, 2H), 2.51 (s, 3H), 2.09 (s, 3H), 1.99-1.91 (m, 2H), 1.78-1.69 (m, 2H).

LC/MS (Method 1, ESIpos): R$_t$=1.19 min, m/z=570 [M+H]$^+$.

Example 65A 1-({3-[2-(3-Chlorophenyl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

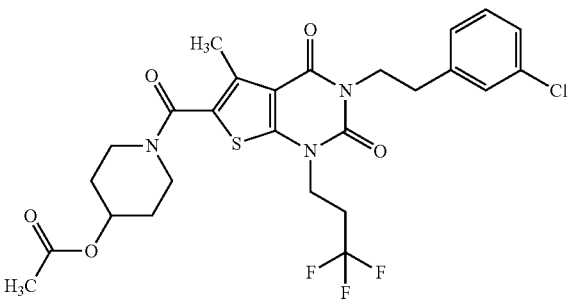 [SMILES: CC(=O)OC1CCN(C(=O)c2sc3c(c2C)c(=O)n(CCc2cccc(Cl)c2)c(=O)n3CCC(F)(F)F)CC1]

Analogously to the process described in Ex. 63A, 70 mg (0.156 mmol) of the compound from Ex. 60A and 37 mg (0.235 mmol) of 2-(3-chlorophenyl)ethyl alcohol gave 74 mg (79% of theory) of the title compound.

$^1$H-NMR (400 MHz, CDCl$_3$, δ/ppm): 7.28-7.17 (m, 4H, partially obscured by the CHCl$_3$ signal), 5.04 (m, 1H), 4.22-4.13 (m, 4H), 3.88-3.81 (m, 2H), 3.56-3.48 (m, 2H), 2.92 (m, 2H), 2.66-2.55 (m, 2H), 2.52 (s, 3H), 2.09 (s, 3H), 1.99-1.91 (m, 2H), 1.78-1.69 (m, 2H).

LC/MS (Method 1, ESIpos): R$_t$=1.24 min, m/z=586/588 [M+H]$^+$.

Example 66A 1-({5-Methyl-3-[2-(3-methylphenyl)ethyl]-2,4-dioxo-1-(3,3,3-trifluoropropyl)-1,2,3,4-tetrahydrothieno[2,3-d]pyrimidin-6-yl}carbonyl)piperidin-4-yl acetate

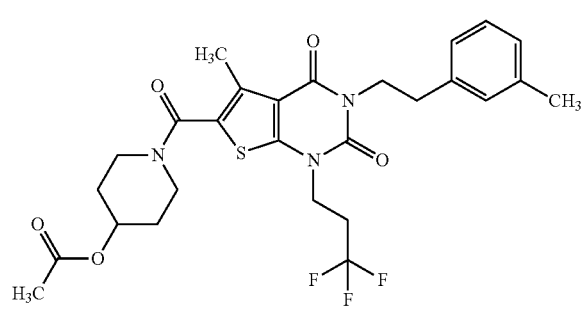 [SMILES: CC(=O)OC1CCN(C(=O)c2sc3c(c2C)c(=O)n(CCc2cccc(C)c2)c(=O)n3CCC(F)(F)F)CC1]

Analogously to the process described in Ex. 63A, 70 mg (0.156 mmol) of the compound from Ex. 60A and 37 mg (0.235 mmol) of 2-(3-methylphenyl)ethyl alcohol gave 61 mg (66% of theory) of the title compound.

$^1$H-NMR (400 MHz, CDCl$_3$, δ/ppm): 7.20 (t, 1H), 7.13 (s, 1H), 7.10 (d, 1H), 7.05 (d, 1H), 5.04 (m, 1H), 4.21-4.14 (m, 4H), 3.89-3.81 (m, 2H), 3.56-3.48 (m, 2H), 2.89 (m, 2H), 2.67-2.55 (m, 2H), 2.53 (s, 3H), 2.34 (s, 3H), 2.09 (s, 3H), 1.99-1.91 (m, 2H), 1.78-1.69 (m, 2H).

LC/MS (Method 1, ESIpos): R$_t$=1.23 min, m/z=566 [M+H]$^+$.

Example 67A 1-({3-[2-(4-Fluorophenyl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

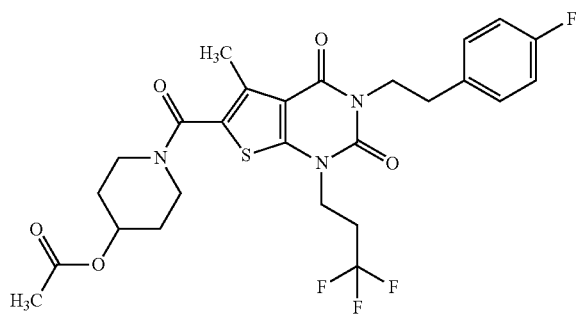 [SMILES: CC(=O)OC1CCN(C(=O)c2sc3c(c2C)c(=O)n(CCc2ccc(F)cc2)c(=O)n3CCC(F)(F)F)CC1]

Analogously to the process described in Ex. 63A, 42 mg (0.094 mmol) of the compound from Ex. 60A and 20 mg (0.141 mmol) of 2-(4-fluorophenyl)ethyl alcohol gave 39 mg (72% of theory) of the title compound.

$^1$H-NMR (400 MHz, CDCl$_3$, δ/ppm): 7.27-7.23 (m, 2H, partially obscured by the CHCl$_3$ signal), 6.99 (t, 2H), 5.04 (m, 1H), 4.20-4.13 (m, 4H), 3.88-3.81 (m, 2H), 3.56-3.48 (m, 2H), 2.91 (m, 2H), 2.66-2.55 (m, 2H), 2.51 (s, 3H), 2.09 (s, 3H), 1.99-1.91 (m, 2H), 1.77-1.69 (m, 2H).

LC/MS (Method 1, ESIpos): R$_t$=1.20 min, m/z=570 [M+H]$^+$.

Example 68A 1-({3-[2-(4-Chlorophenyl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

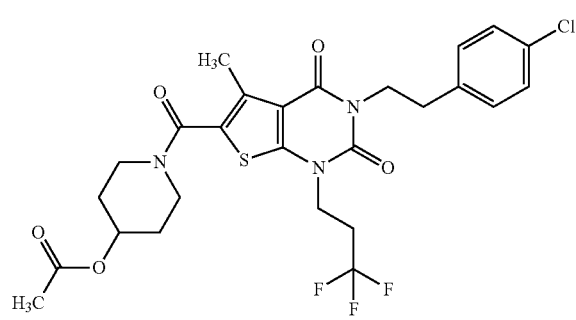 [SMILES: CC(=O)OC1CCN(C(=O)c2sc3c(c2C)c(=O)n(CCc2ccc(Cl)cc2)c(=O)n3CCC(F)(F)F)CC1]

Analogously to the process described in Ex. 63A, 70 mg (0.156 mmol) of the compound from Ex. 60A and 37 mg (0.235 mmol) of 2-(4-chlorophenyl)ethyl alcohol gave 78 mg (85% of theory) of the title compound.

$^1$H-NMR (400 MHz, CDCl$_3$, δ/ppm): 7.27 (d, 2H), 7.22 (d, 2H), 5.04 (m, 1H), 4.20-4.13 (m, 4H), 3.89-3.80 (m, 2H), 3.56-3.48 (m, 2H), 2.91 (m, 2H), 2.65-2.53 (m, 2H), 2.51 (s, 3H), 2.09 (s, 3H), 1.99-1.91 (m, 2H), 1.78-1.69 (m, 2H).

LC/MS (Method 1, ESIpos): R$_t$=1.23 min, m/z=586/588 [M+H]$^+$.

Example 69A 1-({3-[2-(4-Methoxyphenyl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

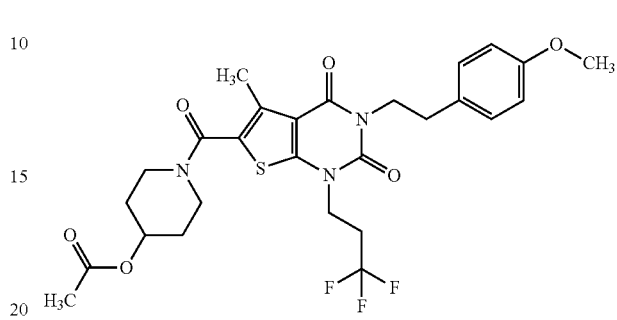

Analogously to the process described in Ex. 63A, 70 mg (0.156 mmol) of the compound from Ex. 60A and 36 mg (0.235 mmol) of 2-(4-methoxyphenyl)ethyl alcohol gave 72 mg (79% of theory) of the title compound.

$^1$H-NMR (400 MHz, CDCl$_3$, δ/ppm): 7.20 (d, 2H), 6.84 (d, 2H), 5.04 (m, 1H), 4.19-4.13 (m, 4H), 3.89-3.80 (m, 2H), 3.79 (s, 3H), 3.55-3.48 (m, 2H), 2.88 (m, 2H), 2.64-2.55 (m, 2H), 2.52 (s, 3H), 2.09 (s, 3H), 1.99-1.91 (m, 2H), 1.77-1.69 (m, 2H).

LC/MS (Method 1, ESIpos): R$_t$=1.14 min, m/z=582 [M+H]$^+$.

Example 70A 1-({5-Methyl-2,4-dioxo-3-[2-(pyrazin-2-yl)ethyl]-1-(3,3,3-trifluoropropyl)-1,2,3,4-tetrahydrothieno[2,3-d]pyrimidin-6-yl}carbonyl)piperidin-4-yl acetate

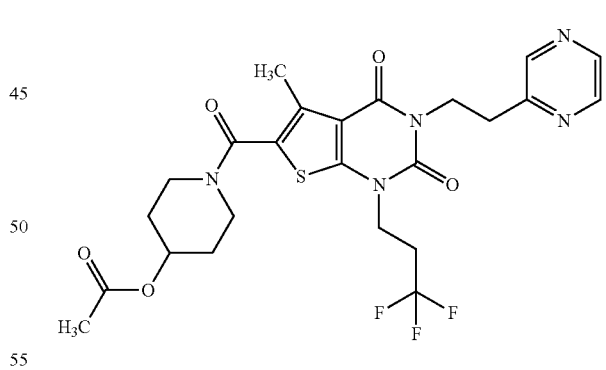

Analogously to the process described in Ex. 63A, 70 mg (0.156 mmol) of the compound from Ex. 60A and 29 mg (0.235 mmol) of 2-(2-hydroxyethyl)pyrazine [commercially available; lit. e.g.: U.S. Pat. No. 5,344,830, Example 18/step A] gave two fractions of the title compound: 14 mg (16% of theory, pure) and 93 mg of a mixture of the title compound with triphenylphosphine oxide. In deviation to the process in Ex. 63A, here the purification by preparative HPLC was carried out according to Method 7.

$^1$H-NMR (400 MHz, CDCl$_3$, δ/ppm): 8.51-8.42 (m, 3H), 5.04 (m, 1H), 4.41 (t, 2H), 4.13 (t, 2H), 3.89-3.80 (m, 2H), 3.55-3.47 (m, 2H), 3.18 (t, 2H), 2.65-2.54 (m, 2H), 2.48 (s, 3H), 2.09 (s, 3H), 1.99-1.91 (m, 2H), 1.78-1.68 (m, 2H).

LC/MS (Method 1, ESIpos): $R_t$=0.93 min, m/z=554 [M+H]$^+$.

Example 71A 1-({5-Methyl-2,4-dioxo-3-[2-phenylpropyl]-1-(3,3,3-trifluoropropyl)-1,2,3,4-tetrahydrothieno[2,3-d]pyrimidin-6-yl}carbonyl)piperidin-4-yl acetate (racemate)

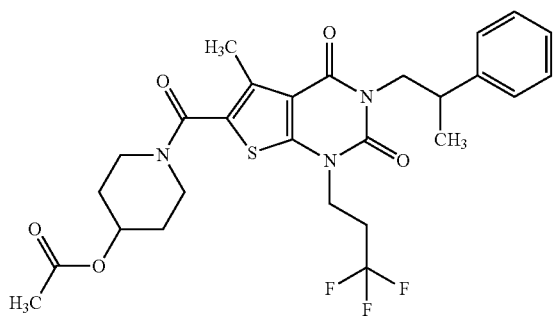 [SMILES: CC(=O)OC1CCN(C(=O)c2sc3c(c2C)c(=O)n(CC(C)c2ccccc2)c(=O)n3CCC(F)(F)F)CC1]

Analogously to the process described in Ex. 63A, 200 mg (0.447 mmol) of the compound from Ex. 60A and 91 mg (0.670 mmol) of racemic 2-phenylpropan-1-ol gave 238 mg (94% of theory) of the title compound.

$^1$H-NMR (400 MHz, DMSO-d$_6$, δ/ppm): 7.34-7.24 (m, 4H), 7.22-7.17 (m, 1H), 4.92 (m, 1H), 4.12-4.05 (m, 3H), 3.94 (m, 1H), 3.79-3.71 (m, 2H), 3.43-3.36 (m, 2H), 3.27-3.19 (m, 1H), 2.78-2.66 (m, 2H), 2.38 (s, 3H), 2.03 (s, 3H), 1.92-1.85 (m, 2H), 1.60-1.51 (m, 2H), 1.19 (d, 3H).

LC/MS (Method 1, ESIpos): $R_t$=1.20 min, m/z=566 [M+H]$^+$.

Example 72A

1-{[3-(2-Methoxy-2-phenylethyl)-5-methyl-2,4-dioxo-1-(3,3,3-trifluoropropyl)-1,2,3,4-tetrahydrothieno[2,3-d]pyrimidin-6-yl]carbonyl}piperidin-4-yl acetate (racemate)

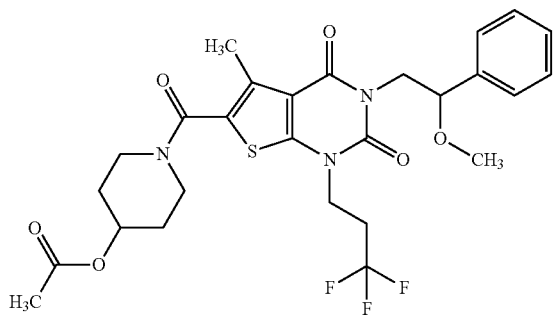 [SMILES: COC(Cn1c(=O)c2c(C)c(C(=O)N3CCC(OC(C)=O)CC3)sc2n(CCC(F)(F)F)c1=O)c1ccccc1]

Analogously to the process described in Ex. 63A, 200 mg (0.447 mmol) of the compound from Ex. 60A and 102 mg (0.670 mmol) of racemic 2-methoxy-2-phenylethanol gave 256 mg (93% of theory, purity 95%) of the title compound.

$^1$H-NMR (400 MHz, DMSO-d$_6$, δ/ppm): 7.41-7.36 (m, 2H), 7.34-7.30 (m, 3H), 4.92 (m, 1H), 4.57 (dd, 1H), 4.35 (dd, 1H), 4.19-4.04 (m, 2H), 3.81 (dd, 1H), 3.79-3.72 (m, 2H), 3.44-3.37 (m, 2H), 3.07 (s, 3H), 2.79-2.67 (m, 2H), 2.39 (s, 3H), 2.03 (s, 3H), 1.93-1.84 (m, 2H), 1.61-1.52 (m, 2H).

LC/MS (Method 1, ESIpos): $R_t$=1.15 min, m/z=582 [M+H]$^+$.

Example 73A 1-({5-Methyl-2,4-dioxo-3-[(1-phenylcyclopropyl)methyl]-1-(3,3,3-trifluoropropyl)-1,2,3,4-tetrahydrothieno[2,3-d]pyrimidin-6-yl}carbonyl)piperidin-4-yl acetate

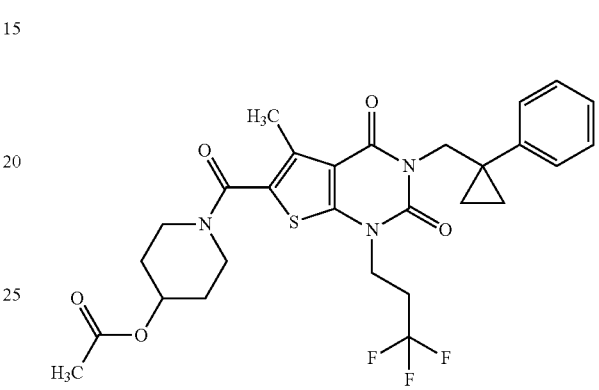

Analogously to the process described in Ex. 63A, 100 mg (0.223 mmol) of the compound from Ex. 60A and 50 mg (0.335 mmol) of (1-phenylcyclopropyl)methanol [lit.: L. K. Sydnes, P. F. F. Pereira, M. Sandberg, H. H. Oevreboe, *J. Chem. Res. Miniprint* 2001 (4), 464-474] gave 57 mg (42% of theory, purity 96%) of the title compound.

$^1$H-NMR (400 MHz, DMSO-d$_6$, δ/ppm): 7.26-7.19 (m, 4H), 7.17-7.13 (m, 1H), 4.91 (m, 1H), 4.16 (s, 2H), 4.00 (t, 2H), 3.78-3.70 (m, 2H), 3.43-3.35 (m, 2H), 2.63-2.51 (m, 2H, partly obscured by DMSO signal), 2.32 (s, 3H), 2.03 (s, 3H), 1.91-1.85 (m, 2H), 1.60-1.51 (m, 2H), 0.95 (m, 2H), 0.72 (m, 2H).

LC/MS (Method 1, ESIpos): $R_t$=1.22 min, m/z=578 [M+H]$^+$.

Example 74A

1-{[5-Methyl-3-(2-methyl-2-phenylpropyl)-2,4-dioxo-1-(3,3,3-trifluoropropyl)-1,2,3,4-tetrahydrothieno[2,3-d]pyrimidin-6-yl]carbonyl}piperidin-4-yl acetate

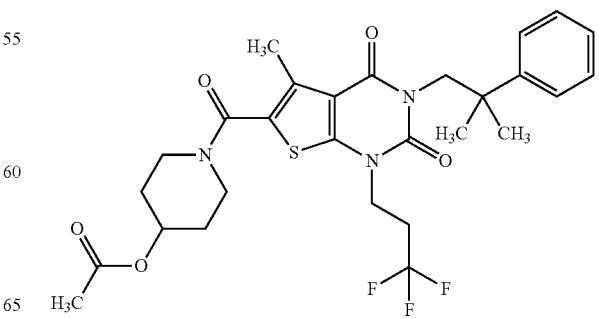

Analogously to the process described in Ex. 63A, 150 mg (0.335 mmol) of the compound from Ex. 60A and 76 mg (0.503 mmol) of 2-methyl-2-phenylpropan-1-ol [lit.: D. Coletta, B. di Giacomo, B. Natalini, M.-H. Ni, R. Pellicciari, *Farmaco* 1999, 54 (9), 600-610] gave 104 mg (51% of theory, purity 95%) of the title compound.

$^1$H-NMR (400 MHz, DMSO-d$_6$, δ/ppm): 7.43 (d, 2H), 7.32 (t, 2H), 7.21 (t, 1H), 4.92 (m, 1H), 4.10-4.05 (m, 4H), 3.79-3.71 (m, 2H), 3.44-3.36 (m, 2H), 2.77-2.65 (m, 2H), 2.35 (s, 3H), 2.03 (s, 3H), 1.92-1.85 (m, 2H), 1.61-1.52 (m, 2H), 1.28 (s, 6H).

LC/MS (Method 1, ESIpos): R$_t$=1.29 min, m/z=580 [M+H]$^+$.

Example 75A 1-({5-Methyl-2,4-dioxo-3 [2-(pyridin-2-yl)ethyl]-1-(3,3,3-trifluoropropyl)-1,2,3,4-tetrahydrothieno[2,3-d]pyrimidin-6-yl}carbonyl)piperidin-4-yl acetate (Formic Acid Salt)

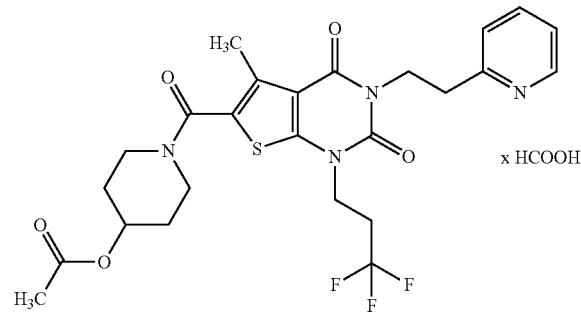 [SMILES: CC(=O)OC1CCN(C(=O)c2sc3c(c2C)c(=O)n(CCc2ccccn2)c(=O)n3CCC(F)(F)F)CC1]

Analogously to the process described in Ex. 63A, 70 mg (0.156 mmol) of the compound from Ex. 60A and 29 mg (0.235 mmol) of 2-(2-hydroxyethyl)pyridine gave 112 mg (95% of theory, purity 80%) of the title compound.

$^1$H-NMR (400 MHz, DMSO-d$_6$, δ/ppm): 8.88 (s, 1H), 8.48 (d, 1H), 7.71 (dt, 1H), 7.28 (d, 1H), 7.23 (dd, 1H), 4.92 (m, 1H), 4.22 (t, 1H), 4.11 (t, 1H), 3.79-3.71 (m, 2H), 3.44-3.36 (m, 2H), 2.99 (t, 2H), 2.81-2.69 (m, 2H), 2.39 (s, 3H), 2.03 (s, 3H), 1.92-1.85 (m, 2H), 1.61-1.51 (m, 2H).

LC/MS (Method 1, ESIpos): R$_t$=0.79 min, m/z=553 [M+H]$^+$.

Example 76A 1-({5-Methyl-2,4-dioxo-3 [2-(pyridin-4-yl)ethyl]-1-(3,3,3-trifluoropropyl)-1,2,3,4-tetrahydrothieno[2,3-d]pyrimidin-6-yl}carbonyl)piperidin-4-yl acetate (Formic Acid Salt)

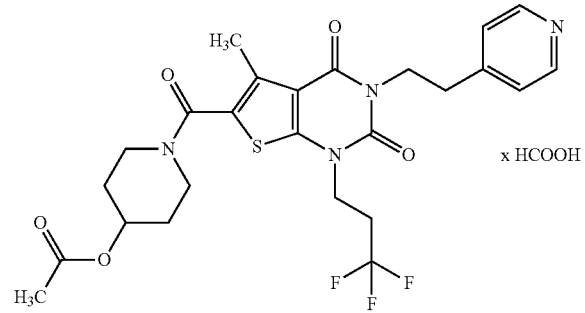 [SMILES: CC(=O)OC1CCN(C(=O)c2sc3c(c2C)c(=O)n(CCc2ccncc2)c(=O)n3CCC(F)(F)F)CC1]

Analogously to the process described in Ex. 63A, 70 mg (0.156 mmol) of the compound from Ex. 60A and 29 mg (0.235 mmol) of 4-(2-hydroxyethyl)pyridine gave 54 mg (50% of theory, purity 80%) of the title compound.

LC/MS (Method 1, ESIpos): R$_t$=0.76 min, m/z=553 [M+H]$^+$.

Example 77A 1-({3-[2-(1H-Imidazol-1-yl)ethyl]-5-methyl-2,4-dioxo-1-(3,3,3-trifluoropropyl)-1,2,3,4-tetrahydrothieno[2,3-d]pyrimidin-6-yl}carbonyl)piperidin-4-yl acetate

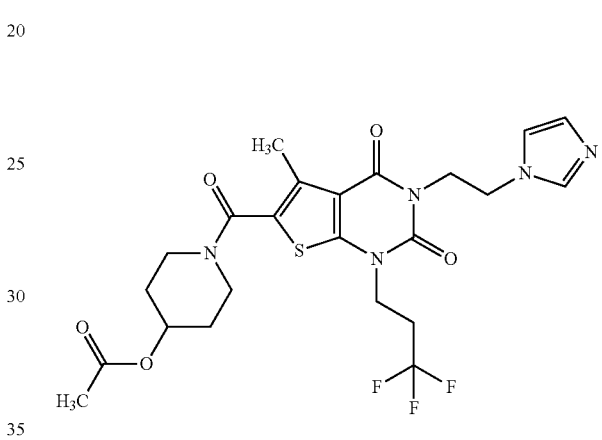

182 mg (0.559 mmol) of caesium carbonate were added to a solution of 100 mg (0.223 mmol) of the compound from Ex. 60A in 3 ml of DMF, and the mixture was stirred at RT for 10 min. 45 mg (0.268 mmol) of 1-(2-chloroethyl)-1H-imidazole hydrochloride [lit.: M. L. Burdeinyi, S. V. Popkov, M. V. Kharchevnikowa, *Russ. Chem. Bull.* 2009, 58 (5), 936-939] were then added. After stirring at RT overnight, conversion was incomplete. Therefore, the mixture was heated at 70° C. for another 1 h. After cooling to RT, the reaction mixture was separated directly by preparative HPLC into its components (Method 5). The product fractions were combined and concentrated. The residue was dissolved in a little methanol and the solution was passed over a bicarbonate cartridge (Polymerlabs, Stratospheres SPE, PL-HCO$_3$ MP SPE, capacity 0.9 mmol). Subsequent evaporation and drying of the residue under high vacuum gave 106 mg (87% of theory) of the title compound as the free base.

$^1$H-NMR (400 MHz, DMSO-d$_6$, δ/ppm): 7.58 (s, 1H), 7.12 (s, 1H), 6.85 (s, 1H), 4.92 (m, 1H), 4.23-4.17 (m, 4H), 4.09 (t, 2H), 3.79-3.71 (m, 2H), 3.43-3.36 (m, 2H), 2.80-2.68 (m, 2H), 2.36 (s, 3H), 2.02 (s, 3H), 1.92-1.84 (m, 2H), 1.60-1.52 (m, 2H).

LC/MS (Method 1, ESIpos): R$_t$=0.67 min, m/z=542 [M+H]$^+$.

Example 78A

1-{[3-(But-3-yn-1-yl)-5-methyl-2,4-dioxo-1-(3,3,3-trifluoropropyl)-1,2,3,4-tetrahydrothieno [2,3-d]pyrimidin-6-yl]carbonyl}piperidin-4-yl acetate

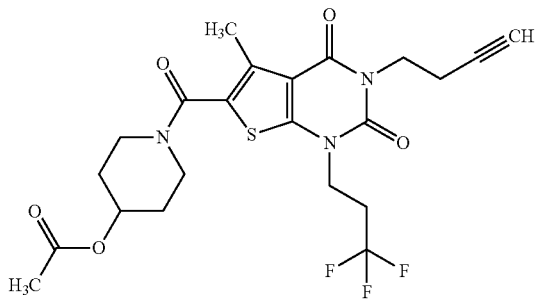 [SMILES: C#CCCn1c(=O)c2c(C)c(C(=O)N3CCC(OC(C)=O)CC3)sc2n(CCC(F)(F)F)c1=O]

80 mg (0.246 mmol) of caesium carbonate were added to a solution of 100 mg (0.223 mmol) of the compound from Ex. 60A in 3 ml of DMF, and the mixture was stirred at RT for 10 min. 37 mg (0.268 mmol) of 4-bromobutyne were then added. The reaction mixture was stirred at RT for about 16 h and then directly separated into its components by means of preparative HPLC (Method 5). The product fractions were combined and concentrated, and the residue was dried under high vacuum. This gave 90 mg (80% of theory) of the title compound.

$^1$H-NMR (400 MHz, DMSO-$d_6$, δ/ppm): 4.92 (m, 1H), 4.13 (t, 2H), 4.01 (t, 2H), 3.79-3.71 (m, 2H), 3.43-3.36 (m, 2H), 2.88 (t, 1H), 2.85-2.73 (m, 2H), 2.49-2.44 (m, 2H), 2.39 (s, 3H), 2.02 (s, 3H), 1.92-1.84 (m, 2H), 1.60-1.51 (m, 2H).

LC/MS (Method 1, ESIpos): $R_t$=0.99 min, m/z=500 [M+H]$^+$.

Example 79A

1-{[3-(2-Methoxyethyl)-5-methyl-2,4-dioxo-1-(3,3,3-trifluoropropyl)-1,2,3,4-tetrahydrothieno [2,3-d]pyrimidin-6-yl]carbonyl}piperidin-4-yl acetate

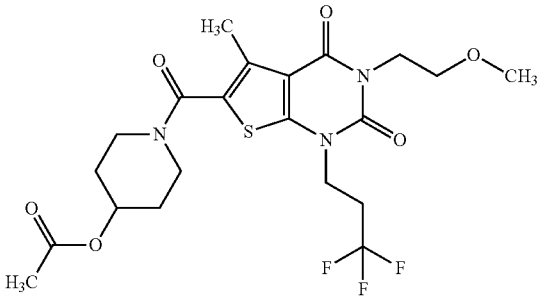 [SMILES: COCCn1c(=O)c2c(C)c(C(=O)N3CCC(OC(C)=O)CC3)sc2n(CCC(F)(F)F)c1=O]

Analogously to the process described in Ex. 78A, 100 mg (0.223 mmol) of the compound from Ex. 60A and 37 mg (0.268 mmol) of 2-bromoethyl methyl ether gave 94 mg (83% of theory) of the title compound.

$^1$H-NMR (400 MHz, DMSO-$d_6$, δ/ppm): 4.92 (m, 1H), 4.13 (t, 2H), 4.06 (t, 2H), 3.79-3.71 (m, 2H), 3.50 (t, 2H), 3.44-3.36 (m, 2H), 3.24 (s, 3H), 2.85-2.73 (m, 2H), 2.39 (s, 3H), 2.02 (s, 3H), 1.91-1.84 (m, 2H), 1.60-1.51 (m, 2H).

LC/MS (Method 1, ESIpos): $R_t$=0.93 min, m/z=506 [M+H]$^+$.

Example 80A

1-{[3-(2-Cyclopropylethyl)-5-methyl-2,4-dioxo-1-(3,3,3-trifluoropropyl)-1,2,3,4-tetrahydrothieno[2,3-d]pyrimidin-6-yl]carbonyl}piperidin-4-yl acetate

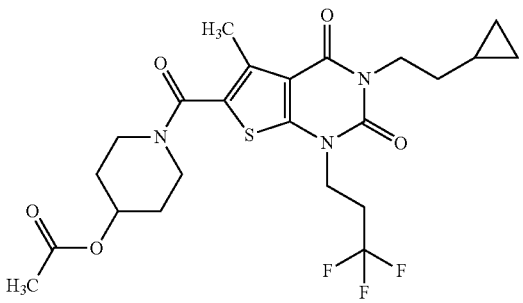 [SMILES: CC(=O)OC1CCN(C(=O)c2sc3c(c2C)c(=O)n(CCC2CC2)c(=O)n3CCC(F)(F)F)CC1]

Analogously to the process described in Ex. 63A, 100 mg (0.223 mmol) of the compound from Ex. 60A and 29 mg (0.335 mmol) of 2-cyclopropylethanol gave 52 mg (45% of theory) of the title compound.

$^1$H-NMR (400 MHz, DMSO-$d_6$, δ/ppm): 4.91 (m, 1H), 4.12 (t, 2H), 3.95 (t, 2H), 3.78-3.71 (m, 2H), 3.43-3.34 (m, 2H, partially obscured by the water signal), 2.85-2.73 (m, 2H), 2.39 (s, 3H), 2.02 (s, 3H), 1.91-1.84 (m, 2H), 1.60-1.51 (m, 2H), 1.44 (quart, 2H), 0.72-0.65 (m, 1H), 0.41-0.37 (m, 2H), 0.02 (m, 2H, partially obscured by the TMS signal).

LC/MS (Method 1, ESIpos): $R_t$=1.12 min, m/z=516 [M+H]$^+$.

Example 81A

1-{[3-Isobutyl-5-methyl-2,4-dioxo-1-(3,3,3-trifluoropropyl)-1,2,3,4-tetrahydrothieno [2,3-d]pyrimidin-6-yl]carbonyl}piperidin-4-yl acetate

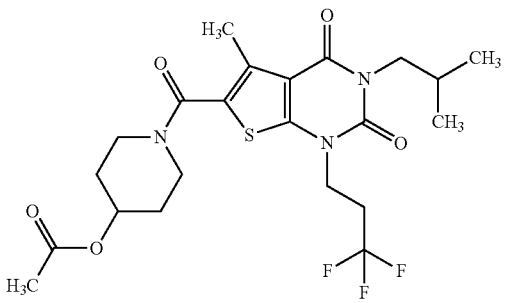 [SMILES: CC(=O)OC1CCN(C(=O)c2sc3c(c2C)c(=O)n(CC(C)C)c(=O)n3CCC(F)(F)F)CC1]

Analogously to the process described in Ex. 63A, 100 mg (0.223 mmol) of the compound from Ex. 60A and 25 mg (0.335 mmol) of 2-methylpropanol gave 95 mg (84% of theory) of the title compound.

$^1$H-NMR (400 MHz, DMSO-$d_6$, δ/ppm): 4.92 (m, 1H), 4.13 (t, 2H), 3.79-3.70 (m, 4H), 3.44-3.36 (m, 2H), 2.85-2.73 (m, 2H), 2.39 (s, 3H), 2.09-1.99 (m, 1H), 2.02 (s, 3H), 1.92-1.84 (m, 2H), 1.60-1.51 (m, 2H), 0.86 (d, 6H).

LC/MS (Method 1, ESIpos): $R_t$=1.11 min, m/z=504 [M+H]$^+$.

Example 82A

1-{[3-(2-Methoxypropyl)-5-methyl-2,4-dioxo-1-(3,3,3-trifluoropropyl)-1,2,3,4-tetrahydrothieno[2,3-d]pyrimidin-6-yl]carbonyl}piperidin-4-yl acetate (racemate)

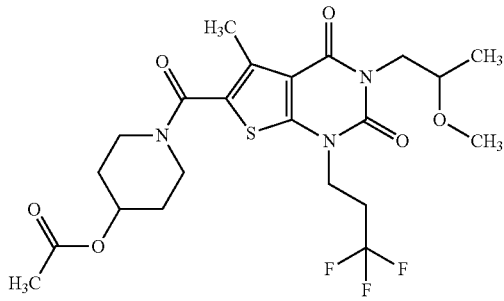 [SMILES: COC(C)Cn1c(=O)c2c(C)c(C(=O)N3CCC(OC(C)=O)CC3)sc2n(CCC(F)(F)F)c1=O]

Analogously to the process described in Ex. 63A, 80 mg (0.179 mmol) of the compound from Ex. 60A and 24 mg (0.268 mmol) of racemic 2-methoxypropanol gave 53 mg (57% of theory) of the title compound. In deviation to the processes described above, here the product obtained after preparative HPLC was chromatographed once more on silica gel (mobile phase: 2:1 cyclohexane/ethyl acetate).

$^1$H-NMR (400 MHz, DMSO-$d_6$, δ/ppm): 4.92 (m, 1H), 4.13 (quart, 2H), 3.79-3.72 (m, 4H), 3.64 (m, 1H), 3.44-3.36 (m, 2H), 3.22 (s, 3H), 2.85-2.73 (m, 2H), 2.39 (s, 3H), 2.02 (s, 3H), 1.92-1.85 (m, 2H), 1.60-1.51 (m, 2H), 1.06 (d, 3H).

LC/MS (Method 1, ESIpos): $R_t$=0.99 min, m/z=520 [M+H]$^+$.

Example 83A 1-({3-Ethyl-5-methyl-2,4-dioxo-1-[2-(trifluoromethoxy)ethyl]-1,2,3,4-tetrahydrothieno[2,3-d]pyrimidin-6-yl}carbonyl)piperidin-4-yl acetate

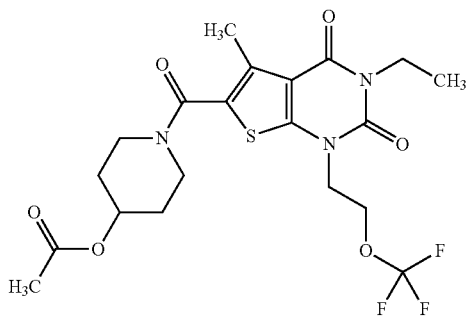 [SMILES: CCn1c(=O)c2c(C)c(C(=O)N3CCC(OC(C)=O)CC3)sc2n(CCOC(F)(F)F)c1=O]

97 mg (0.296 mmol) of caesium carbonate were added to a solution of 75 mg (0.198 mmol) of the compound from Ex. 62A in 2 ml of DMF, and the mixture was stirred at RT for 20 min. 57 mg (0.296 mmol) of 1-bromo-2-(trifluoromethoxy)ethane [commercially available; lit.: P. E. Aldrich, W. A. Sheppard, *J. Org. Chem.* 1964, 29 (1), 11-15] were then added. In a microwave oven (Biotage Initiator Sixty), the reaction mixture was heated at 100° C. for 15 min. After cooling to RT, the mixture was separated directly by preparative HPLC into its components (Method 13). The product fractions were combined and concentrated, and the residue was dried under high vacuum. 66 mg (68% of theory) of the title compound were obtained.

$^1$H-NMR (400 MHz, DMSO-$d_6$, δ/ppm): 4.91 (m, 1H), 4.42 (t, 2H), 4.22 (t, 2H), 3.91 (quart, 2H), 3.78-3.70 (m, 2H), 3.43-3.38 (m, 2H, partially obscured by the water signal), 2.39 (s, 3H), 2.02 (s, 3H), 1.91-1.84 (m, 2H), 1.59-1.50 (m, 2H), 1.12 (t, 3H).

LC/MS (Method 1, ESIpos): $R_t$=1.01 min, m/z=492 [M+H]$^+$.

Example 84A

1-[(3-Ethyl-5-methyl-2,4-dioxo-1-{2-[(trifluoromethyl)sulphanyl]ethyl}-1,2,3,4-tetrahydrothieno[2,3-d]pyrimidin-6-yl)carbonyl]piperidin-4-yl acetate

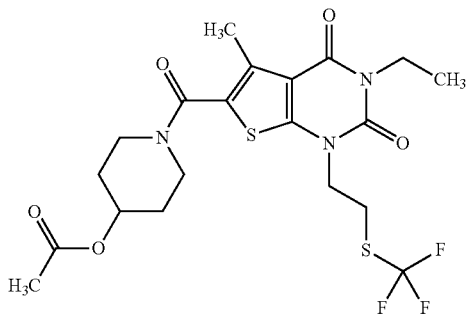 [SMILES: CCn1c(=O)c2c(C)c(C(=O)N3CCC(OC(C)=O)CC3)sc2n(CCSC(F)(F)F)c1=O]

Analogously to the process described in Ex. 83A, 75 mg (0.198 mmol) of the compound from Ex. 62A and 62 mg (0.296 mmol) of 2-bromoethyl trifluoromethyl sulphide gave 74 mg (74% of theory) of the title compound.

$^1$H-NMR (400 MHz, DMSO-$d_6$, δ/ppm): 4.91 (m, 1H), 4.16 (t, 2H), 3.91 (quart, 2H), 3.78-3.71 (m, 2H), 3.43-3.34 (m, 4H, partially obscured by the water signal), 2.39 (s, 3H), 2.02 (s, 3H), 1.92-1.84 (m, 2H), 1.59-1.51 (m, 2H), 1.12 (t, 3H).

LC/MS (Method 1, ESIpos): $R_t$=1.07 min, m/z=508 [M+H]$^+$.

Example 85A 1-({3-Ethyl-5-methyl-2,4-dioxo-1-[2-(trifluoromethyl)prop-2-en-1-yl]-1,2,3,4-tetrahydrothieno[2,3-d]pyrimidin-6-yl}carbonyl)piperidin-4-yl acetate

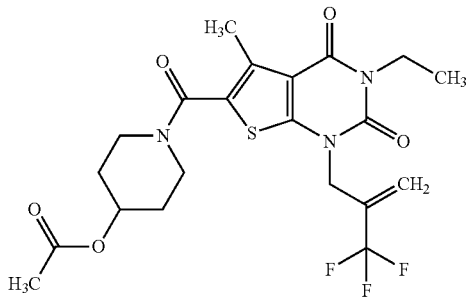 [SMILES: C=C(Cn1c(=O)n(CC)c(=O)c2c(C)c(C(=O)N3CCC(OC(C)=O)CC3)sc21)C(F)(F)F]

Analogously to the process described in Ex. 83A, 75 mg (0.198 mmol) of the compound from Ex. 62A and 56 mg (0.296 mmol) of 2-(bromomethyl)-3,3,3-trifluoropropene gave 77 mg (73% of theory, purity 91%) of the title compound.

$^1$H-NMR (400 MHz, DMSO-$d_6$, δ/ppm): 6.02 (s, 1H), 5.83 (s, 1H), 4.91 (m, 1H), 4.79 (s, 2H), 3.92 (quart, 2H), 3.77-3.69 (m, 2H), 3.43-3.37 (m, 2H, partially obscured by the water signal), 2.40 (s, 3H), 2.02 (s, 3H), 1.91-1.83 (m, 2H), 1.59-1.50 (m, 2H), 1.13 (t, 3H).

LC/MS (Method 1, ESIpos): $R_t$=1.03 min, m/z=488 [M+H]$^+$.

Example 86A 1-({1-[(2,2-Difluorocyclopropyl)methyl]-3-ethyl-5-methyl-2,4-dioxo-1,2,3,4-tetrahydrothieno[2,3-d]pyrimidin-6-yl}carbonyl)piperidin-4-yl acetate (racemate)

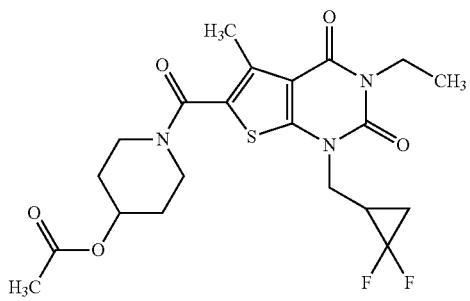 [SMILES: CCn1c(=O)c2c(C)c(C(=O)N3CCC(OC(C)=O)CC3)sc2n(CC2CC2(F)F)c1=O]

Analogously to the process described in Ex. 83A, 75 mg (0.198 mmol) of the compound from Ex. 62A and 51 mg (0.296 mmol) of racemic 2-(bromomethyl)-1,1-difluorocyclopropane gave 68 mg (72% of theory) of the title compound.

$^1$H-NMR (400 MHz, DMSO-$d_6$, δ/ppm): 4.91 (m, 1H), 4.19-4.11 (m, 1H), 4.00-3.90 (m, 1H), 3.91 (quart, 2H), 3.79-3.71 (m, 2H), 3.43-3.36 (m, 2H, partially obscured by the water signal), 2.40 (s, 3H), 2.29-2.17 (m, 1H), 2.02 (s, 3H), 1.91-1.84 (m, 2H), 1.77-1.67 (m, 1H), 1.60-1.45 (m, 3H), 1.13 (t, 3H).

LC/MS (Method 1, ESIpos): $R_t$=1.08 min, m/z=470 [M+H]$^+$.

Example 87A 2-tert-Butyl 4-ethyl 5-{[(2,2-difluoro-2-phenylethyl)carbamoyl]amino}-3-methylthiophene-2,4-dicarboxylate

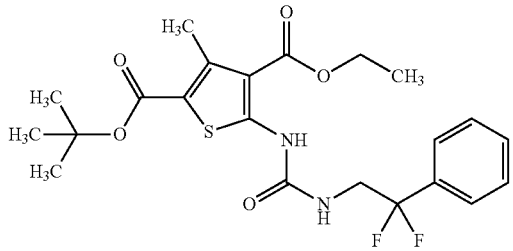 [SMILES: CCOC(=O)c1c(NC(=O)NCC(F)(F)c2ccccc2)sc(C(=O)OC(C)(C)C)c1C]

Analogously to the process described in Ex. 2A, 1.63 g (5.69 mmol) of 2-tert-butyl 4-ethyl 5-amino-3-methylthiophene-2,4-dicarboxylate (Example 1A), 1.85 g (11.4 mmol) of N,N'-carbonyldiimidazole, 3.2 ml (22.8 mmol) of triethylamine and 1.79 g (11.4 mmol) of 2,2-difluoro-2-phenylethanamine [lit.: K. D. Kreuter, M. R. Player et al., *Bioorg. Med. Chem. Lett.* 2008, 18 (9), 2865-2870] gave 2.0 g (71% of theory, purity 95%) of the title compound. In deviation, MPLC purification was carried out using the mobile phase cyclohexane/ethyl acetate 5:1.

$^1$H-NMR (400 MHz, DMSO-$d_6$, δ/ppm): 10.64 (s, 1H), 8.59 (t, 1H), 8.58-7.49 (m, 5H), 4.32 (quart, 2H), 3.92 (dt, 2H), 2.62 (s, 3H), 1.49 (s, 9H), 1.33 (t, 3H).

LC/MS (Method 1, ESIpos): $R_t$=1.37 min, m/z=469 [M+H]$^+$.

Example 88A 2-tert-Butyl 4-ethyl 3-methyl-5-[(propylcarbamoyl)amino]thiophene-2,4-dicarboxylate

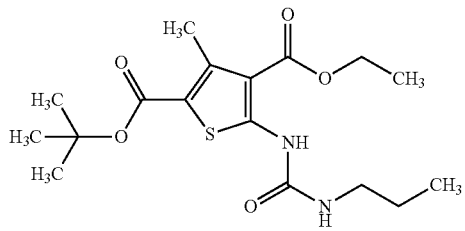 [SMILES: CCCNC(=O)Nc1sc(C(=O)OC(C)(C)C)c(C)c1C(=O)OCC]

Analogously to the process described in Ex. 2A, 15.0 g (52.6 mmol) of 2-tert-butyl 4-ethyl 5-amino-3-methylthiophene-2,4-dicarboxylate (Example 1A), 17.0 g (105 mmol) of N,N'-carbonyldiimidazole, 29 ml (210 mmol) of triethylamine and 17.3 ml (210 mmol) of propylamine gave 12.4 g (63% of theory) of the title compound. In deviation, MPLC purification was carried out using the mobile phase cyclohexane/ethyl acetate 10:1.

$^1$H-NMR (400 MHz, DMSO-$d_6$, δ/ppm): 10.54 (s, 1H), 8.05 (t, 1H), 4.31 (quart, 2H), 3.07 (quart, 2H), 2.62 (s, 3H), 1.50 (s, 9H), 1.50-1.41 (m, 2H), 1.32 (t, 3H), 0.88 (t, 3H).

LC/MS (Method 1, ESIpos): $R_t$=1.30 min, m/z=371 [M+H]$^+$.

Example 89A 2-tert-Butyl 4-ethyl 3-methyl-5-{[(3,3,3-trifluoro-2-methoxypropyl)carbamoyl]amino}thiophene-2,4-dicarboxylate (racemate)

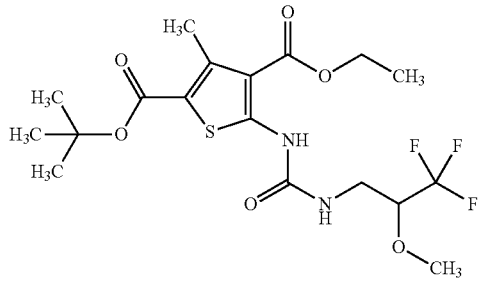 [SMILES: CCOC(=O)c1c(NC(=O)NCC(OC)C(F)(F)F)sc(C(=O)OC(C)(C)C)c1C]

Analogously to the process described in Ex. 2A, 0.99 g (3.48 mmol) of 2-tert-butyl 4-ethyl 5-amino-3-methylthiophene-2,4-dicarboxylate (Example 1A), 1.13 g (6.96 mmol) of N,N'-carbonyldiimidazole, 1.9 ml (13.9 mmol) of triethylamine and 1.25 g (6.96 mmol) of racemic 3,3,3-trifluoro-2-methoxypropane-1-amine hydrochloride gave 1.39 g (87% of theory) of the title compound. In deviation, here MPLC purification was carried out using as mobile phase a cyclohexane/ethyl acetate gradient 10:1→5:1.

$^1$H-NMR (400 MHz, DMSO-$d_6$, δ/ppm): 10.64 (s, 1H), 8.39 (t, 1H), 4.32 (quart, 2H), 4.03-3.96 (m, 1H), 3.57-3.50 (m, 1H), 3.51 (s, 3H), 3.33-3.26 (m, 1H, partially obscured by water signal), 2.63 (s, 3H), 1.50 (s, 9H), 1.33 (t, 3H).

LC/MS (Method 1, ESIpos): $R_t$=1.35 min, m/z=455 [M+H]$^+$.

Example 90A tert-Butyl 3-(2,2-difluoro-2-phenylethyl)-5-methyl-2,4-dioxo-1,2,3,4-tetrahydrothieno[2,3-d]pyrimidine-6-carboxylate

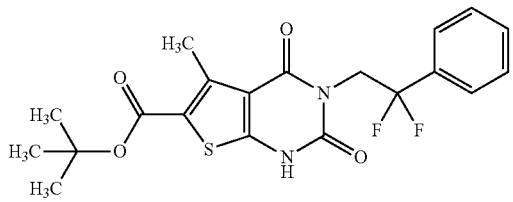 [SMILES: Cc1c(C(=O)OC(C)(C)C)sc2[nH]c(=O)n(CC(F)(F)c3ccccc3)c(=O)c12]

Analogously to the process described under Ex. 8A, 1.96 g (4.18 mmol) of the compound from Ex. 87A gave 1.64 g (92% of theory) of the title compound.

$^1$H-NMR (400 MHz, DMSO-$d_6$, δ/ppm): 12.57 (s, 1H), 7.56-7.49 (m, 5H), 4.56 (t, 2H), 2.69 (s, 3H), 1.52 (s, 9H).

LC/MS (Method 1, ESIpos): $R_t$=1.20 min, m/z=421 [M−H]$^−$.

Example 91A tert-Butyl 5-methyl-2,4-dioxo-3-propyl-1,2,3,4-tetrahydrothieno[2,3-d]pyrimidine-6-carboxylate

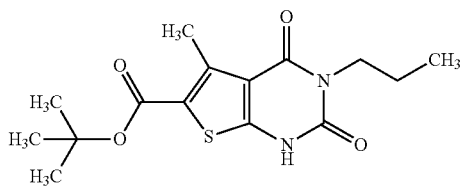 [SMILES: CCCn1c(=O)[nH]c2sc(C(=O)OC(C)(C)C)c(C)c2c1=O]

Analogously to the process described under Ex. 8A, 17.5 g (47.1 mmol) of the compound from Ex. 88A gave 13.9 g (90% of theory) of the title compound.

$^1$H-NMR (400 MHz, DMSO-$d_6$, δ/ppm): 12.38 (s, 1H), 3.77 (dd, 2H), 2.71 (s, 3H), 1.60-1.49 (m, 2H), 1.52 (s, 9H), 0.87 (t, 3H).

LC/MS (Method 1, ESIpos): $R_t$=1.11 min, m/z=325 [M+H]$^+$.

Example 92A tert-Butyl 5-methyl-2,4-dioxo-3-(3,3,3-trifluoro-2-methoxypropyl)-1,2,3,4-tetrahydrothieno[2,3-d]pyrimidine-6-carboxylate (racemate)

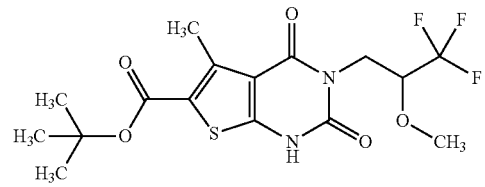 [SMILES: COC(Cn1c(=O)[nH]c2sc(C(=O)OC(C)(C)C)c(C)c2c1=O)C(F)(F)F]

Analogously to the process described under Ex. 8A, 1.38 g (3.04 mmol) of the compound from Ex. 89A gave 1.19 g (96% of theory) of the title compound.

$^1$H-NMR (400 MHz, DMSO-$d_6$, δ/ppm): 12.56 (s, 1H), 4.24-4.16 (m, 2H), 4.00 (quart, 1H), 3.43 (s, 3H), 2.72 (s, 3H), 1.52 (s, 9H).

LC/MS (Method 9, ESIpos): $R_t$=1.43 min, m/z=409 [M+H]$^+$.

Example 93A tert-Butyl 3-(2,2-difluoro-2-phenylethyl)-5-methyl-2,4-dioxo-1-(3,3,3-trifluoropropyl)-1,2,3,4-tetrahydrothieno[2,3-d]pyrimidine-6-carboxylate

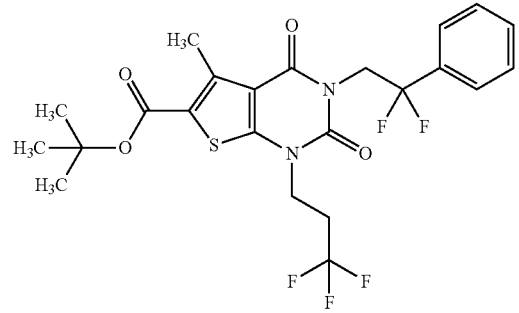 [SMILES: Cc1c(C(=O)OC(C)(C)C)sc2c1c(=O)n(CC(F)(F)c1ccccc1)c(=O)n2CCC(F)(F)F]

926 mg (2.84 mmol) of caesium carbonate were added to a solution of 800 mg (1.89 mmol) of the compound from Ex. 90A in 20 ml of DMF, and the mixture was stirred at RT for 20 min. 636 mg (2.84 mmol) of 3,3,3-trifluoro-1-iodopropane were then added, and the mixture was stirred at 60° C. for 5 h. After cooling to RT, the mixture was diluted with ethyl acetate and washed successively with water and saturated sodium chloride solution. After drying over anhydrous magnesium sulphate, the mixture was filtered and concentrated. The crude product was purified by MPLC (Biotage cartridge with 50 g of silica gel, mobile phase cyclohexane/ethyl acetate 10:1). The product fractions were combined and concentrated. After the residue had been dried under high vacuum, 625 mg (63% of theory) of the title compound were obtained.

$^1$H-NMR (400 MHz, DMSO-$d_6$, δ/ppm): 7.56-7.49 (m, 5H), 4.62 (t, 2H), 4.15 (t, 2H), 2.79-2.67 (m, 2H), 2.73 (s, 3H), 1.54 (s, 9H).

LC/MS (Method 1, ESIpos): $R_t$=1.39 min, m/z=519 [M+H]$^+$.

Example 94A tert-Butyl 3-(2,2-difluoro-2-phenylethyl)-1-(2-methoxyethyl)-5-methyl-2,4-dioxo-1,2,3,4-tetrahydrothieno[2,3-d]pyrimidine-6-carboxylate

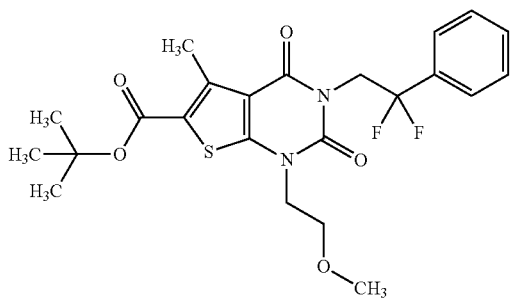 [SMILES: COCCn1c(=O)n(CC(F)(F)c2ccccc2)c(=O)c2c(C)c(C(=O)OC(C)(C)C)sc21]

926 mg (2.84 mmol) of caesium carbonate were added to a solution of 800 mg (1.89 mmol) of the compound from Ex. 90A in 20 ml of DMF, and the mixture was stirred at RT for 10 min. 395 mg (2.84 mmol) of 2-bromoethyl methyl ether were then added, and the mixture was stirred at 65° C. for 4 h. After cooling to RT, the mixture was diluted with ethyl acetate and washed successively with water and saturated sodium chloride solution. After drying over anhydrous magnesium sulphate, the mixture was filtered and concentrated. The crude product was purified by MPLC (Puriflash cartridge with 50 g of silica gel, mobile phase cyclohexane/ethyl acetate 10:1). The product fractions were combined and concentrated. For further purification, the residue was stirred with 20 ml of a mixture of pentane and dichloromethane (20:1) at RT. This gave, after another filtration and drying under high vacuum, 685 mg (75% of theory) of the title compound.

$^1$H-NMR (400 MHz, DMSO-d$_6$, δ/ppm): 7.55-7.49 (m, 5H), 4.62 (t, 2H), 4.06 (t, 2H), 3.58 (t, 2H), 3.24 (s, 3H), 2.72 (s, 3H), 1.53 (s, 9H).

LC/MS (Method 1, ESIpos): R$_t$=1.37 min, m/z=481 [M+H]$^+$.

Example 95A tert-Butyl 5-methyl-2,4-dioxo-3-propyl-1-[2-(trifluoromethoxy)ethyl]-1,2,3,4-tetrahydrothieno[2,3-d]pyrimidine-6-carboxylate

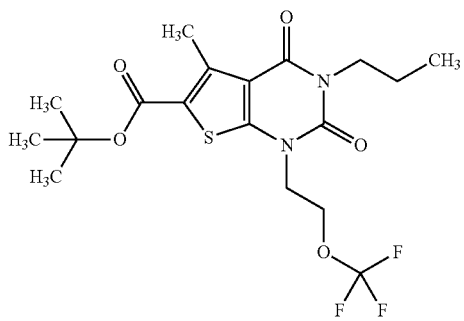 [SMILES: CCCn1c(=O)c2c(C)c(C(=O)OC(C)(C)C)sc2n(CCOC(F)(F)F)c1=O]

1.67 g (5.18 mmol) of caesium carbonate were added to a solution of 1.12 g (3.46 mmol) of the compound from Ex. 91A in 30 ml of DMF, and the mixture was stirred at RT for 20 min. 1.0 g (5.18 mmol) of 1-bromo-2-trifluoromethoxyethane were then added, and the mixture was stirred at 80° C. for 5 h. Subsequently, the mixture was concentrated to dryness and the residue was taken up in ethyl acetate. The mixture was washed successively with water and saturated sodium chloride solution. After drying over anhydrous magnesium sulphate, the mixture was filtered and concentrated. The crude product was purified by MPLC (Biotage cartridge with 100 g of silica gel, mobile phase cyclohexane/ethyl acetate 10:1→5:1). The product fractions were combined and concentrated. Drying of the residue under high vacuum gave 1.28 g (82% of theory, 97% pure) of the title compound.

$^1$H-NMR (400 MHz, DMSO-d$_6$, δ/ppm): 4.42 (t, 2H), 4.25 (t, 2H), 3.83 (t, 2H), 2.75 (s, 3H), 1.61-1.51 (m, 2H), 1.53 (s, 9H), 0.86 (t, 3H).

LC/MS (Method 1, ESIpos): R$_t$=1.37 min; no ionization.

Example 96A tert-Butyl 5-methyl-2,4-dioxo-3-(3,3,3-trifluoro-2-methoxypropyl)-1-(3,3,3-trifluoropropyl)-1,2,3,4-tetrahydrothieno[2,3-d]pyrimidine-6-carboxylate (racemate)

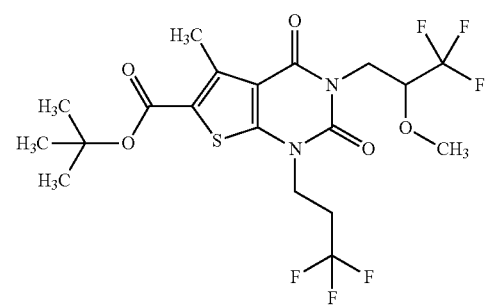 [SMILES: COC(Cn1c(=O)c2c(C)c(C(=O)OC(C)(C)C)sc2n(CCC(F)(F)F)c1=O)C(F)(F)F]

598 mg (1.84 mmol) of caesium carbonate were added to a solution of 500 mg (1.22 mmol) of the compound from Ex. 92A in 5 ml of DMF, and the mixture was stirred at RT for 20 min. 411 mg (1.84 mmol) of 3,3,3-trifluoro-1-iodopropane were then added. The mixture was stirred in a microwave oven (Biotage Initiator with dynamic control of irradiation power) at 100° C. for 2 h. After cooling to RT, about 50 ml of water were added and the mixture was extracted with ethyl acetate. The organic extract was washed with water and saturated sodium chloride solution. After drying over anhydrous magnesium sulphate, the mixture was filtered and concentrated. The residue obtained was purified by preparative HPLC (Method 6). This gave, after combination of the product fractions, concentration and drying under high vacuum, 495 mg (80% of theory) of the title compound.

$^1$H-NMR (400 MHz, DMSO-d$_6$, δ/ppm): 4.29-4.17 (m, 4H), 4.05 (dd, 1H), 3.42 (s, 3H), 2.87-2.76 (m, 2H), 2.76 (s, 3H), 1.54 (s, 9H).

LC/MS (Method 9, ESIpos): R$_t$=1.38 min, m/z=505 [M+H]$^+$.

Example 97A tert-Butyl 3-ethyl-5-methyl-2,4-dioxo-1-[2-(trifluoromethoxy)ethyl]-1,2,3,4-tetrahydrothieno[2,3-d]pyrimidine-6-carboxylate

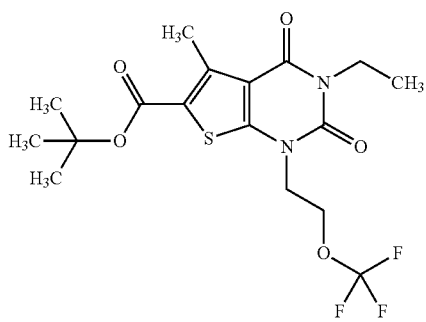 [SMILES: CCn1c(=O)c2c(C)c(C(=O)OC(C)(C)C)sc2n(CCOC(F)(F)F)c1=O]

Analogously to the process described in Ex. 26A, 2.50 g (8.06 mmol) of the compound from Ex. 12A and 2.33 g (12.1 mmol) of 1-bromo-2-trifluoromethoxyethane gave 1.93 g (56% of theory) of the title compound. In deviation from the process described above, here the reaction time at 100° C. was 5 h. MPLC purification was carried out via a Biotage cartridge containing 100 g of silica gel, using a mobile phase gradient of cyclohexane/ethyl acetate 50:1→10:1. Final stirring of the product obtained in this manner was carried out using a mixture of 30 ml of pentane and 0.5 ml of dichloromethane.

$^1$H-NMR (400 MHz, DMSO-$d_6$, δ/ppm): 4.42 (t, 2H), 4.25 (t, 2H), 3.91 (quart, 2H), 2.75 (s, 3H), 1.53 (s, 9H), 1.13 (t, 3H).

LC/MS (Method 1, ESIpos): $R_t$=1.30 min; poor ionization.

Example 98A tert-Butyl 5-methyl-2,4-dioxo-3-propyl-1-(3,3,3-trifluoropropyl)-1,2,3,4-tetrahydrothieno[2,3-d]pyrimidine-6-carboxylate

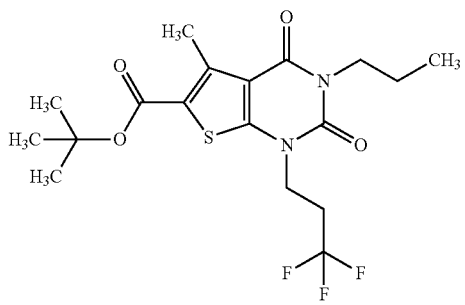 [SMILES: CCCn1c(=O)c2c(C)c(C(=O)OC(C)(C)C)sc2n(CCC(F)(F)F)c1=O]

6.03 g (18.5 mmol) of caesium carbonate were added to a solution of 4.0 g (12.3 mmol) of the compound from Ex. 91A in 120 ml of DMF, and the mixture was stirred at RT for 20 min. 4.14 g (18.5 mmol) of 3,3,3-trifluoro-1-iodopropane were then added, and the mixture was stirred at 70° C. for 5 h. After this time, a further 4.02 g (12.3 mmol) of caesium carbonate and 2.76 g (12.3 mmol) of 3,3,3-trifluoro-1-iodopropane were added, and the mixture was stirred at 70° C. for another 4 h. After cooling to RT, the mixture was diluted with ethyl acetate and washed successively with water and saturated sodium chloride solution. After drying over anhydrous magnesium sulphate, the mixture was filtered and concentrated. The crude product was purified by MPLC (Biotage cartridge with 100 g of silica gel, mobile phase cyclohexane/ethyl acetate 10:1). The product fractions were combined and concentrated. Since the product obtained in this manner was still contaminated, further purification was carried out by preparative HPLC (Method 6). Another evaporation and drying under a high vacuum gave 4.23 g (81% of theory) of the title compound.

$^1$H-NMR (400 MHz, DMSO-$d_6$, δ/ppm): 4.15 (t, 2H), 3.83 (t, 2H), 2.85-2.73 (m, 2H), 2.75 (s, 3H), 1.62-1.51 (m, 2H), 1.53 (s, 9H), 0.87 (t, 3H).

LC/MS (Method 1, ESIpos): $R_t$=1.37 min, m/z=421 [M+H]$^+$.

Example 99A tert-Butyl 1-(2-methoxyethyl)-5-methyl-2,4-dioxo-3-propyl-1,2,3,4-tetrahydrothieno[2,3-d]pyrimidine-6-carboxylate

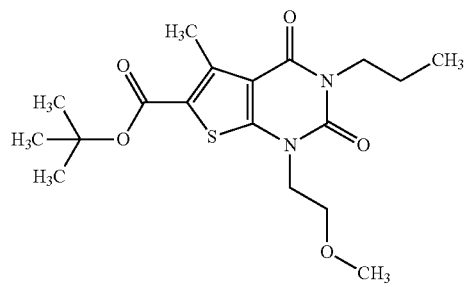 [SMILES: CCCn1c(=O)c2c(C)c(C(=O)OC(C)(C)C)sc2n(CCOC)c1=O]

Analogously to the process described in Ex. 26A, 4.0 g (12.3 mmol) of the compound from Ex. 91A and 2.57 g (18.5 mmol) of 1-bromo-2-methoxyethane gave 3.59 g (76% of theory) of the title compound. In deviation from the process described above, here the reaction time at 100° C. was 5 h. MPLC purification was carried out via a Biotage cartridge containing 100 g of silica gel, using a mobile phase gradient of cyclohexane/ethyl acetate 10:1→5:1. Final stirring of the product obtained in this manner was carried out using a mixture of 60 ml of pentane and 1.5 ml of dichloromethane.

$^1$H-NMR (400 MHz, DMSO-$d_6$, δ/ppm): 4.07 (t, 2H), 3.82 (t, 2H), 3.65 (t, 2H), 3.24 (s, 3H), 2.74 (s, 3H), 1.61-1.50 (m, 2H), 1.53 (s, 9H), 0.87 (t, 3H).

LC/MS (Method 1, ESIpos): $R_t$=1.29 min, m/z=383 [M+H]$^+$.

Example 100A 3-(2,2-Difluoro-2-phenylethyl)-5-methyl-2,4-dioxo-1-(3,3,3-trifluoropropyl)-1,2,3,4-tetrahydrothieno[2,3-d]pyrimidine-6-carboxylic acid

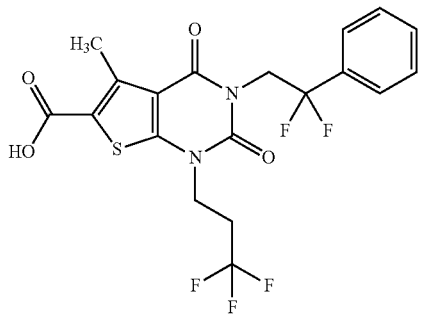 [SMILES: Cc1c(C(=O)O)sc2c1c(=O)n(CC(F)(F)c1ccccc1)c(=O)n2CCC(F)(F)F]

Analogously to the process described in Ex. 43A, 614 mg (1.18 mmol) of the compound from Ex. 93A and 10 ml of trifluoroacetic acid in 20 ml of dichloromethane gave 543 mg (99% of theory) of the title compound.

$^1$H-NMR (400 MHz, DMSO-$d_6$, δ/ppm): 13.52 (s, broad, 1H), 7.56-7.49 (m, 5H), 4.63 (t, 2H), 4.15 (t, 2H), 2.79-2.67 (m, 2H), 2.74 (s, 3H).

LC/MS (Method 1, ESIpos): $R_t$=1.09 min, m/z=461 [M−H]$^-$.

Example 101A 3-(2,2-Difluoro-2-phenylethyl)-1-(2-methoxyethyl)-5-methyl-2,4-dioxo-1,2,3,4-tetrahydrothieno[2,3-d]pyrimidine-6-carboxylic acid

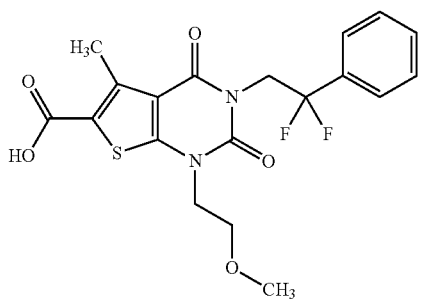 [SMILES: COCCn1c(=O)n(CC(F)(F)c2ccccc2)c(=O)c2c(C)c(C(=O)O)sc21]

Analogously to the process described in Ex. 43A, 673 mg (1.40 mmol) of the compound from Ex. 94A and 10 ml of trifluoroacetic acid in 20 ml of dichloromethane gave 419 mg (67% of theory, purity 96%) of the title compound.

$^1$H-NMR (400 MHz, DMSO-$d_6$, δ/ppm): 13.41 (s, broad, 1H), 7.56-7.49 (m, 5H), 4.62 (t, 2H), 4.06 (t, 2H), 3.59 (t, 2H), 3.24 (s, 3H), 2.73 (s, 3H).

LC/MS (Method 1, ESIpos): $R_t$=0.98 min, m/z=425 [M+H]$^+$.

Example 102A

5-Methyl-2,4-dioxo-3-propyl-1-[2-(trifluoromethoxy)ethyl]-1,2,3,4-tetrahydrothieno[2,3-d]pyrimidine-6-carboxylic acid

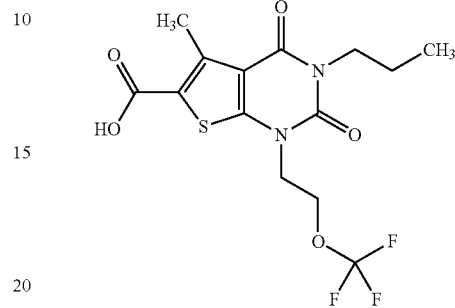

Analogously to the process described in Ex. 43A, 1.25 g (2.86 mmol) of the compound from Ex. 95A and 15 ml of trifluoroacetic acid in 30 ml of dichloromethane gave 1.06 g (95% of theory, purity 97%) of the title compound.

$^1$H-NMR (400 MHz, DMSO-$d_6$, δ/ppm): 13.40 (s, broad, 1H), 4.41 (t, 2H), 4.25 (t, 2H), 3.83 (t, 2H), 2.75 (s, 3H), 1.57 (m, 2H), 0.87 (t, 3H).

LC/MS (Method 9, ESIpos): $R_t$=1.25 min, m/z=381 [M+H]$^+$.

Example 103A

5-Methyl-2,4-dioxo-3-(3,3,3-trifluoro-2-methoxypropyl)-1-(3,3,3-trifluoropropyl)-1,2,3,4-tetrahydrothieno[2,3-d]pyrimidine-6-carboxylic acid (racemate)

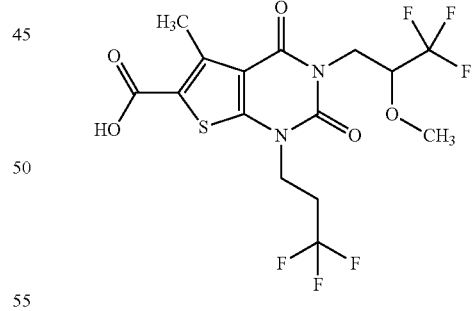

Analogously to the process described in Ex. 43A, 488 mg (0.967 mmol) of the compound from Ex. 96A and 8 ml of trifluoroacetic acid in 16 ml of dichloromethane gave 432 mg (99% of theory) of the title compound.

$^1$H-NMR (400 MHz, DMSO-$d_6$, δ/ppm): 13.50 (s, broad, 1H), 4.29-4.16 (m, 4H), 4.05 (dd, 1H), 3.43 (s, 3H), 2.87-2.75 (m, 2H), 2.76 (s, 3H).

LC/MS (Method 1, ESIpos): $R_t$=1.01 min, m/z=449 [M+H]$^+$.

Example 104A

3-Ethyl-5-methyl-2,4-dioxo-1-[2-(trifluoromethoxy)ethyl]-1,2,3,4-tetrahydrothieno[2,3-d]pyrimidine-6-carboxylic acid

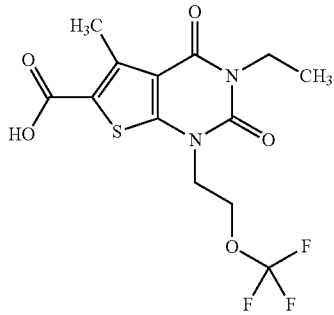 [SMILES: CCn1c(=O)c2c(C)c(C(=O)O)sc2n(CCOC(F)(F)F)c1=O]

30 ml of trifluoroacetic acid were added to a solution of 2.31 g (5.47 mmol) of the compound from Ex. 97A in 60 ml of dichloromethane, and the mixture was stirred at RT for 1 h. The reaction mixture was then concentrated to dryness on a rotary evaporator. The residue that remained was dissolved in about 400 ml of ethyl acetate and washed twice with water and once with saturated sodium chloride solution. After drying over anhydrous magnesium sulphate, the mixture was filtered and concentrated, and the residue was dried under high vacuum. 2.04 g (99% of theory) of the title compound were obtained.

$^1$H-NMR (400 MHz, DMSO-d$_6$, δ/ppm): 13.40 (s, broad, 1H), 4.42 (t, 2H), 4.25 (t, 2H), 3.91 (quart, 2H), 2.76 (s, 3H), 1.13 (t, 3H).

LC/MS (Method 1, ESIpos): R$_t$=0.91 min, m/z=367 [M+H]$^+$.

Example 105A

5-Methyl-2,4-dioxo-3-propyl-1-(3,3,3-trifluoropropyl)-1,2,3,4-tetrahydrothieno[2,3-d]pyrimidine-6-carboxylic acid

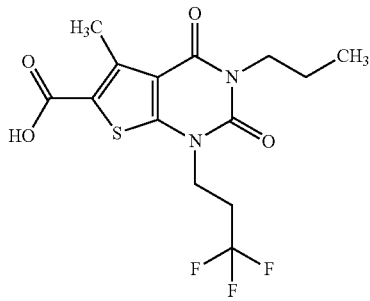 [SMILES: CCCn1c(=O)c2c(C)c(C(=O)O)sc2n(CCC(F)(F)F)c1=O]

Analogously to the process described in Ex. 43A, 4.20 g (9.99 mmol) of the compound from Ex. 98A and 60 ml of trifluoroacetic acid in 120 ml of dichloromethane gave 2.61 g (71% of theory) of the title compound.

$^1$H-NMR (400 MHz, DMSO-d$_6$, δ/ppm): 13.35 (s, broad, 1H), 4.15 (t, 2H), 3.83 (t, 2H), 2.84-2.74 (m, 2H), 2.76 (s, 3H), 1.57 (m, 2H), 0.87 (t, 3H).

LC/MS (Method 1, ESIpos): R$_t$=0.98 min, m/z=365 [M+H]$^+$.

Example 106A 1-(2-Methoxyethyl)-5-methyl-2,4-dioxo-3-propyl-1,2,3,4-tetrahydrothieno[2,3-d]pyrimidine-6-carboxylic acid

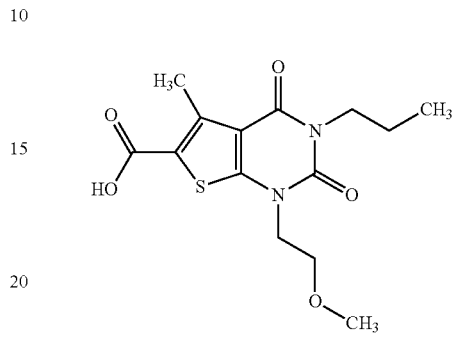

Analogously to the process described in Ex. 43A, 4.15 g (10.8 mmol) of the compound from Ex. 99A and 60 ml of trifluoroacetic acid in 120 ml of dichloromethane gave 3.44 g (97% of theory) of the title compound.

$^1$H-NMR (400 MHz, DMSO-d$_6$, δ/ppm): 13.32 (s, broad, 1H), 4.07 (t, 2H), 3.82 (dd, 2H), 3.65 (t, 2H), 3.24 (s, 3H), 2.75 (s, 3H), 1.57 (m, 2H), 0.87 (t, 3H).

LC/MS (Method 1, ESIpos): R$_t$=0.85 min, m/z=327 [M+H]$^+$.

Example 107A 2-tert-Butyl 4-ethyl 5-amino-3-ethylthiophene-2,4-dicarboxylate

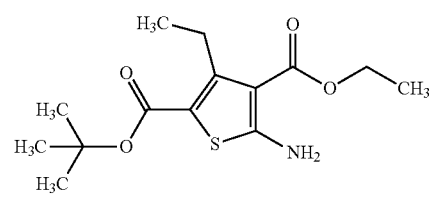 [SMILES: CCOC(=O)c1c(N)sc(C(=O)OC(C)(C)C)c1CC]

6.5 g (37.7 mmol) of tert-butyl 3-oxopentanoate [lit.: S. Luedeke, M. Mueller, M. Richter, Adv. Synth. Catal. 2009, 351 (1-2), 253-259], 4.27 g (37.7 mmol) of ethyl cyanoacetate and 1.33 g (41.5 mmol) of sulphur were initially charged in 10 ml of ethanol and heated to 45° C. 3.8 ml (43.3 mmol) of morpholine were added dropwise to this mixture. The reaction mixture was then stirred at 60° C. for 5 h. All the volatile constituents were then removed on a rotary evaporator. About 250 ml of water were added to the residue that remained, and the mixture was extracted three times with in each case about 200 ml of ethyl acetate. The combined organic extracts were washed with about 200 ml of saturated sodium chloride solution and then dried over anhydrous magnesium sulphate. After filtration, the mixture was concentrated to dryness. The crude product obtained in this manner was purified by MPLC (Biotage cartridge, 340 g of silica gel, mobile phase cyclohexane/ethyl acetate 20:1→10:1). This gave, after combination of the product fractions, concentration and drying under high vacuum, 4.06 g (35% of theory) of the title compound.

¹H-NMR (400 MHz, CDCl₃, δ/ppm): 6.45 (s, broad, 2H), 4.32 (quart, 2H), 3.22 (quart, 2H), 1.54 (s, 9H), 1.37 (t, 3H), 1.16 (t, 3H).

LC/MS (Method 1, ESIpos): $R_t$=1.23 min, m/z=300 [M+H]⁺.

Example 108A 2-tert-Butyl 4-ethyl 3-ethyl-5-[(ethylcarbamoyl)amino]thiophene-2,4-dicarboxylate

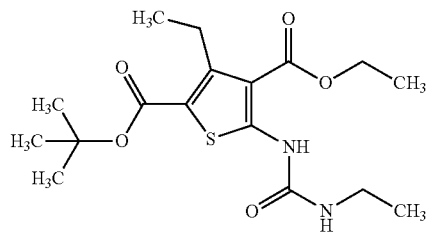 [SMILES: CCNC(=O)Nc1sc(C(=O)OC(C)(C)C)c(CC)c1C(=O)OCC]

Analogously to the process described in Ex. 2A, 1.44 g (4.81 mmol) of the compound from Ex. 107A, 1.56 g (9.62 mmol) of N,N'-carbonyldiimidazole (CDI), 2.7 ml (19.2 mmol) of triethylamine and 9.6 ml (19.2 mmol) of a 2 M solution of ethylamine in THF gave 1.68 g (89% of theory, purity 95%) of the title compound. Here, the reaction time for the reaction with CDI was 4 days, and MPLC purification was carried out using the mobile phase cyclohexane/ethyl acetate 10:1→5:1.

¹H-NMR (400 MHz, CDCl₃, δ/ppm): 10.98 (s, broad, 1H), 4.85 (t, 1H), 4.35 (quart, 2H), 3.37 (m, 2H), 3.27 (quart, 2H), 1.55 (s, 9H), 1.40 (t, 3H), 1.22 (t, 3H), 1.17 (t, 3H).

LC/MS (Method 1, ESIpos): $R_t$=1.24 min, m/z=371 [M+H]⁺.

Example 109A tert-Butyl 3,5-diethyl-2,4-dioxo-1,2,3,4-tetrahydrothieno[2,3-d]pyrimidine-6-carboxylate

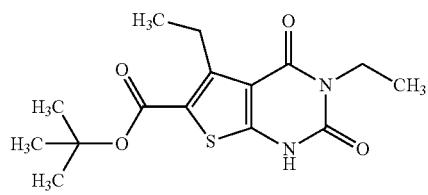 [SMILES: CCc1c(C(=O)OC(C)(C)C)sc2[nH]c(=O)n(CC)c(=O)c12]

Analogously to the process described under Ex. 8A, 1.60 g (4.32 mmol) of the compound from Ex. 108A gave 1.34 g (88% of theory, purity 92%) of the title compound.

¹H-NMR (400 MHz, CDCl₃, δ/ppm): 10.49 (s, broad, 1H), 4.08 (quart, 2H), 3.37 (quart, 2H), 1.58 (s, 9H), 1.29 (t, 3H), 1.23 (t, 3H).

LC/MS (Method 1, ESIpos): $R_t$=1.07 min, m/z=325 [M+H]⁺.

Example 110A tert-Butyl 3,5-diethyl-2,4-dioxo-1-(3,3,3-trifluoropropyl)-1,2,3,4-tetrahydrothieno[2,3-d]pyrimidine-6-carboxylate

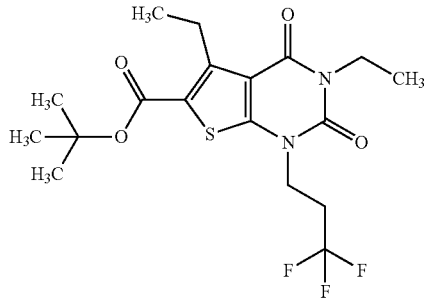

1.48 g (4.53 mmol) of caesium carbonate were added to a solution of 980 mg (3.02 mmol) of the compound from Ex. 109A in 15 ml of DMF, and the mixture was stirred at RT for 20 min. 1.02 g (4.53 mmol) of 3,3,3-trifluoro-1-iodopropane were then added, and the mixture was stirred in a microwave oven (Biotage Initiator with dynamic control of irradiation power) at 100° C. for 2 h. After cooling to RT, about 75 ml of water were added and the mixture was extracted with ethyl acetate. The organic extract was washed with water and saturated sodium chloride solution. After drying over anhydrous magnesium sulphate, the mixture was filtered and concentrated. The residue obtained was first prepurified coarsely by MPLC (Biotage cartridge, 50 g of silica gel, mobile phase cyclohexane/ethyl acetate 20:1). The product-containing fractions were combined and concentrated to dryness. At RT, the residue was stirred in a mixture of 20 ml of pentane and about 0.5 ml of dichloromethane for 16 h. After filtration with suction and drying under high vacuum, a first fraction of 326 mg of the title compound was obtained. The filtrate of stirring was concentrated and the residue was purified by preparative HPLC (Method 6). This gave, after concentration of the product fractions and drying under high vacuum, a second fraction of 565 mg of the title compound. In total, 891 mg (70% of theory) of the title compound were obtained in this manner.

¹H-NMR (400 MHz, CDCl₃, δ/ppm): 4.19 (m, 2H), 4.07 (quart, 2H), 3.38 (quart, 2H), 2.71-2.59 (m, 2H), 1.59 (s, 9H), 1.26 (t, 3H), 1.23 (t, 3H).

LC/MS (Method 1, ESIpos): $R_t$=1.39 min, m/z=421 [M+H]⁺.

Example 111A 3,5-Diethyl-2,4-dioxo-1-(3,3,3-trifluoropropyl)-1,2,3,4-tetrahydrothieno[2,3-d]pyrimidine-6-carboxylic acid

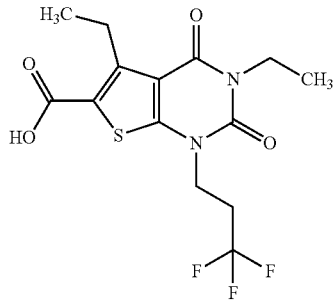 [SMILES: CCc1c(C(=O)O)sc2c1c(=O)n(CC)c(=O)n2CCC(F)(F)F]

Analogously to the process described in Ex. 43A, 1.15 g (2.73 mmol) of the compound from Ex. 110A and 20 ml of trifluoroacetic acid in 60 ml of dichloromethane gave 851 mg (85% of theory) of the title compound.

$^1$H-NMR (400 MHz, DMSO-$d_6$, δ/ppm): 13.43 (s, broad, 1H), 4.15 (t, 2H), 3.92 (quart, 2H), 3.35-3.29 (m, 2H, partially obscured by water signal), 2.86-2.74 (m, 2H), 1.135 (t, 3H), 1.130 (t, 3H).

LC/MS (Method 10, ESIpos): $R_t$=1.26 min, m/z=365 [M+H]$^+$.

Example 112A

3-Ethyl-5-methyl-6-[(3-methyl-4-oxopiperidin-1-yl) carbonyl]-1-(3,3,3-trifluoropropyl)thieno[2,3-d]pyrimidine-2,4(1H,3H)-dione (racemate)

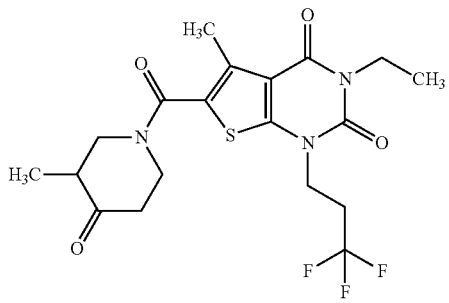 [SMILES: CCn1c(=O)c2c(C)c(C(=O)N3CCC(=O)C(C)C3)sc2n(CCC(F)(F)F)c1=O]

Preparation of the Acid Chloride:

At RT, first 249 µl (2.86 mmol) of oxalyl chloride and then a small drop of DMF were added to a solution of 200 mg (0.571 mmol) of the compound from Ex. 52A in 4 ml of dichloromethane. After the reaction mixture had been stirred at RT for 2.5 h, it was concentrated to dryness on a rotary evaporator. The residue that remained was dried under high vacuum and then reacted further in the next partial step.

Preparation of the Amide:

The acid chloride obtained above was dissolved in 1 ml of dichloromethane and added dropwise to a solution of 171 mg (1.14 mmol) of 3-methylpiperidin-4-one hydrochloride and 398 µl (2.28 mmol) of N,N-diisopropylethylamine in 5 ml of dichloromethane. The reaction mixture was stirred at RT for 2 h. After the mixture had been concentrated to dryness on a rotary evaporator, the crude product was purified by preparative HPLC (Method 6). This gave, after combination of the product fractions, concentration and drying under high vacuum, 236 mg (88% of theory, purity 95%) of the title compound.

$^1$H-NMR (400 MHz, DMSO-$d_6$, δ/ppm): 4.18-4.09 (m, 4H), 3.92 (quart, 2H), 3.53-3.45 (m, 1H), 3.19-3.12 (m, 1H), 2.86-2.74 (m, 2H), 2.71-2.63 (m, 1H), 2.61-2.52 (m, 1H, partially obscured by the DMSO signal), 2.44 (s, 3H), 2.35 (dt, 1H), 1.13 (t, 3H), 0.92 (d, 3H).

LC/MS (Method 1, ESIpos): $R_t$=0.93 min, m/z=446 [M+H]$^+$.

Example 113A

1-[1-Ethyl-2,6-dioxo-4-(pyridinium-1-yl)-1,6-dihydropyrimidin-5(2H)-ylidene]-2,2-difluoroethanolate

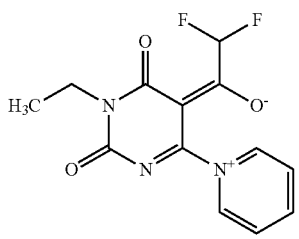 [SMILES: CCN1C(=O)N=C([n+]2ccccc2)/C(=C(\[O-])C(F)F)C1=O]

At RT, 35 ml (430 mmol) of pyridine were added to a suspension of 7.5 g (43.0 mmol) of the compound from Ex. 17A in 110 ml of acetonitrile. 21.4 ml (172 mmol) of difluoroacetic anhydride were then slowly added dropwise. After the addition had ended, stirring was continued at RT for 1 h. About 300 ml of water were then added, and the mixture was extracted four times with about 100 ml of ethyl acetate each time. The organic extract was washed with saturated aqueous sodium chloride solution, dried over anhydrous magnesium sulphate and then concentrated to dryness. At RT, the solid that remained was stirred in a mixture of 50 ml of diisopropyl ether and 50 ml of diethyl ether. This gave, after filtration with suction and drying under high vacuum, 6.38 g (50% of theory) of the title compound.

$^1$H-NMR (400 MHz, DMSO-$d_6$, δ/ppm): 9.20 (d, 2H), 8.80 (t, 1H), 8.25 (t, 2H), 6.97 (t, 1H), 3.89 (quart, 2H), 1.14 (t, 3H).

LC/MS (Method 1, ESIpos): $R_t$=0.46 min, m/z=296 [M+H]$^+$.

Example 114A

Ethyl 5-(difluoromethyl)-3-ethyl-2,4-dioxo-1,2,3,4-tetrahydrothieno[2,3-d]pyrimidine-6-carboxylate

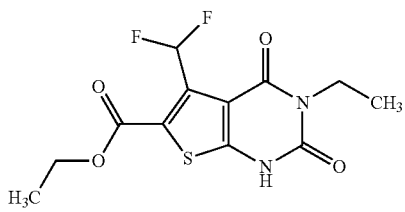 [SMILES: CCOC(=O)c1sc2[nH]c(=O)n(CC)c(=O)c2c1C(F)F]

le;2q1.5 ml (13.8 mmol) of ethyl mercaptoacetate were added to a suspension of 2.04 g (6.92 mmol) of the compound from Ex. 113A in 15 ml of ethanol, and the mixture was stirred at RT for 5 min. 1.61 g (15.2 mmol) of sodium carbonate were then added, and the mixture was heated in a microwave oven (Biotage Initiator with dynamic control of irradiation power) at 120° C. for 1 h. Three such batches were combined and concentrated to dryness on a rotary evaporator. The residue that remained was taken up in about 300 ml of water, acidified slightly by addition of acetic acid and extracted three times with about 100 ml of dichloromethane each. The organic extract was washed with saturated aqueous sodium chloride solution, dried over anhydrous magnesium sulphate, filtered and concentrated. The solid that remained was chromatographed on a silica gel cartridge (Puriflash, cyclohexane/ethyl acetate gradient 3:1→1:1). This gave, after evaporation of the product fractions and drying of the residue under high vacuum, 890 mg (12% of theory) of the title compound.

$^1$H-NMR (400 MHz, DMSO-$d_6$, δ/ppm): 12.59 (s, 1H), 7.71 (t, 1H), 4.32 (quart, 2H), 3.87 (quart, 2H), 1.30 (t, 3H), 1.13 (t, 3H).

LC/MS (Method 1, ESIpos): $R_t$=0.87 min, m/z=319 [M+H]$^+$.

Example 115A

Ethyl 5-(difluoromethyl)-3-ethyl-2,4-dioxo-1-(3,3,3-trifluoropropyl)-1,2,3,4-tetrahydrothieno[2,3-d]-pyrimidine-6-carboxylate

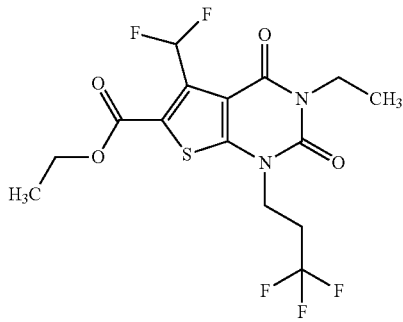 [SMILES: CCOC(=O)c1sc2c(c1C(F)F)c(=O)n(CC)c(=O)n2CCC(F)(F)F]

1.35 g (4.15 mmol) of caesium carbonate were added to a solution of 880 mg (2.76 mmol) of the compound from Ex. 114A in 12 ml of DMF, and the mixture was stirred at RT for 20 min. 929 mg (4.15 mmol) of 3,3,3-trifluoro-1-iodopropane were then added, and the mixture was heated at 80° C. for 2 h. After cooling to RT, the mixture was diluted with about 100 ml of ethyl acetate and, in succession, washed twice with in each case about 100 ml of water and once with about 100 ml of saturated sodium chloride solution. After drying over anhydrous magnesium sulphate, the mixture was filtered and concentrated. The crude product was purified by preparative HPLC (Method 6). The product fractions were combined and concentrated, and the residue was dried under high vacuum. 750 mg (63% of theory) of the title compound were obtained.

$^1$H-NMR (400 MHz, DMSO-$d_6$, δ/ppm): 7.74 (t, 1H), 4.36 (quart, 2H), 4.20 (t, 2H), 3.92 (quart, 2H), 2.88-2.76 (m, 2H), 1.32 (t, 3H), 1.14 (t, 3H).

LC/MS (Method 1, ESIpos): $R_t$=1.13 min, m/z=415 [M+H]$^+$.

Example 116A

Ethyl 5-(difluoromethyl)-3-ethyl-2,4-dioxo-1-[2-(trifluoromethoxy)ethyl]-1,2,3,4-tetrahydrothieno-[2,3-d]pyrimidine-6-carboxylate

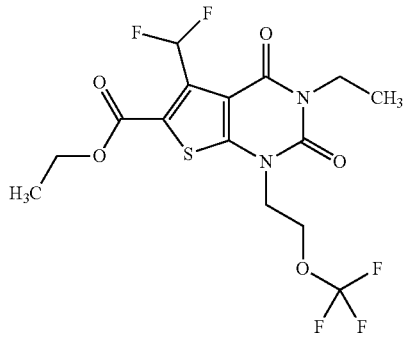 [SMILES: CCOC(=O)c1sc2c(c1C(F)F)c(=O)n(CC)c(=O)n2CCOC(F)(F)F]

Analogously to the process described in Ex. 115A, 500 mg (1.57 mmol) of the compound from Ex. 114A and 455 mg (2.36 mmol) of 1-bromo-2-(trifluoromethoxy)ethane [commercially available; lit.: P. E. Aldrich, W. A. Sheppard, J. Org. Chem. 1964, 29 (1), 11-15] gave 385 mg (56% of theory) of the title compound. Here, purification of the crude product by preparative HPLC was carried out according to Method 5.

$^1$H-NMR (400 MHz, DMSO-$d_6$, δ/ppm): 7.73 (t, 1H), 4.43 (t, 2H), 4.35 (quart, 2H), 4.32 (t, 2H), 3.93 (quart, 2H), 1.31 (t, 3H), 1.14 (t, 3H).

LC/MS (Method 1, ESIpos): $R_t$=1.12 min, m/z=431 [M+H]$^+$.

Example 117A tert-Butyl 5-methyl-2,4-dioxo-3-(2-phenylethyl)-1-[2-(trifluoromethoxy)ethyl]-1,2,3,4-tetrahydrothieno[2,3-d]pyrimidine-6-carboxylate

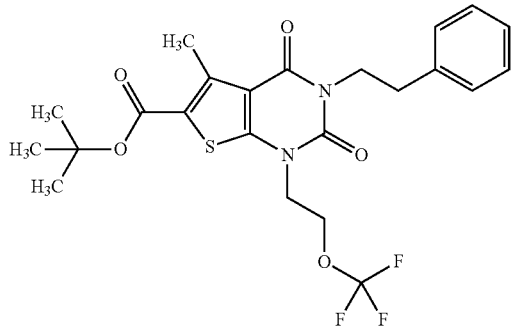 [SMILES: Cc1c(C(=O)OC(C)(C)C)sc2c1c(=O)n(CCc1ccccc1)c(=O)n2CCOC(F)(F)F]

1.26 g (3.88 mmol) of caesium carbonate were added to a solution of 1.0 g (2.59 mmol) of the compound from Ex. 8A in 15 ml of DMF, and the mixture was stirred at RT for 20 min. 749 mg (3.88 mmol) of 1-bromo-2-(trifluoromethoxy)ethane [commercially available; lit.: P. E. Aldrich, W. A. Sheppard, J. Org. Chem. 1964, 29 (1), 11-15] were then added, and the mixture was heated at 80° C. for 2 h. After cooling to RT, about 300 ml of water were added and the mixture was extracted three times in succession with in each case about 75 ml of diethyl ether. The combined organic extract was washed in each case once with about 100 ml of water and about 100 ml of saturated sodium chloride solution. After drying over anhydrous magnesium sulphate, the mixture was filtered and concentrated. At 0° C., the crude product was stirred with 30 ml of pentane, to which a few drops of dichloromethane had been added. The solid was filtered off with suction, and gave, after drying under high vacuum, a first fraction of 665 mg of the title compound. The concentrated mother liquor gave, after purification by preparative HPLC (Method 15), a second fraction of 402 mg of the title compound. A total of 1.07 g (82% of theory) of the title compound were thus obtained.

$^1$H-NMR (400 MHz, CDCl$_3$, δ/ppm): 7.30-7.20 (m, 5H, partially obscured by the CHCl$_3$ signal), 4.28 (t, 2H), 4.22 (t, 2H), 4.21 (t, 2H), 2.97-2.93 (m, 2H), 2.85 (s, 3H), 1.59 (s, 9H).

LC/MS (Method 1, ESIpos): R$_t$=1.43 min, m/z=499 [M+H]$^+$.

Example 118A

5-Methyl-2,4-dioxo-3-(2-phenylethyl)-1-[2-(trifluoromethoxy)ethyl]-1,2,3,4-tetrahydrothieno[2,3-d] pyrimidine-6-carboxylic acid

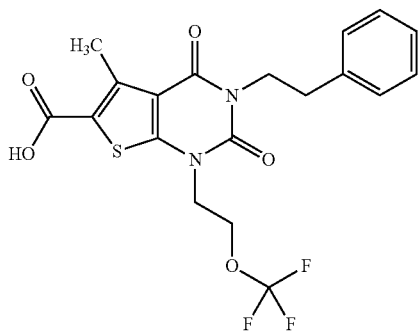 [SMILES: Cc1c(C(=O)O)sc2c1c(=O)n(CCc1ccccc1)c(=O)n2CCOC(F)(F)F]

12.5 ml of trifluoroacetic acid were added to a solution of 1.0 g (2.01 mmol) of the compound from Ex. 117A in 25 ml of dichloromethane, and the mixture was stirred at RT for 1 h. The reaction mixture was then concentrated to dryness on a rotary evaporator. The residue that remained was stirred at RT in a mixture of 40 ml of diethyl ether and 20 ml of pentane overnight. After filtration with suction and drying under high vacuum, a first fraction of 559 mg of the title compound was obtained. The concentrated mother liquor gave, after purification by preparative HPLC (Method 5), a second fraction of 266 mg of the title compound. A total of 825 mg (92% of theory) of the title compound were thus obtained.

$^1$H-NMR (400 MHz, DMSO-d$_6$, δ/ppm): 13.42 (broad, 1H), 7.32-7.27 (m, 2H), 7.24-7.19 (m, 3H), 4.39 (t, 2H), 4.25 (t, 2H), 4.10-4.06 (m, 2H), 2.87-2.82 (m, 2H), 2.75 (s, 3H).

LC/MS (Method 1, ESIpos): R$_t$=1.11 min, m/z=443 [M+H]$^+$.

Example 119A 5-(Difluoromethyl)-3-ethyl-2,4-dioxo-1-(3,3,3-trifluoropropyl)-1,2,3,4-tetrahydrothieno[2,3-d]-pyrimidine-6-carboxylic acid

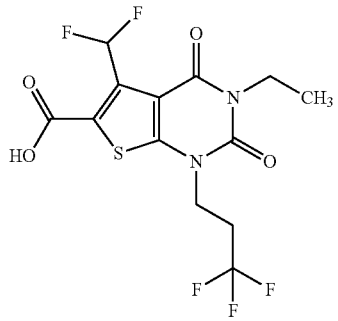 [SMILES: CCn1c(=O)c2c(C(F)F)c(C(=O)O)sc2n(CCC(F)(F)F)c1=O]

Analogously to the process described under Ex. 55A, 733 mg (1.77 mmol) of the compound from Ex. 115A gave 668 mg (95% of theory) of the title compound.

$^1$H-NMR (400 MHz, DMSO-d$_6$, δ/ppm): 7.77 (t, 1H), 4.19 (t, 2H), 3.92 (quart, 2H), 2.88-2.75 (m, 2H), 1.14 (t, 3H).

LC/MS (Method 1, ESIpos): R$_t$=0.85 min, m/z=387 [M+H]$^+$.

Example 120A 5-(Difluoromethyl)-3-ethyl-2,4-dioxo-1-[2-(trifluoromethoxy)ethyl]-1,2,3,4-tetrahydrothieno[2,3-d]-pyrimidine-6-carboxylic acid

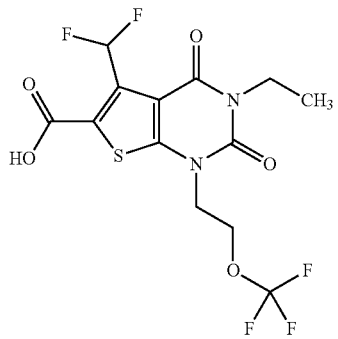 [SMILES: CCn1c(=O)c2c(C(F)F)c(C(=O)O)sc2n(CCOC(F)(F)F)c1=O]

Analogously to the process described under Ex. 55A, 365 mg (0.848 mmol) of the compound from Ex. 116A gave 320 mg (91% of theory) of the title compound. Here, the reaction time was 3 h.

$^1$H-NMR (400 MHz, DMSO-d$_6$, δ/ppm): 14.38 (very broad, 1H), 7.77 (t, 1H), 4.43 (t, 2H), 4.30 (t, 2H), 3.92 (quart, 2H), 1.14 (t, 3H).

LC/MS (Method 1, ESIpos): R$_t$=0.85 min, m/z=403 [M+H]$^+$.

Example 121A

1-{[5-Methyl-2,4-dioxo-3-(2-oxo-2-phenylethyl)-1-(3,3,3-trifluoropropyl)-1,2,3,4-tetrahydrothieno[2,3-d]pyrimidin-6-yl]carbonyl}piperidin-4-yl acetate

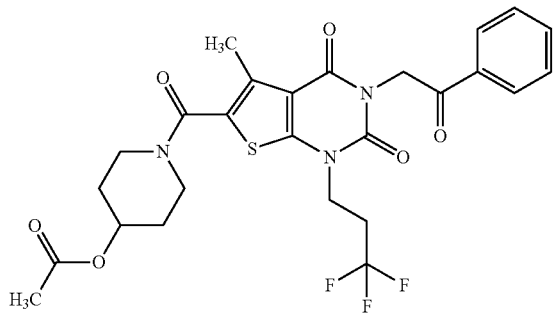 [SMILES: CC(=O)OC1CCN(C(=O)c2sc3c(c2C)c(=O)n(CC(=O)c2ccccc2)c(=O)n3CCC(F)(F)F)CC1]

Analogously to the process described in Ex. 78A, 500 mg (1.12 mmol) of the compound from Ex. 60A and 190 mg (1.23 mmol) of 2-chloroacetophenone gave 573 mg (88% of theory) of the title compound. In this case, purification of the product was carried out by MPLC (Biotage cartridge, 50 g of silica gel, cyclohexane/ethyl acetate gradient 2:1→1:1).

$^1$H-NMR (400 MHz, DMSO-$d_6$, δ/ppm): 8.10 (d, 2H), 7.74 (t, 1H), 7.60 (t, 2H), 5.43 (s, 2H), 4.94-4.90 (m, 1H), 4.19 (t, 2H), 3.80-3.74 (m, 2H), 3.44-3.40 (m, 2H), 2.86-2.78 (m, 2H), 2.38 (s, 3H), 2.03 (s, 3H), 1.92-1.87 (m, 2H), 1.60-1.54 (m, 2H).

LC/MS (Method 1, ESIpos): $R_t$=1.06 min, m/z=566 [M+H]$^+$.

Example 122A

1-{[5-Methyl-2,4-dioxo-3-(3,3,3-trifluoro-2-phenylpropyl)-1-(3,3,3-trifluoropropyl)-1,2,3,4-tetrahydrothieno[2,3-d]pyrimidin-6-yl]carbonyl}piperidin-4-ylacetate (racemate)

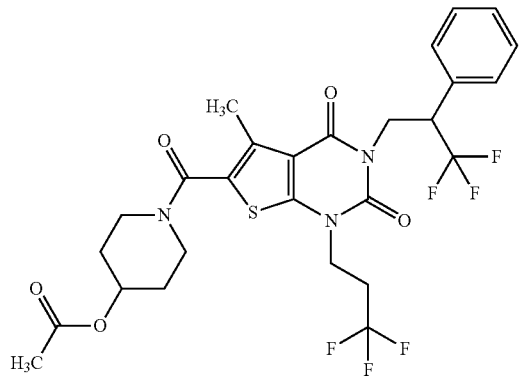 [SMILES: CC(=O)OC1CCN(C(=O)c2sc3c(c2C)c(=O)n(CC(c2ccccc2)C(F)(F)F)c(=O)n3CCC(F)(F)F)CC1]

Analogously to the process described in Ex. 63A, 100 mg (0.223 mmol) of the compound from Ex. 60A and 64 mg (0.335 mmol) of racemic 3,3,3-trifluoro-2-phenylpropanol [prepared analogously to J. Y. Hamilton et al., *Synthesis* 2013, 45 (13), 1857-1862] gave 11 mg (7% of theory) of the title compound. A second batch of 200 mg (0.447 mmol) of the compound from Ex. 60A gave 17 mg (6% of theory) of the title compound.

$^1$H-NMR (400 MHz, CDCl$_3$, δ/ppm): 7.37-7.30 (m, 5H), 5.06-5.00 (m, 1H), 4.62-4.50 (m, 2H), 4.16-3.98 (m, 3H), 3.87-3.79 (m, 2H), 3.54-3.46 (m, 2H), 2.52-2.40 (m, 2H), 2.47 (s, 3H), 2.09 (s, 3H), 1.98-1.90 (m, 2H), 1.77-1.68 (m, 2H).

LC/MS (Method 1, ESIpos): $R_t$=1.19 min, m/z=620 [M+H]$^+$.

Example 123A

1-{[3-(4,4-Difluorobut-3-en-1-yl)-5-methyl-2,4-dioxo-1-(3,3,3-trifluoropropyl)-1,2,3,4-tetrahydrothieno[2,3-d]pyrimidin-6-yl]carbonyl}piperidin-4-ylacetate

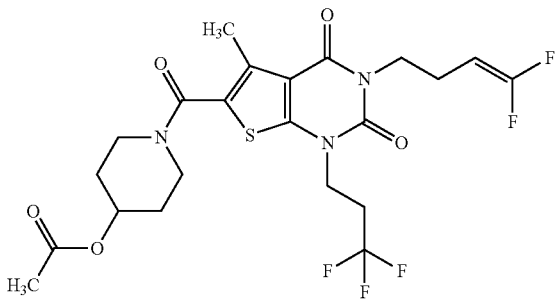 [SMILES: CC(=O)OC1CCN(C(=O)c2sc3c(c2C)c(=O)n(CCC=C(F)F)c(=O)n3CCC(F)(F)F)CC1]

Analogously to the process described in Ex. 78A, 100 mg (0.223 mmol) of the compound from Ex. 60A and 46 mg (0.268 mmol) of 4-bromo-1,1-difluorobutene gave 97 mg (80% of theory) of the title compound.

$^1$H-NMR (400 MHz, DMSO-$d_6$, δ/ppm): 4.95-4.89 (m, 1H), 4.53 (dtd, 1H), 4.13 (t, 2H), 3.93 (t, 2H), 3.79-3.71 (m, 2H), 3.44-3.37 (m, 2H, partially obscured by the water signal), 2.85-2.71 (m, 2H), 2.39 (s, 3H), 2.27 (quart, 2H), 2.02 (s, 3H), 1.92-1.85 (m, 2H), 1.60-1.52 (m, 2H).

LC/MS (Method 1, ESIpos): $R_t$=1.10 min, m/z=538 [M+H]$^+$.

Example 124A

1-{[3-(2-Hydroxy-2-phenylethyl)-5-methyl-2,4-dioxo-1-(3,3,3-trifluoropropyl)-1,2,3,4-tetrahydrothieno[2,3-d]pyrimidin-6-yl]carbonyl}piperidin-4-ylacetate (racemate)

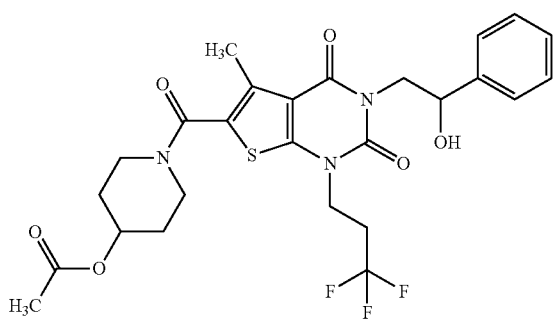

At RT, a little at a time and over a period of about 2 h, a total of 18 mg (0.476 mmol) of solid sodium borohydride was added to a solution of 538 mg (0.951 mmol) of the compound from Ex. 121A in 40 ml of methanol and 1 ml of dichloromethane. After a further 30 min at RT, water was added and the mixture was extracted repeatedly with ethyl acetate. The combined organic extract was washed with saturated sodium chloride solution, dried over anhydrous magnesium sulphate, filtered and concentrated. The residue obtained was purified by preparative HPLC (Method 16). This gave, after evaporation of the product fractions and drying of the residue under high vacuum, 435 mg (80% of theory) of the title compound.

$^1$H-NMR (400 MHz, DMSO-$d_6$, δ/ppm): 7.38-7.31 (m, 4H), 7.28-7.23 (m, 1H), 5.39 (d, 1H), 4.96-4.89 (m, 2H), 4.23 (dd, 1H), 4.11 (t, 2H), 3.82 (dd, 1H), 3.78-3.72 (m, 2H), 3.44-3.37 (m, 2H), 2.79-2.67 (m, 2H), 2.39 (s, 3H), 2.03 (s, 3H), 1.93-1.85 (m, 2H), 1.61-1.52 (m, 2H).

LC/MS (Method 1, ESIpos): $R_t$=0.98 min, m/z=568 [M+H]$^+$.

Example 125A

1-{[3-(2-Hydroxy-2-phenylethyl)-5-methyl-2,4-di-oxo-1-(3,3,3-trifluoropropyl)-1,2,3,4-tetrahydroth-ieno[2,3-d]pyrimidin-6-yl]carbonyl}piperidin-4-ylacetate (enantiomer 1)

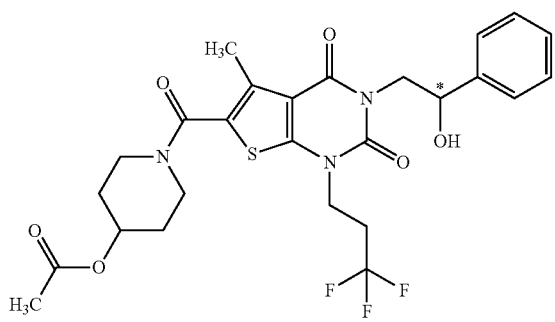

452 mg (0.796 mmol) of the racemic compound from Ex. 124A were dissolved in 20 ml of ethanol/acetonitrile (1:1) and, in 40 portions, separated into the enantiomers by preparative SFC-HPLC on a chiral phase [column: Daicel Chiralpak IC 5 μm 250 mm×20 mm; mobile phase: carbon dioxide/methanol 60:40; flow rate: 80 ml/min, temperature: 40° C.; detection: 210 nm]. This gave, after concentration of the product fractions and drying of the residue under high vacuum, 210 mg (92% of theory) of enantiomer 1.

$^1$H-NMR (400 MHz, DMSO-$d_6$, δ/ppm): 7.38-7.31 (m, 4H), 7.28-7.23 (m, 1H), 5.39 (d, 1H), 4.96-4.89 (m, 2H), 4.23 (dd, 1H), 4.11 (t, 2H), 3.82 (dd, 1H), 3.79-3.71 (m, 2H), 3.47-3.37 (m, 2H), 2.80-2.66 (m, 2H), 2.39 (s, 3H), 2.03 (s, 3H), 1.93-1.85 (m, 2H), 1.61-1.52 (m, 2H).

Chiral analytical SFC [column: Daicel Chiralpak IC 5 μm 250 mm×4.6 mm; mobile phase: carbon dioxide/methanol 60:40; flow rate: 3 ml/min, temperature: 40° C.; detection: 210 nm]: $R_t$=6.53 min; 99.9% ee.

Example 126A

1-{[3-(2-Hydroxy-2-phenylethyl)-5-methyl-2,4-di-oxo-1-(3,3,3-trifluoropropyl)-1,2,3,4-tetrahydroth-ieno[2,3-d]pyrimidin-6-yl]carbonyl}piperidin-4-ylacetate (enantiomer 2)

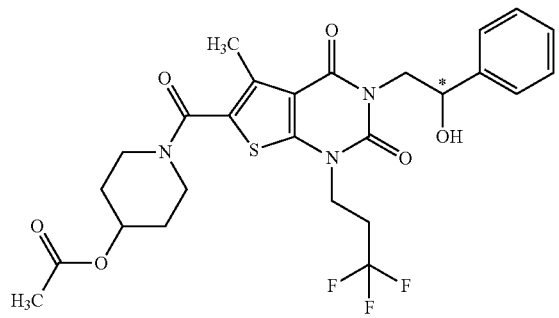

452 mg (0.796 mmol) of the racemic compound from Ex. 124A were dissolved in 20 ml of ethanol/acetonitrile (1:1) and, in 40 portions, separated into the enantiomers by preparative SFC-HPLC on a chiral phase [column: Daicel Chiralpak IC 5 μm 250 mm×20 mm; mobile phase: carbon dioxide/methanol 60:40; flow rate: 80 ml/min, temperature: 40° C.; detection: 210 nm]. This gave, after concentration of the product fractions and drying of the residue under high vacuum, 206 mg (91% of theory) of enantiomer 2.

$^1$H-NMR (400 MHz, DMSO-$d_6$, δ/ppm): 7.38-7.31 (m, 4H), 7.28-7.23 (m, 1H), 5.39 (d, 1H), 4.96-4.89 (m, 2H), 4.23 (dd, 1H), 4.11 (t, 2H), 3.82 (dd, 1H), 3.79-3.71 (m, 2H), 3.47-3.37 (m, 2H), 2.79-2.66 (m, 2H), 2.39 (s, 3H), 2.03 (s, 3H), 1.93-1.85 (m, 2H), 1.61-1.52 (m, 2H).

Chiral analytical SFC [column: Daicel Chiralpak IC 5 μm 250 mm×4.6 mm; mobile phase: carbon dioxide/methanol 60:40; flow rate: 3 ml/min, temperature: 40° C.; detection: 210 nm]: $R_t$=5.04 min; 99.9% ee.

Example 127A

1-{[3-(2-Fluoro-2-phenylethyl)-5-methyl-2,4-dioxo-1-(3,3,3-trifluoropropyl)-1,2,3,4-tetrahydrothieno[2,3-d]pyrimidin-6-yl]carbonyl}piperidin-4-ylacetate (enantiomer 1)

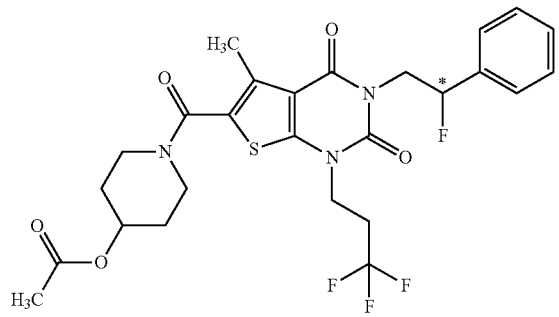 [SMILES: CC(=O)OC1CCN(C(=O)c2sc3c(c2C)c(=O)n(CC(F)c2ccccc2)c(=O)n3CCC(F)(F)F)CC1]

At −20° C., a solution of 28 μl (0.211 mmol) of diethylaminosulphur trifluoride (DAST) in 0.5 ml of dichloromethane was added dropwise to a solution of 100 mg (0.176 mmol) of the compound from Ex. 125A in 5 ml of dichloromethane. The reaction mixture was then stirred at RT for 3 h. The same amount of DAST in dichloromethane was then added again. After a further 4 h of stirring, semisaturated aqueous sodium bicarbonate solution was added and the mixture was extracted with dichloromethane. The organic extract was dried over anhydrous magnesium sulphate, filtered and concentrated. The residue was purified by preparative HPLC (Method 5). This gave, after concentration of the product fractions and drying of the residue under high vacuum, 84 mg (83% of theory) of the title compound.

$^1$H-NMR (400 MHz, DMSO-$d_6$, δ/ppm): 7.49-7.40 (m, 5H), 5.77 (ddd, 1H), 4.92 (m, 1H), 4.63 (m, 1H), 4.16 (t, 2H), 4.00 (ddd, 1H), 3.80-3.72 (m, 2H), 3.45-3.37 (m, 2H), 2.86-2.74 (m, 2H), 2.41 (s, 3H), 2.03 (s, 3H), 1.93-1.85 (m, 2H), 1.61-1.52 (m, 2H).

LC/MS (Method 1, ESIpos): $R_t$=1.11 min, m/z=570 [M+H]$^+$.

Example 128A

1-{[3-(2-Fluoro-2-phenylethyl)-5-methyl-2,4-dioxo-1-(3,3,3-trifluoropropyl)-1,2,3,4-tetrahydrothieno[2,3-d]pyrimidin-6-yl]carbonyl}piperidin-4-ylacetate (enantiomer 2)

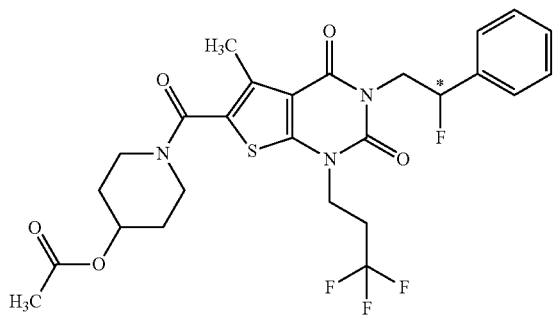 [SMILES: CC(=O)OC1CCN(C(=O)c2sc3c(c2C)c(=O)n(CC(F)c2ccccc2)c(=O)n3CCC(F)(F)F)CC1]

At −20° C., a solution of 20 μl (0.148 mmol) of diethylaminosulphur trifluoride (DAST) in 0.5 ml of dichloromethane was added dropwise to a solution of 70 mg (0.123 mmol) of the compound from Ex. 126A in 4 ml of dichloromethane. The reaction mixture was subsequently stirred at −20° C. for 1 h. The same amount of DAST in dichloromethane was then added again. After a further hour at −20° C., the cooling bath was removed and stirring was continued at RT. After 6 h at RT, semisaturated aqueous sodium bicarbonate solution was added and the mixture was extracted with dichloromethane. The organic extract was dried over anhydrous magnesium sulphate, filtered and concentrated. The residue was purified by preparative HPLC (Method 5). This gave, after concentration of the product fractions and drying of the residue under high vacuum, 62 mg (88% of theory) of the title compound.

$^1$H-NMR (400 MHz, DMSO-$d_6$, δ/ppm): 7.49-7.41 (m, 5H), 5.77 (ddd, 1H), 4.92 (m, 1H), 4.63 (m, 1H), 4.16 (t, 2H), 3.99 (ddd, 1H), 3.81-3.72 (m, 2H), 3.45-3.37 (m, 2H), 2.86-2.74 (m, 2H), 2.41 (s, 3H), 2.03 (s, 3H), 1.93-1.85 (m, 2H), 1.61-1.52 (m, 2H).

LC/MS (Method 1, ESIpos): $R_t$=1.11 min, m/z=570 [M+H]$^+$.

Example 129A

1-{[3-(2-Hydroxy-2-phenylpropyl)-5-methyl-2,4-dioxo-1-(3,3,3-trifluoropropyl)-1,2,3,4-tetrahydrothieno[2,3-d]pyrimidin-6-yl]carbonyl}piperidin-4-ylacetate (racemate)

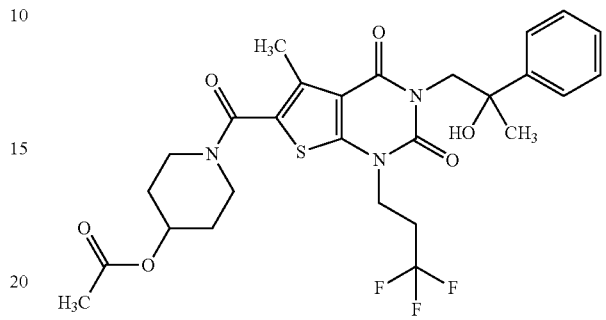

105 mg (0.186 mmol) of the compound from Ex. 121A were dissolved in 3 ml of anhydrous THF, and 186 μl (0.186 mmol) of a 1 M solution of methylmagnesium bromide in THF were added at 0° C. After 3 h at 0° C., an identical amount of Grignard reagent was added. After a further 30 min, about 0.5 ml of saturated aqueous ammonium chloride solution was added, the reaction mixture was then diluted with ethyl acetate and finally anhydrous magnesium sulphate was added in such an amount that the aqueous phase was taken up completely. The mixture was then filtered off with suction and the filtrate was evaporated. The filtrate residue was purified by preparative HPLC (Method 5). This gave, after combination of the product fractions, concentration and drying under high vacuum, 55 mg (50% of theory) of the title compound.

$^1$H-NMR (400 MHz, DMSO-$d_6$, δ/ppm): 7.48 (d, 2H), 7.30 (t, 2H), 7.21 (t, 1H), 5.04 (s, 1H), 4.96-4.89 (m, 1H), 4.18 (quart, 2H), 4.12-4.03 (m, 2H), 3.79-3.72 (m, 2H), 3.44-3.37 (m, 2H), 2.76-2.64 (m, 2H), 2.36 (s, 3H), 2.03 (s, 3H), 1.93-1.85 (m, 2H), 1.61-1.52 (m, 2H), 1.42 (s, 3H).

LC/MS (Method 1, ESIpos): $R_t$=1.10 min, m/z=582 [M+H]$^+$.

Example 130A

1-{[3-Ethyl-5-methyl-1-(3-methylbutyl)-2,4-dioxo-1,2,3,4-tetrahydrothieno[2,3-d]pyrimidin-6-yl]carbonyl}piperidin-4-yl acetate

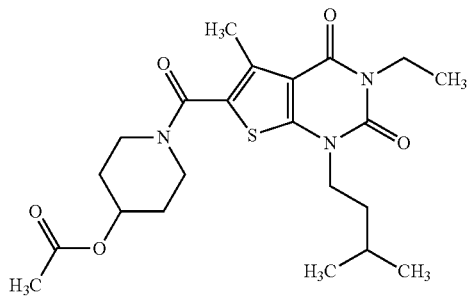 [SMILES: CCn1c(=O)c2c(C)c(C(=O)N3CCC(OC(C)=O)CC3)sc2n(CCC(C)C)c1=O]

Analogously to the process described in Ex. 83A, 150 mg (0.395 mmol) of the compound from Ex. 62A and 117 mg (0.593 mmol) of 1-iodo-3-methylbutane gave 150 mg (84% of theory) of the title compound. In deviation, the reaction time in the microwave oven was 60 min, and purification by preparative HPLC was carried out according to Method 6.

$^1$H-NMR (400 MHz, DMSO-$d_6$, δ/ppm): 4.91 (m, 1H), 3.92-3.87 (m, 2H), 3.91 (quart, 2H), 3.78-3.71 (m, 2H), 3.40 (m, 2H), 2.39 (s, 3H), 2.02 (s, 3H), 1.91-1.84 (m, 2H), 1.65 (sept, 1H), 1.60-1.54 (m, 4H), 1.12 (t, 3H), 0.95 (d, 6H).

LC/MS (Method 1, ESIpos): $R_t$=1.10 min, m/z=450 [M+H]$^+$.

Example 131A

1-{[3-Ethyl-5-methyl-2,4-dioxo-1-(4,4,4-trifluorobutyl)-1,2,3,4-tetrahydrothieno[2,3-d]pyrimidin-6-yl]carbonyl}piperidin-4-yl acetate

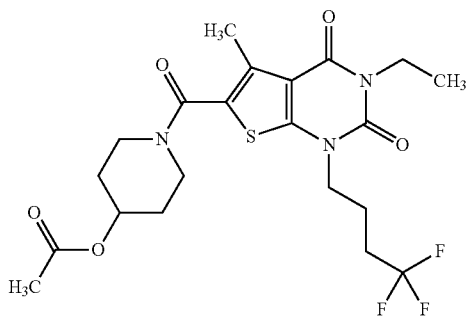

Analogously to the process described in Ex. 83A, 150 mg (0.395 mmol) of the compound from Ex.

62A and 141 mg (0.593 mmol) of 4,4,4-trifluoro-1-iodobutane gave 163 mg (84% of theory) of the title compound. In deviation, the reaction time in the microwave oven was 60 min, and purification by preparative HPLC was carried out according to Method 6.

$^1$H-NMR (400 MHz, DMSO-$d_6$, δ/ppm): 4.92 (m, 1H), 3.97 (t, 2H), 3.90 (quart, 2H), 3.79-3.71 (m, 2H), 3.40 (m, 2H), 2.47-2.38 (m, 2H), 2.39 (s, 3H), 2.02 (s, 3H), 1.95-1.85 (m, 4H), 1.60-1.51 (m, 2H), 1.13 (t, 3H).

LC/MS (Method 1, ESIpos): $R_t$=1.01 min, m/z=490 [M+H]$^+$.

Example 132A

1-{[3-Ethyl-5-methyl-2,4-dioxo-1-(3,4,4-trifluorobut-3-en-1-yl)-1,2,3,4-tetrahydrothieno[2,3-d]pyrimidin-6-yl]carbonyl}piperidin-4-yl acetate

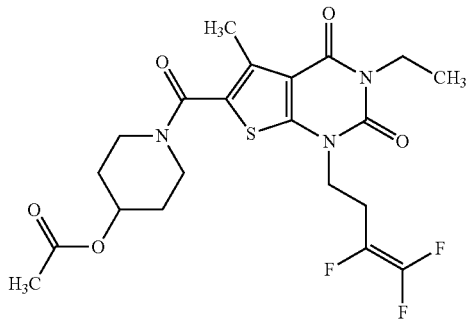 [SMILES: CCn1c(=O)c2c(C)c(C(=O)N3CCC(OC(C)=O)CC3)sc2n(CCC(F)=C(F)F)c1=O]

Analogously to the process described in Ex. 83A, 150 mg (0.395 mmol) of the compound from Ex. 62A and 140 mg (0.593 mmol) of 1,1,2-trifluoro-4-iodobut-1-ene gave 72 mg (37% of theory) of the title compound. In deviation, the reaction time in the microwave oven was 90 min, and purification by preparative HPLC was carried out according to Method 6.

$^1$H-NMR (400 MHz, DMSO-$d_6$, δ/ppm): 4.91 (m, 1H), 4.10 (t, 2H), 3.91 (quart, 2H), 3.78-3.70 (m, 2H), 3.39 (m, 2H), 2.82 (m, 2H), 2.39 (s, 3H), 2.02 (s, 3H), 1.91-1.84 (m, 2H), 1.60-1.51 (m, 2H), 1.12 (t, 3H).

LC/MS (Method 1, ESIpos): $R_t$=1.00 min, m/z=488 [M+H]$^+$.

Example 133A

6-Chloro-3-isobutylpyrimidine-2,4(1H,3H)-dione

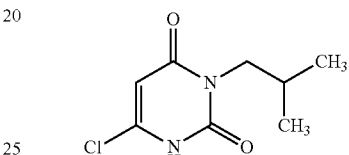

At a temperature of 0° C., 18.8 ml (201 mmol) of phosphorus oxychloride were added carefully to 4 ml of 50% strength aqueous ethanol. Subsequently, likewise at 0° C., 4.15 g (22.6 mmol) of 1-isobutylpyrimidine-2,4,6(1H,3H,5H)-trione [lit.: G. Brückmann, S. D. Isaacs, J. Am. Chem. Soc. 1949, 71 (2), 390-392] were added a little at a time. After the addition had ended, the reaction mixture was heated first for 30 min at 50° C. and then for 2 h at 100° C. After cooling to RT, the reaction mixture was poured into about 80 ml of ice-water. The precipitated solid was filtered off with suction and washed with water. Drying under high vacuum gave 3.20 g (70% of theory) of the title compound.

$^1$H-NMR (400 MHz, DMSO-$d_6$, δ/ppm): 12.33 (br. s, 1H), 5.89 (s, 1H), 3.56 (d, 2H), 1.99 (m, 1H), 0.83 (d, 6H).

LC/MS (Method 1, ESIpos): $R_t$=0.64 min, m/z=203/205 [M+H]$^+$.

Example 134A 2,2-Difluoro-1-[1-isobutyl-2,6-dioxo-4-(pyridinium-1-yl)-1,6-dihydropyrimidin-5(2H)-ylidene]ethanolate

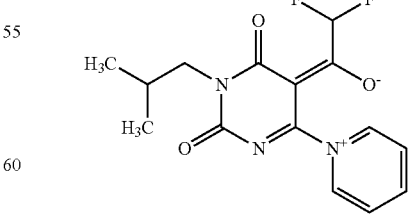

At RT, 13 ml (158 mmol) of pyridine were added to a suspension of 3.2 g (15.8 mmol) of the compound from Ex. 133A in 35 ml of ethyl acetate. 7.9 ml (63.2 mmol) of difluoroacetic anhydride were then slowly added dropwise.

After the dropwise addition had ended, stirring was continued at RT for 1 h. The solid was then filtered off with suction, washed with a little ethyl acetate and pentane and dried under high vacuum. This gave 2.30 g (45% of theory) of the title compound.

$^1$H-NMR (400 MHz, DMSO-$d_6$, δ/ppm): 9.22 (d, 2H), 8.80 (t, 1H), 8.25 (t, 2H), 6.95 (t, 1H), 3.70 (d, 2H), 2.08 (m, 1H), 0.89 (d, 6H).

LC/MS (Method 1, ESIpos): $R_t$=0.66 min, m/z=324 [M+H]$^+$.

Example 135A

Ethyl 5-(difluoromethyl)-3-isobutyl-2,4-dioxo-1,2,3,4-tetrahydrothieno[2,3-d]pyrimidine-6-carboxylate

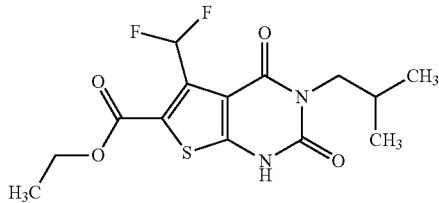 [SMILES: CCOC(=O)c1sc2[nH]c(=O)n(CC(C)C)c(=O)c2c1C(F)F]

757 µl (6.90 mmol) of ethyl mercaptoacetate were added to a suspension of 1.11 g (3.45 mmol) of the compound from Ex. 134A in 14 ml of ethanol, and the mixture was stirred at RT for 5 min. 804 mg (7.59 mmol) of sodium carbonate were then added, and the mixture was heated in a microwave oven (Biotage Initiator with dynamic control of irradiation power) at 125° C. for 2 h. Two such batches were then combined and concentrated to dryness on a rotary evaporator. The residue that remained was taken up in about 300 ml of water, acidified slightly by addition of acetic acid and extracted three times with about 100 ml of dichloromethane each. The organic extract was washed with saturated aqueous sodium chloride solution, dried over anhydrous magnesium sulphate, filtered and concentrated. The residue was suspended in a little dichloromethane and stirred at RT. The solid was then filtered off with suction and dried under high vacuum. This gave a first fraction of 1.59 g of the title compound. The filtrate was concentrated to dryness and chromatographed on a silica gel cartridge (Biotage, 100 g of silica gel, mobile phase cyclohexane/ethyl acetate 3:1→1:1). Evaporation of the product fractions and drying of the residue under high vacuum gave 355 mg of a second fraction of the title compound. A total of 1.94 g (81% of theory) of the title compound were thus obtained.

$^1$H-NMR (400 MHz, DMSO-$d_6$, δ/ppm): 12.59 (s, 1H), 7.70 (t, 1H), 4.32 (quart, 2H), 3.68 (d, 2H), 2.03 (m, 1H), 1.30 (t, 3H), 0.86 (d, 6H).

LC/MS (Method 1, ESIpos): $R_t$=0.98 min, m/z=347 [M+H]$^+$.

Example 136A

Ethyl 5-(difluoromethyl)-3-isobutyl-2,4-dioxo-1-[2-(trifluoromethoxy)ethyl]-1,2,3,4-tetrahydrothieno[2,3-d]pyrimidine-6-carboxylate

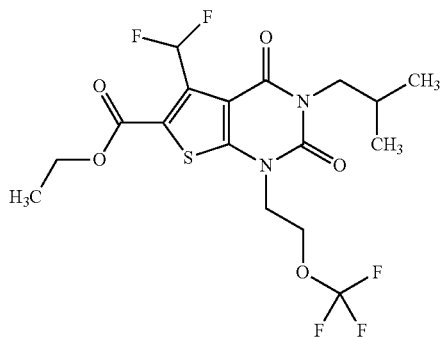 [SMILES: CCOC(=O)c1sc2c(c1C(F)F)c(=O)n(CC(C)C)c(=O)n2CCOC(F)(F)F]

847 mg (2.60 mmol) of caesium carbonate were added to a solution of 600 mg (1.73 mmol) of the compound from Ex. 135A in 9 ml of DMF, and the mixture was stirred at RT for 20 min. 501 mg (2.60 mmol) of 1-bromo-2-(trifluoromethoxy)ethane [commercially available; lit.: P. E. Aldrich, W. A. Sheppard, *J. Org. Chem.* 1964, 29 (1), 11-15] were then added, and the mixture was heated in a microwave oven (Biotage Initiator with dynamic control of irradiation power) at 100° C. for 1 h. After cooling to RT, the mixture was diluted with about 80 ml of ethyl acetate and, in succession, washed twice with in each case about 80 ml of water and once with about 80 ml of saturated sodium chloride solution. After drying over anhydrous magnesium sulphate, the mixture was filtered and concentrated. The crude product was purified by preparative HPLC (Method 5). The product fractions were combined and concentrated, and the residue was dried under high vacuum. 553 mg (69% of theory) of the title compound were obtained.

$^1$H-NMR (400 MHz, DMSO-$d_6$, δ/ppm): 7.72 (t, 1H), 4.42 (t, 2H), 4.35 (quart, 2H), 4.32 (t, 2H), 3.74 (d, 2H), 2.03 (m, 1H), 1.31 (t, 3H), 0.86 (d, 6H).

LC/MS (Method 1, ESIpos): $R_t$=1.23 min, m/z=459 [M+H]$^+$.

Example 137A

Ethyl 5-(difluoromethyl)-3-isobutyl-2,4-dioxo-1-(3,3,3-trifluoropropyl)-1,2,3,4-tetrahydrothieno[2,3-d]pyrimidine-6-carboxylate

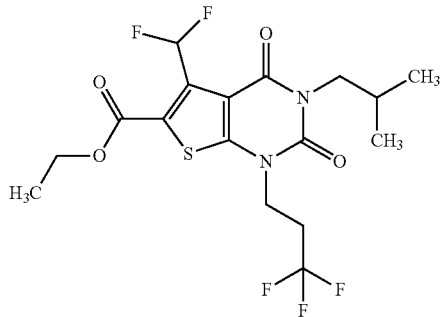 [SMILES: CCOC(=O)c1sc2c(c1C(F)F)c(=O)n(CC(C)C)c(=O)n2CCC(F)(F)F]

Analogously to the process described in Ex. 136A, 600 mg (1.73 mmol) of the compound from Ex. 135A and 582 mg (2.60 mmol) of 3,3,3-trifluoro-1-iodopropane gave 570 mg (74% of theory) of the title compound. Here, purification by preparative HPLC was carried out according to Method 6.

$^1$H-NMR (400 MHz, DMSO-d$_6$, δ/ppm): 7.73 (t, 1H), 4.36 (quart, 2H), 4.21 (t, 2H), 3.73 (d, 2H), 2.81 (m, 2H), 2.03 (m, 1H), 1.32 (t, 3H), 0.87 (d, 6H).

LC/MS (Method 1, ESIpos): R$_t$=1.22 min, m/z=443 [M+H]$^+$.

Example 138A 5-(Difluoromethyl)-3-isobutyl-2,4-dioxo-1-[2-(trifluoromethoxy)ethyl]-1,2,3,4-tetrahydrothieno[2,3-d]pyrimidine-6-carboxylic acid

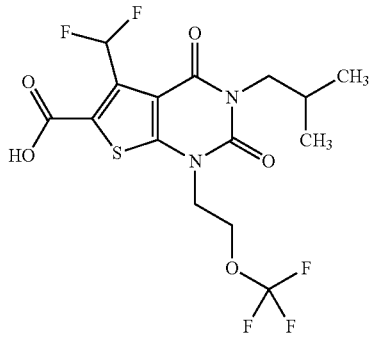 [SMILES: CC(C)Cn1c(=O)c2c(C(F)F)c(C(=O)O)sc2n(CCOC(F)(F)F)c1=O]

1.73 ml (1.73 mmol) of a 1 M solution of lithium hydroxide in water were added to a solution of 530 mg (1.16 mmol) of the compound from Ex. 136A in 12 ml of ethanol, and the mixture was stirred at RT for 3 h. All the volatile constituents were then removed on a rotary evaporator. The residue that remained was taken up in water and acidified with about 1.5 ml of 1 M hydrochloric acid. The product precipitated out and was filtered off with suction, washed with water and dried under high vacuum. 466 mg (93% of theory) of the title compound were obtained.

$^1$H-NMR (400 MHz, DMSO-d$_6$, δ/ppm): 14.43 (very broad, about 1H), 7.76 (t, 1H), 4.42 (t, 2H), 4.30 (t, 2H), 3.74 (d, 2H), 2.03 (m, 1H), 0.86 (d, 6H).

LC/MS (Method 1, ESIpos): R$_t$=0.99 min, m/z=431 [M+H]$^+$.

Example 139A 5-(Difluoromethyl)-3-isobutyl-2,4-dioxo-1-(3,3,3-trifluoropropyl)-1,2,3,4-tetrahydrothieno[2,3-d]pyrimidine-6-carboxylic acid

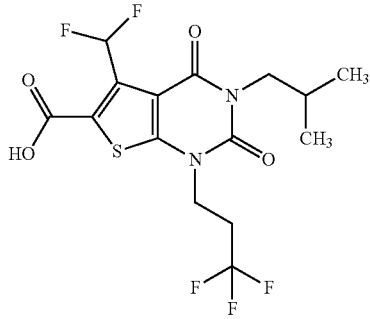 [SMILES: CC(C)Cn1c(=O)c2c(C(F)F)c(C(=O)O)sc2n(CCC(F)(F)F)c1=O]

Analogously to the process described under Ex. 138A, 540 mg (1.22 mmol) of the compound from Ex. 137A gave 463 mg (91% of theory) of the title compound.

$^1$H-NMR (400 MHz, DMSO-d$_6$, δ/ppm): 14.39 (very broad, about 1H), 7.77 (t, 1H), 4.19 (t, 2H), 3.73 (d, 2H), 2.81 (m, 2H), 2.03 (m, 1H), 0.86 (d, 6H).

LC/MS (Method 1, ESIpos): R$_t$=0.98 min, m/z=415 [M+H]$^+$.

Example 140A tert-Butyl 5-(bromomethyl)-2,4-dioxo-3-propyl-1-(3,3,3-trifluoropropyl)-1,2,3,4-tetrahydrothieno[2,3-d]pyrimidine-6-carboxylate

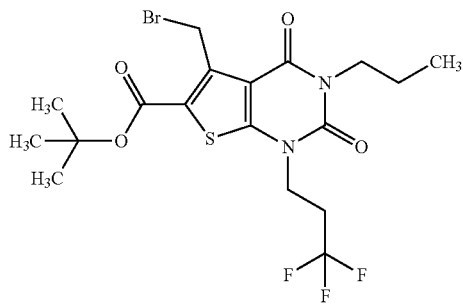 [SMILES: CCCn1c(=O)c2c(CBr)c(C(=O)OC(C)(C)C)sc2n(CCC(F)(F)F)c1=O]

200 mg (0.476 mmol) of the compound from Ex. 98A, 178 mg (0.999 mmol) of N-bromosuccinimide (NBS) and 7.8 mg (0.048 mmol) of 2,2'-azobis(2-methylpropionitrile) (AIBN) in 5 ml of anhydrous acetonitrile were heated under reflux for about 16 h. All the volatile constituents were then substantially removed on a rotary evaporator. The residue that remained was purified by means of filtration with suction through silica gel using dichloromethane as mobile phase. This gave, after combination of the product fractions, concentration and drying under high vacuum, 213 mg (89% of theory) of the title compound.

$^1$H-NMR (400 MHz, DMSO-d$_6$, δ/ppm): 5.21 (s, 2H), 4.17 (t, 2H), 3.85 (t, 2H), 2.87-2.75 (m, 2H), 1.63-1.53 (m, 2H), 1.57 (s, 9H), 0.88 (t, 3H).

LC/MS (Method 1, ESIpos): R$_t$=1.34 min, m/z=499/501 [M+H]$^+$.

Example 141A tert-Butyl 5-(bromomethyl)-3-ethyl-2,4-dioxo-1-(3,3,3-trifluoropropyl)-1,2,3,4-tetrahydrothieno[2,3-d]pyrimidine-6-carboxylate

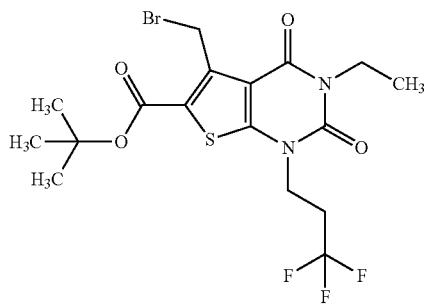 [SMILES: CCn1c(=O)c2c(CBr)c(C(=O)OC(C)(C)C)sc2n(CCC(F)(F)F)c1=O]

Analogously to the process described in Ex. 140A, 4.40 g (10.8 mmol) of the compound from Ex. 35A, 2.02 g (11.4 mmol) of N-bromosuccinimide (NBS) and 89 mg (0.541 mmol) of 2,2'-azobis(2-methylpropionitrile) (AIBN) gave 4.56 g (82% of theory, purity 95%) of the title compound.

$^1$H-NMR (400 MHz, DMSO-$d_6$, δ/ppm): 5.21 (s, 2H), 4.17 (t, 2H), 3.93 (quart, 2H), 2.88-2.76 (m, 2H), 1.57 (s, 9H), 1.15 (t, 3H).

LC/MS (Method 1, ESIpos): $R_t$=1.31 min; no ionization.

Example 142A tert-Butyl 5-formyl-2,4-dioxo-3-propyl-1-(3,3,3-trifluoropropyl)-1,2,3,4-tetrahydrothieno [2,3-d]pyrimidine-6-carboxylate

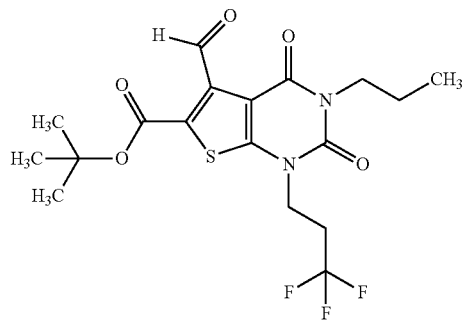 [SMILES: CCCn1c(=O)c2c(C=O)c(C(=O)OC(C)(C)C)sc2n(CCC(F)(F)F)c1=O]

385 mg of molecular sieve (4A) and, at a temperature of −10° C. and a little at a time, a total of 181 mg (1.54 mmol) of N-methylmorpholine N-oxide (NMO) were added to a solution of 385 mg (0.771 mmol) of the compound from Ex. 140A in 5 ml of anhydrous acetonitrile. The reaction mixture was then stirred at RT for 4 h. The mixture was then filtered through a little kieselguhr and the filtrate was concentrated to dryness. The residue obtained was taken up in 20 ml of diisopropyl ether/ethyl acetate (1:1) and washed successively twice with in each case 10 ml of aqueous citric acid solution and once with 10 ml of saturated aqueous sodium chloride solution. After drying over anhydrous magnesium sulphate, the mixture was filtered and concentrated. Drying of the residue under high vacuum gave 247 mg (73% of theory) of the title compound.

$^1$H-NMR (400 MHz, DMSO-$d_6$, δ/ppm): 10.36 (s, 1H), 4.19 (t, 2H), 3.81 (t, 2H), 2.88-2.76 (m, 2H), 1.61-1.51 (m, 2H), 1.50 (s, 9H), 0.86 (t, 3H).

LC/MS (Method 1, ESIpos): $R_t$=1.22 min, m/z=435 [M+H]$^+$.

Example 143A tert-Butyl 3-ethyl-5-formyl-2,4-dioxo-1-(3,3,3-trifluoropropyl)-1,2,3,4-tetrahydrothieno[2,3-d]pyrimidine-6-carboxylate

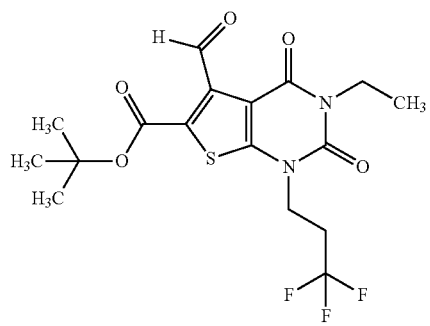 [SMILES: CCn1c(=O)c2c(C=O)c(C(=O)OC(C)(C)C)sc2n(CCC(F)(F)F)c1=O]

Analogously to the process described in Ex. 142A, 3.75 g (7.73 mmol) of the compound from Ex. 141A and 1.81 g (15.4 mmol) of N-methylmorpholine N-oxide (NMO) gave 2.38 g (73% of theory) of the title compound. The reaction time in this case was 5 h.

$^1$H-NMR (400 MHz, DMSO-$d_6$, δ/ppm): 10.36 (s, 1H), 4.19 (t, 2H), 3.88 (quart, 2H), 2.88-2.76 (m, 2H), 1.50 (s, 9H), 1.12 (t, 3H).

LC/MS (Method 1, ESIpos): $R_t$=1.15 min, m/z=421 [M+H]$^+$.

Example 144A tert-Butyl 5-(difluoromethyl)-2,4-dioxo-3-propyl-1-(3,3,3-trifluoropropyl)-1,2,3,4-tetrahydrothieno[2,3-d]pyrimidine-6-carboxylate

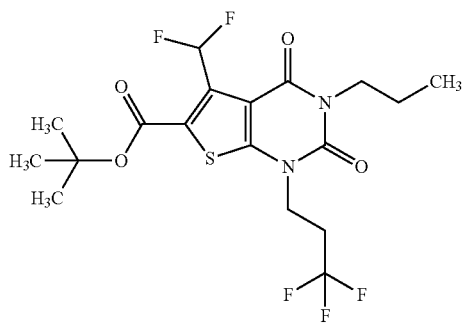 [SMILES: CCCn1c(=O)c2c(C(F)F)c(C(=O)OC(C)(C)C)sc2n(CCC(F)(F)F)c1=O]

At 0° C., 218 mg (1.35 mmol) of N,N-diethylaminosulphur trifluoride (DAST) were added to a solution of 235 mg (0.541 mmol) of the compound from Ex. 142A in 5 ml of dichloromethane. The mixture was then stirred at RT for 3 h. 0.5 ml of saturated aqueous sodium bicarbonate solution were then added, and the mixture was stirred at RT for a few minutes. The mixture was then diluted with 5 ml of ethyl acetate and solid anhydrous magnesium sulphate was added in the amount required to take up the aqueous phase completely. The mixture was filtered, the residue was washed with a little ethyl acetate and the filtrate was concentrated. The solid obtained was purified by preparative HPLC (Method 6). This gave, after concentration of the product fractions and drying under high vacuum, 198 mg (80% of theory) of the title compound.

$^1$H-NMR (400 MHz, DMSO-$d_6$, δ/ppm): 7.71 (t, 1H), 4.19 (t, 2H), 3.84 (t, 2H), 2.87-2.75 (m, 2H), 1.62-1.53 (m, 2H), 1.55 (s, 9H), 0.88 (t, 3H).

LC/MS (Method 1, ESIpos): $R_t$=1.32 min, m/z=457 [M+H]$^+$.

Example 145A tert-Butyl 3-ethyl-5-(fluoromethyl)-2,4-dioxo-1-(3,3,3-trifluoropropyl)-1,2,3,4-tetrahydrothieno[2,3-d]pyrimidine-6-carboxylate

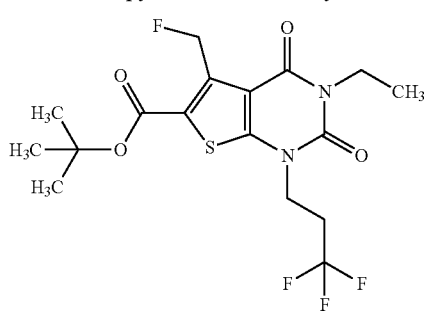

400 mg of molecular sieve (4A) and 2 ml (1.98 mmol) of a 1 M solution of tetra-n-butylammonium fluoride (TBAF) in THF were added to a solution of 800 mg (1.65 mmol) of the compound from Ex. 141A in 16 ml of anhydrous acetonitrile. After the mixture had been stirred at RT for about 16 h, it was filtered and the filtrate was concentrated to dryness. The residue obtained was purified by preparative HPLC (Method 18). This gave, after concentration of the product fractions and drying under high vacuum, 450 mg (60% of theory, purity 94%) of the title compound.

$^1$H-NMR (400 MHz, DMSO-$d_6$, δ/ppm): 5.93 (d, 2H), 4.19 (t, 2H), 3.93 (quart, 2H), 2.88-2.76 (m, 2H), 1.55 (s, 9H), 1.14 (t, 3H).

LC/MS (Method 1, ESIpos): $R_t$=1.21 min, m/z=425 [M+H]$^+$.

Example 146A tert-Butyl 3-ethyl-5-(1-hydroxyethyl)-2,4-dioxo-1-(3,3,3-trifluoropropyl)-1,2,3,4-tetrahydrothieno[2,3-d]pyrimidine-6-carboxylate (racemate)

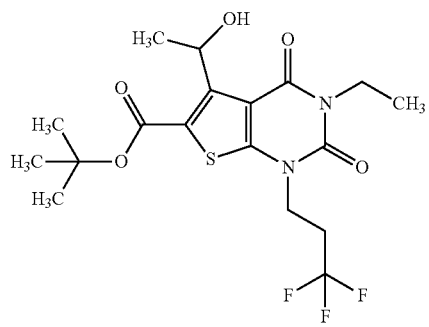 [SMILES: CCn1c(=O)c2c(C(C)O)c(C(=O)OC(C)(C)C)sc2n(CCC(F)(F)F)c1=O]

At 0° C., 1.9 ml of a 1.4 M solution of methylmagnesium bromide in a mixture of THF/toluene were added dropwise to a solution of 1.0 g (2.38 mmol) of the compound from Ex. 143A in 24 ml of anhydrous THF. After the reaction mixture had been stirred at 0° C. for 1 h, 5 ml of water were added at this temperature. The mixture was allowed to warm to RT and then extracted with ethyl acetate. The organic extract was washed successively with water and saturated sodium chloride solution. After drying over anhydrous sodium sulphate, the mixture was filtered and concentrated. The residue obtained was purified by preparative HPLC (Method 18). The product fractions were combined and concentrated, and the residue was dried under high vacuum. 480 mg (46% of theory) of the title compound were obtained.

$^1$H-NMR (400 MHz, DMSO-$d_6$, δ/ppm): 5.76 (broad, 1H), 4.18 (t, 2H), 3.97 (quart, 2H), 2.88-2.76 (m, 2H), 1.54 (s, 9H), 1.41 (d, 3H), 1.16 (t, 3H).

LC/MS (Method 1, ESIpos): $R_t$=1.22 min, m/z=437 [M+H]$^+$.

Example 147A tert-Butyl 3-ethyl-5-(1-fluoroethyl)-2,4-dioxo-1-(3,3,3-trifluoropropyl)-1,2,3,4-tetrahydrothieno[2,3-d]pyrimidine-6-carboxylate (racemate)

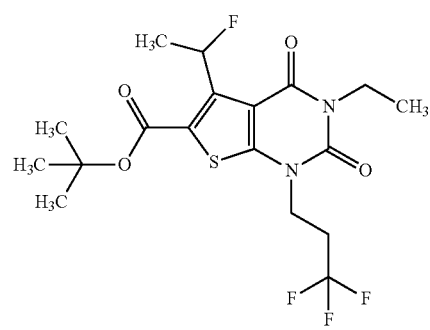 [SMILES: CCn1c(=O)c2c(C(C)F)c(C(=O)OC(C)(C)C)sc2n(CCC(F)(F)F)c1=O]

At 0° C., 405 mg (0.916 mmol) of a 50% strength solution of bis(2-methoxyethyl)aminosulphur trifluoride (Deoxo-Fluor®) in THF were added to a solution of 400 mg (0.916 mmol) of the compound from Ex. 146A in 9.2 ml of dichloromethane After stirring at RT for 30 min, a further 203 mg (0.458 mmol) of Deoxo-Fluor® solution were added. After a further 30 min of stirring, saturated aqueous sodium bicarbonate solution was added and the mixture was extracted with ethyl acetate. The organic extract was washed with water and dried over anhydrous sodium sulphate. This gave, after filtration, concentration and drying under high vacuum, 430 mg (90% of theory, purity 85%) of the title compound.

LC/MS (Method 1, ESIpos): $R_t$=1.28 min, m/z=439 [M+H]$^+$.

Example 148A 5-(Difluoromethyl)-2,4-dioxo-3-propyl-1-(3,3,3-trifluoropropyl)-1,2,3,4-tetrahydrothieno[2,3-d]pyrimidine-6-carboxylic acid

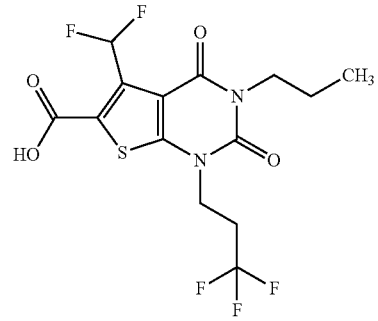 [SMILES: CCCn1c(=O)c2c(C(F)F)c(C(=O)O)sc2n(CCC(F)(F)F)c1=O]

1 ml of trifluoroacetic acid were added to a solution of 190 mg (0.416 mmol) of the compound from Ex. 144A in 2 ml of dichloromethane, and the mixture was stirred at RT for 3 h. The reaction mixture was then concentrated to dryness on a rotary evaporator. The residue that remained was twice dissolved in in each case 5 ml of dichloromethane and in each case concentrated again. After drying under a high vacuum, 166 mg (97% of theory, 97% purity) of the title compound were obtained.

¹H-NMR (400 MHz, DMSO-d₆, δ/ppm): 14.43 (very broad, about 1H), 7.76 (t, 1H), 4.19 (t, 2H), 3.84 (t, 2H), 2.87-2.75 (m, 2H), 1.62-1.53 (m, 2H), 0.88 (t, 3H).

LC/MS (Method 1, ESIpos): $R_t$=0.91 min, m/z=401 [M+H]⁺.

Example 149A

3-Ethyl-5-(fluoromethyl)-2,4-dioxo-1-(3,3,3-trifluoropropyl)-1,2,3,4-tetrahydrothieno[2,3-d]pyrimidine-6-carboxylic acid

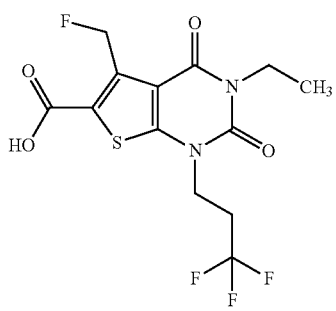

Analogously to the process described under Ex. 148A, 450 mg (1.06 mmol) of the compound from Ex. 145A gave 390 mg (92% of theory, purity 93%) of the title compound.

¹H-NMR (400 MHz, DMSO-d₆, δ/ppm): 14.04 (very broad, about 1H), 5.95 (d, 2H), 4.18 (t, 2H), 3.93 (quart, 2H), 2.87-2.75 (m, 2H), 1.14 (t, 3H).

LC/MS (Method 1, ESIpos): $R_t$=0.86 min, m/z=369 [M+H]⁺.

Example 150A

3-Ethyl-5-(1-fluoroethyl)-2,4-dioxo-1-(3,3,3-trifluoropropyl)-1,2,3,4-tetrahydrothieno[2,3-d]pyrimidine-6-carboxylic acid (racemate)

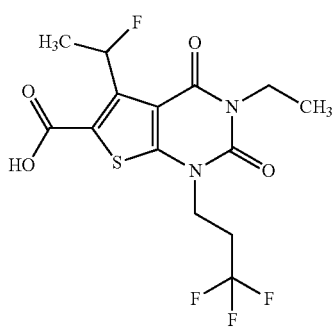 [SMILES: CCn1c(=O)c2c(C(C)F)c(C(=O)O)sc2n(CCC(F)(F)F)c1=O]

Analogously to the process described under Ex. 148A, 430 mg (0.834 mmol, purity 85%) of the compound from Ex. 147A gave 290 mg (77% of theory, purity 85%) of the title compound.

¹H-NMR (400 MHz, DMSO-d₆, δ/ppm): 13.91 (very broad, about 1H), 6.75 (d of quart, 1H), 4.17 (t, 2H), 3.92 (quart, 2H), 2.87-2.75 (m, 2H), 1.73 (dd, 3H), 1.14 (t, 3H).

LC/MS (Method 1, ESIpos): $R_t$=0.89 min, m/z=383 [M+H]⁺.

Example 151A tert-Butyl 5-(bromomethyl)-2,4-dioxo-3-propyl-1-[2-(trifluoromethoxy)ethyl]-1,2,3,4-tetrahydrothieno[2,3-d]pyrimidine-6-carboxylate

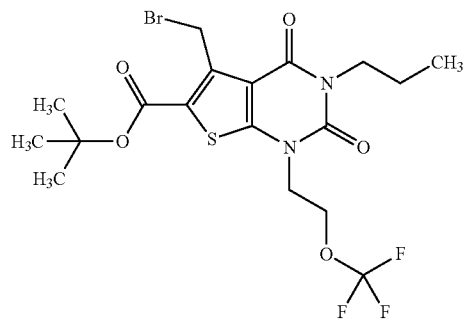 [SMILES: CCCn1c(=O)c2c(CBr)c(C(=O)OC(C)(C)C)sc2n(CCOC(F)(F)F)c1=O]

Analogously to the process described in Ex. 140A, 2.0 g (4.58 mmol) of the compound from Ex. 95A, 856 mg (4.81 mmol) of N-bromosuccinimide (NBS) and 38 mg (0.229 mmol) of 2,2'-azobis(2-methylpropionitrile) (AIBN) gave 1.90 g (80% of theory) of the title compound. The reaction time in this case was 1 h.

¹H-NMR (400 MHz, DMSO-d₆, δ/ppm): 5.20 (s, 2H), 4.42 (t, 2H), 4.27 (t, 2H), 3.86 (t, 2H), 1.63-1.54 (m, 2H), 1.56 (s, 9H), 0.88 (t, 3H).

LC/MS (Method 1, ESIpos): $R_t$=1.37 min, m/z=515/517 [M+H]⁺.

Example 152A tert-Butyl 5-formyl-2,4-dioxo-3-propyl-1-[2-(trifluoromethoxy)ethyl]-1,2,3,4-tetrahydrothieno[2,3-d]pyrimidine-6-carboxylate

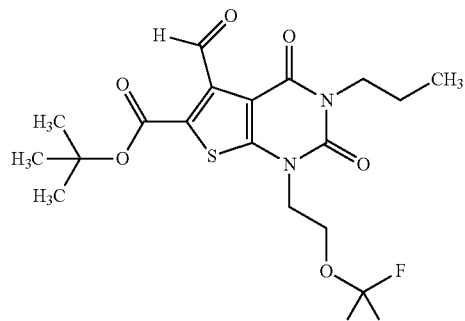

Analogously to the process described in Ex. 142A, 1.80 g (3.49 mmol) of the compound from Ex. 151A and 818 mg (6.99 mmol) of N-methylmorpholine N-oxide (NMO) gave 1.17 g (74% of theory) of the title compound. The reaction time in this case was 5 h.

¹H-NMR (400 MHz, DMSO-d₆, δ/ppm): 10.35 (s, 1H), 4.43 (t, 2H), 4.29 (t, 2H), 3.81 (t, 2H), 1.61-1.51 (m, 2H), 1.50 (s, 9H), 0.85 (t, 3H).

LC/MS (Method 1, ESIpos): $R_t$=1.21 min, m/z=451 [M+H]⁺.

Example 153A tert-Butyl 5-(difluoromethyl)-2,4-dioxo-3-propyl-1-[2-(trifluoromethoxy)ethyl]-1,2,3,4-tetrahydrothieno[2,3-d]pyrimidine-6-carboxylate

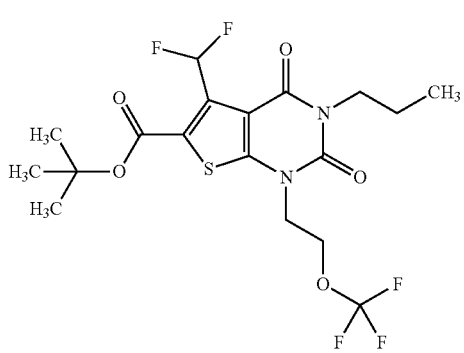 [SMILES: CCCn1c(=O)c2c(C(F)F)c(C(=O)OC(C)(C)C)sc2n(CCOC(F)(F)F)c1=O]

Analogously to the process described in Ex. 144A, 1.11 g (2.47 mmol) of the compound from Ex. 152A and 998 mg (6.19 mmol) of N,N-diethylaminosulphur trifluoride (DAST) gave 935 mg (79% of theory) of the title compound. Here, purification of the product was carried out by chromatography on a silica gel cartridge (Biotage, 50 g of silica gel, mobile phase: 5:1 cyclohexane/ethyl acetate).

$^1$H-NMR (400 MHz, DMSO-$d_6$, δ/ppm): 7.71 (t, 1H), 4.42 (t, 2H), 4.30 (t, 2H), 3.85 (t, 2H), 1.62-1.52 (m, 2H), 1.54 (s, 9H), 0.87 (t, 3H).

LC/MS (Method 1, ESIpos): $R_t$=1.29 min, m/z=473 [M+H]$^+$.

Example 154A 5-(Difluoromethyl)-2,4-dioxo-3-propyl-1-[2-(trifluoromethoxy)ethyl]-1,2,3,4-tetrahydrothieno[2,3-d]pyrimidine-6-carboxylic acid

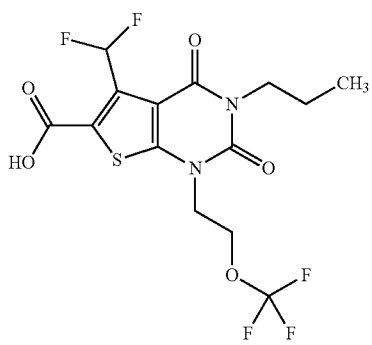 [SMILES: CCCn1c(=O)c2c(C(F)F)c(C(=O)O)sc2n(CCOC(F)(F)F)c1=O]

Analogously to the process described under Ex. 148A, 916 mg (1.94 mmol) of the compound from Ex. 153A gave 806 mg (98% of theory) of the title compound.

$^1$H-NMR (400 MHz, DMSO-$d_6$, δ/ppm): 14.34 (very broad, 1H), 7.76 (t, 1H), 4.42 (t, 2H), 4.30 (t, 2H), 3.85 (t, 2H), 1.62-1.53 (m, 2H), 0.87 (t, 3H).

LC/MS (Method 1, ESIpos): $R_t$=0.88 min, m/z=417 [M+H]$^+$.

Example 155A tert-Butyl 1-ethyl-5-methyl-2,4-dioxo-3-propyl-1,2,3,4-tetrahydrothieno[2,3-d]pyrimidine-6-carboxylate

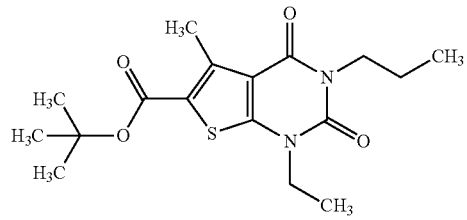 [SMILES: CCCn1c(=O)c2c(C)c(C(=O)OC(C)(C)C)sc2n(CC)c1=O]

4.52 g (13.9 mmol) of caesium carbonate were added to a solution of 3.0 g (9.25 mmol) of the compound from Ex. 91A in 36 ml of DMF, and the mixture was stirred at RT for 10 min. 1.1 ml (13.9 mmol) of iodoethane were then added, and the mixture was stirred in a microwave oven (Biotage Initiator with dynamic control of irradiation power) at 100° C. for 1 h. After cooling to RT, the mixture was diluted with ethyl acetate and washed successively with water and saturated sodium chloride solution. After drying over anhydrous magnesium sulphate, the mixture was filtered and concentrated. The crude product was purified by MPLC (Biotage cartridge with 100 g of silica gel, mobile phase: 20:1 cyclohexane/ethyl acetate). The product fractions were combined and concentrated. After the residue had been dried under high vacuum, 3.06 g (93% of theory) of the title compound were obtained.

$^1$H-NMR (400 MHz, DMSO-$d_6$, δ/ppm): 3.94 (quart, 2H), 3.82 (m, 2H), 2.75 (s, 3H), 1.61-1.51 (m, 2H), 1.53 (s, 9H), 1.25 (t, 3H), 0.87 (t, 3H).

LC/MS (Method 1, ESIpos): $R_t$=1.34 min, m/z=353 [M+H]$^+$.

Example 156A tert-Butyl 5-(bromomethyl)-1-ethyl-2,4-dioxo-3-propyl-1,2,3,4-tetrahydrothieno[2,3-d]pyrimidine-6-carboxylate

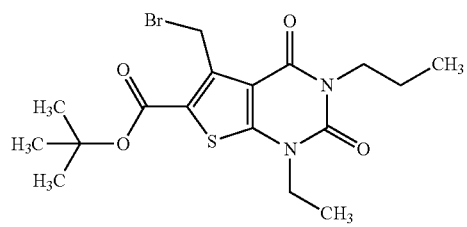 [SMILES: CCCn1c(=O)c2c(CBr)c(C(=O)OC(C)(C)C)sc2n(CC)c1=O]

Analogously to the process described in Ex. 140A, 2.0 g (5.67 mmol) of the compound from Ex. 155A, 1.06 g (5.96 mmol) of N-bromosuccinimide (NBS) and 47 mg (0.284 mmol) of 2,2'-azobis(2-methylpropionitrile) (AIBN) gave 2.22 g (90% of theory) of the title compound. The reaction time in this case was 1 h.

$^1$H-NMR (400 MHz, DMSO-$d_6$, δ/ppm): 5.21 (s, 2H), 3.96 (quart, 2H), 3.84 (m, 2H), 1.63-1.53 (m, 2H), 1.57 (s, 9H), 1.26 (t, 3H), 0.89 (t, 3H).

LC/MS (Method 1, ESIpos): $R_t$=1.38 min, m/z=431/433 [M+H]$^+$.

Example 157A tert-Butyl 1-ethyl-5-formyl-2,4-dioxo-3-propyl-1,2, 3,4-tetrahydrothieno[2,3-d]pyrimidine-6-carboxylate

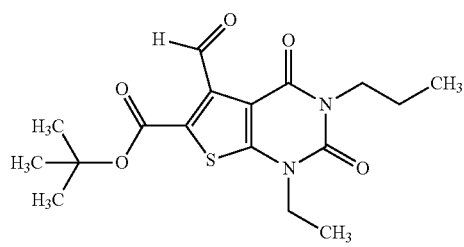 [SMILES: CCCn1c(=O)c2c(C=O)c(C(=O)OC(C)(C)C)sc2n(CC)c1=O]

Analogously to the process described in Ex. 142A, 2.15 g (4.98 mmol) of the compound from Ex. 156A and 1.17 g (9.97 mmol) of N-methylmorpholine N-oxide (NMO) gave 1.38 g (75% of theory) of the title compound. Here, the reaction time was about 16 h.

$^1$H-NMR (400 MHz, DMSO-$d_6$, δ/ppm): 10.35 (s, 1H), 3.97 (quart, 2H), 3.80 (m, 2H), 1.62-1.51 (m, 2H), 1.50 (s, 9H), 1.27 (t, 3H), 0.86 (t, 3H).

LC/MS (Method 1, ESIpos): $R_t$=1.16 min, m/z=367 [M+H]$^+$.

Example 158A tert-Butyl 5-(difluoromethyl)-1-ethyl-2,4-dioxo-3-propyl-1,2,3,4-tetrahydrothieno[2,3-d]pyrimidine-6-carboxylate

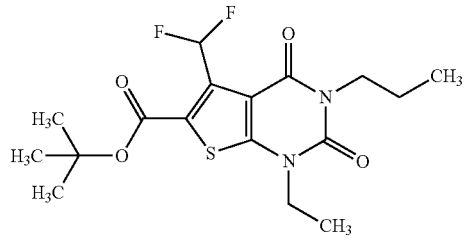 [SMILES: CCCn1c(=O)c2c(C(F)F)c(C(=O)OC(C)(C)C)sc2n(CC)c1=O]

Analogously to the process described in Ex. 144A, 1.32 g (3.60 mmol) of the compound from Ex. 157A and 1.45 g (9.01 mmol) of N,N-diethylaminosulphur trifluoride (DAST) gave 1.08 g (77% of theory) of the title compound. Here, purification of the product was carried out by chromatography on a silica gel cartridge (Biotage, 100 g of silica gel, mobile phase: 5:1 cyclohexane/ethyl acetate).

$^1$H-NMR (400 MHz, DMSO-$d_6$, δ/ppm): 7.72 (t, 1H), 3.98 (quart, 2H), 3.83 (m, 2H), 1.62-1.53 (m, 2H), 1.55 (s, 9H), 1.27 (t, 3H), 0.88 (t, 3H).

LC/MS (Method 1, ESIpos): $R_t$=1.25 min, m/z=389 [M+H]$^+$.

Example 159A 5-(Difluoromethyl)-1-ethyl-2,4-dioxo-3-propyl-1,2, 3,4-tetrahydrothieno[2,3-d]pyrimidine-6-carboxylic acid

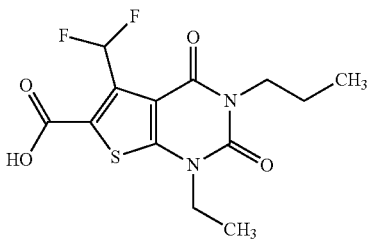 [SMILES: CCCn1c(=O)c2c(C(F)F)c(C(=O)O)sc2n(CC)c1=O]

Analogously to the process described under Ex. 148A, 1.0 g (2.57 mmol) of the compound from Ex. 158A gave 855 mg (99% of theory) of the title compound.

$^1$H-NMR (400 MHz, DMSO-$d_6$, δ/ppm): 14.28 (very broad, about 1H), 7.76 (t, 1H), 3.98 (quart, 2H), 3.83 (m, 2H), 1.62-1.53 (m, 2H), 1.27 (t, 3H), 0.88 (t, 3H).

LC/MS (Method 1, ESIpos): $R_t$=0.74 min, m/z=333 [M+H]$^+$.

Example 160A

3-Isobutyl-5-methyl-2,4-dioxo-1-(3,3,3-trifluoropropyl)-1,2,3,4-tetrahydrothieno [2,3-d]pyrimidine-6-carboxylic acid

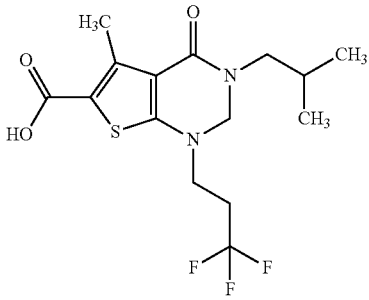 [SMILES: Cc1c(C(=O)O)sc2c1C(=O)N(CC(C)C)CN2CCC(F)(F)F]

758 mg (2.33 mmol) of caesium carbonate were added to a solution of 250 mg (0.776 mmol) of the compound from Ex. 59A in 7.5 ml of anhydrous DMF, and the mixture was stirred at RT for 10 min. 211 µl (1.94 mmol) of 1-bromo-3-methylpropane were then added, and the mixture was stirred initially at RT for 3 h and then at 60° C. for 16 h. After cooling to RT, 2 ml of 2 M aqueous sodium hydroxide solution were added and the reaction mixture was stirred at RT for a further 2 h. The mixture was then poured onto about 50 ml of water and extracted with dichloromethane. The organic extract was discarded and the aqueous phase was brought to a pH of about 4 with 1 M hydrochloric acid. The mixture was extracted with ethyl acetate. The organic extract was dried over anhydrous magnesium sulphate, filtered and concentrated. The residue obtained was purified by preparative HPLC (Method 5). This gave, after evaporation of the product fractions and drying of the residue under high vacuum, 132 mg (44% of theory) of the title compound.

$^1$H-NMR (400 MHz, DMSO-d$_6$, δ/ppm): 13.42 (broad, 1H), 4.15 (t, 2H), 3.72 (d, 2H), 2.85-2.71 (m, 2H), 2.75 (s, 3H), 2.09-1.98 (m, 1H), 0.86 (d, 6H).

LC/MS (Method 1, ESIpos): R$_t$=0.99 min, m/z=379 [M+H]$^+$.

Example 161A 3-(Cyclopropylmethyl)-5-methyl-2,4-dioxo-1-(3,3,3-trifluoropropyl)-1,2,3,4-tetrahydrothieno[2,3-d]pyrimidine-6-carboxylic acid

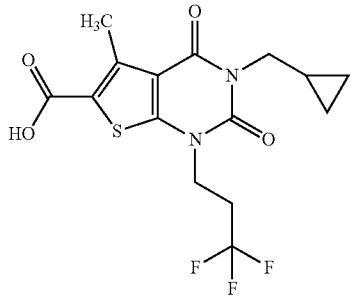 [SMILES: Cc1c(C(=O)O)sc2c1c(=O)n(CC1CC1)c(=O)n2CCC(F)(F)F]

758 mg (2.33 mmol) of caesium carbonate were added to a solution of 250 mg (0.776 mmol) of the compound from Ex. 59A in 7.5 ml of anhydrous DMF, and the mixture was stirred at RT for 10 min. 262 mg (1.94 mmol) of (bromomethyl)cyclopropane were then added and the mixture was stirred at RT for about 16 h. 2 ml of 2 M aqueous sodium hydroxide solution were then added and the mixture was stirred at RT for a further 3 h. The mixture was then poured onto about 50 ml of water. The solid that precipitated out was filtered off and discarded. The filtrate was adjusted to a pH of about 4-5 using 1 M hydrochloric acid. The product which precipitated out was filtered off with suction, washed with a little water and dried under high vacuum. This gave 160 mg (52% of theory, purity 95%) of the title compound which was used further without further purification.

$^1$H-NMR (400 MHz, DMSO-d$_6$, δ/ppm): 13.44 (broad, about 1H), 4.16 (t, 2H), 3.77 (d, 2H), 2.86-2.73 (m, 2H), 2.76 (s, 3H), 1.20-1.13 (m, 1H), 0.45-0.40 (m, 2H), 0.36-0.32 (m, 2H).

LC/MS (Method 1, ESIpos): R$_t$=0.95 min, m/z=377 [M+H]$^+$.

Example 162A 3-(2-Methoxypropyl)-5-methyl-2,4-dioxo-1-(3,3,3-trifluoropropyl)-1,2,3,4-tetrahydrothieno[2,3-d]pyrimidine-6-carboxylic acid (racemate)

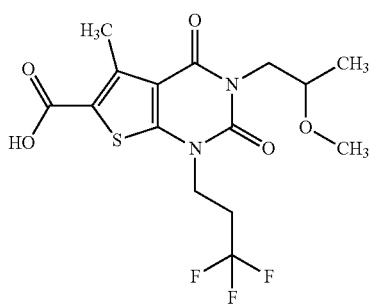 [SMILES: COC(C)Cn1c(=O)c2c(C)c(C(=O)O)sc2n(CCC(F)(F)F)c1=O]

1st Step: 2-Methoxypropyl 3-(2-methoxypropyl)-5-methyl-2,4-dioxo-1-(3,3,3-trifluoropropyl)-1,2,3,4-tetrahydrothieno[2,3-d]pyrimidine-6-carboxylate

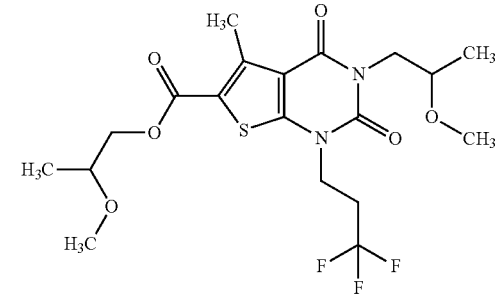 [SMILES: COC(C)COC(=O)c1sc2c(c1C)c(=O)n(CC(C)OC)c(=O)n2CCC(F)(F)F]

1.52 g (4.66 mmol) of caesium carbonate were added to a solution of 500 mg (1.55 mmol) of the compound from Ex. 59A in 15 ml of anhydrous DMF, and the mixture was stirred at RT for 10 min. 948 mg (3.88 mmol) of racemic 2-methoxypropyl-4-methylbenzene sulphonate [prepared analogously to a published method starting from racemic methyl 2-methoxypropionate; lit.: A. Terfort, H. Brunner, J. Chem. Soc. Perkin Trans. 1, 1996 (12), 1467-1479] were then added, and the mixture was stirred initially at RT for 16 h. Since the reaction was still incomplete, the mixture was then stirred at 80° C. for another about 18 h. After cooling to RT, about 100 ml of water were added and the mixture was extracted with dichloromethane. The organic extract was dried over anhydrous magnesium sulphate, filtered and concentrated. The residue obtained was purified by preparative HPLC (Method 6). Concentration of the product fractions gave 130 mg (18% of theory) of the title compound.

$^1$H-NMR (400 MHz, DMSO-d$_6$, δ/ppm): 4.31 (dd, 1H), 4.22-4.13 (m, 3H), 4.06 (dd, 1H), 3.77 (dd, 1H), 3.67-3.59 (m, 2H), 3.29 (s, 3H), 3.22 (s, 3H), 2.86-2.74 (m, 2H), 2.79 (s, 3H), 1.15 (d, 3H), 1.06 (d, 3H).

LC/MS (Method 1, ESIpos): R$_t$=1.12 min, m/z=467 [M+H]$^+$.

2nd Step: 3-(2-Methoxypropyl)-5-methyl-2,4-dioxo-1-(3,3,3-trifluoropropyl)-1,2,3,4-tetrahydrothieno[2,3-d]pyrimidino-6-carboxylic acid (racemate)

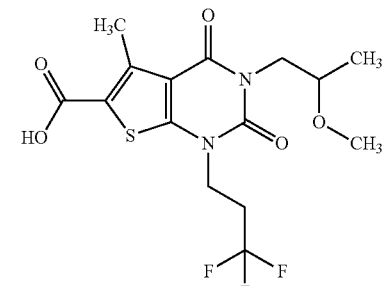

125 mg (0.268 mmol) of the compound from the preceding step were dissolved in 5 ml of ethanol, 1.34 ml (1.34 mmol) of a 1 M solution of lithium hydroxide in water were added and the mixture was stirred at RT for 2 h. The ethanol was then removed on a rotary evaporator and the residue was diluted with water and acidified by addition of 1 M hydrochloric acid. It was then extracted with ethyl acetate. The organic extract was dried over anhydrous magnesium sulphate, filtered and concentrated. This gave 103 mg (63% of theory, purity 66%) of the title compound which was reacted further without further purification.

$^1$H-NMR (400 MHz, DMSO-$d_6$, δ/ppm): 13.41 (broad, 1H), 4.19-4.13 (m, 2H), 4.05 (dd, 1H), 3.77 (dd, 1H), 3.67-3.59 (m, 1H), 3.22 (s, 3H), 2.85-2.73 (m, 2H), 2.76 (s, 3H), 1.06 (d, 3H).

LC/MS (Method 1, ESIpos): $R_t$=0.84 min, m/z=395 [M+H]$^+$.

Example 163A

Ethyl 2-[(ethylcarbamoyl)amino]-4-methylthiophene-3-carboxylate

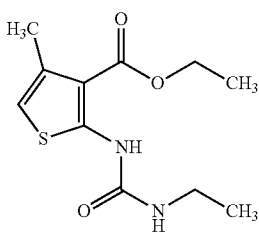 [SMILES: CCNC(=O)Nc1scc(C)c1C(=O)OCC]

96 ml (1.21 mol) of ethyl isocyanate were added to a solution of 150 g (0.810 mol) of ethyl 2-amino-4-methylthiophene-3-carboxylate and 113 ml (0.810 mol) of triethylamine in 1.5 litres of THF. The reaction mixture was heated under reflux for 2 days. After cooling to RT, the mixture was poured into about 2 litres of water and extracted four times with a total of 1.1 litres of dichloromethane. The organic extract was dried over anhydrous sodium sulphate and then filtered and concentrated to dryness. After the residue had been dried under high vacuum, 200 g (89% of theory, purity about 93%) of the title compound were obtained, this being employed in the next reaction step without further purification.

$^1$H-NMR (300 MHz, DMSO-$d_6$, δ/ppm): 10.28 (s, 1H), 7.83 (broad, 1H), 6.39 (s, 1H), 4.27 (quart, 2H), 3.13 (m, 2H), 2.26 (s, 3H), 1.31 (t, 3H), 1.06 (t, 3H).

LC/MS (Method 1, ESIpos): $R_t$=0.92 min, m/z=257 [M+H]$^+$.

Example 164A

3-Ethyl-5-methylthieno[2,3-d]pyrimidine-2,4(1H,3H)-dione

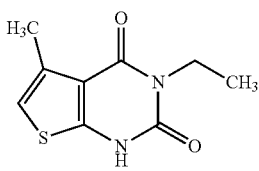

67 g (261 mmol) of the compound from Ex. 163A were dissolved in 1.6 litres of ethanol and 141 ml (392 mmol) of a 21% strength solution of sodium ethoxide in ethanol were added. After the mixture had been stirred at RT for about 16 h, it was poured into about 500 ml of cold water and adjusted to a pH of about 5 by addition of glacial acetic acid. The resulting precipitate was filtered off with suction, washed with water until neutral and dried. 50 g (91% of theory) of the title compound were obtained.

$^1$H-NMR (300 MHz, DMSO-$d_6$, δ/ppm): 6.66 (s, 1H), 3.86 (quart, 2H), 2.35 (s, 3H), 1.11 (t, 3H).

LC/MS (Method 1, ESIpos): $R_t$=0.67 min, m/z=211 [M+H]$^+$.

Example 165A

3-Ethyl-5-methyl-2,4-dioxo-1,2,3,4-tetrahydrothieno[2,3-d]pyrimidine-6-carbaldehyde

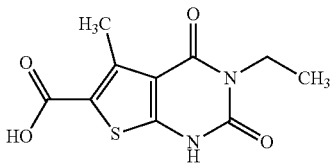 [SMILES: CCn1c(=O)[nH]c2sc(C(=O)O)c(C)c2c1=O]

4.5 ml (48.5 mmol) of phosphorus oxychloride were added carefully to a solution of 850 mg (4.04 mmol) of the compound from Ex. 164A in 3.1 ml (40.4 mmol) of DMF. After the strongly exothermic reaction had subsided, the mixture was stirred for a further 15 min. The reaction mixture was then carefully stirred into 100 ml of ice-water. After 1 h of stirring, the precipitated product was filtered off with suction, washed with water until neutral and dried. 936 mg (97% of theory) of the title compound were obtained.

$^1$H-NMR (400 MHz, DMSO-$d_6$, δ/ppm): 12.58 (broad, 1H), 10.06 (s, 1H), 3.86 (quart, 2H), 2.76 (s, 3H), 1.12 (t, 3H).

LC/MS (Method 1, ESIpos): $R_t$=0.68 min, m/z=239 [M+H]$^+$.

Example 166A

3-Ethyl-5-methyl-1-(3,3,3-trifluoropropyl)thieno[2,3-d]pyrimidine-2,4(1H,3H)-dione

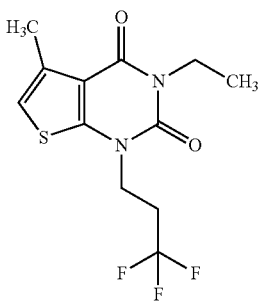 [SMILES: CCn1c(=O)c2c(C)csc2n(CCC(F)(F)F)c1=O]

2.0 g (9.51 mmol) of the compound from Ex. 164A and 3.29 g (23.8 mmol) of potassium carbonate in 50 ml of anhydrous DMF were stirred at RT for 15 min, and 3.3 ml (28.5 mmol) of 1,1,1-trifluoro-3-iodopropane were then added. Since, after stirring overnight at RT, conversion was incomplete, a further 1.31 g (9.51 mmol) of potassium carbonate and 1.1 ml (9.51 mmol) of 1,1,1-trifluoro-3-iodopropane were added and the mixture was stirred at 60°

C. for 2 h. After cooling to RT, the mixture was diluted with ethyl acetate and washed successively twice with water and once with saturated sodium chloride solution. After drying over anhydrous magnesium sulphate, the mixture was filtered and the filtrate was evaporated to dryness. The crude product was purified by chromatography on a silica gel cartridge (Biotage, 340 g of silica gel, mobile phase: cyclohexane/ethyl acetate 24:1→10:1). Concentration and drying of the product fractions gave 2.06 g (70% of theory) of the title compound.

$^1$H-NMR (400 MHz, DMSO-d$_6$, δ/ppm): 6.88 (s, 1H), 4.12 (t, 2H), 3.91 (quart, 2H), 2.84-2.71 (m, 2H), 2.39 (s, 3H), 1.12 (t, 3H).

LC/MS (Method 1, ESIpos): R$_t$=1.02 min, m/z=307 [M+H]$^+$.

Example 167A

3-Ethyl-5-methyl-2,4-dioxo-1-(3,3,3-trifluoropropyl)-1,2,3,4-tetrahydrothieno[2,3-d]pyrimidine-6-carbaldehyde

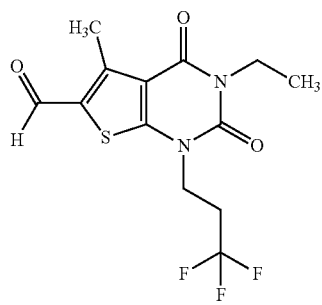 [SMILES: CCn1c(=O)c2c(C)c(C=O)sc2n(CCC(F)(F)F)c1=O]

Method A:

5.0 g (21.0 mmol) of the compound from Ex. 165A and 7.25 g (52.5 mmol) of potassium carbonate in a mixture of 95 ml of acetonitrile and 15 ml of DMF were stirred at RT for 15 min, and 14.1 g (63.0 mmol) of 1,1,1-trifluoro-3-iodopropane were then added. The reaction mixture was stirred at a temperature of 78° C. for about 16 h. After cooling to RT, the mixture was diluted with 500 ml of ethyl acetate and, in succession, washed twice with in each case 100 ml of water and once with 50 ml of saturated sodium chloride solution. After drying over anhydrous sodium sulphate, the mixture was filtered and the filtrate was evaporated to dryness. The crude product was purified by chromatography (80 g of silica gel, mobile phase: heptane/ethyl acetate 100:0→60:40). This gave, after concentration of the product fractions and drying of the residue, 2.99 g (42% of theory) of the title compound.

Method B:

7.8 ml (83.2 mmol) of phosphorus oxychloride were added carefully to a solution of 5.10 g (16.6 mmol) of the compound from Ex. 166A in 25.6 ml (333 mmol) of DMF. After the strongly exothermic reaction had almost subsided, the mixture was stirred for a further 30 min at 100° C. After cooling to RT, the reaction mixture was carefully stirred into 100 ml of ice-water. After 1 h of stirring, the precipitated product was filtered off with suction, washed with water until neutral and dried. This gave 5.08 g (85% of theory, 94% pure) of the title compound.

$^1$H-NMR (400 MHz, DMSO-d$_6$, δ/ppm): 10.11 (s, 1H), 4.18 (t, 2H), 3.91 (quart, 2H), 2.86-2.74 (m, 2H), 2.80 (s, 3H), 1.14 (t, 3H).

LC/MS (Method 1, ESIpos): R$_t$=0.98 min, m/z=335 [M+H]$^+$.

WORKING EXAMPLES

Example 1

6-[(4-Hydroxypiperidin-1-yl)carbonyl]-5-methyl-3-(2-phenylethyl)-1-(3,3,3-trifluoropropyl)thieno[2,3-d]pyrimidine-2,4(1H,3H)-dione

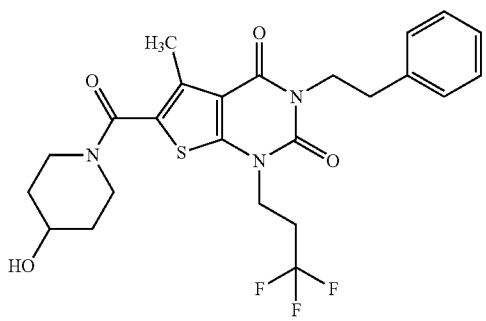 [SMILES: Cc1c(C(=O)N2CCC(O)CC2)sc2c1c(=O)n(CCc1ccccc1)c(=O)n2CCC(F)(F)F]

Preparation of the acid chloride: At RT, first 61 μl (0.70 mmol) of oxalyl chloride and then a small drop of DMF were added to a solution of 60 mg (0.140 mmol) of the compound from Ex. 43A in 2 ml of dichloromethane. After the reaction mixture had been stirred at RT for 2 h, it was evaporated to dryness on a rotary evaporator. The residue that remained was dried under high vacuum and then reacted further in the next partial step.

Preparation of the amide: The acid chloride obtained above was dissolved in 2 ml of anhydrous THF, and this solution was added dropwise to a solution of 17 mg (0.170 mmol) of 4-hydroxypiperidine and 49 μl (0.280 mmol) of N,N-diisopropylethylamine in 2 ml of anhydrous THF. A few drops of dichloromethane were then added, and the reaction mixture was stirred at RT for 1 h. After the mixture had been evaporated to dryness on a rotary evaporator, the crude product was purified by preparative HPLC (Method 5). This gave, after combination of the product fractions, evaporation and drying of the residue under high vacuum, 69 mg (96% of theory) of the title compound.

$^1$H-NMR (400 MHz, CDCl$_3$, δ/ppm): 7.32-7.21 (m, 5H, partially obscured by the CHCl$_3$ signal), 4.22 (t, 2H), 4.14 (t, 2H), 4.03 (m, 1H), 3.98-3.90 (br. m, 2H), 3.45-3.37 (m, 2H), 2.94 (t, 2H), 2.64-2.52 (m, 2H), 2.51 (s, 3H), 1.98-1.91 (m, 2H), 1.65-1.55 (m, 2H, partially obscured by the water signal).

LC/MS (Method 1, ESIpos): R$_t$=1.04 min, m/z=510 [M+H]$^+$.

Example 2

1-(4,4-Difluorobut-3-en-1-yl)-6-[(4-hydroxypiperidin-1-yl)carbonyl]-5-methyl-3-(2-phenylethyl)thieno[2,3-d]pyrimidine-2,4(1H,3H)-dione

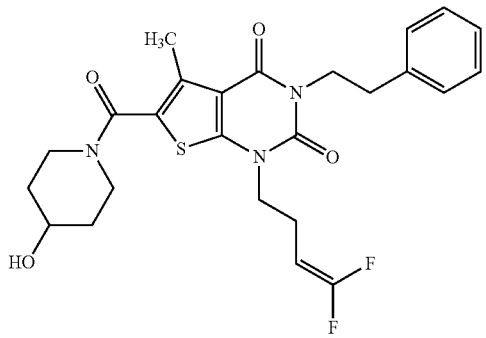 [SMILES: Cc1c(C(=O)N2CCC(O)CC2)sc2c1c(=O)n(CCc1ccccc1)c(=O)n2CCC=C(F)F]

Analogously to the process described in Ex. 1, 70 mg (0.170 mmol) of the compound from Ex. 44A and 20 mg (0.20 mmol) of 4-hydroxypiperidine gave 42 mg (50% of theory) of the title compound. In deviation to the process described above, the reaction time in the second partial step (amide formation) was not 1 h but about 16 h.

$^1$H-NMR (400 MHz, DMSO-$d_6$, δ/ppm): 7.33-7.29 (m, 2H), 7.27-7.20 (m, 3H), 4.82 (d, 1H), 4.62 (d of t of d, 1H), 4.07 (dd, 2H), 3.93 (t, 2H), 3.82-3.71 (br. m, 3H), 3.24 (m, 2H), 2.83 (dd, 2H), 2.41-2.33 (m, 2H), 2.38 (s, 3H), 1.80-1.72 (m, 2H), 1.40-1.30 (m, 2H).

LC/MS (Method 1, ESIpos): $R_t$=1.04 min, m/z=504 [M+H]$^+$.

Example 3

6-[(4-Hydroxypiperidin-1-yl)carbonyl]-1-(2-methoxyethyl)-5-methyl-3-(2-phenylethyl)thieno[2,3-d]pyrimidine-2,4(1H,3H)-dione

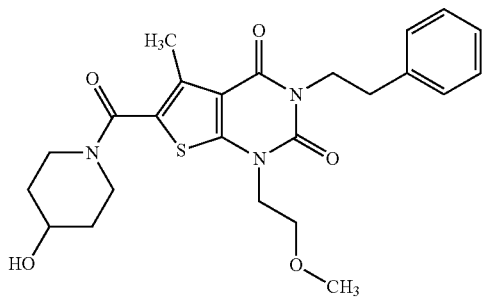 [SMILES: COCCn1c(=O)n(CCc2ccccc2)c(=O)c2c(C)c(C(=O)N3CCC(O)CC3)sc21]

Analogously to the process described in Ex. 1, 100 mg (0.260 mmol) of the compound from Ex. 45A and 31 mg (0.310 mmol) of 4-hydroxypiperidine gave 102 mg (82% of theory) of the title compound. In deviation to the process described above, the reaction time in the second partial step (amide formation) was not 1 h but about 16 h. Here, purification by preparative HPLC was carried out according to Method 6.

$^1$H-NMR (400 MHz, DMSO-$d_6$, δ/ppm): 7.33-7.29 (m, 2H), 7.26-7.20 (m, 3H), 4.82 (d, 1H), 4.09-4.02 (m, 4H), 3.82-3.71 (m, 3H), 3.62 (t, 2H), 3.27-3.19 (m, 2H), 2.25 (s, 3H), 2.84 (m, 2H), 2.37 (s, 3H), 1.80-1.73 (m, 2H), 1.40-1.30 (m, 2H).

LC/MS (Method 1, ESIpos): $R_t$=0.93 min, m/z=472 [M+H]$^+$.

Example 4

3-[2-(2-Fluorophenyl)ethyl]-6-[(4-hydroxypiperidin-1-yl)carbonyl]-5-methyl-1-(3,3,3-trifluoropropyl)thieno[2,3-d]pyrimidine-2,4(1H,3H)-dione

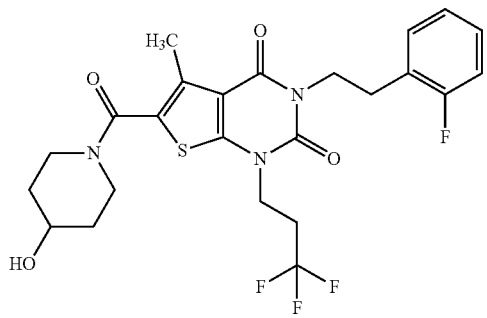 [SMILES: Cc1c(C(=O)N2CCC(O)CC2)sc2c1c(=O)n(CCc1ccccc1Cl)c(=O)n2CCC(F)(F)F]

Analogously to the process described in Ex. 1, 95 mg (0.210 mmol) of the compound from Ex. 46A and 29 mg (0.287 mmol) of 4-hydroxypiperidine gave 112 mg (99% of theory) of the title compound. In deviation to the process described above, the reaction time in the second partial step (amide formation) was not 1 h but about 16 h.

$^1$H-NMR (400 MHz, DMSO-$d_6$, δ/ppm): 7.30-7.24 (m, 2H), 7.17-7.10 (m, 2H), 4.82 (d, 1H), 4.13-4.06 (m, 4H), 3.82-3.71 (m, 3H), 3.24 (m, 2H), 2.90 (t, 2H), 2.78-2.66 (m, 2H), 2.36 (s, 3H), 1.80-1.72 (m, 2H), 1.40-1.31 (m, 2H).

LC/MS (Method 1, ESIpos): $R_t$=1.03 min, m/z=528 [M+H]$^+$.

Example 5

1-(4,4-Difluorobut-3-en-1-yl)-3-[2-(2-fluorophenyl)ethyl]-6-[(4-hydroxypiperidin-1-yl)carbonyl]-5-methylthieno[2,3-d]pyrimidine-2,4(1H,3H)-dione

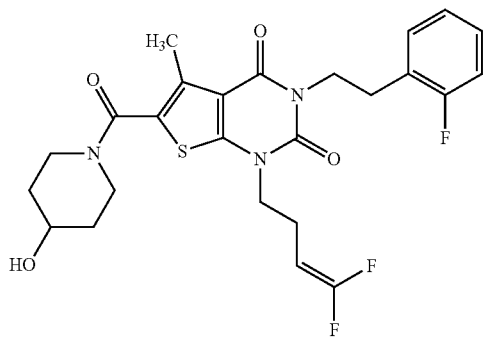

Analogously to the process described in Ex. 1, 75 mg (0.170 mmol) of the compound from Ex. 47A and 41 mg (0.405 mmol) of 4-hydroxypiperidine gave 88 mg (99% of theory) of the title compound. In deviation to the process described above, the reaction time in the first partial step (acid chloride formation) was 3 h and in the second partial step (amide formation) was about 16 h.

¹H-NMR (400 MHz, DMSO-d₆, δ/ppm): 7.30-7.24 (m, 2H), 7.16-7.10 (m, 2H), 4.81 (d, 1H), 4.60 (d of t of d, 1H), 4.10 (m, 2H), 3.91 (m, 2H), 3.81-3.71 (m, 3H), 3.23 (m, 2H), 2.90 (m, 2H), 2.36 (s, 3H), 1.80-1.72 (m, 2H), 1.40-1.30 (m, 2H).

LC/MS (Method 1, ESIpos): R$_t$=1.04 min, m/z=522 [M+H]⁺.

Example 6

3-[2-(2-Chlorophenyl)ethyl]-6-[(4-hydroxypiperidin-1-yl)carbonyl]-5-methyl-1-(3,3,3-trifluoropropyl)thieno [2,3-d]pyrimidine-2,4(1H,3H)-dione

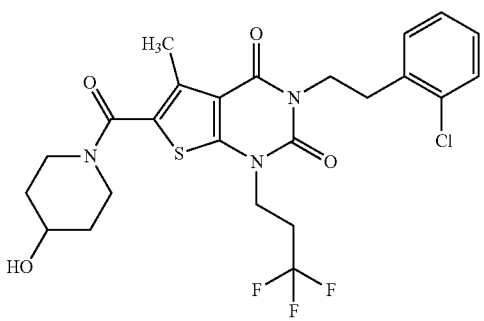

Preparation of the acid chloride: At RT, first 71 μl (0.810 mmol) of oxalyl chloride and then a small drop of DMF were added to a solution of 75 mg (0.160 mmol) of the compound from Ex. 48A in 2.5 ml of dichloromethane After the reaction mixture had been stirred at RT for 2 h, it was evaporated to dryness on a rotary evaporator. The residue that remained was dried under high vacuum and then reacted further in the next partial step.

Preparation of the amide: The acid chloride obtained above was dissolved in 2 ml of dichloromethane, and this solution was added dropwise to a solution of 25 mg (0.240 mmol) of 4-hydroxypiperidine and 57 μl (0.330 mmol) of N,N-diisopropylethylamine in 2.5 ml of anhydrous THF. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 83 mg (94% of theory) of the title compound.

¹H-NMR (400 MHz, DMSO-d₆, δ/ppm): 7.43-7.40 (m, 1H), 7.31-7.24 (m, 3H), 4.82 (d, 1H), 4.15-4.07 (m, 4H), 3.82-3.71 (m, 3H), 3.24 (m, 2H), 2.99 (t, 2H), 2.78-2.66 (m, 2H), 2.36 (s, 3H), 1.80-1.73 (m, 2H), 1.40-1.31 (m, 2H).

LC/MS (Method 1, ESIpos): R$_t$=1.08 min, m/z=544/546 [M+H]⁺.

Example 7

3-[2-(2-Chlorophenyl)ethyl]-1-(4,4-difluorobut-3-en-1-yl)-6-[(4-hydroxypiperidin-1-yl)carbonyl]-5-methylthieno[2,3-d]pyrimidine-2,4(1H,3H)-dione

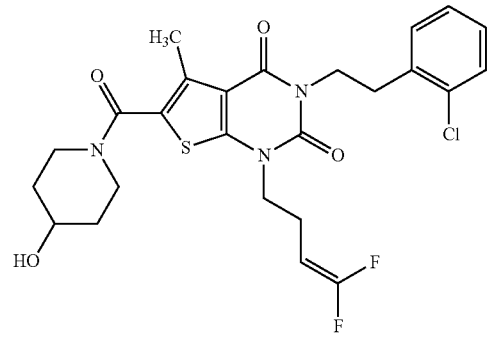 [SMILES: Cc1c(C(=O)N2CCC(O)CC2)sc2c1c(=O)n(CCc1ccccc1Cl)c(=O)n2CCC=C(F)F]

Analogously to the process described in Ex. 6, 75 mg (0.160 mmol) of the compound from Ex. 49A and 25 mg (0.250 mmol) of 4-hydroxypiperidine gave 85 mg (95% of theory) of the title compound.

¹H-NMR (400 MHz, DMSO-d₆, δ/ppm): 7.43-7.40 (m, 1H), 7.32-7.23 (m, 3H), 4.82 (d, 1H), 4.60 (d of t of d, 1H), 4.13 (m, 2H), 3.91 (t, 2H), 3.81-3.71 (m, 3H), 3.23 (m, 2H), 2.99 (t, 2H), 2.38-2.32 (m, 2H), 2.35 (s, 3H), 1.80-1.73 (m, 2H), 1.40-1.30 (m, 2H).

LC/MS (Method 1, ESIpos): R$_t$=1.10 min, m/z=538/540 [M+H]⁺.

Example 8

6-[(4-Hydroxypiperidin-1-yl)carbonyl]-5-methyl-3-[2-(2-methylphenyl)ethyl]-1-(3,3,3-trifluoropropyl)thieno[2,3-d]pyrimidine-2,4(1H,3H)-dione

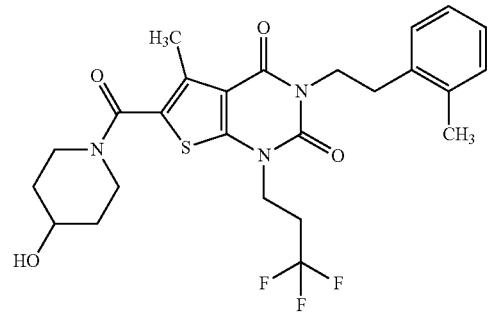 [SMILES: Cc1ccccc1CCn1c(=O)c2c(C)c(C(=O)N3CCC(O)CC3)sc2n(CCC(F)(F)F)c1=O]

59 mg (0.104 mmol) of the compound from Ex. 63A were dissolved in 3 ml of ethanol, and 210 μl (0.210 mmol) of a 1 M solution of lithium hydroxide in water were added. After 1 h of stirring at RT, the reaction mixture was separated directly by preparative HPLC into its components (Method 5). The product fractions were combined and concentrated, and the residue was dried under high vacuum. 51 mg (93% of theory) of the title compound were obtained.

¹H-NMR (400 MHz, CDCl₃, δ/ppm): 7.22-7.10 (m, 4H), 4.19-4.12 (m, 4H), 4.03 (m, 1H), 3.98-3.90 (m, 2H), 3.44-3.37 (m, 2H), 2.94 (m, 2H), 2.65-2.54 (m, 2H), 2.52 (s, 3H), 2.47 (s, 3H), 1.98-1.90 (m, 2H), 1.65-1.57 (m, 2H, partially obscured by the water signal).

LC/MS (Method 1, ESIpos): $R_t$=1.06 min, m/z=524 [M+H]$^+$.

Example 9

3-[2-(3-Fluorophenyl)ethyl]-6-[(4-hydroxypiperidin-1-yl)carbonyl]-5-methyl-1-(3,3,3-trifluoropropyl)thieno[2,3-d]pyrimidine-2,4(1H,3H)-dione

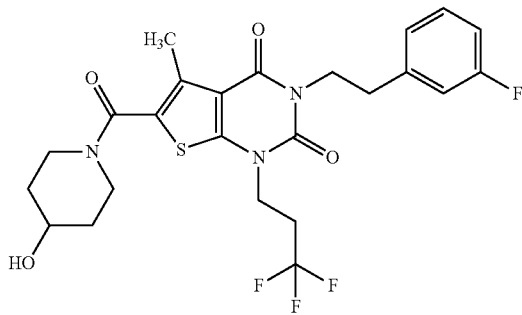 [SMILES: Cc1c(C(=O)N2CCC(O)CC2)sc2c1c(=O)n(CCc1cccc(F)c1)c(=O)n2CCC(F)(F)F]

Analogously to the process described in Ex. 8, 53 mg (0.093 mmol) of the compound from Ex. 64 gave 37 mg (75% of theory) of the title compound. In deviation to the process described above, here the reaction time was 3 h.

$^1$H-NMR (400 MHz, CDCl$_3$, δ/ppm): 7.07 (d, 1H), 7.00 (d, 1H), 6.92 (dt, 1H), 4.23-4.13 (m, 4H), 4.04 (m, 1H), 3.98-3.90 (m, 2H), 3.45-3.37 (m, 2H), 2.94 (m, 2H), 2.66-2.55 (m, 2H), 2.51 (s, 3H), 1.98-1.91 (m, 2H), 1.66-1.57 (m, 2H, partially obscured by the water signal).

LC/MS (Method 1, ESIpos): $R_t$=1.01 min, m/z=528 [M+H]$^+$.

Example 10

3-[2-(3-Chlorophenyl)ethyl]-6-[(4-hydroxypiperidin-1-yl)carbonyl]-5-methyl-1-(3,3,3-trifluoropropyl)thieno[2,3-d]pyrimidine-2,4(1H,3H)-dione

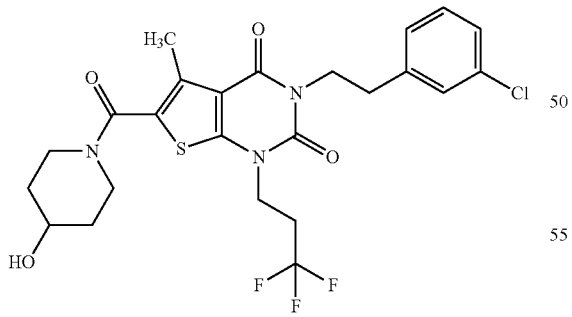

Analogously to the process described in Ex. 8, 60 mg (0.10 mmol) of the compound from Ex. 65A gave 45 mg (77% of theory, purity 95%) of the title compound. In deviation to the process described above, here the reaction time was 3 h.

$^1$H-NMR (400 MHz, CDCl$_3$, δ/ppm): 7.29-7.17 (m, 4H, partially obscured by the CHCl$_3$ signal), 4.22-4.13 (m, 4H), 4.03 (m, 1H), 3.98-3.89 (m, 2H), 3.45-3.37 (m, 2H), 2.92 (m, 2H), 2.67-2.55 (m, 2H), 2.51 (s, 3H), 1.98-1.90 (m, 2H), 1.66-1.56 (m, 2H, partially obscured by the water signal).

LC/MS (Method 1, ESIpos): $R_t$=1.06 min, m/z=544/546 [M+H]$^+$.

Example 11

6-[(4-Hydroxypiperidin-1-yl)carbonyl]-5-methyl-3-[2-(3-methylphenyl)ethyl]-1-(3,3,3-trifluoropropyl)thieno[2,3-d]pyrimidine-2,4(1H,3H)-dione

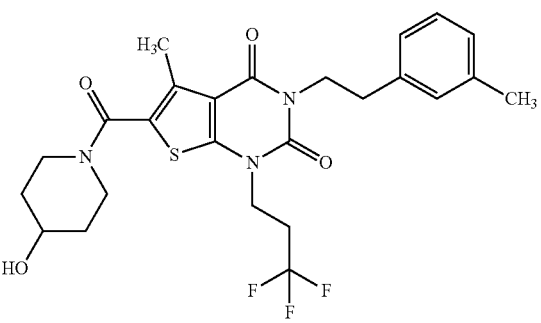 [SMILES: Cc1cccc(CCn2c(=O)c3c(C)c(C(=O)N4CCC(O)CC4)sc3n(CCC(F)(F)F)c2=O)c1]

Analogously to the process described in Ex. 8, 55 mg (0.10 mmol) of the compound from Ex. 66A gave 44 mg (86% of theory) of the title compound.

$^1$H-NMR (400 MHz, CDCl$_3$, δ/ppm): 7.20 (t, 1H), 7.14 (s, 1H), 7.10 (d, 1H), 7.04 (d, 1H), 4.21-4.14 (m, 4H), 4.03 (m, 1H), 3.98-3.90 (m, 2H), 3.44-3.37 (m, 2H), 2.89 (m, 2H), 2.66-2.55 (m, 2H), 2.52 (s, 3H), 2.33 (s, 3H), 1.98-1.90 (m, 2H), 1.66-1.56 (m, 2H, partially obscured by the water signal).

LC/MS (Method 1, ESIpos): $R_t$=1.09 min, m/z=524 [M+H]$^+$.

Example 12

3-[2-(4-Fluorophenyl)ethyl]-6-[(4-hydroxypiperidin-1-yl)carbonyl]-5-methyl-1-(3,3,3-trifluoropropyl)thieno[2,3-d]pyrimidine-2,4(1H,3H)-dione

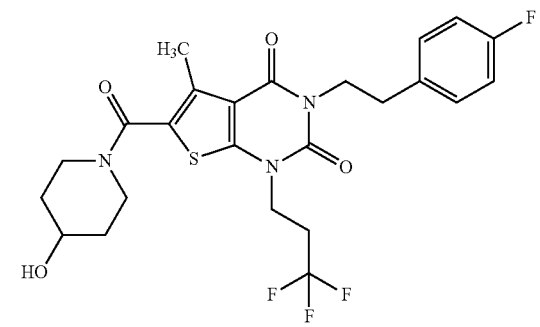 [SMILES: Cc1c(C(=O)N2CCC(O)CC2)sc2c1c(=O)n(CCc1ccc(F)cc1)c(=O)n2CCC(F)(F)F]

Analogously to the process described in Ex. 8, 35 mg (0.061 mmol) of the compound from Ex. 67A gave 30 mg (93% of theory) of the title compound. In deviation to the process described above, here the reaction time was 2 h.

$^1$H-NMR (400 MHz, CDCl$_3$, δ/ppm): 7.27-7.23 (m, 2H, partially obscured by the CHCl$_3$ signal), 6.99 (t, 2H), 4.20-4.13 (m, 4H), 4.03 (m, 1H), 3.97-3.90 (m, 2H), 3.45-3.37

(m, 2H), 2.91 (m, 2H), 2.66-2.54 (m, 2H), 2.51 (s, 3H), 1.98-1.90 (m, 2H), 1.66-1.55 (m, 2H, partially obscured by the water signal).

LC/MS (Method 1, ESIpos): $R_t$=1.02 min, m/z=528 [M+H]$^+$.

Example 13

3-[2-(4-Chlorophenyl)ethyl]-6-[(4-hydroxypiperidin-1-yl)carbonyl]-5-methyl-1-(3,3,3-trifluoropropyl)thieno[2,3-d]pyrimidine-2,4(1H,3H)-dione

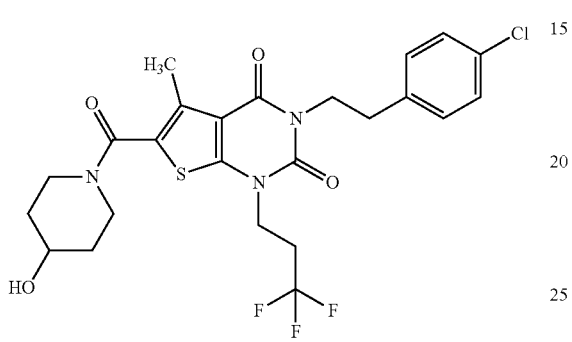

Analogously to the process described in Ex. 8, 74 mg (0.126 mmol) of the compound from Ex. 68A gave 60 mg (87% of theory) of the title compound. In deviation to the process described above, here the reaction time was 2 h.

$^1$H-NMR (400 MHz, CDCl$_3$, δ/ppm): 7.27 (d, 2H), 7.22 (d, 2H), 4.20-4.13 (m, 4H), 4.04 (m, 1H), 3.97-3.90 (m, 2H), 3.45-3.37 (m, 2H), 2.91 (m, 2H), 2.65-2.53 (m, 2H), 2.51 (s, 3H), 1.98-1.90 (m, 2H), 1.66-1.56 (m, 2H, partially obscured by the water signal).

LC/MS (Method 1, ESIpos): $R_t$=1.10 min, m/z=544/546 [M+H]$^+$.

Example 14

6-[(4-Hydroxypiperidin-1-yl)carbonyl]-3-[2-(4-methoxyphenyl)ethyl]-5-methyl-1-(3,3,3-trifluoropropyl)thieno[2,3-d]pyrimidine-2,4(1H,3H)-dione

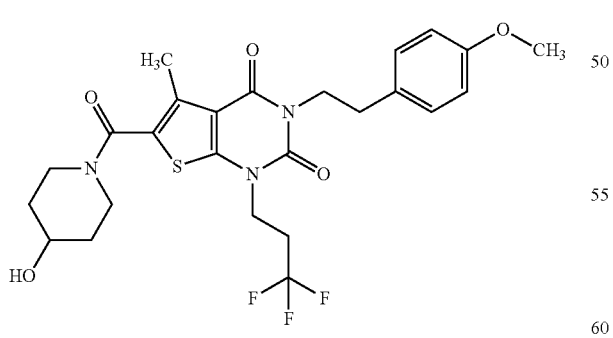

Analogously to the process described in Ex. 8, 66 mg (0.11 mmol) of the compound from Ex. 69A gave 54 mg (87% of theory) of the title compound. In deviation to the process described above, here the reaction time was 2 h.

$^1$H-NMR (400 MHz, CDCl$_3$, δ/ppm): 7.20 (d, 2H), 6.84 (d, 2H), 4.19-4.12 (m, 4H), 4.03 (m, 1H), 3.98-3.90 (m, 2H), 3.79 (s, 3H), 3.44-3.37 (m, 2H), 2.88 (m, 2H), 2.64-2.54 (m, 2H), 2.51 (s, 3H), 1.98-1.91 (m, 2H), 1.65-1.55 (m, 2H, partially obscured by the water signal).

LC/MS (Method 1, ESIpos): $R_t$=0.98 min, m/z=540 [M+H]$^+$.

Example 15

3-[2-(2-Chlorophenyl)ethyl]-1-(4,4-difluorobut-3-en-1-yl)-6-[(4-hydroxypiperidin-1-yl)carbonyl]-5-methylthieno[2,3-d]pyrimidine-2,4(1H,3H)-dione

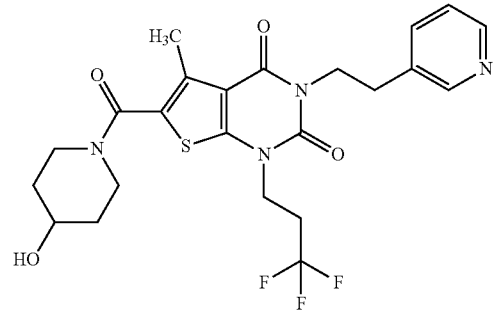 [SMILES: Cc1c(C(=O)N2CCC(O)CC2)sc2c1c(=O)n(CCc1cccnc1)c(=O)n2CCC(F)(F)F]

Analogously to the process described in Ex. 6, 75 mg (0.160 mmol) of the compound from Ex. 50A and 25 mg (0.250 mmol) of 4-hydroxypiperidine gave 62 mg (70% of theory, purity 93%) of the title compound. In addition to the process described above, here the product obtained after preparative HPLC purification was dissolved in a little methanol, and the solution was passed through a bicarbonate cartridge (from Polymerlabs, Stratospheres SPE, PL-HCO$_3$ MP SPE, capacity 0.9 mmol) to yield, after subsequent evaporation and drying of the residue under high vacuum, the free base.

$^1$H-NMR (400 MHz, DMSO-d$_6$, δ/ppm): 8.44-8.41 (m, 2H), 7.66 (d, 1H), 7.32 (dd, 1H), 4.82 (d, 1H), 4.13-4.08 (m, 4H), 3.82-3.71 (m, 3H), 3.24 (m, 2H), 2.88 (t, 2H), 2.81-2.68 (m, 2H), 2.36 (s, 3H), 1.80-1.72 (m, 2H), 1.41-1.31 (m, 2H).

LC/MS (Method 1, ESIpos): $R_t$=0.60 min, m/z=511 [M+H]$^+$.

Example 16

1-(4,4-Difluorobut-3-en-1-yl)-6-[(4-hydroxypiperidin-1-yl)carbonyl]-5-methyl-3-[2-(pyridin-3-yl)ethyl]thieno[2,3-d]pyrimidine-2,4(1H,3H)-dione

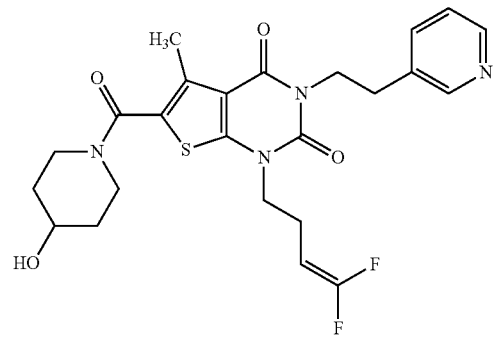 [SMILES: Cc1c(C(=O)N2CCC(O)CC2)sc2c1c(=O)n(CCc1cccnc1)c(=O)n2CCC=C(F)F]

Analogously to the process described in Ex. 6, 75 mg (0.160 mmol) of the compound from Ex. 51A and 25 mg (0.250 mmol) of 4-hydroxypiperidine gave 50 mg (61% of theory) of the title compound. In addition to the process described above, here the product obtained after preparative HPLC purification was dissolved in a little methanol, and the solution was passed through a bicarbonate cartridge (from Polymerlabs, Stratospheres SPE, PL-HCO$_3$ MP SPE, capacity 0.9 mmol) to yield, after subsequent evaporation and drying of the residue under high vacuum, the free base.

$^1$H-NMR (400 MHz, DMSO-d$_6$, δ/ppm): 8.44-8.41 (m, 2H), 7.66 (d, 1H), 7.32 (dd, 1H), 4.82 (broad, 1H), 4.61 (d of t of d, 1H), 4.10 (m, 2H), 3.92 (t, 2H), 3.81-3.72 (m, 3H), 3.24 (m, 2H), 2.88 (t, 2H), 2.39-2.33 (m, 2H), 2.36 (s, 3H), 1.80-1.72 (m, 2H), 1.40-1.31 (m, 2H).

LC/MS (Method 1, ESIpos): R$_t$=0.63 min, m/z=505 [M+H]$^+$.

Example 17

6-[(4-Hydroxypiperidin-1-yl)carbonyl]-5-methyl-3-[2-(pyrazin-2-yl)ethyl]-1-(3,3,3-trifluoropropyl)thieno[2,3-d]pyrimidine-2,4(1H,3H)-dione

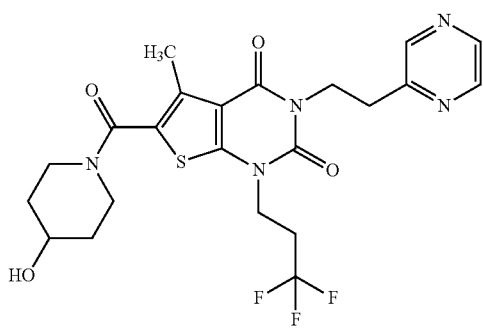 [SMILES: Cc1c(C(=O)N2CCC(O)CC2)sc2c1c(=O)n(CCc1cnccn1)c(=O)n2CCC(F)(F)F]

Analogously to the process described in Ex. 8, 90 mg (0.08 mmol, purity about 50%) of the compound from Ex. 70A gave 35 mg (85% of theory) of the title compound. In addition to the process described above, here the product obtained after preparative HPLC purification was dissolved in a little methanol, and the solution was passed through a bicarbonate cartridge (from Polymerlabs, Stratospheres SPE, PL-HCO$_3$ MP SPE, capacity 0.9 mmol) to yield, after subsequent evaporation and drying of the residue under high vacuum, the free base.

$^1$H-NMR (400 MHz, DMSO-d$_6$, δ/ppm): 8.50 (d, 1H), 8.49 (s, 1H), 8.43 (d, 1H), 4.42 (t, 2H), 4.13 (t, 2H), 4.04 (m, 1H), 3.98-3.90 (m, 2H), 3.44-3.37 (m, 2H), 3.18 (t, 2H), 2.65-2.53 (m, 2H), 2.48 (s, 3H), 1.98-1.90 (m, 2H), 1.66-1.56 (m, 2H, obscured by the water signal).

LC/MS (Method 1, ESIpos): R$_t$=0.77 min, m/z=512 [M+H]$^+$.

Example 18

3-Ethyl-6-[(4-hydroxypiperidin-1-yl)carbonyl]-5-methyl-1-(3,3,3-trifluoropropyl)thieno[2,3-d]pyrimidine-2,4(1H,3H)-dione

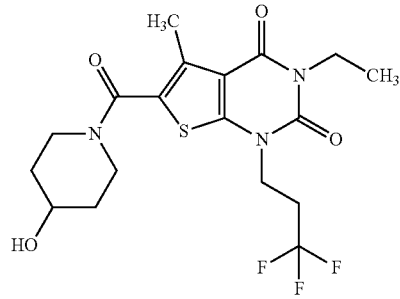 [SMILES: CCn1c(=O)c2c(C)c(C(=O)N3CCC(O)CC3)sc2n(CCC(F)(F)F)c1=O]

Preparation of the Acid Chloride: At RT, first 2.5 ml (28.6 mmol) of oxalyl chloride and then a drop of DMF were added to a solution of 2.0 g (5.71 mmol) of the compound from Ex. 52A in 60 ml of dichloromethane. After the reaction mixture had been stirred at RT for 2 h, it was evaporated to dryness on a rotary evaporator. The residue that remained was dried under high vacuum and then reacted further in the next partial step.

Preparation of the Amide: The acid chloride obtained above was dissolved in 30 ml of anhydrous THF, and this solution was added dropwise to a solution of 693 mg (6.85 mmol) of 4-hydroxypiperidine and 2 ml (11.4 mmol) of N,N-diisopropylethylamine in 30 ml of anhydrous THF. The reaction mixture was then stirred at RT for about 16 h. After the mixture had been evaporated to dryness on a rotary evaporator, about 100 ml of water were added to the residue and the mixture was extracted three times with in each case about 150 ml of ethyl acetate. The combined organic extract was washed with saturated aqueous sodium chloride solution, dried over anhydrous magnesium sulphate, filtered and evaporated. At RT, the residue obtained in this manner was stirred in a mixture of 30 ml of pentane and 0.5 ml of diethyl ether for 2 h. The mixture was then filtered and the solid was washed with a little pentane and dried under a high vacuum. This gave 2.32 g (91% of theory) of the title compound.

$^1$H-NMR (400 MHz, DMSO-d$_6$, δ/ppm): 4.81 (d, 1H), 4.13 (t, 2H), 3.91 (quart, 2H), 3.82-3.71 (m, 3H), 3.24 (m, 2H), 2.85-2.73 (m, 2H), 2.38 (s, 3H), 1.80-1.72 (m, 2H), 1.39-1.30 (m, 2H), 1.13 (t, 3H).

LC/MS (Method 1, ESIpos): R$_t$=0.84 min, m/z=434 [M+H]$^+$.

Example 19

1-(4,4-Difluorobut-3-en-1-yl)-3-ethyl-6-[(4-hydroxypiperidin-1-yl)carbonyl]-5-methylthieno[2,3-d]pyrimidine-2,4(1H,3H)-dione

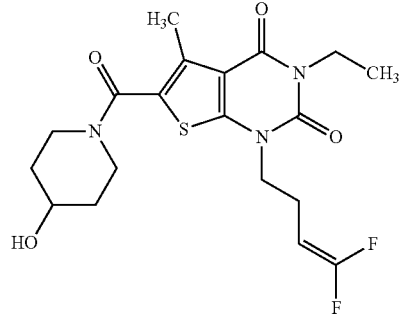 [SMILES: CCn1c(=O)c2c(C)c(C(=O)N3CCC(O)CC3)sc2n(CCC=C(F)F)c1=O]

Analogously to the process described in Ex. 1, 70 mg (0.20 mmol) of the compound from Ex. 53A and 25 mg (0.240 mmol) of 4-hydroxypiperidine gave 70 mg (80% of theory) of the title compound. In deviation to the process described above, the reaction time in the first partial step (acid chloride formation) was only 1 h and in the second partial step (amide formation) was not 1 h but about 16 h.

$^1$H-NMR (400 MHz, DMSO-$d_6$, δ/ppm): 4.81 (d, 1H), 4.63 (d of t of d, 1H), 3.96-3.88 (m, 4H), 3.81-3.71 (m, 3H), 3.23 (m, 2H), 2.42-2.36 (m, 2H), 2.38 (s, 3H), 1.79-1.72 (m, 2H), 1.39-1.30 (m, 2H), 1.12 (t, 3H).

LC/MS (Method 1, ESIpos): $R_t$=0.84 min, m/z=428 [M+H]$^+$.

Example 20

3-Ethyl-6-[(4-hydroxypiperidin-1-yl)carbonyl]-1-(2-methoxyethyl)-5-methylthieno[2,3-d]pyrimidine-2,4(1H,3H)-dione

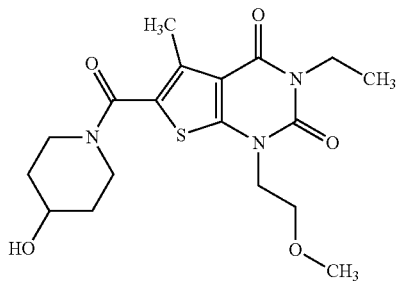 [SMILES: CCn1c(=O)c2c(C)c(C(=O)N3CCC(O)CC3)sc2n(CCOC)c1=O]

Analogously to the process described in Ex. 1, 75 mg (0.220 mmol) of the compound from Ex. 54A and 27 mg (0.270 mmol) of 4-hydroxypiperidine gave 57 mg (64% of theory) of the title compound. In deviation to the process described above, the reaction time in the first partial step (acid chloride formation) was only 1 h.

$^1$H-NMR (400 MHz, DMSO-$d_6$, δ/ppm): 4.81 (d, 1H), 4.05 (t, 2H), 3.91 (quart, 2H), 3.82-3.70 (m, 3H), 3.65 (t, 2H), 3.26-3.19 (m, 2H), 3.25 (s, 3H), 2.37 (s, 3H), 1.79-1.72 (m, 2H), 1.39-1.30 (m, 2H), 1.12 (t, 3H).

LC/MS (Method 1, ESIpos): $R_t$=0.72 min, m/z=396 [M+H]$^+$.

Example 21

3-Ethyl-6-[(4-hydroxy-4-methylpiperidin-1-yl)carbonyl]-5-methyl-1-(3,3,3-trifluoropropyl)thieno[2,3-d]pyrimidine-2,4(1H,3H)-dione

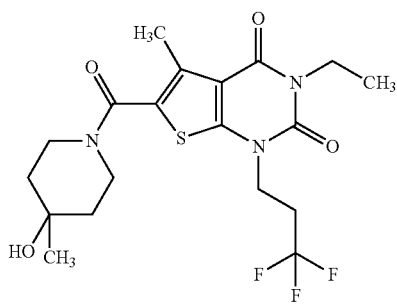 [SMILES: CCn1c(=O)c2c(C)c(C(=O)N3CCC(C)(O)CC3)sc2n(CCC(F)(F)F)c1=O]

Preparation of the Acid Chloride: At RT, first 125 μl (1.43 mmol) of oxalyl chloride and then a drop of DMF were added to a solution of 100 mg (0.290 mmol) of the compound from Ex. 52A in 3 ml of dichloromethane After the reaction mixture had been stirred at RT for 1 h, it was evaporated to dryness on a rotary evaporator. The residue that remained was dried under high vacuum and then reacted further in the next partial step.

Preparation of the Amide: The acid chloride obtained above was dissolved in 3 ml of anhydrous THF, and 40 mg (0.340 mmol) of 4-methylpiperidin-4-ol [commercially available; lit. e.g.: J. M. McManus et al., *J. Med. Chem.* 1965, 8 (6), 766-776] and 100 μl (0.570 mmol) of N,N-diisopropylethylamine were added. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 113 mg (88% of theory) of the title compound.

$^1$H-NMR (400 MHz, DMSO-$d_6$, δ/ppm): 4.47 (s, 1H), 4.12 (t, 2H), 3.91 (quart, 2H), 3.72 (broad, 2H), 3.36 (broad, 2H), 2.85-2.73 (m, 2H), 2.38 (s, 3H), 1.53-1.40 (m, 4H), 1.15 (s, 3H), 1.13 (t, 3H).

LC/MS (Method 1, ESIpos): $R_t$=0.90 min, m/z=448 [M+H]$^+$.

Example 22

3-Ethyl-6-{[4-hydroxy-4-(trifluoromethyl)piperidin-1-yl]carbonyl}-5-methyl-1-(3,3,3-trifluoropropyl)thieno[2,3-d]pyrimidine-2,4(1H,3H)-dione

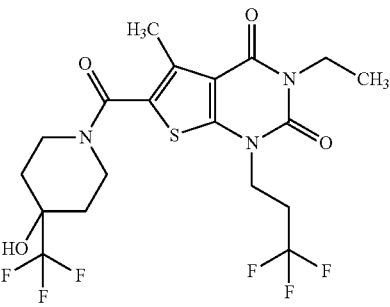 [SMILES: CCn1c(=O)c2c(C)c(C(=O)N3CCC(O)(C(F)(F)F)CC3)sc2n(CCC(F)(F)F)c1=O]

Analogously to the process described in Ex. 21, 100 mg (0.290 mmol) of the compound from Ex. 52A and 70 mg (0.340 mmol) of 4-trifluoromethylpiperidin-4-ol [commercially available; lit. e.g.: WO 2005/103002-A2, intermediate product 1] gave 135 mg (94% of theory) of the title compound.

$^1$H-NMR (400 MHz, DMSO-$d_6$, δ/ppm): 6.19 (s, 1H), 4.13 (t, 2H), 4.02 (broad, 2H), 3.91 (quart, 2H), 3.22 (br. t, 2H), 2.86-2.73 (m, 2H), 2.40 (s, 3H), 1.76-1.61 (m, 4H), 1.12 (t, 3H).

LC/MS (Method 1, ESIpos): $R_t$=0.97 min, m/z=502 [M+H]$^+$.

Example 23

3-Ethyl-6-[(3-hydroxy-8-azabicyclo[3.2.1]oct-8-yl)carbonyl]-5-methyl-1-(3,3,3-trifluoropropyl)thieno[2,3-d]pyrimidine-2,4(1H,3H)-dione

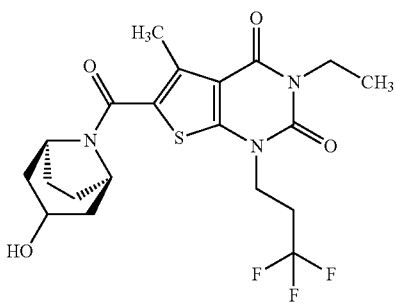 [SMILES: CCn1c(=O)c2c(C)c(C(=O)N3[C@@H]4CC[C@H]3CC(O)C4)sc2n(CCC(F)(F)F)c1=O]

In succession, solutions of 35 mg (0.10 mmol) of the compound from Ex. 52A and 45.6 mg (0.120 mmol) of HATU in in each case 300 μl of DMF and 35 μl (0.20 mmol) of N,N-diisopropylethylamine were added to 12.7 mg (0.10 mmol) of 8-azabicyclo[3.2.1]octan-3-ol [G. B. Kok et al., *J. Org. Chem.* 2010, 75 (14), 4806-4811]. After a reaction time of about 16 h at RT, the reaction mixture was separated directly by preparative HPLC into its components (Method 8). The product fractions were combined and concentrated, and the residue was dried under high vacuum. This gave 29 mg (52% of theory, 80% pure) of the title compound.

LC/MS (Method 3, ESIpos): $R_t$=0.98 min, m/z=460 [M+H]$^+$.

Example 24

6-[(4-Hydroxypiperidin-1-yl)carbonyl]-3-(2-phenylethyl)-5-(trifluoromethyl)-1-(3,3,3-trifluoropropyl)thieno[2,3-d]pyrimidine-2,4(1H,3H)-dione

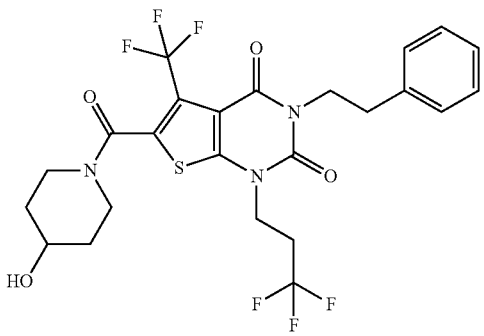 [SMILES: O=C(c1sc2c(c1C(F)(F)F)c(=O)n(CCc1ccccc1)c(=O)n2CCC(F)(F)F)N1CCC(O)CC1]

Preparation of the Acid Chloride: At RT, first 67 μl (0.760 mmol) of oxalyl chloride and then a small drop of DMF were added to a solution of 75 mg (0.150 mmol) of the compound from Ex. 55A in 2.2 ml of dichloromethane After the reaction mixture had been stirred at RT for 2 h, it was evaporated to dryness on a rotary evaporator. The residue that remained was dried under high vacuum and then reacted further in the next partial step.

Preparation of the Amide: The acid chloride obtained above was dissolved in 2 ml of anhydrous THF, and this solution was added dropwise to a solution of 20 mg (0.20 mmol) of 4-hydroxypiperidine and 53 μl (0.310 mmol) of N,N-diisopropylethylamine in 1 ml of dichloromethane. The reaction mixture was then stirred at RT for 1 h. The mixture was evaporated to dryness on a rotary evaporator, and the residue was purified by preparative HPLC (Method 5). This gave, after combination of the product fractions, evaporation and drying of the residue under high vacuum, 72 mg (84% of theory) of the title compound.

$^1$H-NMR (400 MHz, DMSO-d$_6$, δ/ppm): 7.34-7.29 (m, 2H), 7.27-7.21 (m, 3H), 4.86 (d, 1H), 4.16 (m, 2H), 4.07 (m, 2H), 3.97 (broad, 1H), 3.76 (broad, 1H), 3.45 (broad, 1H), 3.35-3.21 (m, 1H), 3.16 (m, 1H), 2.87-2.73 (m, 4H), 1.84-1.65 (broad, 2H), 1.45-1.28 (broad, 2H).

LC/MS (Method 1, ESIpos): $R_t$=1.07 min, m/z=564 [M+H]$^+$.

Example 25

3-Ethyl-6-[(4-hydroxypiperidin-1-yl)carbonyl]-5-(trifluoromethyl)-1-(3,3,3-trifluoropropyl)thieno[2,3-d]pyrimidine-2,4(1H,3H)-dione

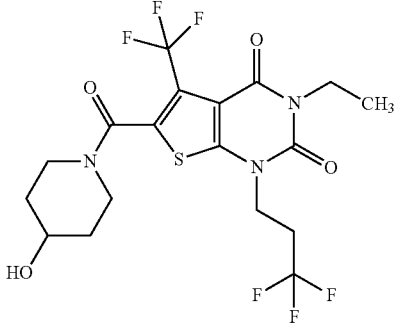 [SMILES: CCn1c(=O)c2c(C(F)(F)F)c(C(=O)N3CCC(O)CC3)sc2n(CCC(F)(F)F)c1=O]

Analogously to the process described in Ex. 24, 55 mg (0.140 mmol) of the compound from Ex. 56A and 18 mg (0.180 mmol) of 4-hydroxypiperidine gave 64 mg (97% of theory) of the title compound. In deviation to the process described above, the reaction time in the second partial step (amide formation) was about 16 h.

$^1$H-NMR (400 MHz, DMSO-d$_6$, δ/ppm): 4.85 (d, 1H), 4.16 (t, 2H), 4.02-3.88 (m, 3H), 3.76 (broad, 1H), 3.45 (m, 1H), 3.32-3.22 (br. m, 1H), 3.15 (m, 1H), 2.88-2.76 (m, 2H), 1.83-1.64 (broad, 2H), 1.43-1.25 (broad, 2H), 1.13 (t, 3H).

LC/MS (Method 1, ESIpos): $R_t$=0.87 min, m/z=488 [M+H]$^+$.

Example 26

5-Methyl-6-[(3-oxopiperazin-1-yl)carbonyl]-3-(2-phenylethyl)-1-(3,3,3-trifluoropropyl)thieno[2,3-d]pyrimidine-2,4(1H,3H)-dione

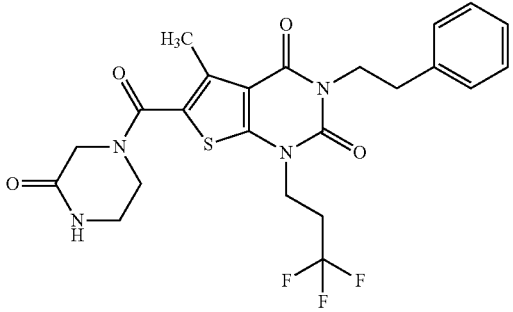 [SMILES: Cc1c(C(=O)N2CCNC(=O)C2)sc2c1c(=O)n(CCc1ccccc1)c(=O)n2CCC(F)(F)F]

Preparation of the Acid Chloride: At RT, first 77 µl (0.880 mmol) of oxalyl chloride and then a small drop of DMF were added to a solution of 75 mg (0.180 mmol) of the compound from Ex. 43A in 2 ml of dichloromethane After the reaction mixture had been stirred at RT for 1 h, it was evaporated to dryness on a rotary evaporator. The residue that remained was dried under high vacuum and then reacted further in the next partial step.

Preparation of the Amide: The acid chloride obtained above was dissolved in 2 ml of anhydrous THF, and 21 mg (0.210 mmol) of piperazin-2-one and 61 µl (0.350 mmol) of N,N-diisopropylethylamine were added. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 85 mg (95% of theory) of the title compound.

$^1$H-NMR (400 MHz, DMSO-$d_6$, δ/ppm): 8.16 (s, 1H), 7.33-7.28 (m, 2H), 7.26-7.21 (m, 3H), 4.13 (t, 2H), 4.07 (m, 2H), 4.05 (s, 2H), 3.69 (m, 2H), 3.25 (m, 2H), 2.84 (m, 2H), 2.82-2.71 (m, 2H), 2.41 (s, 3H).

LC/MS (Method 1, ESIpos): $R_t$=0.97 min, m/z=509 [M+H]$^+$.

Example 27

1-(4,4-Difluorobut-3-en-1-yl)-5-methyl-6-[(3-oxopiperazin-1-yl)carbonyl]-3-(2-phenylethyl)thieno[2,3-d]pyrimidine-2,4(1H,3H)-dione

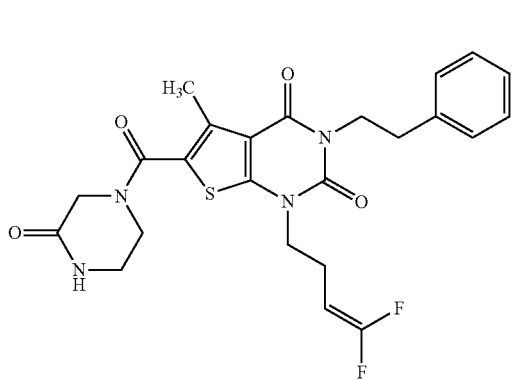 [SMILES: Cc1c(C(=O)N2CCNC(=O)C2)sc2c1c(=O)n(CCc1ccccc1)c(=O)n2CCC=C(F)F]

Analogously to the process described in Ex. 26, 75 mg (0.180 mmol) of the compound from Ex. 44A and 21 mg (0.210 mmol) of piperazin-2-one gave 88 mg (93% of theory) of the title compound.

$^1$H-NMR (400 MHz, DMSO-$d_6$, δ/ppm): 8.16 (s, 1H), 7.34-7.29 (m, 2H), 7.26-7.20 (m, 3H), 4.62 (d oft of d, 1H), 4.07 (m, 2H), 4.04 (s, 2H), 3.94 (t, 2H), 3.68 (m, 2H), 3.25 (m, 2H), 2.83 (m, 2H), 2.40 (s, 3H), 2.38 (m, 2H).

LC/MS (Method 1, ESIpos): $R_t$=1.00 min, m/z=503 [M+H]$^+$.

Example 28

1-(2-Methoxyethyl)-5-methyl-6-[(3-oxopiperazin-1-yl)carbonyl]-3-(2-phenylethyl)thieno[2,3-d]pyrimidine-2,4(1H,3H)-dione

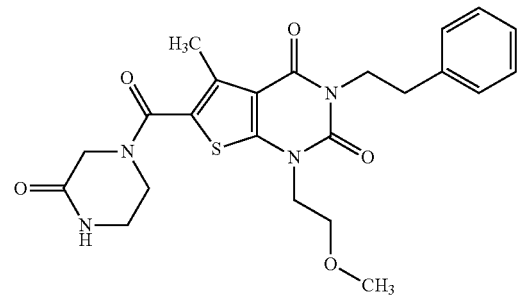 [SMILES: COCCn1c(=O)n(CCc2ccccc2)c(=O)c2c(C)c(C(=O)N3CCNC(=O)C3)sc21]

Analogously to the process described in Ex. 26, 75 mg (0.190 mmol) of the compound from Ex. 45A and 23 mg (0.230 mmol) of piperazin-2-one gave 82 mg (90% of theory) of the title compound.

$^1$H-NMR (400 MHz, DMSO-$d_6$, δ/ppm): 8.15 (s, 1H), 7.34-7.29 (m, 2H), 7.26-7.20 (m, 3H), 4.09-4.03 (m, 4H), 4.04 (s, 2H), 3.68 (m, 2H), 3.62 (t, 2H), 3.26-3.22 (m, 2H), 3.25 (s, 3H), 2.84 (m, 2H), 2.39 (s, 3H).

LC/MS (Method 1, ESIpos): $R_t$=0.86 min, m/z=471 [M+H]$^+$.

Example 29

3-[2-(2-Fluorophenyl)ethyl]-5-methyl-6-[(3-oxopiperazin-1-yl)carbonyl]-1-(3,3,3-trifluoropropyl)thieno[2,3-d]pyrimidine-2,4(1H,3H)-dione

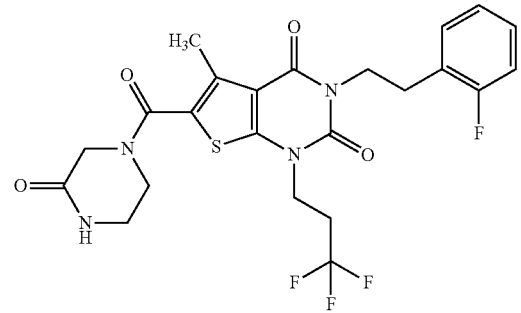 [SMILES: Cc1c(C(=O)N2CCNC(=O)C2)sc2c1c(=O)n(CCc1ccccc1F)c(=O)n2CCC(F)(F)F]

Preparation of the Acid Chloride: At RT, first 74 µl (0.840 mmol) of oxalyl chloride and then a small drop of DMF were added to a solution of 75 mg (0.170 mmol) of the compound from Ex. 46A in 1.9 ml of dichloromethane After the reaction mixture had been stirred at RT for 1 h, it was evaporated to dryness on a rotary evaporator. The residue that remained was dried under high vacuum and then reacted further in the next partial step.

Preparation of the Amide: The acid chloride obtained above was dissolved in 1.9 ml of anhydrous THF, and 20 mg (0.20 mmol) of piperazin-2-one and 59 µl (0.340 mmol) of N,N-diisopropylethylamine were added. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 65 mg (73% of theory) of the title compound.

¹H-NMR (400 MHz, DMSO-d₆, δ/ppm): 8.16 (s, 1H), 7.29-7.24 (m, 2H), 7.17-7.10 (m, 2H), 4.13-4.07 (m, 4H), 4.04 (s, 2H), 3.68 (m, 2H), 3.25 (m, 2H), 2.91 (t, 2H), 2.78-2.66 (m, 2H), 2.38 (s, 3H).

LC/MS (Method 1, ESIpos): $R_t$=0.98 min, m/z=527 [M+H]⁺.

Example 30

1-(4,4-Difluorobut-3-en-1-yl)-3-[2-(2-fluorophenyl)ethyl]-5-methyl-6-[(3-oxopiperazin-1-yl)carbonyl]thieno[2,3-d]pyrimidine-2,4(1H,3H)-dione

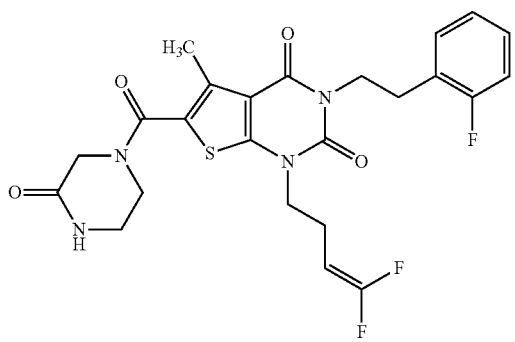 [SMILES: Cc1c(C(=O)N2CCNC(=O)C2)sc2c1c(=O)n(CCc1ccccc1F)c(=O)n2CCC=C(F)F]

Analogously to the process described in Ex. 29, 75 mg (0.170 mmol) of the compound from Ex. 47A and 21 mg (0.210 mmol) of piperazin-2-one gave 60 mg (64% of theory, purity 95%) of the title compound.

¹H-NMR (400 MHz, DMSO-d₆, δ/ppm): 8.16 (s, 1H), 7.29-7.24 (m, 2H), 7.16-7.10 (m, 2H), 4.60 (d of t of d, 1H), 4.10 (t, 2H), 4.04 (s, 2H), 3.92 (t, 2H), 3.68 (m, 2H), 3.24 (m, 2H), 2.90 (t, 2H), 2.39-2.32 (m, 2H), 2.37 (s, 3H).

LC/MS (Method 1, ESIpos): $R_t$=0.98 min, m/z=521 [M+H]⁺.

Example 31

3-[2-(2-Chlorophenyl)ethyl]-5-methyl-6-[(3-oxopiperazin-1-yl)carbonyl]-1-(3,3,3-trifluoropropyl)thieno[2,3-d]pyrimidine-2,4(1H,3H)-dione

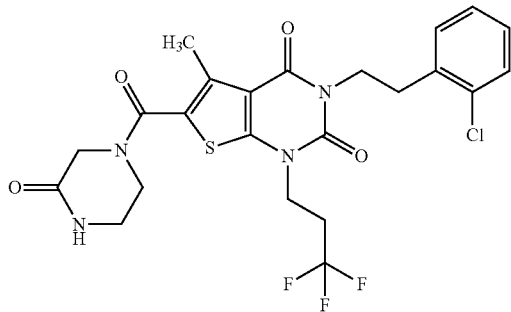 [SMILES: Cc1c(C(=O)N2CCNC(=O)C2)sc2c1c(=O)n(CCc1ccccc1Cl)c(=O)n2CCC(F)(F)F]

Preparation of the Acid Chloride: At RT, first 71 μl (0.810 mmol) of oxalyl chloride and then a small drop of DMF were added to a solution of 75 mg (0.160 mmol) of the compound from Ex. 48A in 2.5 ml of dichloromethane After the reaction mixture had been stirred at RT for 2 h, it was evaporated to dryness on a rotary evaporator. The residue that remained was dried under high vacuum and then reacted further in the next partial step.

Preparation of the Amide: The acid chloride obtained above was dissolved in 2 ml of dichloromethane, and this solution was added dropwise to a solution of 24 mg (0.240 mmol) of piperazin-2-one and 57 μl (0.330 mmol) of N,N-diisopropylethylamine in 2.5 ml of anhydrous THF. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 75 mg (84% of theory) of the title compound.

¹H-NMR (400 MHz, DMSO-d₆, δ/ppm): 8.16 (s, 1H), 7.43-7.40 (m, 1H), 7.31-7.24 (m, 3H), 4.15-4.08 (m, 4H), 4.04 (s, 2H), 3.68 (m, 2H), 3.25 (m, 2H), 3.00 (t, 2H), 2.78-2.67 (m, 2H), 2.38 (s, 3H).

LC/MS (Method 1, ESIpos): $R_t$=1.01 min, m/z=543/545 [M+H]⁺.

Example 32

3-[2-(2-Chlorophenyl)ethyl]-1-(4,4-difluorobut-3-en-1-yl)-5-methyl-6-[(3-oxopiperazin-1-yl)carbonyl]thieno[2,3-d]pyrimidine-2,4(1H,3H)-dione

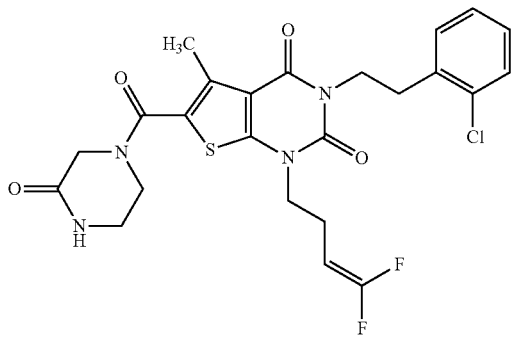 [SMILES: Cc1c(C(=O)N2CCNC(=O)C2)sc2c1c(=O)n(CCc1ccccc1Cl)c(=O)n2CCC=C(F)F]

Analogously to the process described in Ex. 31, 75 mg (0.170 mmol) of the compound from Ex. 49A and 25 mg (0.250 mmol) of piperazin-2-one gave 71 mg (80% of theory) of the title compound.

¹H-NMR (400 MHz, DMSO-d₆, δ/ppm): 8.15 (s, 1H), 7.43-7.39 (m, 1H), 7.32-7.23 (m, 3H), 4.60 (d of t of d, 1H), 4.13 (t, 2H), 4.04 (s, 2H), 3.91 (t, 2H), 3.68 (m, 2H), 3.25 (m, 2H), 2.99 (t, 2H), 2.39-2.32 (m, 2H), 2.37 (s, 3H).

LC/MS (Method 1, ESIpos): $R_t$=1.03 min, m/z=537/539 [M+H]⁺.

Example 33

5-Methyl-6-[(3-oxopiperazin-1-yl)carbonyl]-3-[2-(pyridin-3-yl)ethyl]-1-(3,3,3-trifluoropropyl)thieno[2,3-d]pyrimidine-2,4(1H,3H)-dione

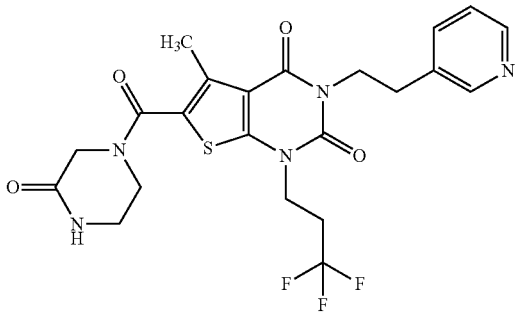 [SMILES: Cc1c(C(=O)N2CCNC(=O)C2)sc2c1c(=O)n(CCc1cccnc1)c(=O)n2CCC(F)(F)F]

Preparation of the Acid Chloride: At RT, first 71 μl (0.810 mmol) of oxalyl chloride and then a small drop of DMF were added to a solution of 75 mg (0.160 mmol) of the compound from Ex. 50A in 2.5 ml of dichloromethane After the reaction mixture had been stirred at RT for 2 h, it was evaporated to dryness on a rotary evaporator. The residue that remained was dried under high vacuum and then reacted further in the next partial step.

Preparation of the Amide: The acid chloride obtained above was dissolved in 4 ml of dichloromethane, and this solution was added dropwise to a solution of 24 mg (0.240 mmol) of piperazin-2-one and 84 μL (0.490 mmol) of N,N-diisopropylethylamine in 2.5 ml of anhydrous THF. The reaction mixture was then stirred at RT for about 16 h. After the mixture had been evaporated to dryness on a rotary evaporator, the crude product was purified by preparative HPLC (Method 5). After combination and concentration of the product fractions, the residue was dissolved in a little methanol and the solution was passed over a bicarbonate cartridge (Polymerlabs, Stratospheres SPE, PL-HCO$_3$ MP SPE, capacity 0.9 mmol). Subsequent evaporation and drying under high vacuum gave 86 mg (100% of theory) of the title compound as the free base.

$^1$H-NMR (400 MHz, DMSO-d$_6$, δ/ppm): 8.44-8.42 (m, 2H), 8.16 (s, 1H), 7.66 (m, 1H), 7.32 (m, 1H), 4.13-4.08 (m, 4H), 4.05 (s, 2H), 3.68 (m, 2H), 3.24 (m, 2H), 2.89 (t, 2H), 2.81-2.69 (m, 2H), 2.38 (s, 3H).

LC/MS (Method 1, ESIpos): R$_t$=0.57 min, m/z=510 [M+H]$^+$.

Example 34

1-(4,4-Difluorobut-3-en-1-yl)-5-methyl-6-[(3-oxopiperazin-1-yl)carbonyl]-3-[2-(pyridin-3-yl)ethyl]thieno[2,3-d]pyrimidine-2,4(1H,3H)-dione

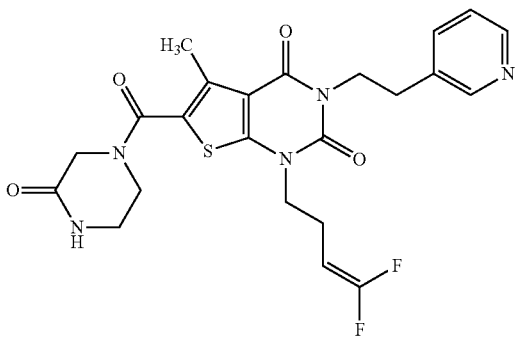 [SMILES: Cc1c(C(=O)N2CCNC(=O)C2)sc2c1c(=O)n(CCc1cccnc1)c(=O)n2CCC=C(F)F]

Analogously to the process described in Ex. 33, 75 mg (0.160 mmol) of the compound from Ex. 51A and 25 mg (0.250 mmol) of piperazin-2-one gave 52 mg (63% of theory) of the title compound.

$^1$H-NMR (400 MHz, DMSO-d$_6$, δ/ppm): 8.44-8.41 (m, 2H), 8.16 (s, 1H), 7.66 (m, 1H), 7.32 (m, 1H), 4.61 (d oft of d, 1H), 4.11 (t, 2H), 4.04 (s, 2H), 3.92 (t, 2H), 3.68 (m, 2H), 3.24 (m, 2H), 2.88 (t, 2H), 2.40-2.33 (m, 2H), 2.38 (s, 3H).

LC/MS (Method 1, ESIpos): R$_t$=0.59 min, m/z=504 [M+H]$^+$.

Example 35

3-Ethyl-5-methyl-6-[(3-oxopiperazin-1-yl)carbonyl]-1-(3,3,3-trifluoropropyl)thieno[2,3-d]pyrimidine-2,4(1H,3H)-dione

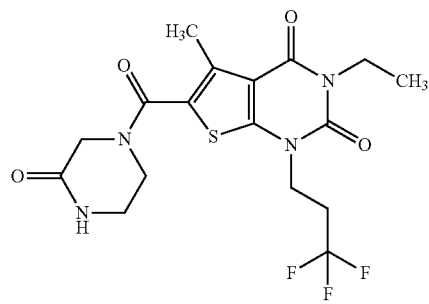 [SMILES: CCn1c(=O)c2c(C)c(C(=O)N3CCNC(=O)C3)sc2n(CCC(F)(F)F)c1=O]

Analogously to the process described in Ex. 26, 100 mg (0.290 mmol) of the compound from Ex. 52A and 34 mg (0.340 mmol) of piperazin-2-one gave 49 mg (39% of theory) of the title compound.

$^1$H-NMR (400 MHz, DMSO-d$_6$, δ/ppm): 8.15 (s, 1H), 4.13 (t, 2H), 4.04 (s, 2H), 3.91 (quart, 2H), 3.68 (m, 2H), 3.24 (m, 2H), 2.85-2.73 (m, 2H), 2.40 (s, 3H), 1.13 (t, 3H).

LC/MS (Method 1, ESIpos): R$_t$=0.76 min, m/z=433 [M+H]$^+$.

Example 36

1-(4,4-Difluorobut-3-en-1-yl)-3-ethyl-5-methyl-6-[(3-oxopiperazin-1-yl)carbonyl]thieno[2,3-d]pyrimidine-2,4(1H,3H)-dione

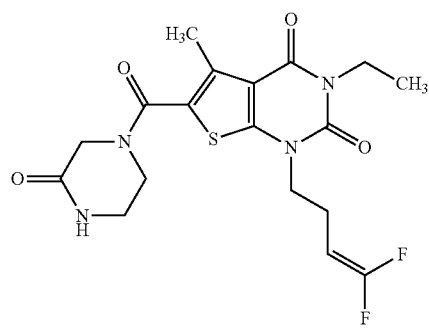 [SMILES: CCn1c(=O)c2c(C)c(C(=O)N3CCNC(=O)C3)sc2n(CCC=C(F)F)c1=O]

Analogously to the process described in Ex. 26, 75 mg (0.220 mmol) of the compound from Ex. 53A and 26 mg (0.260 mmol) of piperazin-2-one gave 73 mg (74% of theory) of the title compound.

¹H-NMR (400 MHz, DMSO-d₆, δ/ppm): 8.15 (s, 1H), 4.63 (d of t of d, 1H), 4.04 (s, 2H), 3.96-3.88 (m, 4H), 3.68 (m, 2H), 3.23 (m, 2H), 2.43-2.37 (m, 2H), 2.40 (s, 3H), 1.12 (t, 3H).

LC/MS (Method 1, ESIpos): $R_t$=0.81 min, m/z=427 [M+H]⁺.

Example 37

3-Ethyl-1-(2-methoxyethyl)-5-methyl-6-[(3-oxopiperazin-1-yl)carbonyl]thieno[2,3-d]pyrimidine-2,4(1H,3H)-dione

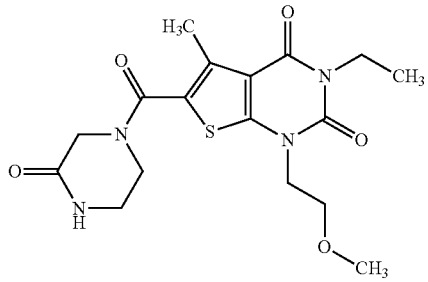 [SMILES: CCn1c(=O)c2c(C)c(C(=O)N3CCNC(=O)C3)sc2n(CCOC)c1=O]

Analogously to the process described in Ex. 26, 75 mg (0.240 mmol) of the compound from Ex. 54A and 29 mg (0.290 mmol) of piperazin-2-one gave 84 mg (88% of theory) of the title compound.

¹H-NMR (400 MHz, DMSO-d₆, δ/ppm): 8.15 (s, 1H), 4.05 (t, 2H), 4.04 (s, 2H), 3.91 (quart, 2H), 3.69-3.63 (m, 4H), 3.25 (s, 3H), 3.25-3.21 (m, 2H), 2.39 (s, 3H), 1.13 (t, 3H).

LC/MS (Method 1, ESIpos): $R_t$=0.63 min, m/z=395 [M+H]⁺.

Example 38

6-[(2,2-Dimethyl-3-oxopiperazin-1-yl)carbonyl]-3-ethyl-5-methyl-1-(3,3,3-trifluoropropyl)thieno[2,3-d]pyrimidine-2,4(1H,3H)-dione

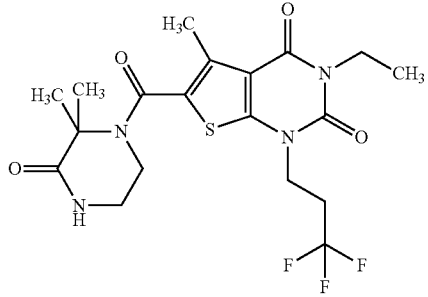 [SMILES: CCn1c(=O)c2c(C)c(C(=O)N3CCNC(=O)C3(C)C)sc2n(CCC(F)(F)F)c1=O]

Analogously to the process described under Ex. 23, 12.8 mg (0.10 mmol) of 3,3-dimethylpiperazin-2-one [A. Benjahad et al., *Tetrahedron Lett.* 1994, 35 (51), 9545-9548] and 35 mg (0.10 mmol) of the compound from Ex. 52A gave 33 mg (53% of theory, purity 75%) of the title compound.

LC/MS (Method 3, ESIpos): $R_t$=0.97 min, m/z=461 [M+H]⁺.

Example 39

3-Ethyl-5-methyl-6-[(2-methyl-3-oxopiperazin-1-yl)carbonyl]-1-(3,3,3-trifluoropropyl)thieno[2,3-d]pyrimidine-2,4(1H,3H)-dione (racemate)

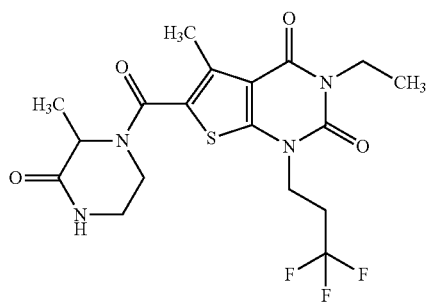 [SMILES: CCn1c(=O)c2c(C)c(C(=O)N3CCNC(=O)C3C)sc2n(CCC(F)(F)F)c1=O]

Analogously to the process described under Ex. 23, 11.4 mg (0.10 mmol) of 3-methylpiperazin-2-one [K. M. Beck et al., *J. Amer. Chem. Soc.* 1952, 74 (3), 605-608] and 35 mg (0.10 mmol) of the compound from Ex. 52A gave 20 mg (46% of theory) of the title compound.

LC/MS (Method 3, ESIpos): $R_t$=0.91 min, m/z=447 [M+H]⁺.

Example 40

3-Ethyl-6-[(2-ethyl-3-oxopiperazin-1-yl)carbonyl]-5-methyl-1-(3,3,3-trifluoropropyl)thieno[2,3-d]pyrimidine-2,4(1H,3H)-dione (racemate)

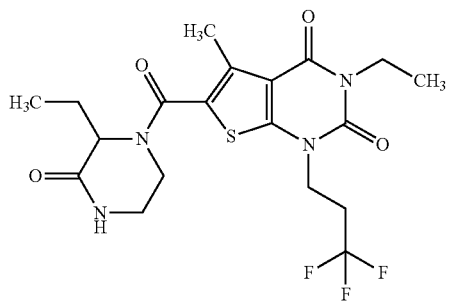 [SMILES: CCC1C(=O)NCCN1C(=O)c1sc2c(c1C)c(=O)n(CC)c(=O)n2CCC(F)(F)F]

Analogously to the process described under Ex. 23, 12.8 mg (0.10 mmol) of 3-ethylpiperazin-2-one [S. R. Aspinall, *J. Amer. Chem. Soc.* 1940, 62 (5), 1202-1204] and 35 mg (0.10 mmol) of the compound from Ex. 52A gave 15 mg (32% of theory) of the title compound.

LC/MS (Method 3, ESIpos): $R_t$=0.94 min, m/z=461 [M+H]⁺.

Example 41

6-[(3-Oxopiperazin-1-yl)carbonyl]-3-(2-phenyl-ethyl)-5-(trifluoromethyl)-1-(3,3,3-trifluoropropyl)thieno[2,3-d]pyrimidine-2,4(1H,3H)-dione

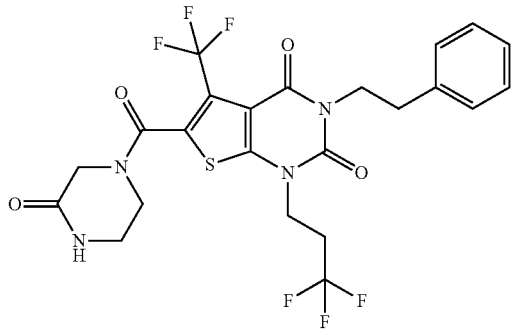 [SMILES: O=C1CN(C(=O)c2sc3c(c2C(F)(F)F)c(=O)n(CCc2ccccc2)c(=O)n3CCC(F)(F)F)CCN1]

Preparation of the Acid Chloride: At RT, first 66 µl (0.760 mmol) of oxalyl chloride and then a small drop of DMF were added to a solution of 75 mg (0.150 mmol) of the compound from Ex.
55A in 2.2 ml of dichloromethane After the reaction mixture had been stirred at RT for 2 h, it was evaporated to dryness on a rotary evaporator. The residue that remained was dried under high vacuum and then reacted further in the next partial step.

Preparation of the Amide: The acid chloride obtained above was dissolved in 2.2 ml of anhydrous THF, and this solution was added dropwise to a solution of 20 mg (0.20 mmol) of piperazin-2-one and 53 µl (0.310 mmol) of N,N-diisopropylethylamine in 1 ml of dichloromethane. The reaction mixture was then stirred at RT for about 16 h. After the mixture had been evaporated to dryness on a rotary evaporator, the crude product was purified by preparative HPLC (Method 5). This gave, after combination of the product fractions, evaporation and drying of the residue under high vacuum, 22 mg (24% of theory) of the title compound.

$^1$H-NMR (400 MHz, DMSO-$d_6$, δ/ppm): 8.20 (s, 1H), 7.34-7.29 (m, 2H), 7.27-7.21 (m, 3H), 4.17 (m, 2H), 4.11-4.04 (m, 3H), 3.89-3.76 (m, 2H), 3.51 (m, 1H), 3.30-3.12 (m, 2H), 2.88-2.74 (m, 4H).

LC/MS (Method 1, ESIpos): $R_t$=1.02 min, m/z=563 [M+H]$^+$.

Example 42

3-Ethyl-6-[(3-oxopiperazin-1-yl)carbonyl]-5-(trifluoromethyl)-1-(3,3,3-trifluoropropyl)thieno[2,3-d]pyrimidine-2,4(1H,3H)-dione

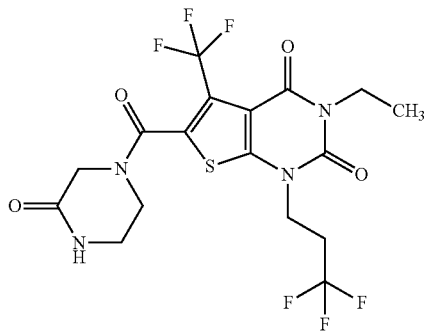 [SMILES: CCn1c(=O)c2c(C(F)(F)F)c(C(=O)N3CCNC(=O)C3)sc2n(CCC(F)(F)F)c1=O]

Analogously to the process described in Ex. 41, 55 mg (0.140 mmol) of the compound from Ex. 56A and 18 mg (0.180 mmol) of piperazin-2-one gave 56 mg (85% of theory) of the title compound.

$^1$H-NMR (400 MHz, DMSO-$d_6$, δ/ppm): 8.19 (s, 1H), 4.17 (m, 2H), 4.09 (broad, 1H), 3.92 (quart, 2H), 3.85 (broad, 1H), 3.79 (broad, 1H), 3.50 (m, 1H), 3.26 (broad, 1H), 3.18 (broad, 1H), 2.88-2.76 (m, 2H), 1.14 (t, 3H).

LC/MS (Method 1, ESIpos): $R_t$=0.82 min, m/z=487 [M+H]$^+$.

Example 43

6-[(4-Hydroxypiperidin-1-yl)carbonyl]-5-methyl-3-(2-phenylpropyl)-1-(3,3,3-trifluoropropyl)thieno[2,3-d]pyrimidine-2,4(1H,3H)-dione (racemate)

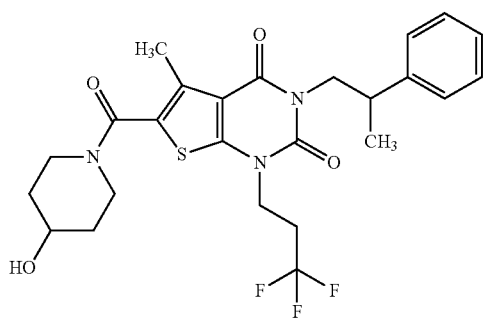 [SMILES: Cc1c(C(=O)N2CCC(O)CC2)sc2c1c(=O)n(CC(C)c1ccccc1)c(=O)n2CCC(F)(F)F]

230 mg (0.407 mmol) of the compound from Ex. 71A were dissolved in 8 ml of ethanol, and 813 µl (0.813 mmol) of a 1 M solution of lithium hydroxide in water were added. After 1 h of stirring at RT, the reaction mixture was separated directly by preparative HPLC into its components (Method 5). The product fractions were combined and concentrated, and the residue was dried under high vacuum. 176 mg (82% of theory) of the title compound were obtained.

$^1$H-NMR (400 MHz, DMSO-$d_6$, δ/ppm): 7.31-7.24 (m, 4H), 7.22-7.18 (m, 1H), 4.82 (d, 1H), 4.12-4.05 (m, 3H), 3.95 (dd, 1H), 3.82-3.71 (m, 3H), 3.28-3.19 (m, 3H), 2.77-2.65 (m, 2H), 2.36 (s, 3H), 1.80-1.72 (m, 2H), 1.40-1.31 (m, 2H), 1.19 (d, 3H).

LC/MS (Method 1, ESIpos): $R_t$=1.06 min, m/z=524 [M+H]$^+$.

Separation of the Enantiomers:

168 mg (0.321 mmol) of the racemic compound from Ex. 43 were dissolved in 2 ml of ethanol and, in 8 portions, separated into the enantiomers by preparative HPLC on a chiral phase (see Examples 44 and 45) [column: Daicel Chiralpak AD-H, 5 µm, 250 mm×20 mm; mobile phase: isohexane/ethanol 1:1; flow rate: 20 ml/min, temperature: 23° C.; detection: 220 nm]:

Example 44

6-[(4-Hydroxypiperidin-1-yl)carbonyl]-5-methyl-3-(2-phenylpropyl)-1-(3,3,3-trifluoropropyl)thieno[2,3-d]pyrimidine-2,4(1H,3H)-dione (enantiomer 1)

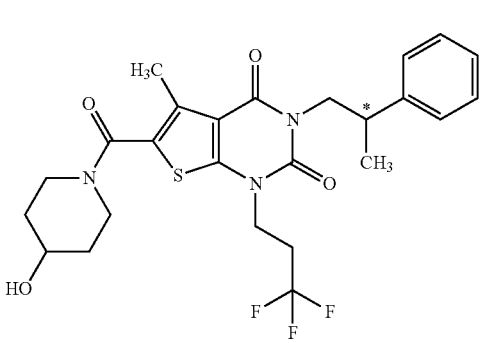 [SMILES: Cc1c(C(=O)N2CCC(O)CC2)sc2c1c(=O)n(CC(C)c1ccccc1)c(=O)n2CCC(F)(F)F]

Yield: 54 mg (64% of theory)

$^1$H-NMR (400 MHz, DMSO-$d_6$, δ/ppm): 7.31-7.24 (m, 4H), 7.22-7.18 (m, 1H), 4.82 (s, broad, 1H), 4.12-4.05 (m, 3H), 3.95 (dd, 1H), 3.82-3.71 (m, 3H), 3.28-3.19 (m, 3H), 2.77-2.65 (m, 2H), 2.36 (s, 3H), 1.80-1.72 (m, 2H), 1.40-1.31 (m, 2H), 1.19 (d, 3H).

Analytical HPLC [column: Daicel Chiralpak AD-H, 5 μm, 250 mm×4.6 mm; mobile phase: isohexane/ethanol 1:1; flow rate: 1 ml/min, temperature: 30° C.; detection: 220 nm]: $R_t$=4.39 min, 99.9% ee.

Example 45

6-[(4-Hydroxypiperidin-1-yl)carbonyl]-5-methyl-3-(2-phenylpropyl)-1-(3,3,3-trifluoropropyl)thieno[2,3-d]pyrimidine-2,4(1H,3H)-dione (enantiomer 2)

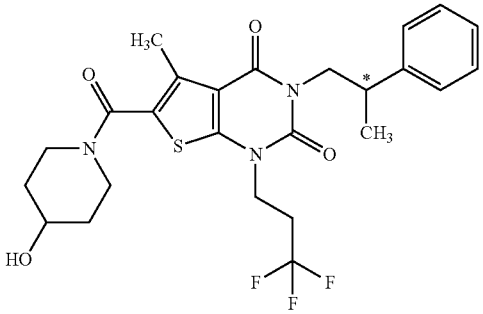 [SMILES: Cc1c(C(=O)N2CCC(O)CC2)sc2c1c(=O)n(CC(C)c1ccccc1)c(=O)n2CCC(F)(F)F]

Yield: 58 mg (69% of theory)

$^1$H-NMR (400 MHz, DMSO-$d_6$, δ/ppm): 7.31-7.24 (m, 4H), 7.22-7.18 (m, 1H), 4.82 (s, broad, 1H), 4.12-4.05 (m, 3H), 3.95 (dd, 1H), 3.82-3.71 (m, 3H), 3.28-3.19 (m, 3H), 2.77-2.65 (m, 2H), 2.36 (s, 3H), 1.80-1.72 (m, 2H), 1.40-1.31 (m, 2H), 1.19 (d, 3H).

Analytical HPLC [column: Daicel Chiralpak AD-H, 5 μm, 250 mm×4.6 mm; mobile phase: isohexane/ethanol 1:1; flow rate: 1 ml/min, temperature: 30° C.; detection: 220 nm]: $R_t$=6.76 min, 99.9% ee.

Example 46

6-[(4-Hydroxypiperidin-1-yl)carbonyl]-3-(2-methoxy-2-phenylethyl)-5-methyl-1-(3,3,3-trifluoropropyl)thieno[2,3-d]pyrimidine-2,4(1H,3H)-dione (racemate)

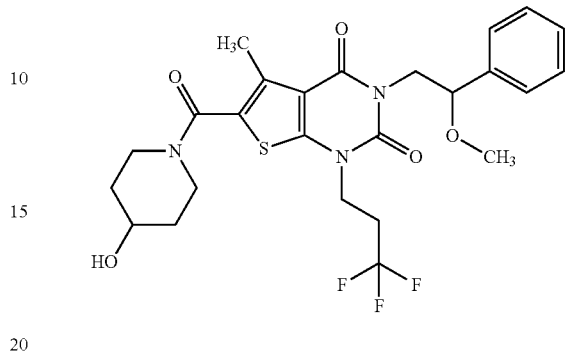

249 mg (0.428 mmol) of the compound from Ex. 72A were dissolved in 8 ml of ethanol, and 856 μl (0.856 mmol) of a 1 M solution of lithium hydroxide in water were added. After 1 h of stirring at RT, the reaction mixture was separated directly by preparative HPLC into its components (Method 5). The product fractions were combined and concentrated, and the residue was dried under high vacuum. 172 mg (74% of theory) of the title compound were obtained.

$^1$H-NMR (400 MHz, DMSO-$d_6$, δ/ppm): 7.41-7.37 (m, 2H), 7.34-7.30 (m, 3H), 4.82 (d, 1H), 4.58 (dd, 1H), 4.35 (dd, 1H), 4.18-4.04 (m, 2H), 3.84-3.71 (m, 4H), 3.28-3.20 (m, 2H), 3.07 (s, 3H), 2.79-2.67 (m, 2H), 2.37 (s, 3H), 1.80-1.73 (m, 2H), 1.41-1.31 (m, 2H).

LC/MS (Method 1, ESIpos): $R_t$=1.00 min, m/z=540 [M+H]$^+$.

Separation of the Enantiomers:

160 mg (0.298 mmol) of the racemic compound from Ex. 46 were dissolved in 6 ml of ethanol and, in 6 portions, separated into the enantiomers by preparative HPLC on a chiral phase (see Examples 47 and 48) [column: Daicel Chiralcel OZ-H, 5 μm, 250 mm×20 mm; mobile phase: ethanol; flow rate: 25 ml/min, temperature: 50° C.; detection: 220 nm]:

Example 47

6-[(4-Hydroxypiperidin-1-yl)carbonyl]-3-(2-methoxy-2-phenylethyl)-5-methyl-1-(3,3,3-trifluoropropyl)thieno[2,3-d]pyrimidine-2,4(1H,3H)-dione (enantiomer 2)

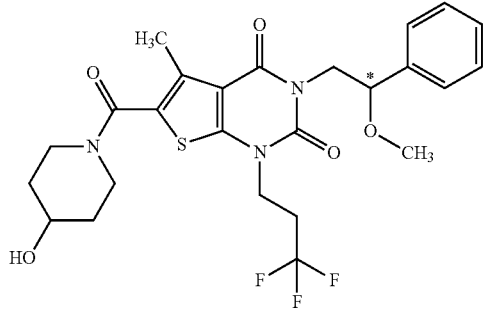 [SMILES: COC(Cn1c(=O)c2c(C)c(C(=O)N3CCC(O)CC3)sc2n(CCC(F)(F)F)c1=O)c1ccccc1]

Yield: 68 mg (85% of theory)

$^1$H-NMR (400 MHz, DMSO-$d_6$, δ/ppm): 7.41-7.37 (m, 2H), 7.34-7.30 (m, 3H), 4.82 (d, 1H), 4.57 (dd, 1H), 4.35 (dd, 1H), 4.18-4.04 (m, 2H), 3.84-3.71 (m, 4H), 3.28-3.20 (m, 2H), 3.07 (s, 3H), 2.79-2.67 (m, 2H), 2.37 (s, 3H), 1.80-1.73 (m, 2H), 1.41-1.31 (m, 2H).

Analytical HPLC [column: Daicel Chiralcel OZ-H, 5 μm, 250 mm×4.6 mm; mobile phase: ethanol; flow rate: 1 ml/min, temperature: 50° C.; detection: 220 nm]: $R_t$=14.25 min, 99.9% ee.

Example 48

6-[(4-Hydroxypiperidin-1-yl)carbonyl]-3-(2-methoxy-2-phenylethyl)-5-methyl-1-(3,3,3-trifluoropropyl)thieno[2,3-d]pyrimidine-2,4(1H,3H)-dione (enantiomer 1)

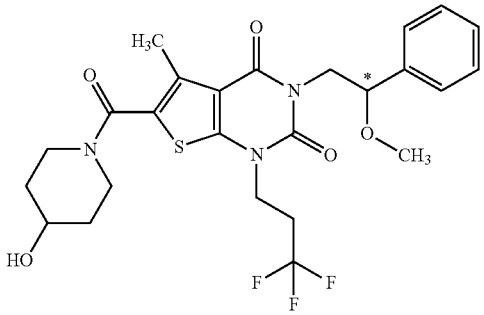 [SMILES: COC(Cn1c(=O)c2c(C)c(C(=O)N3CCC(O)CC3)sc2n(CCC(F)(F)F)c1=O)c1ccccc1]

Yield: 70 mg (87% of theory)

$^1$H-NMR (400 MHz, DMSO-$d_6$, δ/ppm): 7.41-7.37 (m, 2H), 7.34-7.30 (m, 3H), 4.82 (d, 1H), 4.58 (dd, 1H), 4.35 (dd, 1H), 4.18-4.04 (m, 2H), 3.84-3.71 (m, 4H), 3.28-3.20 (m, 2H), 3.07 (s, 3H), 2.79-2.67 (m, 2H), 2.37 (s, 3H), 1.80-1.73 (m, 2H), 1.41-1.31 (m, 2H).

Analytical HPLC [column: Daicel Chiralcel OZ-H, 5 μm, 250 mm×4.6 mm; mobile phase: ethanol; flow rate: 1 ml/min, temperature: 50° C.; detection: 220 nm]: $R_t$=6.54 min, 99.9% ee.

Example 49

6-[(4-Hydroxypiperidin-1-yl)carbonyl]-5-methyl-3-[(1-phenylcyclopropyl)methyl]-1-(3,3,3-trifluoropropyl)thieno[2,3-d]pyrimidine-2,4(1H,3H)-dione

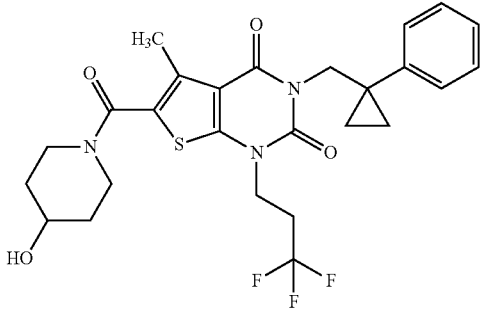 [SMILES: Cc1c(C(=O)N2CCC(O)CC2)sc2c1c(=O)n(CC1(c3ccccc3)CC1)c(=O)n2CCC(F)(F)F]

Analogously to the process described in Ex. 43, 54 mg (0.094 mmol) of the compound from Ex. 73A gave 38 mg (75% of theory) of the title compound.

$^1$H-NMR (400 MHz, DMSO-$d_6$, δ/ppm): 7.26-7.19 (m, 4H), 7.17-7.12 (m, 1H), 4.82 (d, 1H), 4.16 (s, 2H), 3.99 (t, 2H), 3.81-3.71 (m, 3H), 3.26-3.20 (m, 2H), 2.63-2.52 (m, 2H, partially obscured by DMSO signal), 2.31 (s, 3H), 1.80-1.73 (m, 2H), 1.40-1.31 (m, 2H), 0.95 (m, 2H), 0.72 (m, 2H).

LC/MS (Method 1, ESIpos): $R_t$=1.08 min, m/z=536 [M+H]$^+$.

Example 50

6-[(4-Hydroxypiperidin-1-yl)carbonyl]-5-methyl-3-(2-methyl-2-phenylpropyl)-1-(3,3,3-trifluoropropyl)thieno[2,3-d]pyrimidine-2,4(1H,3H)-dione

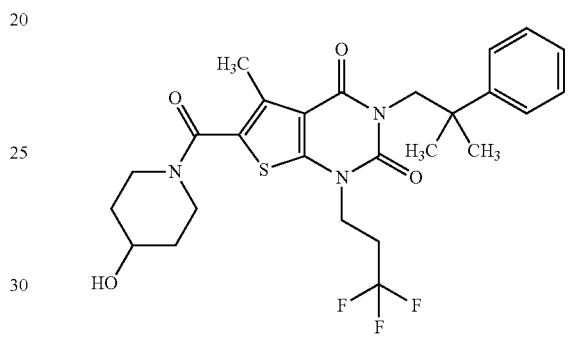

Analogously to the process described in Ex. 43, 96 mg (0.166 mmol) of the compound from Ex. 74A gave 68 mg (76% of theory) of the title compound.

$^1$H-NMR (400 MHz, DMSO-$d_6$, δ/ppm): 7.43 (d, 2H), 7.32 (t, 2H), 7.21 (t, 1H), 4.82 (d, 1H), 4.11-4.04 (m, 4H), 3.82-3.71 (m, 3H), 3.28-3.21 (m, 2H), 2.77-2.65 (m, 2H), 2.34 (s, 3H), 1.80-1.73 (m, 2H), 1.40-1.31 (m, 2H), 1.28 (s, 6H).

LC/MS (Method 1, ESIpos): $R_t$=1.08 min, m/z=538 [M+H]$^+$.

Example 51

3-(2,2-Difluoro-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione

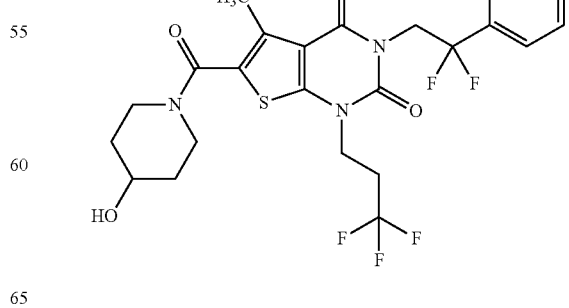

21 mg (0.208 mmol) of 4-hydroxypiperidine, 39 μl (0.225 mmol) of N,N-diisopropylethylamine and 79 mg (0.208 mmol) of HATU were added successively to a solution of 80 mg (0.173 mmol) of the compound from Ex. 100A in 2.5 ml of anhydrous DMF. After a reaction time of about 16 h at RT, the reaction mixture was separated directly by preparative HPLC into its components (Method 5). The product fractions were combined and concentrated, and the residue was dried under high vacuum. 88 mg (93% of theory) of the title compound were obtained.

$^1$H-NMR (400 MHz, DMSO-$d_6$, δ/ppm): 7.57-7.49 (m, 5H), 4.80 (broad, 1H), 4.62 (t, 2H), 4.12 (t, 2H), 2.82-2.72 (m, 3H), 3.29-3.21 (m, 2H), 2.79-2.67 (m, 2H), 2.36 (s, 3H), 1.81-1.73 (m, 2H), 1.41-1.31 (m, 2H).

LC/MS (Method 1, ESIpos): $R_t$=0.98 min, m/z=546 [M+H]$^+$.

Example 52

3-(2,2-Difluoro-2-phenylethyl)-6-[(4-hydroxypiperidin-1-yl)carbonyl]-1-(2-methoxyethyl)-5-methylthieno[2,3-d]pyrimidine-2,4(1H,3H)-dione

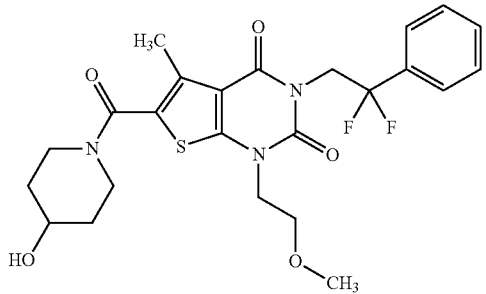 [SMILES: COCCn1c(=O)n(CC(F)(F)c2ccccc2)c(=O)c2c(C)c(C(=O)N3CCC(O)CC3)sc21]

Analogously to the process described in Ex. 51, 80 mg (0.188 mmol) of the compound from Ex. 101A and 23 mg (0.226 mmol) of 4-hydroxypiperidine gave 90 mg (94% of theory) of the title compound.

$^1$H-NMR (400 MHz, DMSO-$d_6$, δ/ppm): 7.57-7.50 (m, 5H), 4.80 (d, 1H), 4.62 (t, 2H), 4.04 (t, 2H), 3.82-3.71 (m, 3H), 3.59 (t, 2H), 3.27-3.21 (m, 2H), 3.25 (s, 3H), 2.35 (s, 3H), 1.81-1.73 (m, 2H), 1.40-1.32 (m, 2H).

LC/MS (Method 1, ESIpos): $R_t$=0.90 min, m/z=508 [M+H]$^+$.

Example 53

6-[(4-Hydroxypiperidin-1-yl)carbonyl]-5-methyl-3-[2-(pyridin-2-yl)ethyl]-1-(3,3,3-trifluoropropyl)thieno[2,3-d]pyrimidine-2,4(1H,3H)-dione

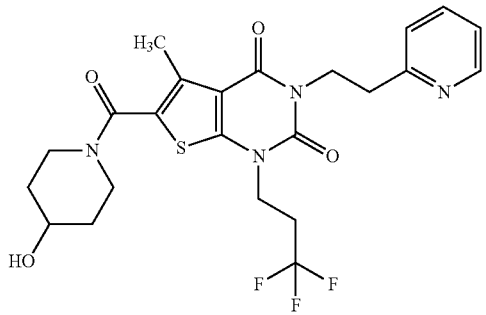 [SMILES: Cc1c(C(=O)N2CCC(O)CC2)sc2c1c(=O)n(CCc1ccccn1)c(=O)n2CCC(F)(F)F]

Analogously to the process described in Ex. 43, 110 mg (0.199 mmol) of the compound from Ex. 75A gave 35 mg (33% of theory, purity 96%) of the title compound. In addition to the process described above, here the product obtained after preparative HPLC was dissolved once more in a little methanol, and the solution was passed through a bicarbonate cartridge (from Polymerlabs, Stratospheres SPE, PL-HCO$_3$ MP SPE, capacity 0.9 mmol) to convert the formic acid salt into the free base.

$^1$H-NMR (400 MHz, DMSO-$d_6$, δ/ppm): 8.47 (d, 1H), 7.71 (dt, 1H), 7.28 (d, 1H), 7.23 (dd, 1H), 4.82 (d, 1H), 4.22 (t, 1H), 4.11 (t, 1H), 3.82-3.72 (m, 3H), 3.28-3.21 (m, 2H), 2.99 (t, 2H), 2.81-2.69 (m, 2H), 2.38 (s, 3H), 1.80-1.73 (m, 2H), 1.40-1.31 (m, 2H).

LC/MS (Method 1, ESIpos): $R_t$=0.63 min, m/z=511 [M+H]$^+$.

Example 54

6-[(4-Hydroxypiperidin-1-yl)carbonyl]-5-methyl-3-[2-(pyridin-4-yl)ethyl]-1-(3,3,3-trifluoropropyl)thieno[2,3-d]pyrimidine-2,4(1H,3H)-dione

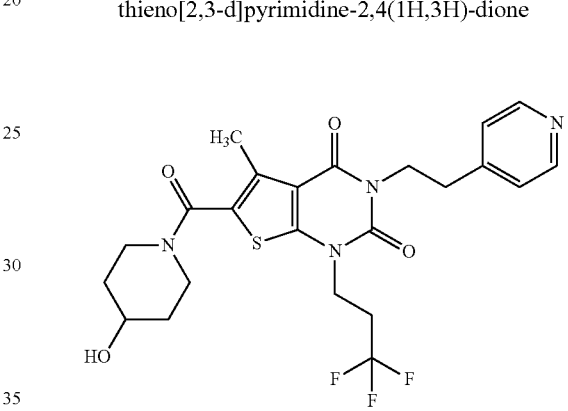

Analogously to the process described in Ex. 43, 54 mg (0.098 mmol) of the compound from Ex. 76A gave 24 mg (43% of theory, purity 90%) of the title compound.

$^1$H-NMR (400 MHz, DMSO-$d_6$, δ/ppm): 8.47 (d, 2H), 7.26 (d, 2H), 4.82 (d, 1H), 4.14-4.09 (m, 4H), 3.81-3.71 (m, 3H), 3.28-3.20 (m, 2H), 2.88 (t, 2H), 2.82-2.70 (m, 2H), 2.37 (s, 3H), 1.80-1.73 (m, 2H), 1.40-1.31 (m, 2H).

LC/MS (Method 1, ESIpos): $R_t$=0.58 min, m/z=511 [M+H]$^+$.

Example 55

6-[(4-Hydroxypiperidin-1-yl)carbonyl]-3-[2-(1H-imidazol-1-yl)ethyl]-5-methyl-1-(3,3,3-trifluoropropyl)thieno[2,3-d]pyrimidine-2,4(1H,3H)-dione

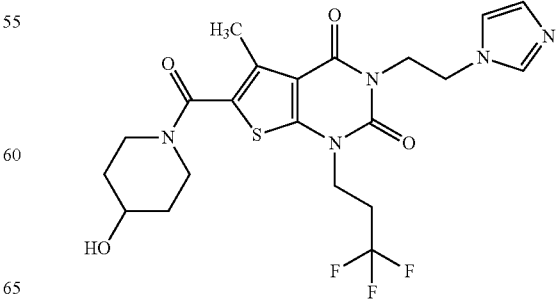

Analogously to the process described in Ex. 43, 100 mg (0.185 mmol) of the compound from Ex. 77A gave 18 mg (19% of theory) of the title compound. In addition to the process described above, here the product obtained after preparative HPLC was dissolved once more in a little methanol, and the solution was passed through a bicarbonate cartridge (from Polymerlabs, Stratospheres SPE, PL-HCO₃ MP SPE, capacity 0.9 mmol) to convert the formic acid salt into the free base.

¹H-NMR (400 MHz, DMSO-d₆, δ/ppm): 7.56 (s, 1H), 7.11 (s, 1H), 6.84 (s, 1H), 4.82 (d, 1H), 4.22-4.17 (m, 4H), 4.08 (t, 2H), 3.81-3.71 (m, 3H), 3.27-3.20 (m, 2H), 2.80-2.68 (m, 2H), 2.34 (s, 3H), 1.80-1.73 (m, 2H), 1.40-1.31 (m, 2H).

LC/MS (Method 1, ESIpos): R$_t$=0.49 min, m/z=500 [M+H]⁺.

Example 56

3-Ethyl-6-[(4-hydroxypiperidin-1-yl)carbonyl]-5-methyl-1-[2-(trifluoromethoxy)ethyl]thieno[2,3-d]pyrimidine-2,4(1H,3H)-dione

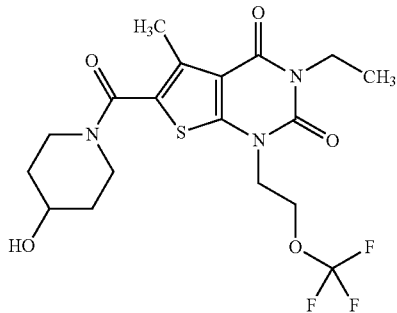

Analogously to the process described in Ex. 43, 59 mg (0.121 mmol) of the compound from Ex. 83A gave 44 mg (80% of theory) of the title compound. In this case, the reaction time was 2 h, and purification by preparative HPLC was carried out according to Method 12.

¹H-NMR (400 MHz, DMSO-d₆, δ/ppm): 4.41 (t, 2H), 4.22 (t, 2H), 3.91 (quart, 2H), 3.80-3.71 (m, 3H), 3.26-3.19 (m, 2H), 2.37 (s, 3H), 1.79-1.71 (m, 2H), 1.39-1.29 (m, 2H), 1.12 (t, 3H).

LC/MS (Method 1, ESIpos): R$_t$=0.83 min, m/z=450 [M+H]⁺.

Example 57

3-Ethyl-6-[(4-hydroxypiperidin-1-yl)carbonyl]-5-methyl-1-{2-[(trifluoromethyl)sulphanyl]ethyl}thieno[2,3-d]pyrimidine-2,4(1H,3H)-dione

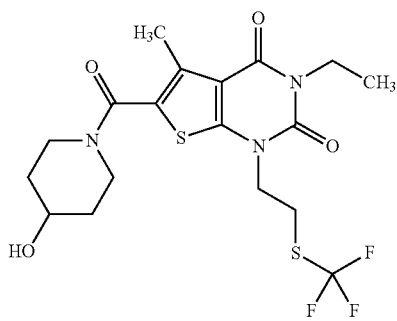

Analogously to the process described in Ex. 43, 67 mg (0.133 mmol) of the compound from Ex. 84A gave 47 mg (76% of theory) of the title compound. In this case, the reaction time was 2 h, and purification by preparative HPLC was carried out according to Method 12.

¹H-NMR (400 MHz, DMSO-d₆, δ/ppm): 4.16 (t, 2H), 3.91 (quart, 2H), 3.81-3.71 (m, 3H), 3.37 (t, 2H), 3.26-3.20 (m, 2H), 2.38 (s, 3H), 1.79-1.72 (m, 2H), 1.39-1.30 (m, 2H), 1.12 (t, 3H).

LC/MS (Method 1, ESIpos): R$_t$=0.90 min, m/z=466 [M+H]⁺.

Example 58

3-Ethyl-6-[(4-hydroxypiperidin-1-yl)carbonyl]-5-methyl-1-[2-(trifluoromethyl)prop-2-en-1-yl]thieno[2,3-d]pyrimidine-2,4(1H,3H)-dione

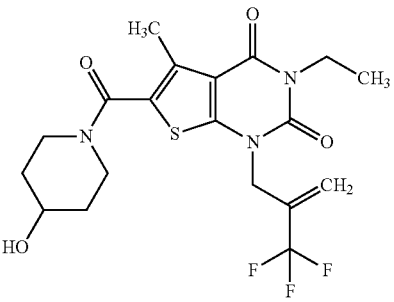 [SMILES: C=C(Cn1c(=O)n(CC)c(=O)c2c(C)c(C(=O)N3CCC(O)CC3)sc21)C(F)(F)F]

Analogously to the process described in Ex. 43, 69 mg (0.142 mmol) of the compound from Ex. 85A gave 49 mg (78% of theory) of the title compound. In this case, the reaction time was 2 h, and purification by preparative HPLC was carried out according to Method 14.

¹H-NMR (400 MHz, DMSO-d₆, δ/ppm): 6.02 (s, 1H), 5.83 (s, 1H), 4.78 (s, 2H), 3.93 (quart, 2H), 3.80-3.70 (m, 3H), 3.26-3.19 (m, 2H), 2.38 (s, 3H), 1.78-1.71 (m, 2H), 1.38-1.29 (m, 2H), 1.13 (t, 3H).

LC/MS (Method 1, ESIpos): R$_t$=0.84 min, m/z=446 [M+H]⁺.

Example 59

1-[(2,2-Difluorocyclopropyl)methyl]-3-ethyl-6-[(4-hydroxypiperidin-1-yl)carbonyl]-5-methylthieno[2,3-d]pyrimidine-2,4(1H,3H)-dione (racemate)

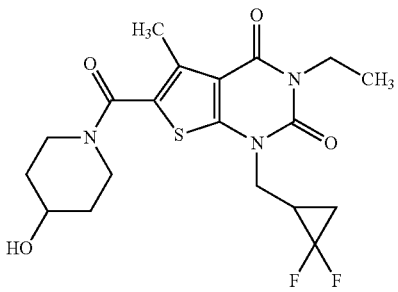 [SMILES: CCn1c(=O)c2c(C)c(C(=O)N3CCC(O)CC3)sc2n(CC2CC2(F)F)c1=O]

Analogously to the process described in Ex. 43, 62 mg (0.132 mmol) of the compound from Ex. 86A gave 57 mg (100% of theory) of the title compound. In this case, the reaction time was 2 h, and purification by preparative HPLC was carried out according to Method 14.

$^1$H-NMR (400 MHz, DMSO-$d_6$, δ/ppm): 4.15 (m, 1H), 4.00-3.88 (m, 4H), 3.81-3.70 (m, 3H), 3.27-3.20 (m, 2H), 2.38 (s, 3H), 2.28-2.17 (m, 1H), 1.79-1.67 (m, 3H), 1.53-1.44 (m, 1H), 1.39-1.30 (m, 2H), 1.13 (t, 3H).

LC/MS (Method 1, ESIpos): $R_t$=0.80 min, m/z=428 [M+H]$^+$.

Example 60

6-[(4-Hydroxypiperidin-1-yl)carbonyl]-5-methyl-3-propyl-1-[2-(trifluoromethoxy)ethyl]thieno[2,3-d]pyrimidine-2,4(1H,3H)-dione

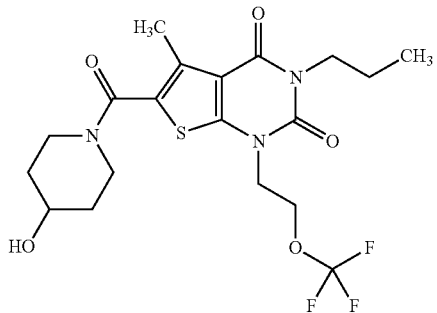 [SMILES: CCCn1c(=O)c2c(C)c(C(=O)N3CCC(O)CC3)sc2n(CCOC(F)(F)F)c1=O]

32 mg (0.316 mmol) of 4-hydroxypiperidine, 60 µl (0.342 mmol) of N,N-diisopropylethylamine and 120 mg (0.316 mmol) of HATU were added successively to a solution of 100 mg (0.263 mmol) of the compound from Ex. 102A in 3 ml of anhydrous DMF. After a reaction time of about 16 h at RT, the reaction mixture was separated directly by preparative HPLC into its components (Method 5). The product fractions were combined and concentrated, and the residue was dried under high vacuum. 101 mg (82% of theory) of the title compound were obtained.

$^1$H-NMR (400 MHz, DMSO-$d_6$, δ/ppm): 4.79 (d, 1H), 4.41 (t, 2H), 4.22 (t, 2H), 3.84 (t, 2H), 3.80-3.70 (m, 3H), 3.26-3.19 (m, 2H), 2.37 (s, 3H), 1.79-1.71 (m, 2H), 1.57 (m, 2H), 1.39-1.30 (m, 2H), 0.87 (t, 3H).

LC/MS (Method 1, ESIpos): $R_t$=0.88 min, m/z=464 [M+H]$^+$.

Example 61

3-(But-3-yn-1-yl)-6-[(4-hydroxypiperidin-1-yl)carbonyl]-5-methyl-1-(3,3,3-trifluoropropyl)thieno[2,3-d]pyrimidine-2,4(1H,3H)-dione

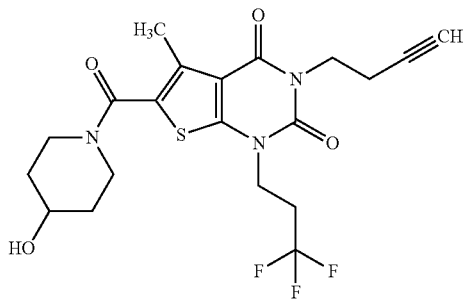 [SMILES: C#CCCn1c(=O)c2c(C)c(C(=O)N3CCC(O)CC3)sc2n(CCC(F)(F)F)c1=O]

Analogously to the process described in Ex. 43, 81 mg (0.162 mmol) of the compound from Ex. 79A gave 48 mg (64% of theory) of the title compound.

$^1$H-NMR (400 MHz, DMSO-$d_6$, δ/ppm): 4.81 (d, 1H), 4.13 (t, 2H), 4.01 (t, 2H), 3.81-3.71 (m, 3H), 3.27-3.20 (m, 2H), 2.88 (t, 1H), 2.85-2.72 (m, 2H), 2.51-2.44 (m, 2H, partially obscured by DMSO signal), 2.38 (s, 3H), 1.79-1.72 (m, 2H), 1.39-1.31 (m, 2H).

LC/MS (Method 1, ESIpos): $R_t$=0.83 min, m/z=458 [M+H]$^+$.

Example 62

6-[(4-Hydroxypiperidin-1-yl)carbonyl]-3-(2-methoxyethyl)-5-methyl-1-(3,3,3-trifluoropropyl)thieno[2,3-d]pyrimidine-2,4(1H,3H)-dione

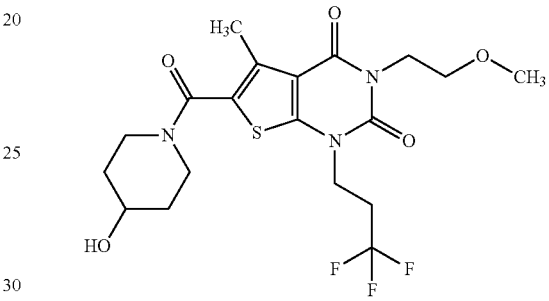

Analogously to the process described in Ex. 43, 88 mg (0.174 mmol) of the compound from Ex. 79A gave 40 mg (49% of theory) of the title compound. Here, the product obtained after preparative HPLC was triturated again with pentane.

$^1$H-NMR (400 MHz, DMSO-$d_6$, δ/ppm): 4.81 (d, 1H), 4.13 (t, 2H), 4.06 (t, 2H), 3.82-3.71 (m, 3H), 3.50 (t, 2H), 3.27-3.20 (m, 2H), 3.24 (s, 3H), 2.85-2.72 (m, 2H), 2.37 (s, 3H), 1.79-1.72 (m, 2H), 1.40-1.30 (m, 2H).

LC/MS (Method 1, ESIpos): $R_t$=0.77 min, m/z=464 [M+H]$^+$.

Example 63

3-(2-Cyclopropylethyl)-6-[(4-hydroxypiperidin-1-yl)carbonyl]-5-methyl-1-(3,3,3-trifluoropropyl)thieno[2,3-d]pyrimidine-2,4(1H,3H)-dione

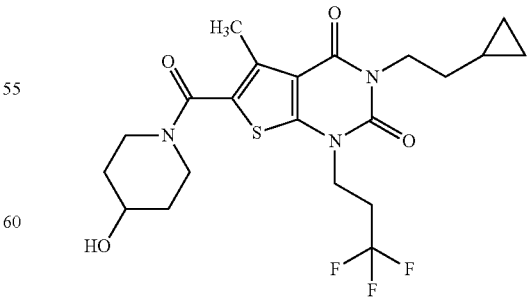

Analogously to the process described in Ex. 43, 50 mg (0.097 mmol) of the compound from Ex. 80A gave 37 mg (80% of theory) of the title compound.

¹H-NMR (400 MHz, DMSO-d₆, δ/ppm): 4.81 (d, 1H), 4.12 (t, 2H), 3.95 (t, 2H), 3.81-3.71 (m, 3H), 3.27-3.20 (m, 2H), 2.85-2.73 (m, 2H), 2.37 (s, 3H), 1.79-1.72 (m, 2H), 1.44 (quart, 2H), 1.39-1.30 (m, 2H), 0.72-0.65 (m, 1H), 0.41-0.37 (m, 2H), 0.01 (m, 2H, substantially obscured by the TMS signal).

LC/MS (Method 1, ESIpos): $R_t$=0.95 min, m/z=474 [M+H]⁺.

Example 64

6-[(4-Hydroxypiperidin-1-yl)carbonyl]-3-isobutyl-5-methyl-1-(3,3,3-trifluoropropyl)thieno[2,3-d]pyrimidine-2,4(1H,3H)-dione

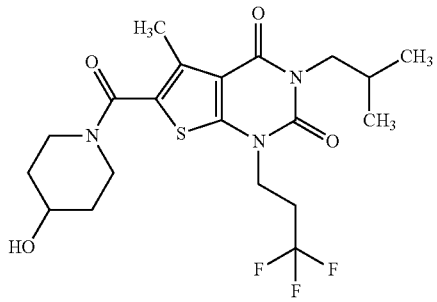 [SMILES: Cc1c(C(=O)N2CCC(O)CC2)sc2c1c(=O)n(CC(C)C)c(=O)n2CCC(F)(F)F]

Analogously to the process described in Ex. 43, 87 mg (0.173 mmol) of the compound from Ex. 81A gave 65 mg (81% of theory) of the title compound.

¹H-NMR (400 MHz, DMSO-d₆, δ/ppm): 4.81 (d, 1H), 4.13 (t, 2H), 3.82-3.70 (m, 5H), 3.27-3.20 (m, 2H), 2.85-2.73 (m, 2H), 2.37 (s, 3H), 2.09-1.99 (m, 1H), 1.80-1.72 (m, 2H), 1.40-1.30 (m, 2H), 0.86 (d, 6H).

LC/MS (Method 1, ESIpos): $R_t$=0.96 min, m/z=462 [M+H]⁺.

Example 65

6-[(4-Hydroxypiperidin-1-yl)carbonyl]-3-(2-methoxypropyl)-5-methyl-1-(3,3,3-trifluoropropyl)thieno[2,3-d]pyrimidine-2,4(1H,3H)-dione (racemate)

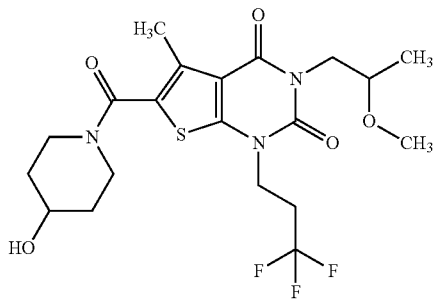 [SMILES: COC(C)Cn1c(=O)c2c(C)c(C(=O)N3CCC(O)CC3)sc2n(CCC(F)(F)F)c1=O]

Analogously to the process described in Ex. 43, 50 mg (0.096 mmol) of the compound from Ex. 82A gave 26 mg (51% of theory, purity 90%) of the title compound.

¹H-NMR (400 MHz, DMSO-d₆, δ/ppm): 4.81 (d, 1H), 4.13 (m, 2H), 4.06 (m, 1H), 3.82-3.71 (m, 4H), 3.64 (m, 1H), 3.28-3.23 (m, 2H), 3.22 (s, 3H), 2.85-2.73 (m, 2H), 2.38 (s, 3H), 1.80-1.72 (m, 2H), 1.40-1.30 (m, 2H), 1.06 (d, 3H).

LC/MS (Method 1, ESIpos): $R_t$=0.81 min, m/z=478 [M+H]⁺.

Example 66

6-[(4-Hydroxypiperidin-1-yl)carbonyl]-5-methyl-3-(3,3,3-trifluoro-2-methoxypropyl)-1-(3,3,3-trifluoropropyl)thieno[2,3-d]pyrimidine-2,4(1H,3H)-dione (racemate)

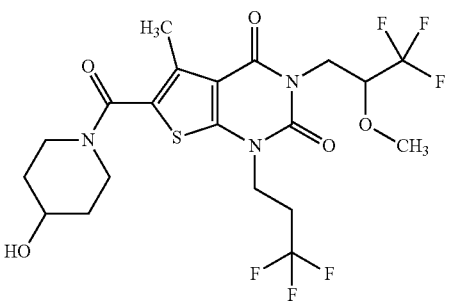 [SMILES: COC(Cn1c(=O)c2c(C)c(C(=O)N3CCC(O)CC3)sc2n(CCC(F)(F)F)c1=O)C(F)(F)F]

Analogously to the process described in Ex. 51, 140 mg (0.312 mmol) of the compound from Ex. 103A and 38 mg (0.375 mmol) of 4-hydroxypiperidine gave 162 mg (97% of theory) of the title compound.

¹H-NMR (400 MHz, DMSO-d₆, δ/ppm): 4.81 (d, 1H), 4.29-4.14 (m, 4H), 4.05 (dd, 1H), 3.82-3.71 (m, 3H), 3.43 (s, 3H), 3.28-3.21 (m, 2H), 2.87-2.75 (m, 2H), 2.38 (s, 3H), 1.80-1.73 (m, 2H), 1.41-1.32 (m, 2H).

LC/MS (Method 1, ESIpos): $R_t$=0.92 min, m/z=532 [M+H]⁺.

Example 67

6-[(4-Hydroxy-4-methylpiperidin-1-yl)carbonyl]-5-methyl-3-(2-phenylethyl)-1-(3,3,3-trifluoropropyl)thieno[2,3-d]pyrimidine-2,4(1H,3H)-dione

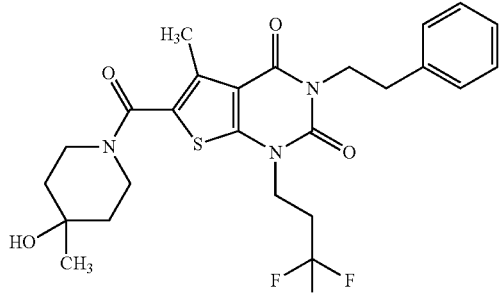

26 mg (0.225 mmol) of 4-methylpiperidin-4-ol [commercially available; lit. e.g.: J. M. McManus et al., *J. Med. Chem.* 1965, 8 (6), 766-776], 43 µl (0.244 mmol) of N,N-diisopropylethylamine and 86 mg (0.225 mmol) of HATU were added in succession to a solution of 80 mg (0.188 mmol) of the compound from Ex. 43A in 2 ml of anhydrous DMF. After a reaction time of about 16 h at RT, the reaction mixture was separated directly by preparative HPLC into its components (Method 6). The product fractions were combined and concentrated, and the residue was dried under high vacuum. 79 mg (80% of theory) of the title compound were obtained.

$^1$H-NMR (400 MHz, DMSO-d$_6$, δ/ppm): 7.33-7.29 (m, 2H), 7.26-7.20 (m, 3H), 4.47 (broad, 1H), 4.12 (t, 2H), 4.06 (m, 2H), 3.79-3.65 (m, broad, 2H), 3.37-3.29 (m, broad, 2H, substantially obscured by the water signal), 2.83 (m, 2H), 2.82-2.70 (m, 2H), 2.38 (s, 3H), 1.54-1.41 (m, 4H), 1.16 (s, 3H).

LC/MS (Method 1, ESIpos): R$_t$=1.07 min, m/z=524 [M+H]$^+$.

Example 68

6-{[4-Hydroxy-4-(hydroxymethyl)piperidin-1-yl]carbonyl}-5-methyl-3-(2-phenylethyl)-1-(3,3,3-trifluoropropyl)thieno[2,3-d]pyrimidine-2,4(1H,3H)-dione

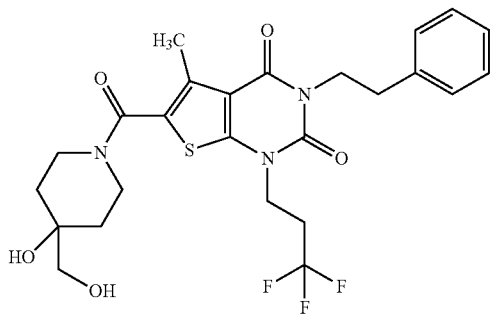 [SMILES: Cc1c(C(=O)N2CCC(O)(CO)CC2)sc2c1c(=O)n(CCc1ccccc1)c(=O)n2CCC(F)(F)F]

38 mg (0.225 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 43 µl (0.244 mmol) of N,N-diisopropylethylamine and 86 mg (0.225 mmol) of HATU were added in succession to a solution of 80 mg (0.188 mmol) of the compound from Ex. 43A in 2 ml of anhydrous DMF. After a reaction time of about 16 h at RT, the reaction mixture was separated directly by preparative HPLC into its components (Method 11). The product fractions were combined and concentrated, and the residue was dried under high vacuum. 84 mg (83% of theory) of the title compound were obtained.

$^1$H-NMR (400 MHz, CDCl$_3$, δ/ppm): 7.32-7.21 (m, 5H, partially obscured by the CHCl$_3$ signal), 4.21 (m, 2H), 4.14 (m, 2H), 4.05 (broad, 2H), 3.52 (d, 2H), 3.49-3.40 (m, 2H), 2.96-2.92 (m, 2H), 2.64-2.52 (m, 2H), 2.51 (s, 3H), 2.15 (s, 1H), 1.86 (t, 1H), 1.76-1.70 (m, 2H), 1.57-1.51 (m, 2H, partially obscured by the water signal).

LC/MS (Method 1, ESIpos): R$_t$=0.94 min, m/z=540 [M+H]$^+$.

Example 69

6-{[4-Hydroxy-4-(trifluoromethyl)piperidin-1-yl]carbonyl}-5-methyl-3-(2-phenylethyl)-1-(3,3,3-trifluoropropyl)thieno[2,3-d]pyrimidine-2,4(1H,3H)-dione

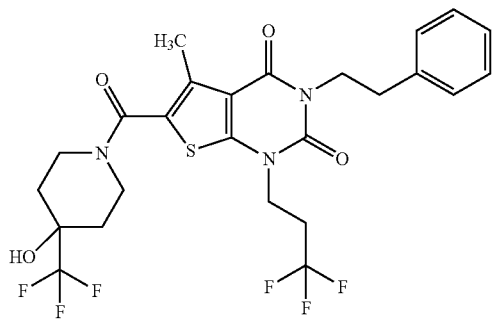 [SMILES: Cc1c(C(=O)N2CCC(O)(C(F)(F)F)CC2)sc2c1c(=O)n(CCc1ccccc1)c(=O)n2CCC(F)(F)F]

Analogously to the process described in Ex. 51, 80 mg (0.188 mmol) of the compound from Ex. 43A and 46 mg (0.225 mmol) of 4-(trifluoromethyl)piperidin-4-ol [commercially available; lit. e.g.: WO 2005/103002-A2, intermediate 1] gave 90 mg (83% of theory) of the title compound. In this case, preparative HPLC was carried out according to Method 6.

$^1$H-NMR (400 MHz, DMSO-d$_6$, δ/ppm): 7.34-7.29 (m, 2H), 7.26-7.21 (m, 3H), 6.20 (s, 1H), 4.13 (t, 2H), 4.07 (m, 2H), 4.00 (broad, 2H), 3.27-3.19 (m, 2H), 2.85-2.81 (m, 2H), 2.82-2.71 (m, 2H), 2.40 (s, 3H), 1.77-1.61 (m, 4H).

LC/MS (Method 1, ESIpos): R$_t$=1.14 min, m/z=577 [M+H]$^+$.

Example 70

3-(2,2-Difluoro-2-phenylethyl)-6-{[4-hydroxy-4-(hydroxymethyl)piperidin-1-yl]carbonyl}-5-methyl-1-(3,3,3-trifluoropropyl)thieno[2,3-d]pyrimidine-2,4(1H,3H)-dione

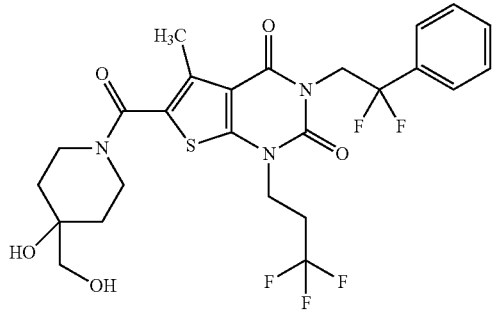 [SMILES: Cc1c(C(=O)N2CCC(O)(CO)CC2)sc2c1c(=O)n(CC(F)(F)c1ccccc1)c(=O)n2CCC(F)(F)F]

35 mg (0.208 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 75 µl (0.433 mmol) of N,N-diisopropylethylamine and 79 mg (0.208 mmol) of HATU were added in succession to a solution of 80 mg (0.173 mmol) of the compound from Ex. 100A in 2.5 ml of anhydrous DMF. After a reaction time of about 16 h at RT, the reaction mixture was separated directly by preparative HPLC into its components (Method 5). The product fractions were combined and concentrated, and the residue was dried under high vacuum. This gave 73 mg (69% of theory, 95% pure) of the title compound.

$^1$H-NMR (400 MHz, DMSO-d$_6$, δ/ppm): 7.57-7.50 (m, 5H), 4.62 (t, 2H), 4.39 (broad, 1H), 4.12 (t, 2H), 3.92-3.78 (m, broad, 2H), 3.34-3.24 (m, 2H, partially obscured by the water signal), 3.21 (s, 2H), 2.79-2.67 (m, 2H), 2.36 (s, 3H), 1.60-1.51 (m, 2H), 1.44-1.38 (m, 2H).

LC/MS (Method 1, ESIpos): R$_t$=0.93 min, m/z=576 [M+H]$^+$.

Example 71

3-(2,2-Difluoro-2-phenylethyl)-6-{[4-hydroxy-4-(hydroxymethyl)piperidin-1-yl]carbonyl}-1-(2-methoxyethyl)-5-methylthieno[2,3-d]pyrimidine-2,4(1H,3H)-dione

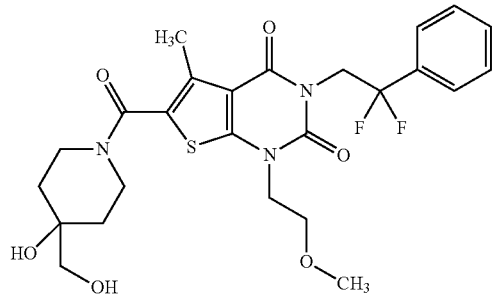 [SMILES: COCCn1c(=O)n(CC(F)(F)c2ccccc2)c(=O)c2c(C)c(C(=O)N3CCC(O)(CO)CC3)sc21]

Analogously to the process described in Ex. 51, 80 mg (0.188 mmol) of the compound from Ex. 101A and 38 mg (0.226 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 75 mg (74% of theory) of the title compound.

$^1$H-NMR (400 MHz, DMSO-d$_6$, δ/ppm): 7.56-7.51 (m, 5H), 4.62 (t, 2H), 4.36 (broad, 1H), 4.04 (t, 2H), 3.91-3.77 (m, broad, 2H), 3.31-3.25 (m, 2H, partially obscured by the water signal), 3.25 (s, 3H), 3.21 (s, 2H), 2.35 (s, 3H), 1.59-1.51 (m, 2H), 1.44-1.38 (m, 2H).

LC/MS (Method 1, ESIpos): R$_t$=0.86 min, m/z=538 [M+H]$^+$.

Example 72

3-Ethyl-6-[(9-hydroxy-3-azabicyclo[3.3.1]non-3-yl)carbonyl]-5-methyl-1-(3,3,3-trifluoropropyl)thieno[2,3-d]pyrimidine-2,4(1H,3H)-dione (α-epimer)

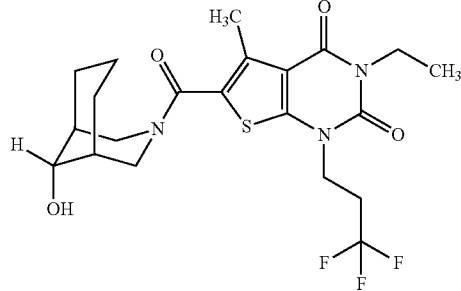 [SMILES: CCn1c(=O)c2c(C)c(C(=O)N3CC4CCCC(C3)C4O)sc2n(CCC(F)(F)F)c1=O]

48 mg (0.343 mmol) of 3-azabicyclo[3.3.1]nonan-9-ol [epimer mixture, commercially available; lit. e.g.: A. I. Moskalenko, V. I. Boev, *Russ. J. Org. Chem.* 2010, 46 (10), 1527-1533 (as hydrochloride)], 114 μl (0.657 mmol) of N,N-diisopropylethylamine and 130 mg (0.343 mmol) of HATU were added in succession to a solution of 100 mg (0.285 mmol) of the compound from Ex. 52A in 3 ml of anhydrous DMF. After a reaction time of about 16 h at RT, the reaction mixture was separated directly by preparative HPLC into its components (Method 5). Two fractions were obtained: 36 mg (26% of theory) of the title compound (α-epimer, as shown) and 41 mg (29% of theory) of the corresponding β-epimer. The assignment was carried out analogously to the literature cited above via the chemical shift of the epimeric CHOH protons (α: 3.81 ppm, β: 3.62 ppm; in DMSO-d$_6$).

$^1$H-NMR (400 MHz, DMSO-d$_6$, δ/ppm): 4.89 (d, 1H), 4.70-3.60 (very broad, 2H), 4.13 (t, 2H), 3.91 (quart, 2H), 3.81 (m, 1H), 3.50-3.00 (very broad, 2H, partially obscured by the water signal), 2.85-2.73 (m, 2H), 2.35 (s, 3H), 2.04-1.93 (m, 2H), 1.77-1.71 (m, 2H), 1.63-1.52 (m, 1H), 1.42-1.33 (m, 3H), 1.13 (t, 3H).

LC/MS (Method 9, ESIpos): R$_t$=1.14 min, m/z=474 [M+H]$^+$.

Example 73

3-Ethyl-6-[(4-hydroxy-3-methylpiperidin-1-yl)carbonyl]-5-methyl-1-(3,3,3-trifluoropropyl)thieno[2,3-d]pyrimidine-2,4(1H,3H)-dione (enantiomer pair 1)

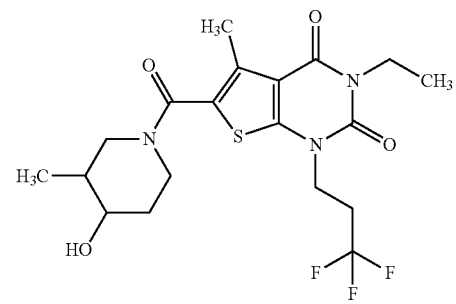 [SMILES: CCn1c(=O)c2c(C)c(C(=O)N3CCC(O)C(C)C3)sc2n(CCC(F)(F)F)c1=O]

16 mg (0.427 mmol) of sodium borohydride were added to a suspension of 190 mg (0.427 mmol) of the racemic compound from Ex. 112A in 20 ml of methanol, and the mixture was stirred at RT for 2 h. The reaction mixture was then concentrated on a rotary evaporator to a small residual volume. This residue was then subjected to coarse pre-purification by preparative HPLC (Method 5) such that all four stereoisomers of the target product were isolated together (185 mg). Separation of the stereoisomers was then carried out by preparative HPLC on a chiral phase [column: Daicel Chiralpak IC 5 μm 250 mm×20 mm; mobile phase: isohexane/ethanol 7:3; flow rate: 15 ml/min; temperature: 25° C.; detection: 220 nm]. To this end, the stereoisomer mixture obtained (185 mg) was dissolved in 3 ml of ethanol and passed through the column in 10 portions. In this manner, separation into the two diastereomeric enantiomer pairs was achieved. Concentration of the respective product fractions and drying under high vacuum gave 37 mg (18% of theory) of the title compound (enantiomer pair 1) and 62 mg (30% of theory) of the diastereomeric enantiomer pair 2. Retention times ($R_t$) on an analytic HPLC column on a chiral phase were 8.11 and 8.48 min (enantiomer pair 1) and 9.82 and 10.06 min (enantiomer pair 2), respectively [column: Daicel Chiralpak IC 5 μm 250 mm×4.6 mm; mobile phase: isohexan/ethanol/diethylamine 70:30:0.2; flow rate: 1 ml/min, temperature: 25° C.; detection: 235 nm].

$^1$H-NMR (400 MHz, DMSO-$d_6$, δ/ppm): 4.72 (broad, 1H), 4.12 (t, 2H), 3.91 (quart, 2H), 3.74 (m, 1H), 3.62-3.48 (m, broad, 2H), 3.43 (m, 1H, partially obscured by the water signal), 3.17 (dd, 1H), 2.85-2.73 (m, 2H), 2.37 (s, 3H), 1.76-1.68 (m, 1H), 1.65-1.54 (m, 2H), 1.13 (t, 3H), 0.83 (d, 3H).

LC/MS (Method 1, ESIpos): $R_t$=0.87 min, m/z=448 [M+H]$^+$.

Example 74

3-Ethyl-6-{[4-hydroxy-4-(hydroxymethyl)piperidin-1-yl]carbonyl}-5-methyl-1-(3,3,3-trifluoropropyl)thieno[2,3-d]pyrimidine-2,4(1H,3H)-dione

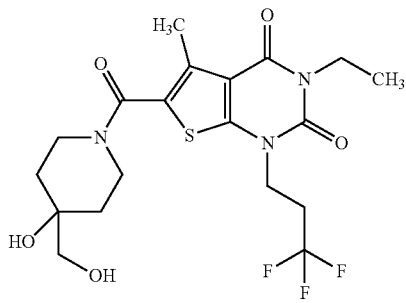 [SMILES: CCn1c(=O)c2c(C)c(C(=O)N3CCC(O)(CO)CC3)sc2n(CCC(F)(F)F)c1=O]

Analogously to the process described in Ex. 51, 100 mg (0.285 mmol) of the compound from Ex. 52A and 57 mg (0.343 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 88 mg (66% of theory) of the title compound. In deviation from the process described above, here the first preparative HPLC (according to Method 5) was followed by a second HPLC purification (according to Method 7).

$^1$H-NMR (400 MHz, DMSO-$d_6$, δ/ppm): 4.65 (t, 1H), 4.38 (s, 1H), 4.12 (t, 2H), 3.91 (quart, 2H), 3.84 (broad, 2H), 3.27 (broad, 2H, partially obscured by the water signal), 3.20 (d, 2H), 2.85-2.73 (m, 2H), 2.38 (s, 3H), 1.59-1.50 (m, 2H), 1.43-1.37 (m, 2H), 1.12 (t, 3H).

LC/MS (Method 1, ESIpos): $R_t$=0.78 min, m/z=464 [M+H]$^+$.

Example 75

3-Ethyl-6-{[4-hydroxy-4-(hydroxymethyl)piperidin-1-yl]carbonyl}-5-methyl-1-[2-(trifluoromethoxy)ethyl]thieno[2,3-d]pyrimidine-2,4(1H,3H)-dione

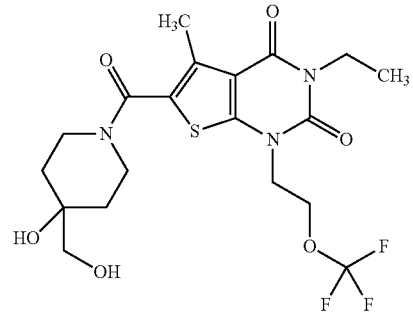 [SMILES: CCn1c(=O)c2c(C)c(C(=O)N3CCC(O)(CO)CC3)sc2n(CCOC(F)(F)F)c1=O]

52 mg (0.311 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 113 μl (0.648 mmol) of N,N-diisopropylethylamine and 118 mg (0.311 mmol) of HATU were added in succession to a solution of 100 mg (0.259 mmol, purity 95%) of the compound from Ex. 104A in 1.7 ml of anhydrous DMF. After a reaction time of about 16 h at RT, the reaction mixture was separated directly by preparative HPLC into its components (Method 7). The product fractions were combined and concentrated, and the residue was dried under high vacuum. 103 mg (82% of theory) of the title compound were obtained.

$^1$H-NMR (400 MHz, DMSO-$d_6$, δ/ppm): 4.63 (t, 1H), 4.41 (t, 2H), 4.36 (s, 1H), 4.22 (t, 2H), 3.91 (quart, 2H), 3.82 (broad, 2H), 3.25 (broad, 2H, partially obscured by the water signal), 3.20 (d, 2H), 2.37 (s, 3H), 1.54 (dt, 2H), 1.43-1.37 (m, 2H), 1.13 (t, 3H).

LC/MS (Method 9, ESIpos): $R_t$=0.98 min, m/z=480 [M+H]$^+$.

Example 76

6-[(4-Hydroxy-4-methylpiperidin-1-yl)carbonyl]-5-methyl-3-propyl-1-(3,3,3-trifluoropropyl)thieno[2,3-d]pyrimidine-2,4(1H,3H)-dione

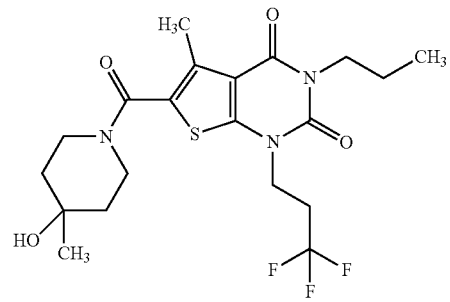 [SMILES: CCCn1c(=O)c2c(C)c(C(=O)N3CCC(C)(O)CC3)sc2n(CCC(F)(F)F)c1=O]

38 mg (0.329 mmol) of 4-methylpiperidin-4-ol [commercially available; lit. e.g.: J. M. McManus et al., *J. Med. Chem.* 1965, 8 (6), 766-776], 62 µl (0.357 mmol) of N,N-diisopropylethylamine and 125 mg (0.329 mmol) of HATU were added in succession to a solution of 100 mg (0.274 mmol) of the compound from Ex. 105A in 3 ml of anhydrous DMF. After a reaction time of about 16 h at RT, the reaction mixture was separated directly by preparative HPLC into its components (Method 5). The product fractions were combined and concentrated, and the residue was dried under high vacuum. 95 mg (75% of theory) of the title compound were obtained.

$^1$H-NMR (400 MHz, DMSO-$d_6$, δ/ppm): 4.46 (s, 1H), 4.12 (t, 2H), 3.83 (t, 2H), 3.72 (broad, 2H), 3.34 (m, broad, 2H, partially obscured by the water signal), 2.85-2.72 (m, 2H), 2.68 (s, 3H), 1.61-1.41 (m, 6H), 1.15 (s, 3H), 0.87 (t, 3H).

LC/MS (Method 1, ESIpos): $R_t$=0.93 min, m/z=462 [M+H]$^+$.

Example 77

6-{[4-Hydroxy-4-(hydroxymethyl)piperidin-1-yl]carbonyl}-5-methyl-3-propyl-1-(3,3,3-trifluoropropyl)thieno[2,3-d]pyrimidine-2,4(1H,3H)-dione

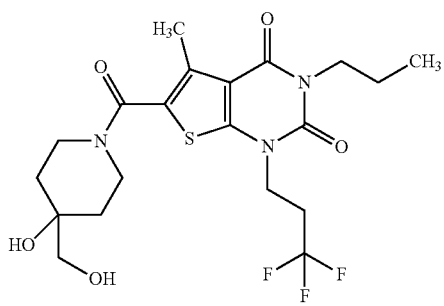 [SMILES: CCCn1c(=O)c2c(C)c(C(=O)N3CCC(O)(CO)CC3)sc2n(CCC(F)(F)F)c1=O]

Analogously to the process described in Ex. 51, 100 mg (0.274 mmol) of the compound from Ex. 105A and 55 mg (0.329 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 116 mg (88% of theory) of the title compound.

$^1$H-NMR (400 MHz, DMSO-$d_6$, δ/ppm): 4.63 (t, 1H), 4.36 (s, 1H), 4.12 (t, 2H), 3.85 (broad, 2H), 3.83 (t, 2H), 3.28 (broad, 2H, partially obscured by the water signal), 3.21 (d, 2H), 2.85-2.73 (m, 2H), 2.38 (s, 3H), 1.61-1.51 (m, 4H), 1.44-1.37 (m, 2H), 0.87 (t, 3H).

LC/MS (Method 1, ESIpos): $R_t$=0.83 min, m/z=478 [M+H]$^+$.

Example 78

6-{[4-Hydroxy-4-(hydroxymethyl)piperidin-1-yl]carbonyl}-1-(2-methoxyethyl)-5-methyl-3-propylthieno[2,3-d]pyrimidine-2,4(1H,3H)-dione

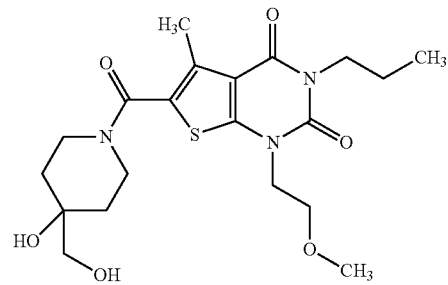 [SMILES: CCCn1c(=O)c2c(C)c(C(=O)N3CCC(O)(CO)CC3)sc2n(CCOC)c1=O]

Analogously to the process described in Ex. 51, 100 mg (0.306 mmol) of the compound from Ex. 106A and 62 mg (0.368 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 76 mg (56% of theory) of the title compound. In deviation from the process described above, here the first preparative HPLC (according to Method 5) was followed by a second HPLC purification (according to Method 7).

$^1$H-NMR (400 MHz, DMSO-$d_6$, δ/ppm): 4.63 (t, 1H), 4.35 (s, 1H), 4.04 (t, 2H), 3.85 (broad, 2H), 3.83 (t, 2H), 3.65 (t, 2H), 3.26 (broad, 2H, partially obscured by the water signal), 3.24 (s, 3H), 3.20 (d, 2H), 2.36 (s, 3H), 1.61-1.50 (m, 4H), 1.43-1.37 (m, 2H), 0.87 (t, 3H).

LC/MS (Method 1, ESIpos): $R_t$=0.70 min, m/z=440 [M+H]$^+$.

Example 79

6-[(4-Hydroxy-4-methylpiperidin-1-yl)carbonyl]-5-methyl-3-propyl-1-[2-(trifluoromethoxy)ethyl]thieno[2,3-d]pyrimidine-2,4(1H,3H)-dione

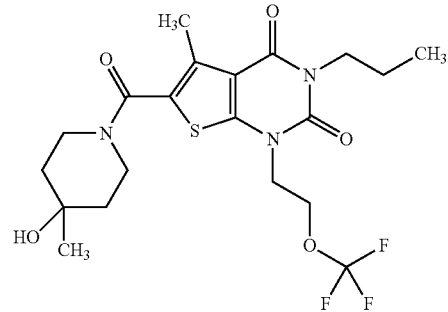 [SMILES: CCCn1c(=O)c2c(C)c(C(=O)N3CCC(C)(O)CC3)sc2n(CCOC(F)(F)F)c1=O]

36 mg (0.316 mmol) of 4-methylpiperidin-4-ol [commercially available; lit. e.g.: J. M. McManus et al., *J. Med. Chem.* 1965, 8 (6), 766-776], 59 µl (0.342 mmol) of N,N-diisopropylethylamine and 120 mg (0.316 mmol) of HATU were added in succession to a solution of 100 mg (0.263 mmol) of the compound from Ex. 102A in 3 ml of anhydrous DMF. After a reaction time of about 16 h at RT, the reaction mixture was separated directly by preparative HPLC into its components (Method 5). The product fractions were combined and concentrated, and the residue was dried under high vacuum. 108 mg (86% of theory) of the title compound were obtained.

¹H-NMR (400 MHz, DMSO-d₆, δ/ppm): 4.46 (s, 1H), 4.41 (t, 2H), 4.22 (t, 2H), 3.84 (t, 2H), 3.71 (broad, 2H), 3.34 (m, broad, 2H, partially obscured by the water signal), 2.37 (s, 3H), 1.62-1.40 (m, 6H), 1.15 (s, 3H), 0.87 (t, 3H).

LC/MS (Method 1, ESIpos): R$_t$=0.94 min, m/z=478 [M+H]⁺.

Example 80

6-{[4-Hydroxy-4-(hydroxymethyl)piperidin-1-yl] carbonyl}-5-methyl-3-propyl-1-[2-(trifluoromethoxy)ethyl]thieno[2,3-d]pyrimidine-2,4(1H,3H)-dione

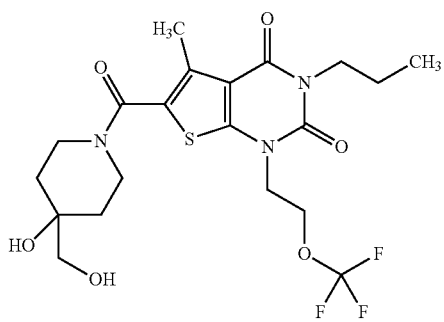 [SMILES: CCCn1c(=O)c2c(C)c(C(=O)N3CCC(O)(CO)CC3)sc2n(CCOC(F)(F)F)c1=O]

53 mg (0.316 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 114 µl (0.657 mmol) of N,N-diisopropylethylamine and 120 mg (0.316 mmol) of HATU were added in succession to a solution of 100 mg (0.263 mmol) of the compound from Ex. 102A in 3 ml of anhydrous DMF. After a reaction time of about 16 h at RT, the reaction mixture was separated directly by preparative HPLC into its components (Method 5). The product fractions were combined and concentrated, and the residue was dried under high vacuum. 78 mg (60% of theory) of the title compound were obtained.

¹H-NMR (400 MHz, DMSO-d₆, δ/ppm): 4.63 (t, 1H), 4.41 (t, 2H), 4.36 (s, 1H), 4.22 (t, 2H), 3.84 (t, 2H), 3.82 (broad, 2H), 3.27 (broad, 2H, partially obscured by the water signal), 3.20 (d, 2H), 2.37 (s, 3H), 1.62-1.50 (m, 4H), 1.43-1.37 (m, 2H), 0.87 (t, 3H).

LC/MS (Method 1, ESIpos): R$_t$=0.82 min, m/z=494 [M+H]⁺.

Example 81

6-{[4-Hydroxy-4-(hydroxymethyl)piperidin-1-yl] carbonyl}-5-methyl-3-(3,3,3-trifluoro-2-methoxypropyl)-1-(3,3,3-trifluoropropyl)thieno[2,3-d]pyrimidine-2,4(1H,3H)-dione (racemate)

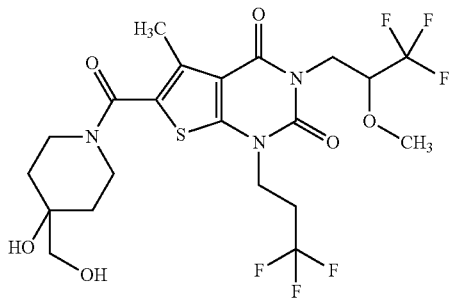 [SMILES: COC(Cn1c(=O)c2c(C)c(C(=O)N3CCC(O)(CO)CC3)sc2n(CCC(F)(F)F)c1=O)C(F)(F)F]

Analogously to the process described in Ex. 51, 140 mg (0.312 mmol) of the compound from Ex. 103A and 63 mg (0.375 mmol) of 4-(hydroxymethyl) piperidin-4-ol hydrochloride [commercially available; lit. e.g.: WO 2005/103037-A2, Example A3b (free base); US 2011/288065-A1, Example 105/Step 1 (hydrochloride)] gave 140 mg (79% of theory) of the title compound.

¹H-NMR (400 MHz, DMSO-d₆, δ/ppm): 4.64 (t, 1H), 4.37 (s, 1H), 4.29-4.14 (m, 4H), 4.05 (dd, 1H), 3.85 (broad, 2H), 3.43 (s, 3H), 3.28 (broad, 2H, partially obscured by the water signal), 3.21 (d, 2H), 2.87-2.75 (m, 2H), 2.38 (s, 3H), 1.56 (dt, 2H), 1.44-1.38 (m, 2H).

LC/MS (Method 1, ESIpos): R$_t$=0.87 min, m/z=562 [M+H]⁺.

Example 82

3-Ethyl-6-[(4-hydroxy-4-methylpiperidin-1-yl)carbonyl]-5-(trifluoromethyl)-1-(3,3,3-trifluoropropyl) thieno[2,3-d]pyrimidine-2,4(1H,3H)-dione

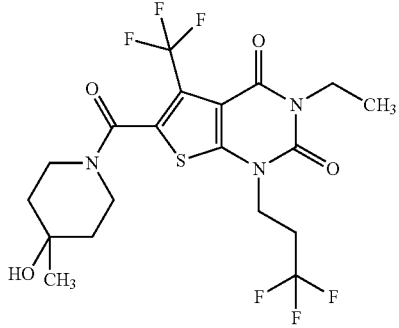 [SMILES: CCn1c(=O)c2c(C(F)(F)F)c(C(=O)N3CCC(C)(O)CC3)sc2n(CCC(F)(F)F)c1=O]

31 mg (0.272 mmol) of 4-methylpiperidin-4-ol [commercially available; lit. e.g.: J. M. McManus et al., *J. Med. Chem.* 1965, 8 (6), 766-776], 56 µl (0.322 mmol) of N,N-diisopropylethylamine and 113 mg (0.297 mmol) of HATU were added in succession to a solution of 100 mg (0.247 mmol) of the compound from Ex. 56A in 2 ml of anhydrous DMF. After a reaction time of about 16 h at RT, the reaction mixture was separated directly by preparative HPLC into its components (Method 5). The product fractions were combined and concentrated, and the residue was dried under high vacuum. This gave 96 mg (75% of theory, 97% pure) of the title compound.

$^1$H-NMR (400 MHz, CDCl$_3$, δ/ppm): 4.38 (m, broad, 1H), 4.24-4.06 (m, 2H), 4.09 (quart, 2H), 3.57-3.43 (m, 1H), 3.41-3.26 (m, 2H), 2.72-2.61 (m, 2H), 1.70-1.48 (m, 4H), 1.33 (s, 3H), 1.27 (t, 3H).

LC/MS (Method 1, ESIpos): $R_t$=0.91 min, m/z=502 [M+H]$^+$.

Example 83

3-Ethyl-6-{[4-hydroxy-4-(hydroxymethyl)piperidin-1-yl]carbonyl}-5-(trifluoromethyl)-1-(3,3,3-trifluoropropyl)thieno[2,3-d]pyrimidine-2,4(1H,3H)-dione

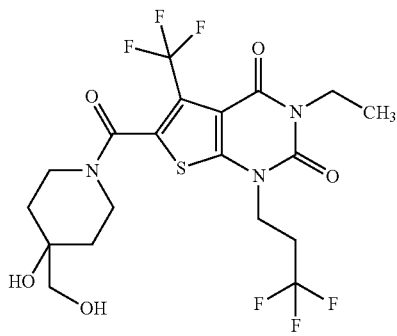 [SMILES: CCn1c(=O)c2c(C(F)(F)F)c(C(=O)N3CCC(O)(CO)CC3)sc2n(CCC(F)(F)F)c1=O]

Analogously to the process described in Ex. 51, 100 mg (0.247 mmol) of the compound from Ex. 56A and 46 mg (0.272 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 79 mg (61% of theory) of the title compound.

$^1$H-NMR (400 MHz, DMSO-d$_6$, δ/ppm): 4.23 (d, 2H), 4.16 (t, 2H), 3.92 (m, 2H), 3.20 (s, 2H), 3.10 (t, 2H), 2.87-2.75 (m, 2H), 1.60-1.32 (m, 4H), 1.13 (t, 3H).

LC/MS (Method 1, ESIpos): $R_t$=0.79 min, m/z=518 [M+H]$^+$.

Example 84

5-(Difluoromethyl)-6-[(4-hydroxypiperidin-1-yl)carbonyl]-3-(2-phenylethyl)-1-(3,3,3-trifluoropropyl)thieno[2,3-d]pyrimidine-2,4(1H,3H)-dione

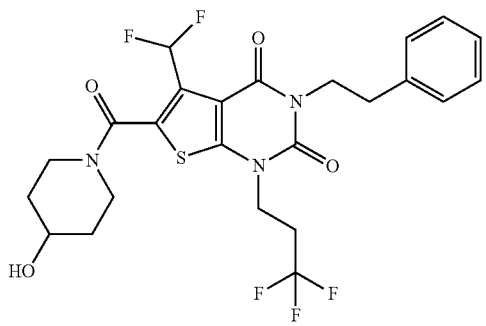 [SMILES: O=C(c1sc2c(c1C(F)F)c(=O)n(CCc1ccccc1)c(=O)n2CCC(F)(F)F)N1CCC(O)CC1]

17 mg (0.165 mmol) of 4-hydroxypiperidine, 29 μl (0.165 mmol) of N,N-diisopropylethylamine and 58 mg (0.152 mmol) of HATU were added successively to a solution of 60 mg (0.127 mmol, purity 97%) of the compound from Ex. 57A in 1.9 ml of anhydrous DMF. After a reaction time of about 16 h at RT, the reaction mixture was separated directly by preparative HPLC into its components (Method 6). The product fractions were combined and concentrated, and the residue was dried under high vacuum. 60 mg (88% of theory) of the title compound were obtained.

$^1$H-NMR (400 MHz, DMSO-d$_6$, δ/ppm): 7.34 (t, 1H), 7.33-7.29 (m, 2H), 7.27-7.23 (m, 3H), 4.84 (d, 1H), 4.15 (t, 2H), 4.07 (m, 2H), 3.96 (broad, 1H), 3.79-3.71 (m, 1H), 3.49 (broad, 1H), 3.22 (broad, 2H), 2.87-2.72 (m, 4H), 1.74 (broad, 2H), 1.41-1.31 (m, 2H).

LC/MS (Method 2, ESIpos): $R_t$=2.27 min, m/z=546 [M+H]$^+$.

Example 85

5-(Difluoromethyl)-6-[(4-hydroxy-4-methylpiperidin-1-yl)carbonyl]-3-(2-phenylethyl)-1-(3,3,3-trifluoropropyl)thieno[2,3-d]pyrimidine-2,4(1H,3H)-dione

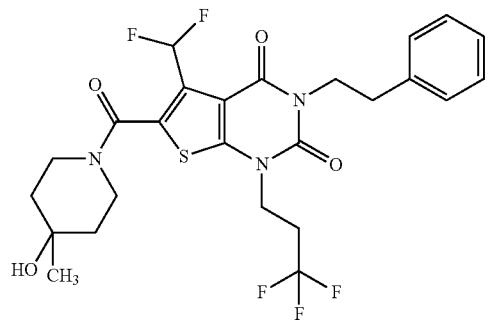 [SMILES: CC1(O)CCN(C(=O)c2sc3c(c2C(F)F)c(=O)n(CCc2ccccc2)c(=O)n3CCC(F)(F)F)CC1]

33 mg (0.274 mmol) of 4-methylpiperidin-4-ol [commercially available; lit. e.g.: J. M. McManus et al., *J. Med. Chem.* 1965, 8 (6), 766-776], 48 μl (0.274 mmol) of N,N-diisopropylethylamine and 96 mg (0.253 mmol) of HATU were added in succession to a solution of 100 mg (0.211 mmol, purity 97%) of the compound from Ex. 57A in 3.2 ml of anhydrous DMF. After a reaction time of about 16 h at RT, the reaction mixture was separated directly by preparative HPLC into its components (Method 6). The product fractions were combined and concentrated, and the residue was dried under high vacuum. 102 mg (86% of theory) of the title compound were obtained.

$^1$H-NMR (400 MHz, DMSO-d$_6$, δ/ppm): 7.33 (t, 1H), 7.32-7.29 (m, 2H), 7.26-7.21 (m, 3H), 4.48 (s, 1H), 4.15 (t, 2H), 4.08 (m, 2H), 4.08 (broad, 1H), 3.37-3.19 (m, broad, 3H, partially obscured by the water signal), 2.89-2.72 (m, 4H), 1.56-1.40 (m, broad, 4H), 1.15 (s, 3H).

LC/MS (Method 1, ESIpos): $R_t$=1.06 min, m/z=560 [M+H]$^+$.

Example 86

5-(Difluoromethyl)-6-{[4-hydroxy-4-(hydroxymethyl)piperidin-1-yl]carbonyl}-3-(2-phenylethyl)-1-(3,3,3-trifluoropropyl)thieno[2,3-d]pyrimidine-2,4(1H,3H)-dione

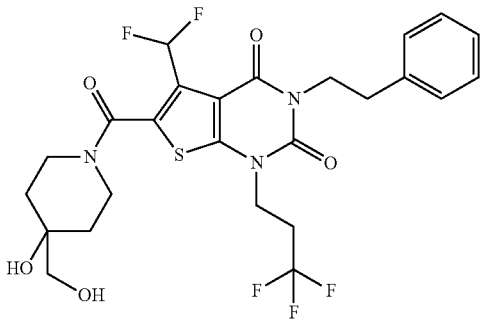 [SMILES: O=C(c1sc2c(c1C(F)F)c(=O)n(CCc1ccccc1)c(=O)n2CCC(F)(F)F)N1CCC(O)(CO)CC1]

31 mg (0.225 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 39 µl (0.225 mmol) of N,N-diisopropylethylamine and 79 mg (0.208 mmol) of HATU were added in succession to a solution of 80 mg (0.173 mmol) of the compound from Ex. 57A in 2.5 ml of anhydrous DMF. After a reaction time of about 16 h at RT, the reaction mixture was separated directly by preparative HPLC into its components (Method 6). The product fractions were combined and concentrated, and the residue was dried under high vacuum. Stirring with a mixture of 10 ml of pentane and 1 ml of diisopropyl ether for 20 min at RT, filtration with suction and once more drying under high vacuum gave 55 mg (55% of theory, purity 96%) of the title compound.

$^1$H-NMR (400 MHz, DMSO-$d_6$, δ/ppm): 7.33 (t, 1H), 7.32-7.29 (m, 2H), 7.26-7.21 (m, 3H), 4.67 (t, 1H), 4.39 (s, 1H), 4.22 (broad, 1H), 4.15 (t, 2H), 4.08 (m, 2H), 3.39 (broad, 2H, partially obscured by the water signal), 3.20 (d, 2H), 3.10 (broad, 1H), 2.88-2.73 (m, 4H), 1.54 (dt, 2H), 1.51-1.31 (broad, 2H).

LC/MS (Method 1, ESIpos): $R_t$=0.96 min, m/z=576 [M+H]$^+$.

Example 87

3,5-Diethyl-6-[(4-hydroxypiperidin-1-yl)carbonyl]-1-(3,3,3-trifluoropropyl)thieno[2,3-d]pyrimidine-2,4(1H,3H)-dione

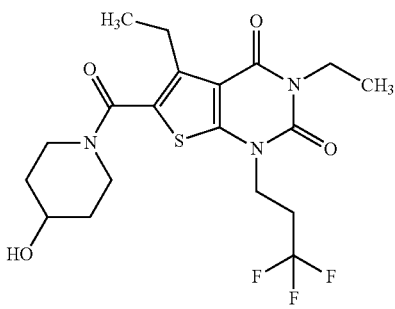 [SMILES: CCc1c(C(=O)N2CCC(O)CC2)sc2c1c(=O)n(CC)c(=O)n2CCC(F)(F)F]

Analogously to the process described in Ex. 51, 80 mg (0.220 mmol) of the compound from Ex. 111A and 24 mg (0.242 mmol) of 4-hydroxypiperidine gave 96 mg (97% of theory) of the title compound.

$^1$H-NMR (400 MHz, DMSO-$d_6$, δ/ppm): 4.80 (d, 1H), 4.12 (t, 2H), 3.92 (quart, 2H), 3.82-3.71 (m, 3H), 3.23 (m, 2H), 2.86-2.74 (m, 4H), 1.79-1.72 (m, 2H), 1.39-1.29 (m, 2H), 1.13 (t, 3H), 1.12 (t, 3H).

LC/MS (Method 1, ESIpos): $R_t$=0.86 min, m/z=448 [M+H]$^+$.

Example 88

3,5-Diethyl-6-[(4-hydroxy-4-methylpiperidin-1-yl)carbonyl]-1-(3,3,3-trifluoropropyl)thieno[2,3-d]pyrimidine-2,4(1H,3H)-dione

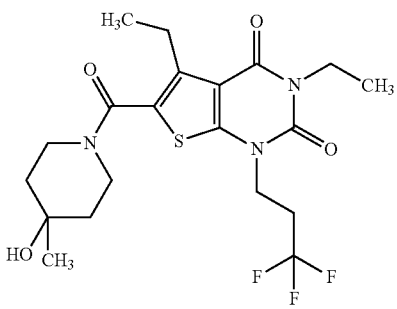 [SMILES: CCc1c(C(=O)N2CCC(C)(O)CC2)sc2c1c(=O)n(CC)c(=O)n2CCC(F)(F)F]

28 mg (0.242 mmol) of 4-methylpiperidin-4-ol [commercially available; lit. e.g.: J. M. McManus et al., J. Med. Chem. 1965, 8 (6), 766-776], 96 µl (0.549 mmol) of N,N-diisopropylethylamine and 100 mg (0.263 mmol) of HATU were added in succession to a solution of 80 mg (0.220 mmol) of the compound from Ex. 111A in 2 ml of anhydrous DMF. After a reaction time of about 16 h at RT, the reaction mixture was separated directly by preparative HPLC into its components (Method 5). The product fractions were combined and concentrated, and the residue was dried under high vacuum. 96 mg (95% of theory) of the title compound were obtained.

$^1$H-NMR (400 MHz, DMSO-$d_6$, δ/ppm): 4.47 (s, 1H), 4.12 (t, 2H), 3.93 (quart, 2H), 3.72 (broad, 2H), 3.37-3.28 (m, broad, 2H, partially obscured by the water signal), 2.86-2.74 (m, 4H), 1.53-1.39 (m, 4H), 1.15 (s, 3H), 1.13 (t, 3H), 1.11 (t, 3H).

LC/MS (Method 1, ESIpos): $R_t$=0.91 min, m/z=462 [M+H]$^+$.

Example 89

3,5-Diethyl-6-{[4-hydroxy-4-(hydroxymethyl)piperidin-1-yl]carbonyl}-1-(3,3,3-trifluoropropyl)thieno[2,3-d]pyrimidine-2,4(1H,3H)-dione

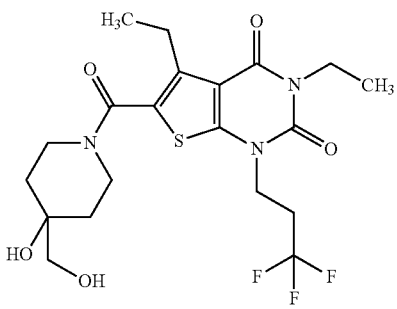

40 mg (0.242 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)], 96 µl (0.549 mmol) of N,N-diisopropylethylamine and 100 mg (0.263 mmol) of HATU were added in succession to a solution of 80 mg (0.220 mmol) of the compound from Ex. 111A in 2 ml of anhydrous DMF. After a reaction time of about 16 h at RT, the reaction mixture was separated directly by preparative HPLC into its components (Method 5). The product fractions were combined and concentrated, and the residue was dried under high vacuum. 89 mg (85% of theory) of the title compound were obtained.

$^1$H-NMR (400 MHz, DMSO-$d_6$, δ/ppm): 4.64 (t, 1H), 4.37 (s, 1H), 4.12 (t, 2H), 3.92 (quart, 2H), 3.85 (broad, 2H), 3.30-3.21 (m, broad, 2H, partially obscured by the water signal), 3.21 (d, 2H), 2.86-2.74 (m, 4H), 1.54 (dt, 2H), 1.43-1.37 (m, 2H), 1.13 (t, 3H), 1.12 (t, 3H).

LC/MS (Method 1, ESIpos): $R_t$=0.80 min, m/z=478 [M+H]$^+$.

Example 90

6-[(4-Hydroxypiperidin-1-yl)carbonyl]-3-(2-phenylethyl)-1-(3,3,3-trifluoropropyl)thieno[2,3-d]pyrimidine-2,4(1H,3H)-dione

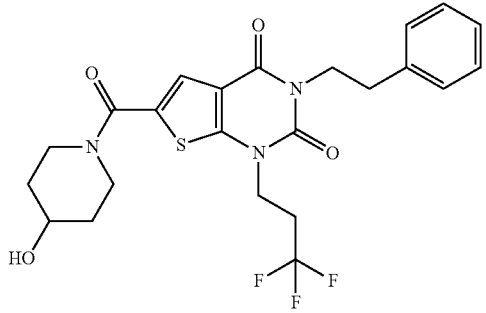 [SMILES: O=C(c1cc2c(=O)n(CCc3ccccc3)c(=O)n(CCC(F)(F)F)c2s1)N1CCC(O)CC1]

Analogously to the process described in Ex. 51, 85 mg (0.196 mmol, purity 96%) of the compound from Ex. 58A and 22 mg (0.215 mmol) of 4-hydroxypiperidine gave 79 mg (81% of theory) of the title compound.

$^1$H-NMR (400 MHz, DMSO-$d_6$, δ/ppm): 7.55 (s, 1H), 7.32-7.28 (m, 2H), 7.25-7.19 (m, 3H), 4.15 (t, 2H), 4.09 (m, 2H), 4.00-3.92 (m, 2H), 3.39 (broad, 2H), 2.85 (t, 2H), 2.84-2.71 (m, 2H), 1.84-1.77 (m, 2H), 1.45-1.36 (m, 2H).

LC/MS (Method 1, ESIpos): $R_t$=0.99 min, m/z=496 [M+H]$^+$.

Example 91

6-[(4-Hydroxy-4-methylpiperidin-1-yl)carbonyl]-3-(2-phenylethyl)-1-(3,3,3-trifluoropropyl)thieno[2,3-d]pyrimidine-2,4(1H,3H)-dione

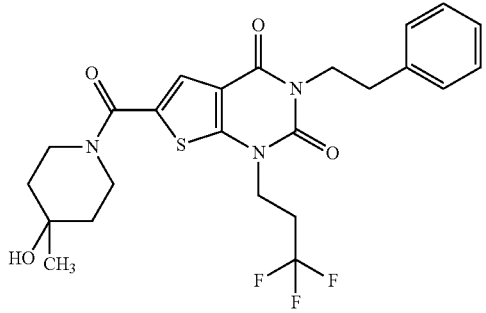 [SMILES: CC1(O)CCN(C(=O)c2cc3c(=O)n(CCc4ccccc4)c(=O)n(CCC(F)(F)F)c3s2)CC1]

Analogously to the process described in Ex. 51, 85 mg (0.196 mmol, purity 96%) of the compound from Ex. 58A and 22 mg (0.215 mmol) of 4-methylpiperidin-4-ol [commercially available; lit. e.g.: J. M. McManus et al., *J. Med. Chem.* 1965, 8 (6), 766-776] gave 44 mg (44% of theory) of the title compound.

$^1$H-NMR (400 MHz, DMSO-$d_6$, δ/ppm): 7.55 (s, 1H), 7.32-7.28 (m, 2H), 7.24-7.19 (m, 3H), 4.15 (t, 2H), 4.09 (m, 2H), 4.00-3.93 (m, 2H), 3.42 (broad, 2H), 2.85 (t, 2H), 2.83-2.71 (m, 2H), 1.57-1.47 (m, 4H), 1.17 (s, 3H).

LC/MS (Method 1, ESIpos): $R_t$=1.02 min, m/z=510 [M+H]$^+$.

Example 92

6-{[4-Hydroxy-4-(hydroxymethyl)piperidin-1-yl]carbonyl}-3-(2-phenylethyl)-1-(3,3,3-trifluoropropyl)thieno[2,3-d]pyrimidine-2,4(1H,3H)-dione

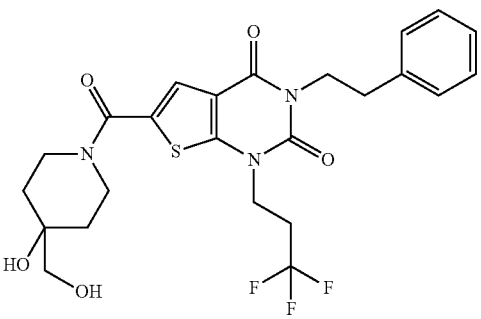 [SMILES: O=C(c1cc2c(=O)n(CCc3ccccc3)c(=O)n(CCC(F)(F)F)c2s1)N1CCC(O)(CO)CC1]

Analogously to the process described in Ex. 51, 85 mg (0.196 mmol, purity 96%) of the compound from Ex. 58A and 36 mg (0.215 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 86 mg (83% of theory) of the title compound.

$^1$H-NMR (400 MHz, CDCl$_3$, δ/ppm): 7.52 (s, 1H), 7.32-7.21 (m, 5H, partially obscured by the CHCl$_3$ signal), 4.29 (broad, 2H), 4.24 (m, 2H), 4.17 (t, 2H), 3.53 (d, 2H), 3.50 (broad, 2H), 2.95 (t, 2H), 2.65-2.54 (m, 2H), 2.21 (broad, 1H), 1.94 (broad, 1H), 1.80-1.74 (m, 2H), 1.61 (m, 2H, partially obscured by the water signal).

LC/MS (Method 1, ESIpos): $R_t$=0.92 min, m/z=526 [M+H]$^+$.

Example 93

3-(2,2-Difluoro-2-phenylethyl)-5-methyl-6-[(3-oxopiperazin-1-yl)carbonyl]-1-(3,3,3-trifluoropropyl)thieno[2,3-d]pyrimidine-2,4(1H,3H)-dione

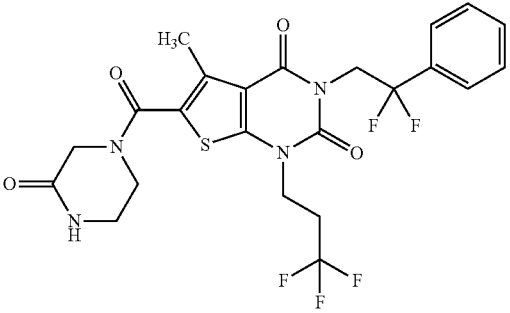 [SMILES: Cc1c(C(=O)N2CCNC(=O)C2)sc2c1c(=O)n(CC(F)(F)c1ccccc1)c(=O)n2CCC(F)(F)F]

21 mg (0.208 mmol) of 2-oxopiperazine, 39 μl (0.225 mmol) of N,N-diisopropylethylamine and 79 mg (0.208 mmol) of HATU were added successively to a solution of 80 mg (0.173 mmol) of the compound from Ex. 100A in 2.5 ml of anhydrous DMF. After a reaction time of about 16 h at RT, the reaction mixture was separated directly by preparative HPLC into its components (Method 5). The product fractions were combined and concentrated, and the residue was dried under high vacuum. 80 mg (84% of theory) of the title compound were obtained.

$^1$H-NMR (400 MHz, DMSO-$d_6$, δ/ppm): 8.16 (s, 1H), 7.57-7.49 (m, 5H), 4.63 (t, 2H), 4.13 (t, 2H), 4.05 (s, 2H), 3.69 (t, 2H), 3.25 (m, 2H), 2.79-2.67 (m, 2H), 2.38 (s, 3H).

LC/MS (Method 1, ESIpos): $R_t$=0.94 min, m/z=545 [M+H]$^+$.

Example 94

3-(2,2-Difluoro-2-phenylethyl)-1-(2-methoxyethyl)-5-methyl-6-[(3-oxopiperazin-1-yl)carbonyl]thieno[2,3-d]pyrimidine-2,4(1H,3H)-dione

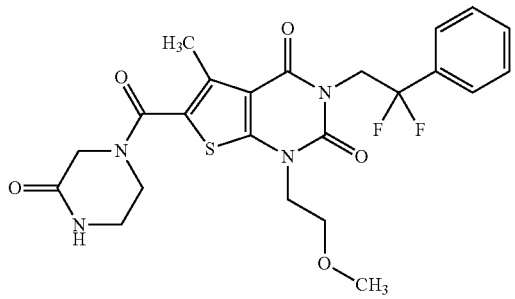 [SMILES: COCCn1c(=O)n(CC(F)(F)c2ccccc2)c(=O)c2c(C)c(C(=O)N3CCNC(=O)C3)sc21]

Analogously to the process described in Ex. 51, 80 mg (0.188 mmol) of the compound from Ex. 101A and 23 mg (0.226 mmol) of oxopiperazine gave 33 mg (32% of theory, purity 95%) of the title compound. In this case, the product was purified by preparative HPLC (twice, in each case Method 5) and finally by stirring with pentane.

$^1$H-NMR (400 MHz, DMSO-$d_6$, δ/ppm): 8.13 (s, 1H), 7.56-7.50 (m, 5H), 4.63 (t, 2H), 4.05 (s, 2H), 4.04 (t, 2H), 3.69 (t, 2H), 3.59 (t, 2H), 3.24 (s, 3H), 3.24 (m, 2H), 2.37 (s, 3H).

LC/MS (Method 1, ESIpos): $R_t$=0.83 min, m/z=507 [M+H]$^+$.

Example 95

5-Methyl-6-[(3-oxopiperazin-1-yl)carbonyl]-3-propyl-1-(3,3,3-trifluoropropyl)thieno[2,3-d]pyrimidine-2,4(1H,3H)-dione

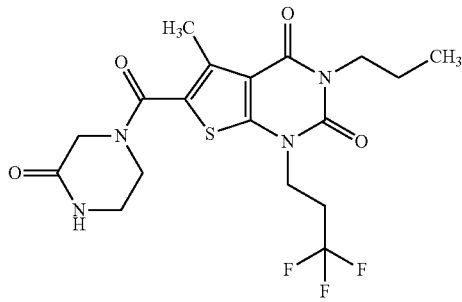 [SMILES: CCCn1c(=O)c2c(C)c(C(=O)N3CCNC(=O)C3)sc2n(CCC(F)(F)F)c1=O]

Analogously to the process described in Ex. 51, 100 mg (0.274 mmol) of the compound from Ex. 105A and 33 mg (0.329 mmol) of 2-oxopiperazine gave 106 mg (86% of theory) of the title compound.

$^1$H-NMR (400 MHz, DMSO-$d_6$, δ/ppm): 8.13 (s, 1H), 4.13 (t, 2H), 4.05 (s, 2H), 3.83 (t, 2H), 3.69 (t, 2H), 3.24 (m, 2H), 2.84-2.74 (m, 2H), 2.40 (s, 3H), 1.57 (sext, 2H), 0.87 (t, 3H).

LC/MS (Method 1, ESIpos): $R_t$=0.84 min, m/z=447 [M+H]$^+$.

Example 96

5-Methyl-6-[(3-oxopiperazin-1-yl)carbonyl]-3-propyl-1-[2-(trifluoromethoxy)ethyl]thieno[2,3-d]pyrimidine-2,4(1H,3H)-dione

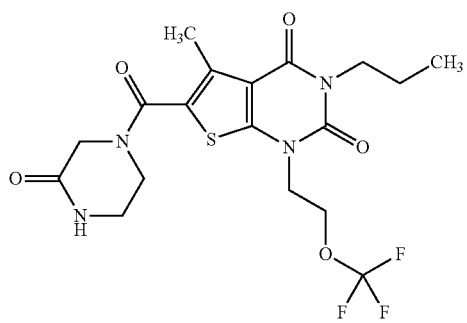 [SMILES: CCCn1c(=O)c2c(C)c(C(=O)N3CCNC(=O)C3)sc2n(CCOC(F)(F)F)c1=O]

Analogously to the process described in Ex. 51, 100 mg (0.263 mmol) of the compound from Ex. 102A and 32 mg (0.316 mmol) of 2-oxopiperazine gave 78 mg (64% of theory) of the title compound.

$^1$H-NMR (400 MHz, DMSO-$d_6$, δ/ppm): 8.13 (s, 1H), 4.41 (t, 2H), 4.23 (t, 2H), 4.04 (s, 2H), 3.84 (t, 2H), 3.67 (t, 2H), 3.23 (m, 2H), 2.39 (s, 3H), 1.57 (sext, 2H), 0.87 (t, 3H).

LC/MS (Method 1, ESIpos): $R_t$=0.83 min, m/z=463 [M+H]$^+$.

Example 97

5-(Difluoromethyl)-6-[(3-oxopiperazin-1-yl)carbonyl]-3-(2-phenylethyl)-1-(3,3,3-trifluoropropyl)thieno[2,3-d]pyrimidine-2,4(1H,3H)-dione

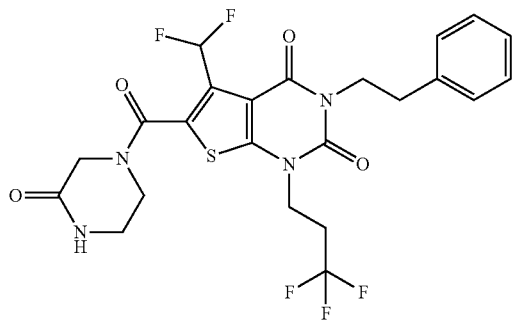 [SMILES: O=C1CN(C(=O)c2sc3c(c2C(F)F)c(=O)n(CCc2ccccc2)c(=O)n3CCC(F)(F)F)CCN1]

28 mg (0.281 mmol) of 2-oxopiperazine, 49 μl (0.281 mmol) of N,N-diisopropylethylamine and 99 mg (0.260 mmol) of HATU were added successively to a solution of 100 mg (0.216 mmol) of the compound from Ex. 57A in 3.1 ml of anhydrous DMF. After a reaction time of about 16 h at RT, the reaction mixture was separated directly by preparative HPLC into its components (Method 6). The product fractions were combined and concentrated, and the residue was dried under high vacuum. Stirring with a mixture of 10 ml of pentane and 1 ml of diisopropyl ether for 20 min at RT, filtration with suction and once more drying under high vacuum gave 78 mg (66% of theory) of the title compound.

$^1$H-NMR (400 MHz, DMSO-d$_6$, δ/ppm): 8.18 (s, 1H), 7.36 (t, 1H), 7.34-7.29 (m, 2H), 7.27-7.21 (m, 3H), 4.15 (t, 2H), 4.08 (m, 2H), 3.90 (broad, 1H), 3.77 (broad, 1H), 3.52 (broad, 2H), 3.22 (broad, 2H), 2.86-2.71 (m, 4H).

LC/MS (Method 1, ESIpos): R$_t$=0.98 min, m/z=545 [M+H]$^+$.

Example 98

3,5-Diethyl-6-[(3-oxopiperazin-1-yl)carbonyl]-1-(3,3,3-trifluoropropyl)thieno[2,3-d]pyrimidine-2,4(1H,3H)-dione

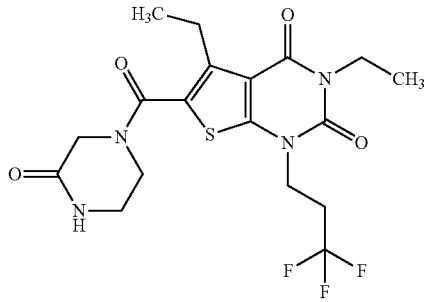 [SMILES: CCc1c(C(=O)N2CCNC(=O)C2)sc2c1c(=O)n(CC)c(=O)n2CCC(F)(F)F]

Analogously to the process described in Ex. 51, 80 mg (0.220 mmol) of the compound from Ex. 111A and 24 mg (0.242 mmol) of 2-oxopiperazine gave 93 mg (95% of theory) of the title compound.

$^1$H-NMR (400 MHz, DMSO-d$_6$, δ/ppm): 8.14 (s, 1H), 4.13 (t, 2H), 4.04 (s, 2H), 3.93 (quart, 2H), 3.67 (t, 2H), 3.23 (m, 2H), 2.86-2.74 (m, 4H), 1.13 (t, 3H), 1.11 (t, 3H).

LC/MS (Method 1, ESIpos): R$_t$=0.79 min, m/z=447 [M+H]$^+$.

Example 99

6-[(4-Hydroxypiperidin-1-yl)carbonyl]-5-methyl-3-(2-phenylethyl)-1-[2-(trifluoromethoxy)ethyl]thieno[2,3-d]pyrimidine-2,4(1H,3H)-dione

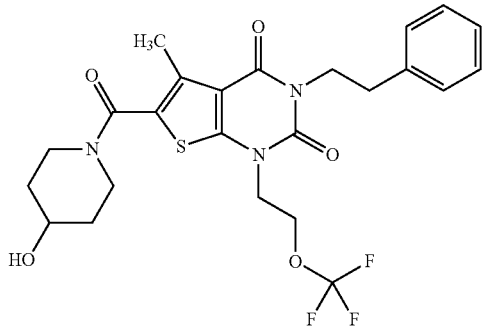 [SMILES: Cc1c(C(=O)N2CCC(O)CC2)sc2c1c(=O)n(CCc1ccccc1)c(=O)n2CCOC(F)(F)F]

Analogously to the process described in Ex. 51, 65 mg (0.147 mmol) of the compound from Ex. 118A and 17 mg (0.162 mmol) of 4-hydroxypiperidine gave 72 mg (93% of theory) of the title compound.

$^1$H-NMR (400 MHz, DMSO-d$_6$, δ/ppm): 7.32-7.28 (m, 2H), 7.25-7.20 (m, 3H), 4.80 (d, 1H), 4.39 (t, 2H), 4.22 (t, 2H), 4.08 (m, 2H), 3.80-3.71 (m, 3H), 3.23 (m, 2H), 2.84 (m, 2H), 2.37 (s, 3H), 1.79-1.72 (m, 2H), 1.40-1.30 (m, 2H).

LC/MS (Method 1, ESIpos): R$_t$=1.05 min, m/z=526 [M+H]$^+$.

Example 100

3-(2-Hydroxy-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 1)

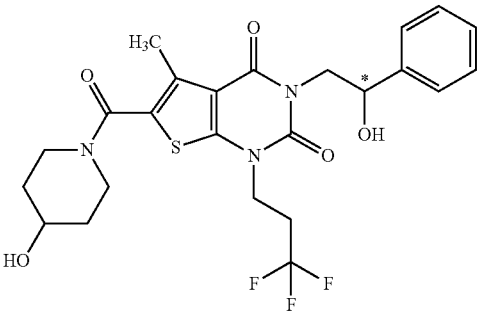

Analogously to the process described in Ex. 43, 50 mg (0.088 mmol) of the compound from Ex. 125A gave 18 mg (38% of theory) of the title compound.

$^1$H-NMR (400 MHz, DMSO-d$_6$, δ/ppm): 7.37-7.31 (m, 4H), 7.28-7.23 (m, 1H), 5.40 (d, 1H), 4.96-4.91 (m, 1H), 4.80 (d, 1H), 4.23 (dd, 1H), 4.11 (t, 2H), 3.85-3.72 (m, 4H), 3.31-3.21 (m, 2H, partially obscured by the water signal), 2.77-2.66 (m, 2H), 2.38 (s, 3H), 1.80-1.73 (m, 2H), 1.41-1.31 (m, 2H).

LC/MS (Method 1, ESIpos): R$_t$=0.86 min, m/z=526 [M+H]$^+$.

Chiral analytical HPLC [column: Daicel Chiralcel OD-H, 5 μm, 250 mm×4.6 mm; eluent: isohexane/ethanol 1:1; flow rate: 1 ml/min, temperature: 30° C.; detection: 220 nm]: R$_t$=6.65 min; 98% ee.

Example 101

3-(2-Hydroxy-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 2)

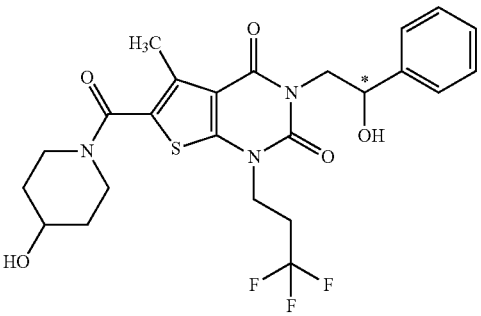 [SMILES: Cc1c(C(=O)N2CCC(O)CC2)sc2c1c(=O)n(CC(O)c1ccccc1)c(=O)n2CCC(F)(F)F]

Analogously to the process described in Ex. 43, 50 mg (0.088 mmol) of the compound from Ex. 126A gave 13 mg (29% of theory) of the title compound.

¹H-NMR (400 MHz, DMSO-d₆, δ/ppm): 7.38-7.32 (m, 4H), 7.28-7.23 (m, 1H), 5.40 (d, 1H), 4.96-4.91 (m, 1H), 4.80 (d, 1H), 4.23 (dd, 1H), 4.11 (t, 2H), 3.85-3.72 (m, 4H), 3.31-3.21 (m, 2H, partially obscured by the water signal), 2.77-2.66 (m, 2H), 2.38 (s, 3H), 1.80-1.73 (m, 2H), 1.40-1.31 (m, 2H).

LC/MS (Method 1, ESIpos): R$_t$=0.86 min, m/z=526 [M+H]⁺.

Chiral analytical HPLC [column: Daicel Chiralcel OD-H, 5 μm, 250 mm×4.6 mm; eluent: isohexane/ethanol 1:1; flow rate: 1 ml/min, temperature: 30° C.; detection: 220 nm]: R$_t$=4.98 min; >99% ee.

Example 102

3-(2-Fluoro-2-phenylethyl)-6-[(4-hydroxypiperidin-1-yl)carbonyl]-5-methyl-1-(3,3,3-trifluoropropyl)thieno [2,3-d]pyrimidine-2,4(1H,3H)-dione (enantiomer 1)

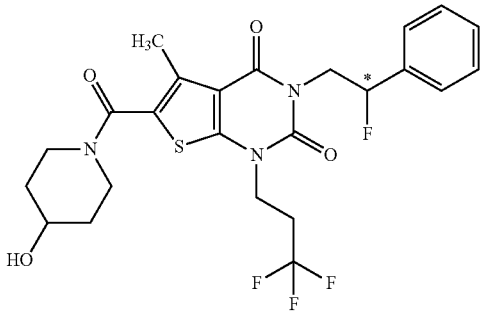 [SMILES: Cc1c(C(=O)N2CCC(O)CC2)sc2c1c(=O)n(CC(F)c1ccccc1)c(=O)n2CCC(F)(F)F]

Analogously to the process described in Ex. 43, 75 mg (0.133 mmol) of the compound from Ex. 127A gave 57 mg (81% of theory) of the title compound. In this case, the reaction time was 30 min.

¹H-NMR (400 MHz, DMSO-d₆, δ/ppm): 7.49-7.40 (m, 5H), 5.77 (ddd, 1H), 4.80 (d, 1H), 4.63 (m, 1H), 4.15 (t, 2H), 4.00 (ddd, 1H), 3.83-3.72 (m, 3H), 3.29-3.22 (m, 2H), 2.86-2.74 (m, 2H), 2.40 (s, 3H), 1.81-1.73 (m, 2H), 1.41-1.32 (m, 2H).

LC/MS (Method 1, ESIpos): R$_t$=0.98 min, m/z=528 [M+H]⁺.

Example 103

3-(2-Fluoro-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 2)

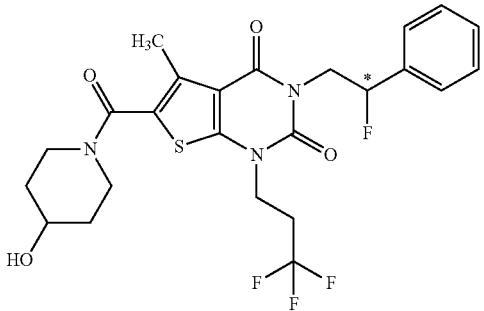 [SMILES: Cc1c(C(=O)N2CCC(O)CC2)sc2c1c(=O)n(CC(F)c1ccccc1)c(=O)n2CCC(F)(F)F]

Analogously to the process described in Ex. 43, 58 mg (0.102 mmol) of the compound from Ex. 128A gave 41 mg (76% of theory) of the title compound. In this case, the reaction time was 30 min.

¹H-NMR (400 MHz, DMSO-d₆, δ/ppm): 7.49-7.40 (m, 5H), 5.77 (ddd, 1H), 4.82 (d, 1H), 4.63 (m, 1H), 4.16 (t, 2H), 3.99 (ddd, 1H), 3.82-3.71 (m, 3H), 3.29-3.21 (m, 2H), 2.86-2.74 (m, 2H), 2.40 (s, 3H), 1.80-1.73 (m, 2H), 1.41-1.32 (m, 2H).

LC/MS (Method 1, ESIpos): R$_t$=0.98 min, m/z=528 [M+H]⁺.

Example 104

6-[(4-Hydroxypiperidin-1-yl)carbonyl]-5-methyl-3-(3,3,3-trifluoro-2-phenylpropyl)-1-(3,3,3-trifluoropropyl)thieno[2,3-d]pyrimidine-2,4(1H,3H)-dione (racemate)

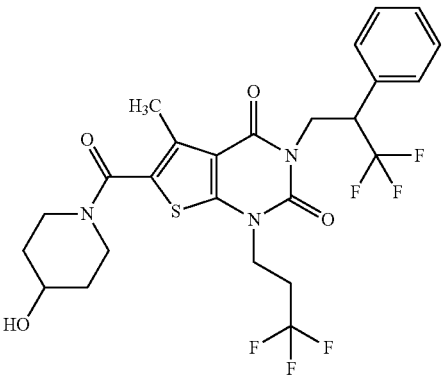 [SMILES: Cc1c(C(=O)N2CCC(O)CC2)sc2c1c(=O)n(CC(c1ccccc1)C(F)(F)F)c(=O)n2CCC(F)(F)F]

Analogously to the process described in Ex. 43, 25 mg (0.040 mmol) of the compound from Ex. 122A gave 20 mg (81% of theory, purity 95%) of the title compound.

¹H-NMR (400 MHz, CDCl₃, δ/ppm): 7.37-7.31 (m, 5H), 4.62-4.50 (m, 2H), 4.16-4.08 (m, 2H), 4.06-3.98 (m, 2H), 3.95-3.88 (m, 2H), 3.43-3.36 (m, 2H), 2.51-2.40 (m, 2H), 2.47 (s, 3H), 1.97-1.90 (m, 2H), 1.65-1.56 (m, 2H), 1.51 (broad, 1H).

LC/MS (Method 1, ESIpos): R$_t$=1.04 min, m/z=578 [M+H]⁺.

Example 105

3-(2-Hydroxy-2-phenylpropyl)-6-[(4-hydroxypiperidin-1-yl)carbonyl]-5-methyl-1-(3,3,3-trifluoropropyl)thieno[2,3-d]pyrimidine-2,4(1H,3H)-dione (racemate)

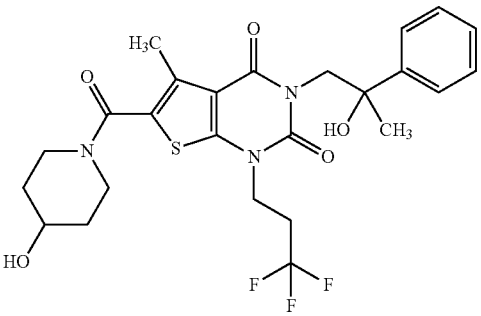 [SMILES: Cc1c(C(=O)N2CCC(O)CC2)sc2c1c(=O)n(CC(C)(O)c1ccccc1)c(=O)n2CCC(F)(F)F]

Analogously to the process described in Ex. 43, 67 mg (0.115 mmol) of the compound from Ex. 129A gave 17 mg (27% of theory) of the title compound.

¹H-NMR (400 MHz, DMSO-d₆, δ/ppm): 7.48 (d, 2H), 7.30 (t, 2H), 7.21 (t, 1H), 5.05 (s, 1H), 4.81 (d, 1H), 4.18 (quart, 2H), 4.12-4.03 (m, 2H), 3.81-3.72 (m, 3H), 3.28-3.21 (m, 2H), 2.75-2.63 (m, 2H), 2.34 (s, 3H), 1.80-1.74 (m, 2H), 1.42 (s, 3H), 1.41-1.32 (m, 2H).

LC/MS (Method 1, ESIpos): R$_t$=0.93 min, m/z=540 [M+H]⁺.

Example 106

3-(4,4-Difluorobut-3-en-1-yl)-6-[(4-hydroxypiperidin-1-yl)carbonyl]-5-methyl-1-(3,3,3-trifluoropropyl)thieno [2,3-d]pyrimidine-2,4(1H,3H)-dione

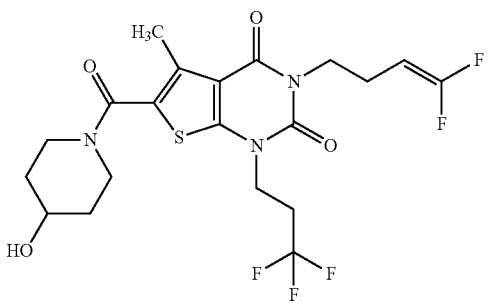 [SMILES: Cc1c(C(=O)N2CCC(O)CC2)sc2c1c(=O)n(CCC=C(F)F)c(=O)n2CCC(F)(F)F]

Analogously to the process described in Ex. 43, 90 mg (0.167 mmol) of the compound from Ex. 123A gave 66 mg (79% of theory) of the title compound.

¹H-NMR (400 MHz, DMSO-d₆, δ/ppm): 4.80 (d, 1H), 4.53 (dtd, 1H), 4.13 (t, 2H), 3.92 (t, 2H), 3.81-3.71 (m, 3H), 3.27-3.21 (m, 2H), 2.84-2.71 (m, 2H), 2.38 (s, 3H), 2.32-2.22 (m, 2H), 1.80-1.72 (m, 2H), 1.40-1.30 (m, 2H).

LC/MS (Method 1, ESIpos): R$_t$=0.96 min, m/z=496 [M+H]⁺.

Example 107

6-[(4-Hydroxypiperidin-1-yl)carbonyl]-5-methyl-3-(3,3,3-trifluoro-2-methoxypropyl)-1-(3,3,3-trifluoropropyl)thieno[2,3-d]pyrimidine-2,4(1H,3H)-dione (enantiomer 1)

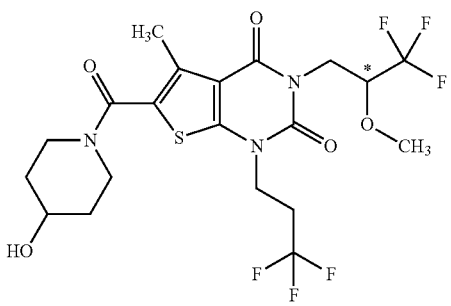 [SMILES: COC(Cn1c(=O)c2c(C)c(C(=O)N3CCC(O)CC3)sc2n(CCC(F)(F)F)c1=O)C(F)(F)F]

134 mg (0.252 mmol) of the racemic compound from Ex. 66 were dissolved in 4 ml of isopropanol and, in 13 portions, separated into the enantiomers by preparative HPLC on a chiral phase [column. Daicel Chiralcel OX-H, 5 μm, 250 mm×20 mm; mobile phase: isohexane/isopropanol 65:35; flow rate: 15 ml/min, temperature: 40° C.; detection: 220 nm]. This gave, after concentration of the product fractions and drying of the residue under high vacuum, 32 mg (47% of theory) of enantiomer 1.

¹H-NMR (400 MHz, DMSO-d₆, δ/ppm): 4.81 (d, 1H), 4.29-4.14 (m, 4H), 4.05 (dd, 1H), 3.82-3.71 (m, 3H), 3.43 (s, 3H), 3.28-3.21 (m, 2H), 2.87-2.75 (m, 2H), 2.38 (s, 3H), 1.80-1.73 (m, 2H), 1.40-1.31 (m, 2H).

LC/MS (Method 1, ESIpos): R$_t$=0.92 min, m/z=532 [M+H]⁺.

Chiral analytical HPLC [column: LUX Cellulose 4, 5 μm, 250 mm×4.6 mm; mobile phase: isohexane/isopropanol 60:40; flow rate: 1 ml/min, temperature: 40° C.; detection: 220 nm]: R$_t$=7.47 min; 99.9% ee.

Example 108

6-[(4-Hydroxypiperidin-1-yl)carbonyl]-5-methyl-3-(3,3,3-trifluoro-2-methoxypropyl)-1-(3,3,3-trifluoropropyl)thieno[2,3-d]pyrimidine-2,4(1H,3H)-dione (enantiomer 2)

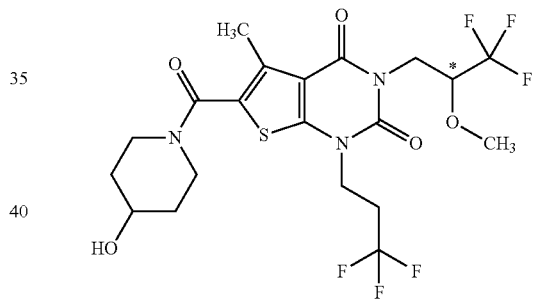

134 mg (0.252 mmol) of the racemic compound from Ex. 66 were dissolved in 4 ml of isopropanol and, in 13 portions, separated into the enantiomers by preparative HPLC on a chiral phase [column: Daicel Chiralcel OX-H, 5 μm, 250 mm×20 mm; mobile phase: isohexane/isopropanol 65:35; flow rate: 15 ml/min, temperature: 40° C.; detection: 220 nm]. This gave, after concentration of the product fractions and drying of the residue under high vacuum, 53 mg (79% of theory) of enantiomer 2.

¹H-NMR (400 MHz, DMSO-d₆, δ/ppm): 4.81 (d, 1H), 4.29-4.14 (m, 4H), 4.05 (dd, 1H), 3.82-3.71 (m, 3H), 3.43 (s, 3H), 3.28-3.21 (m, 2H), 2.87-2.75 (m, 2H), 2.38 (s, 3H), 1.80-1.73 (m, 2H), 1.40-1.31 (m, 2H).

LC/MS (Method 1, ESIpos): R$_t$=0.92 min, m/z=532 [M+H]⁺.

Chiral analytical HPLC [column: LUX Cellulose 4, 5 μm, 250 mm×4.6 mm; mobile phase: isohexane/isopropanol 60:40; flow rate: 1 ml/min, temperature: 40° C.; detection: 220 nm]: R$_t$=9.67 min; 99.9% ee.

Example 109

6-[(4-Hydroxy-4-methylpiperidin-1-yl)carbonyl]-5-methyl-3-(2-phenylethyl)-1-[2-(trifluoromethoxy)ethyl]thieno[2,3-d]pyrimidine-2,4(1H,3H)-dione

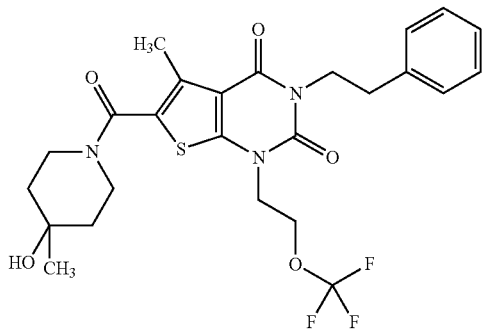 [SMILES: Cc1c(C(=O)N2CCC(C)(O)CC2)sc2c1c(=O)n(CCc1ccccc1)c(=O)n2CCOC(F)(F)F]

Analogously to the process described in Ex. 51, 65 mg (0.147 mmol) of the compound from Ex. 118A and 19 mg (0.162 mmol) of 4-methylpiperidin-4-ol [commercially available; lit. e.g.: J. M. McManus et al., *J. Med. Chem.* 1965, 8 (6), 766-776] gave 65 mg (79% of theory) of the title compound.

$^1$H-NMR (400 MHz, DMSO-d$_6$, δ/ppm): 7.33-7.28 (m, 2H), 7.25-7.20 (m, 3H), 4.46 (s, 1H), 4.39 (t, 2H), 4.22 (t, 2H), 4.08 (m, 2H), 3.76-3.65 (broad, 2H), 3.37-3.29 (m, 2H, partially obscured by the water signal), 2.84 (m, 2H), 2.37 (s, 3H), 1.54-1.40 (m, 4H), 1.15 (s, 3H).

LC/MS (Method 1, ESIpos): R$_t$=1.10 min, m/z=540 [M+H]$^+$.

Example 110

6-{[4-Hydroxy-4-(hydroxymethyl)piperidin-1-yl]carbonyl}-5-methyl-3-(2-phenylethyl)-1-[2-(trifluoromethoxy)ethyl]thieno[2,3-d]pyrimidine-2,4(1H,3H)-dione

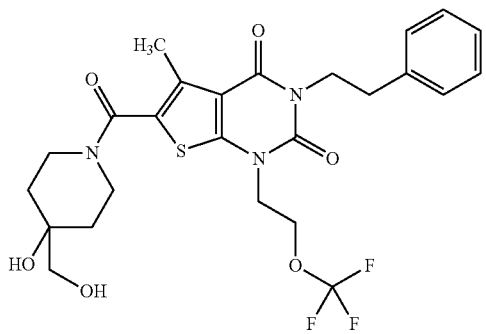 [SMILES: Cc1c(C(=O)N2CCC(O)(CO)CC2)sc2c1c(=O)n(CCc1ccccc1)c(=O)n2CCOC(F)(F)F]

Analogously to the process described in Ex. 51, 65 mg (0.147 mmol) of the compound from Ex. 118A and 27 mg (0.162 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 73 mg (90% of theory) of the title compound.

$^1$H-NMR (400 MHz, DMSO-d$_6$, δ/ppm): 7.32-7.28 (m, 2H), 7.25-7.20 (m, 3H), 4.63 (t, 1H), 4.39 (t, 2H), 4.36 (s, 1H), 4.22 (t, 2H), 4.08 (m, 2H), 3.89-3.77 (broad, 2H), 3.31-3.22 (m, 2H, partially obscured by the water signal), 3.21 (d, 2H), 2.84 (m, 2H), 2.38 (s, 3H), 1.59-1.51 (m, 2H), 1.43-1.37 (m, 2H).

LC/MS (Method 1, ESIpos): R$_t$=0.99 min, m/z=556 [M+H]$^+$.

Example 111

3-Ethyl-6-[(4-hydroxy-4-methylpiperidin-1-yl)carbonyl]-5-methyl-1-[2-(trifluoromethoxy)ethyl]thieno[2,3-d]pyrimidine-2,4(1H,3H)-dione

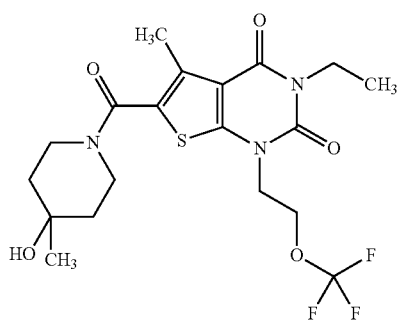 [SMILES: CCn1c(=O)c2c(C)c(C(=O)N3CCC(C)(O)CC3)sc2n(CCOC(F)(F)F)c1=O]

Analogously to the process described in Ex. 51, 100 mg (0.273 mmol) of the compound from Ex. 104A and 38 mg (0.328 mmol) of 4-methylpiperidin-4-ol [commercially available; lit. e.g.: J. M. McManus et al., *J. Med. Chem.* 1965, 8 (6), 766-776] gave 98 mg (77% of theory) of the title compound. The reaction time in this case was 1 h.

$^1$H-NMR (400 MHz, DMSO-d$_6$, δ/ppm): 4.45 (s, 1H), 4.41 (t, 2H), 4.22 (t, 2H), 3.91 (quart, 2H), 3.75-3.65 (broad, 2H), 3.37-3.29 (m, 2H, partially obscured by the water signal), 2.37 (s, 3H), 1.53-1.40 (m, 4H), 1.15 (s, 3H), 1.13 (t, 3H).

LC/MS (Method 1, ESIpos): R$_t$=0.88 min, m/z=464 [M+H]$^+$.

Example 112

3-Ethyl-6-[(4-ethyl-4-hydroxypiperidin-1-yl)carbonyl]-5-methyl-1-[2-(trifluoromethoxy)ethyl]thieno[2,3-d]pyrimidine-2,4(1H,3H)-dione

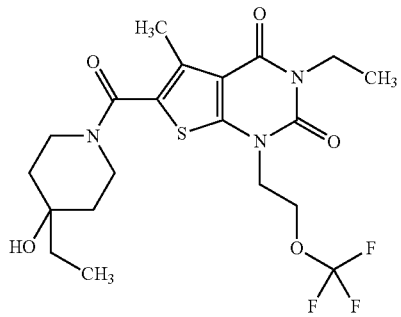 [SMILES: CCn1c(=O)c2c(C)c(C(=O)N3CCC(O)(CC)CC3)sc2n(CCOC(F)(F)F)c1=O]

Analogously to the process described in Ex. 51, 80 mg (0.218 mmol) of the compound from Ex. 104A and 44 mg (0.262 mmol) of 4-ethylpiperidin-4-ol hydrochloride [commercially available; lit. e.g.: US 2004/0067931-A1, Example 3.232 (free base)] gave 97 mg (93% of theory) of the title compound.

$^1$H-NMR (400 MHz, DMSO-$d_6$, δ/ppm): 4.41 (t, 2H), 4.26 (s, 1H), 4.22 (t, 2H), 3.91 (quart, 2H), 3.82-3.72 (broad, 2H), 3.33-3.25 (m, 2H, partially obscured by the water signal), 2.37 (s, 3H), 1.51-1.45 (m, 2H), 1.42-1.34 (m, 2H), 1.40 (quart, 2H), 1.13 (t, 3H), 0.83 (t, 3H).

LC/MS (Method 1, ESIpos): $R_t$=0.94 min, m/z=478 [M+H]$^+$.

Example 113

3-Ethyl-6-[(4-ethyl-4-hydroxypiperidin-1-yl)carbonyl]-5-methyl-1-(3,3,3-trifluoropropyl)thieno[2,3-d]pyrimidine-2,4(1H,3H)-dione

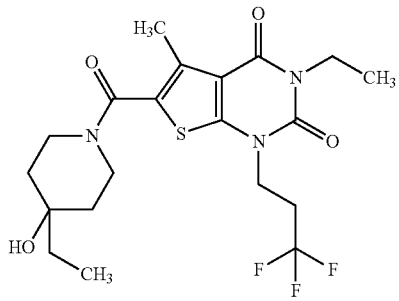 [SMILES: CCn1c(=O)c2c(C)c(C(=O)N3CCC(O)(CC)CC3)sc2n(CCC(F)(F)F)c1=O]

Analogously to the process described in Ex. 51, 80 mg (0.228 mmol) of the compound from Ex. 52A and 45 mg (0.274 mmol) of 4-ethylpiperidin-4-ol hydrochloride [commercially available; lit. e.g.: US 2004/0067931-A1, Example 3.232 (free base)] gave 94 mg (89% of theory) of the title compound.

$^1$H-NMR (400 MHz, DMSO-$d_6$, δ/ppm): 4.26 (s, 1H), 4.12 (t, 2H), 3.91 (quart, 2H), 3.84-3.73 (broad, 2H), 3.33-3.25 (m, 2H, partially obscured by the water signal), 2.85-2.73 (m, 2H), 2.38 (s, 3H), 1.52-1.46 (m, 2H), 1.41 (quart, 2H), 1.41-1.35 (m, 2H), 1.13 (t, 3H), 0.84 (t, 3H).

LC/MS (Method 1, ESIpos): $R_t$=0.90 min, m/z=462 [M+H]$^+$.

Example 114

6-{[4-Hydroxy-4-(hydroxymethyl)piperidin-1-yl]carbonyl}-5-methyl-3-(3,3,3-trifluoro-2-methoxypropyl)-1-(3,3,3-trifluoropropyl)thieno[2,3-d]pyrimidine-2,4(1H,3H)-dione (enantiomer 1)

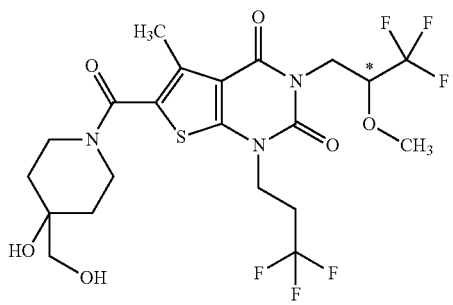 [SMILES: COC(Cn1c(=O)c2c(C)c(C(=O)N3CCC(O)(CO)CC3)sc2n(CCC(F)(F)F)c1=O)C(F)(F)F]

120 mg (0.214 mmol) of the racemic compound from Ex. 81 were dissolved in 4 ml of isopropanol and, in 13 portions, separated into the enantiomers by preparative HPLC on a chiral phase [column: Daicel Chiralcel OX-H, 5 μm, 250 mm×20 mm; mobile phase: isohexane/isopropanol 60:40; flow rate: 15 ml/min, temperature: 30° C.; detection: 220 nm]. This gave, after concentration of the product fractions and drying of the residue under high vacuum, 54 mg (86% of theory, chem. purity 95%, >99% ee) of enantiomer 1. Re-purification by preparative HPLC (Method 5) gave 44 mg (73% of theory) of the title compound in pure form.

$^1$H-NMR (400 MHz, CDCl$_3$, δ/ppm): 4.46 (dd, 1H), 4.21-3.97 (m, 6H), 3.51 (s, 5H), 3.45 (br. t, 2H), 2.71-2.60 (m, 2H), 2.50 (s, 3H), 2.21 (broad, 1H), 1.95 (broad, 1H), 1.76-1.70 (m, 2H), 1.58-1.51 (m, 2H, partially obscured by the water signal).

LC/MS (Method 1, ESIpos): $R_t$=0.88 min, m/z=562 [M+H]$^+$.

Chiral analytical HPLC [column: LUX Cellulose 4, 5 μm, 250 mm×4.6 mm; mobile phase: isohexane/isopropanol 60:40; flow rate: 1 ml/min, temperature: 40° C.; detection: 220 nm]: $R_t$=8.11 min.

Example 115

6-{[4-Hydroxy-4-(hydroxymethyl)piperidin-1-yl]carbonyl}-5-methyl-3-(3,3,3-trifluoro-2-methoxypropyl)-1-(3,3,3-trifluoropropyl)thieno[2,3-d]pyrimidine-2,4(1H,3H)-dione (enantiomer 2)

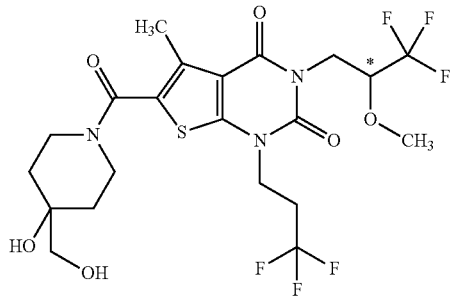 [SMILES: COC(Cn1c(=O)c2c(C)c(C(=O)N3CCC(O)(CO)CC3)sc2n(CCC(F)(F)F)c1=O)C(F)(F)F]

120 mg (0.214 mmol) of the racemic compound from Ex. 81 were dissolved in 4 ml of isopropanol and, in 13 portions, separated into the enantiomers by preparative HPLC on a chiral phase [column: Daicel Chiralcel OX-H, 5 μm, 250 mm×20 mm; mobile phase: isohexane/isopropanol 60:40; flow rate: 15 ml/min, temperature: 30° C.; detection: 220 nm]. This gave, after concentration of the product fractions and drying of the residue under high vacuum, 58 mg (92% of theory, chem. purity 95%, >99% ee) of enantiomer 2. Re-purification by preparative HPLC (Method 5) gave 45 mg (75% of theory) of the title compound in pure form.

$^1$H-NMR (400 MHz, CDCl$_3$, δ/ppm): 4.46 (dd, 1H), 4.21-3.97 (m, 6H), 3.51 (s, 5H), 3.45 (br. t, 2H), 2.71-2.60 (m, 2H), 2.50 (s, 3H), 2.20 (broad, 1H), 1.94 (broad, 1H), 1.76-1.70 (m, 2H), 1.57-1.51 (m, 2H, partially obscured by the water signal).

LC/MS (Method 1, ESIpos): $R_t$=0.88 min, m/z=562 [M+H]$^+$.

Chiral analytical HPLC [column: LUX Cellulose 4, 5 μm, 250 mm×4.6 mm; mobile phase: isohexane/isopropanol 60:40; flow rate: 1 ml/min, temperature: 40° C.; detection: 220 nm]: $R_t$=10.96 min.

Example 116

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (cis-racemate)

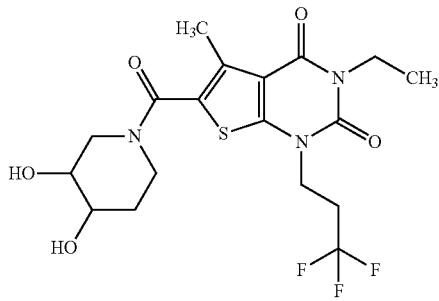 [SMILES: CCn1c(=O)c2c(C)c(C(=O)N3CCC(O)C(O)C3)sc2n(CCC(F)(F)F)c1=O]

Analogously to the process described in Ex. 51, 200 mg (0.571 mmol) of the compound from Ex. 52A and 105 mg (0.685 mmol) of racemic cis-3,4-dihydroxypiperidine hydrochloride [commercially available; lit. e.g.: H. H. Jensen et al., *Chemistry Eur. J.* 2002, 8 (5), 1218-1226] gave 160 mg (62% of theory) of the title compound. Purification was carried out by preparative HPLC (twice) according to Method 5.

$^1$H-NMR (400 MHz, CDCl$_3$, δ/ppm): 4.23-4.11 (m, 2H), 4.07 (quart, 2H), 3.97 (dt, 1H), 3.89-3.82 (m, 2H), 3.81 (t, 1H), 3.61-3.55 (m, 1H), 3.42-3.36 (m, 1H), 2.70-2.59 (m, 2H), 2.51 (s, 3H), 1.98-1.89 (m, 1H), 1.79-1.72 (m, 1H), 1.25 (t, 3H).

LC/MS (Method 1, ESIpos): R$_t$=0.76 min, m/z=450 [M+H]$^+$.

Example 117

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (cis-enantiomer 1)

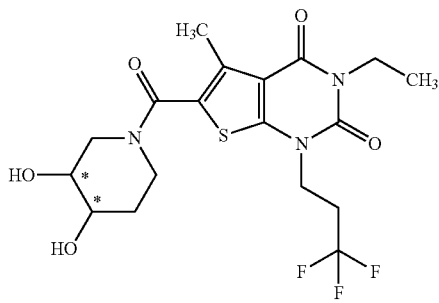 [SMILES: CCn1c(=O)c2c(C)c(C(=O)N3CCC(O)C(O)C3)sc2n(CCC(F)(F)F)c1=O]

149 mg (0.332 mmol) of the racemic compound from Ex. 116 were dissolved in a mixture of 1 ml of methanol and 0.5 ml of isopropanol and, in 6 portions, separated into the enantiomers by preparative HPLC on a chiral phase [column: Daicel Chiralpak IC 5 μm 250 mm×20 mm; mobile phase: isohexane/ethanol 50:50; flow rate: 20 ml/min, temperature: 23° C.; detection: 220 nm]. This gave, after concentration of the product fractions and drying of the residue under high vacuum, 49 mg (63% of theory, chem. purity 97%, 95% ee) of enantiomer 1. Subsequent stirring with pentane gave 38 mg (51% of theory) of the title compound in pure form.

$^1$H-NMR (400 MHz, CDCl$_3$, δ/ppm): 4.23-4.11 (m, 2H), 4.07 (quart, 2H), 3.99-3.94 (m, 1H), 3.89-3.82 (m, 2H), 3.81 (t, 1H), 3.61-3.55 (m, 1H), 3.42-3.36 (m, 1H), 2.70-2.59 (m, 2H), 2.51 (s, 3H), 2.26 (d, 1H), 2.11 (d, 1H), 1.98-1.89 (m, 1H), 1.79-1.72 (m, 1H), 1.25 (t, 3H).

Chiral analytical HPLC [column: Daicel Chiralpak IE-3, 3 μm 50 mm×4.6 mm; mobile phase: isohexane/ethanol 50:50; flow rate: 1 ml/min, temperature: 40° C.; detection: 220 nm]: R$_t$=1.96 min.

Example 118

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (cis-enantiomer 2)

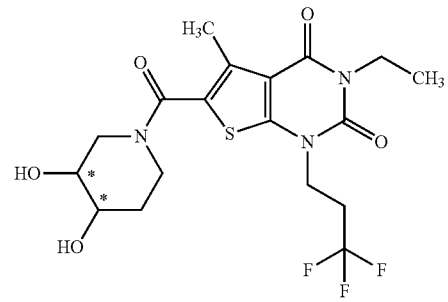

149 mg (0.332 mmol) of the racemic compound from Ex. 116 were dissolved in a mixture of 1 ml of methanol and 0.5 ml of isopropanol and, in 6 portions, separated into the enantiomers by preparative HPLC on a chiral phase [column: Daicel Chiralpak IC 5 μm 250 mm×20 mm; mobile phase: isohexane/ethanol 50:50; flow rate: 20 ml/min, temperature: 23° C.; detection: 220 nm]. This gave, after concentration of the product fractions and drying of the residue under high vacuum, 56 mg (74% of theory, chem. purity 97%, 94% ee) of enantiomer 2. Subsequent stirring with pentane gave 50 mg (67% of theory) of the title compound in pure form.

$^1$H-NMR (400 MHz, CDCl$_3$, δ/ppm): 4.23-4.11 (m, 2H), 4.07 (quart, 2H), 3.99-3.94 (m, 1H), 3.89-3.82 (m, 2H), 3.81 (t, 1H), 3.61-3.55 (m, 1H), 3.42-3.36 (m, 1H), 2.70-2.59 (m, 2H), 2.51 (s, 3H), 2.31 (broad, 1H), 2.14 (broad, 1H), 1.98-1.89 (m, 1H), 1.79-1.72 (m, 1H), 1.25 (t, 3H).

Chiral analytical HPLC [column: Daicel Chiralpak IE-3, 3 μm 50 mm×4.6 mm; mobile phase: isohexane/ethanol 50:50; flow rate: 1 ml/min, temperature: 40° C.; detection: 220 nm]: R$_t$=1.62 min.

Example 119

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (cis-racemate)

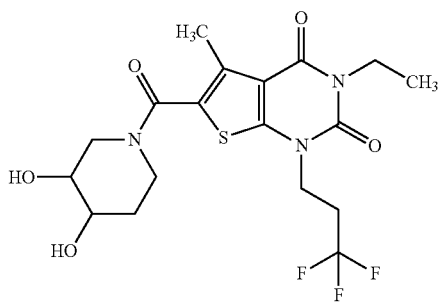 [SMILES: CCn1c(=O)c2c(C)c(C(=O)N3CCC(O)C(O)C3)sc2n(CCC(F)(F)F)c1=O]

Analogously to the process described in Ex. 51, 200 mg (0.571 mmol) of the compound from Ex. 52A and 105 mg (0.685 mmol) of racemic trans-3,4-dihydroxypiperidine hydrochloride [commercially available; lit. e.g.: H. H. Jensen et al., *Chemistry Eur. J.* 2002, 8 (5), 1218-1226] gave 161 mg (62% of theory) of the title compound. Purification was carried out by preparative HPLC (twice) according to Method 5.

$^1$H-NMR (400 MHz, CDCl$_3$, δ/ppm): 4.24-4.13 (m, 3H), 4.11-4.02 (m, 3H), 3.74-3.66 (m, 1H), 3.60-3.53 (m, 1H), 3.22-3.05 (m, 2H), 2.70-2.59 (m, 2H), 2.51 (s, 3H), 2.11-2.03 (m, 1H), 1.62-1.51 (m, 1H), 1.26 (t, 3H).

LC/MS (Method 1, ESIpos): R$_t$=0.76 min, m/z=450 [M+H]$^+$.

Example 120

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (trans-enantiomer 1)

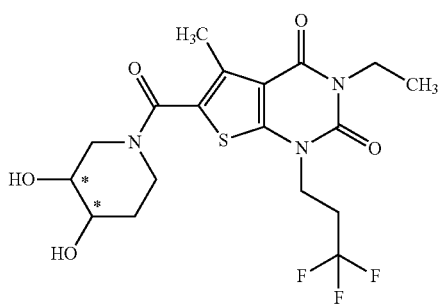 [SMILES: CCn1c(=O)c2c(C)c(C(=O)N3CCC(O)C(O)C3)sc2n(CCC(F)(F)F)c1=O]

146 mg (0.325 mmol) of the racemic compound from Ex. 119 were dissolved in 3 ml of isopropanol and, in 4 portions, separated into the enantiomers by preparative HPLC on a chiral phase [column: Daicel Chiralpak IC 5 μm 250 mm×20 mm; mobile phase: isohexane/isopropanol 40:60; flow rate: 15 ml/min, temperature: 35° C.; detection: 220 nm]. This gave, after concentration of the product fractions and drying of the residue under high vacuum, 62 mg (84% of theory) of enantiomer 1.

$^1$H-NMR (400 MHz, CDCl$_3$, δ/ppm): 4.20 (broad, 1H), 4.17 (m, 2H), 4.08 (broad, 1H), 4.07 (quart, 2H), 3.73-3.67 (m, 1H), 3.59-3.53 (m, 1H), 3.17 (t, 1H), 3.09 (dd, 1H), 2.70-2.59 (m, 2H), 2.51 (s, 3H), 2.48 (broad, 1H), 2.25 (broad, 1H), 2.10-2.04 (m, 1H), 1.61-1.51 (m, 1H, partially obscured by the water signal), 1.25 (t, 3H).

Chiral analytical HPLC [column: Daicel Chiralpak IC 5 μm 250 mm×4.6 mm; mobile phase: 40% isohexane/60% isopropanol with 0.2% TFA and 1% water; flow rate: 1 ml/min, temperature: 40° C.; detection: 220 nm]: R$_t$=6.69 min; >99% ee.

Example 121

6-[(3,4-Dihydroxypiperidin-1-yl)carbonyl]-3-ethyl-5-methyl-1-(3,3,3-trifluoropropyl)thieno [2,3-d]pyrimidine-2,4(1H,3H)-dione (trans-enantiomer 2)

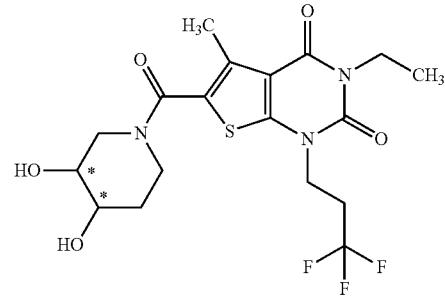 [SMILES: CCn1c(=O)c2c(C)c(C(=O)N3CCC(O)C(O)C3)sc2n(CCC(F)(F)F)c1=O]

146 mg (0.325 mmol) of the racemic compound from Ex. 119 were dissolved in 3 ml of isopropanol and, in 4 portions, separated into the enantiomers by preparative HPLC on a chiral phase [column: Daicel Chiralpak IC 5 μm 250 mm×20 mm; mobile phase: isohexane/isopropanol 40:60; flow rate: 15 ml/min, temperature: 35° C.; detection: 220 nm]. This gave, after concentration of the product fractions and drying of the residue under high vacuum, 62 mg (84% of theory) of enantiomer 2.

$^1$H-NMR (400 MHz, CDCl$_3$, δ/ppm): 4.20 (broad, 1H), 4.17 (m, 2H), 4.08 (broad, 1H), 4.07 (quart, 2H), 3.73-3.67 (m, 1H), 3.59-3.53 (m, 1H), 3.17 (t, 1H), 3.09 (dd, 1H), 2.70-2.59 (m, 2H), 2.51 (br. s, 4H), 2.27 (broad, 1H), 2.10-2.04 (m, 1H), 1.61-1.51 (m, 1H, partially obscured by the water signal), 1.26 (t, 3H).

Chiral analytical HPLC [column: Daicel Chiralpak IC 5 μm 250 mm×4.6 mm; mobile phase: 40% isohexane/60% isopropanol with 0.2% TFA and 1% water; flow rate: 1 ml/min, temperature: 40° C.; detection: 220 nm]: R$_t$=5.74 min; >99% ee.

Example 122

5-(Difluoromethyl)-3-ethyl-6-[(4-hydroxypiperidin-1-yl)carbonyl]-1-(3,3,3-trifluoropropyl)thieno[2,3-d]pyrimidine-2,4(1H,3H)-dione

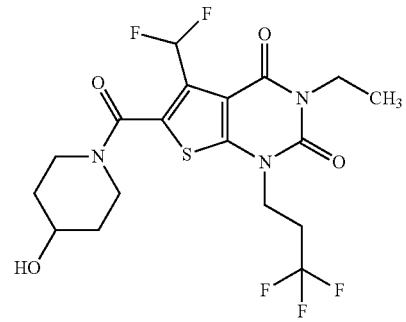 [SMILES: CCn1c(=O)c2c(C(F)F)c(C(=O)N3CCC(O)CC3)sc2n(CCC(F)(F)F)c1=O]

23 mg (0.228 mmol) of 4-hydroxypiperidine, 95 mg (0.249 mmol) of HATU and 54 μl (0.311 mmol) of N,N-diisopropylethylamine were added successively to a solution of 80 mg (0.207 mmol) of the compound from Ex. 119A in 3 ml of anhydrous DMF. After a reaction time of about 16 h at RT, the reaction mixture was separated directly by preparative HPLC (Method 5) into its components. The product fractions were combined and concentrated, and the residue was dried under high vacuum. 86 mg (88% of theory) of the title compound were obtained.

$^1$H-NMR (400 MHz, DMSO-$d_6$, δ/ppm): 7.33 (t, 1H), 4.81 (broad, 1H), 4.15 (t, 2H), 3.94 (broad, 1H), 3.92 (quart, 2H), 3.75 (m, 1H), 3.50 (broad, 1H), 3.21 (broad, 2H), 2.89-2.73 (m, 2H), 1.73 (broad, 2H), 1.36 (broad, 2H), 1.14 (t, 3H).

LC/MS (Method 1, ESIpos): $R_t$=0.83 min, m/z=470 [M+H]$^+$.

Example 123

5-(Difluoromethyl)-3-ethyl-6-[(4-hydroxypiperidin-1-yl)carbonyl]-1-[2-(trifluoromethoxy)ethyl]thieno[2,3-d]pyrimidine-2,4(1H,3H)-dione

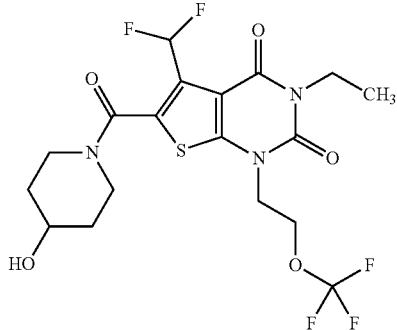 [SMILES: CCn1c(=O)c2c(C(F)F)c(C(=O)N3CCC(O)CC3)sc2n(CCOC(F)(F)F)c1=O]

Analogously to the process described in Ex. 122, 100 mg (0.249 mmol) of the compound from Ex. 120A and 30 mg (0.298 mmol) of 4-hydroxypiperidine gave 70 mg (58% of theory) of the title compound.

$^1$H-NMR (400 MHz, DMSO-$d_6$, δ/ppm): 7.33 (t, 1H), 4.81 (broad, 1H), 4.43 (t, 2H), 4.26 (t, 2H), 3.96 (broad, 1H), 3.93 (quart, 2H), 3.74 (m, 1H), 3.46 (broad, 1H), 3.20 (broad, 2H), 1.72 (broad, 2H), 1.35 (broad, 2H), 1.14 (t, 3H).

LC/MS (Method 1, ESIpos): $R_t$=0.84 min, m/z=486 [M+H]$^+$.

Example 124

5-(Difluoromethyl)-3-ethyl-6-[(4-hydroxy-4-methyl-piperidin-1-yl)carbonyl]-1-(3,3,3-trifluoropropyl)thieno[2,3-d]pyrimidine-2,4(1H,3H)-dione

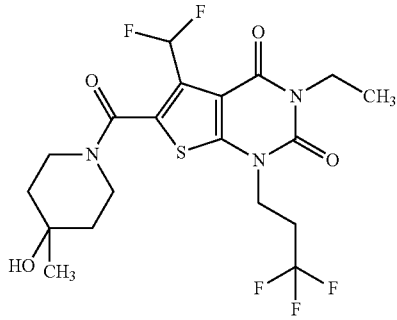 [SMILES: CCn1c(=O)c2c(C(F)F)c(C(=O)N3CCC(C)(O)CC3)sc2n(CCC(F)(F)F)c1=O]

Analogously to the process described in Ex. 122, 80 mg (0.207 mmol) of the compound from Ex. 119A and 26 mg (0.228 mmol) of 4-methylpiperidin-4-ol [commercially available; lit. e.g.: J. M. McManus et al., *J. Med. Chem.* 1965, 8 (6), 766-776] gave 87 mg (83% of theory, purity 96%) of the title compound.

$^1$H-NMR (400 MHz, DMSO-$d_6$, δ/ppm): 7.33 (t, 1H), 4.47 (broad, 1H), 4.15 (t, 2H), 4.06 (broad, 1H), 3.92 (quart, 2H), 3.24 (broad, 3H), 2.89-2.73 (m, 2H), 1.56-1.40 (broad, 4H), 1.15 (s, 3H), 1.14 (t, 3H).

LC/MS (Method 1, ESIpos): $R_t$=0.88 min, m/z=484 [M+H]$^+$.

Example 125

5-(Difluoromethyl)-3-ethyl-6-[(4-ethyl-4-hydroxypiperidin-1-yl)carbonyl]-1-(3,3,3-trifluoropropyl)thieno[2,3-d]pyrimidine-2,4(1H,3H)-dione

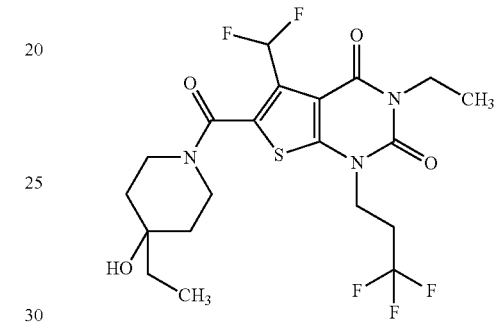

Analogously to the process described in Ex. 122, 80 mg (0.207 mmol) of the compound from Ex. 119A and 41 mg (0.249 mmol) of 4-ethylpiperidin-4-ol hydrochloride [commercially available; lit. e.g.: US 2004/0067931-A1, Example 3.232 (free base)] gave 86 mg (83% of theory) of the title compound.

$^1$H-NMR (400 MHz, DMSO-$d_6$, δ/ppm): 7.33 (t, 1H), 4.27 (s, 1H), 4.16 (broad, 1H), 4.15 (t, 2H), 3.92 (quart, 2H), 3.36 (broad, 2H), 3.13 (broad, 1H), 2.87-2.75 (m, 2H), 1.50 (broad, 2H), 1.40 (quart, 2H), 1.39 (broad, 2H), 1.14 (t, 3H), 0.83 (t, 3H).

LC/MS (Method 1, ESIpos): $R_t$=0.92 min, m/z=498 [M+H]$^+$.

Example 126

5-(Difluoromethyl)-3-ethyl-6-{[4-hydroxy-4-(hydroxymethyl)piperidin-1-yl]carbonyl}-trifluoropropyl)thieno[2,3-d]pyrimidine-2,4(1H,3H)-dione

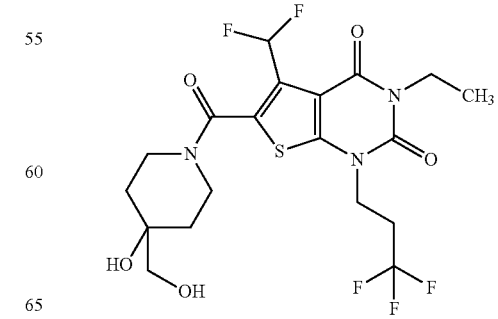

Analogously to the process described in Ex. 122, 80 mg (0.207 mmol) of the compound from Ex. 119A and 38 mg (0.228 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 88 mg (85% of theory) of the title compound.

¹H-NMR (400 MHz, DMSO-d₆, δ/ppm): 7.32 (t, 1H), 4.63 (broad, 1H), 4.36 (broad, 1H), 4.21 (broad, 1H), 4.15 (t, 2H), 3.92 (quart, 2H), 3.37 (broad, 2H), 3.20 (s, 2H), 3.10 (broad, 1H), 2.89-2.73 (m, 2H), 1.53 (dt, 2H), 1.40 (broad, 2H), 1.14 (t, 3H).

LC/MS (Method 1, ESIpos): $R_t$=0.77 min, m/z=500 [M+H]⁺.

Example 127

5-(Difluoromethyl)-3-ethyl-6-[(4-hydroxy-4-methylpiperidin-1-yl)carbonyl]-1-[2-(trifluoromethoxy)ethyl]thieno[2,3-d]pyrimidine-2,4(1H,3H)-dione

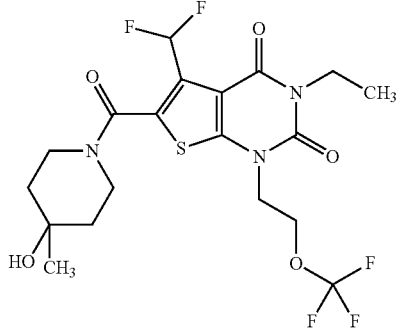 [SMILES: CCn1c(=O)c2c(C(F)F)c(C(=O)N3CCC(C)(O)CC3)sc2n(CCOC(F)(F)F)c1=O]

Analogously to the process described in Ex. 122, 100 mg (0.249 mmol) of the compound from Ex. 120A and 34 mg (0.298 mmol) of 4-methylpiperidin-4-ol [commercially available; lit. e.g.: J. M. McManus et al., *J. Med. Chem.* 1965, 8 (6), 766-776] gave 82 mg (66% of theory) of the title compound.

¹H-NMR (400 MHz, DMSO-d₆, δ/ppm): 7.32 (t, 1H), 4.47 (s, 1H), 4.42 (t, 2H), 4.25 (t, 2H), 4.05 (broad, 1H), 3.92 (quart, 2H), 3.25 (broad, 3H), 1.57-1.38 (broad, 4H), 1.14 (s, 3H), 1.14 (t, 3H).

LC/MS (Method 1, ESIpos): $R_t$=0.88 min, m/z=500 [M+H]⁺.

Example 128

3,5-Diethyl-6-[(4-ethyl-4-hydroxypiperidin-1-yl)carbonyl]-1-(3,3,3-trifluoropropyl)thieno[2,3-d]pyrimidine-2,4(1H,3H)-dione

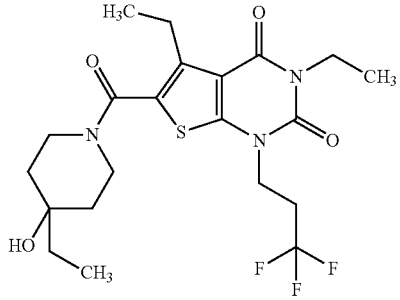 [SMILES: CCc1c(C(=O)N2CCC(O)(CC)CC2)sc2c1c(=O)n(CC)c(=O)n2CCC(F)(F)F]

Analogously to the process described in Ex. 122, 80 mg (0.220 mmol) of the compound from Ex. 111A and 44 mg (0.263 mmol) of 4-ethylpiperidin-4-ol hydrochloride [commercially available; lit. e.g.: US 2004/0067931-A1, Example 3.232 (free base)] gave 100 mg (95% of theory) of the title compound.

¹H-NMR (400 MHz, DMSO-d₆, δ/ppm): 4.27 (s, 1H), 4.12 (t, 2H), 3.92 (quart, 2H), 3.80 (broad, 2H), 3.27 (broad, 2H, partially obscured by water signal), 2.86-2.74 (m, 2H), 2.79 (quart, 2H), 1.49 (broad, 2H), 1.41 (quart, 2H), 1.38 (broad, 2H), 1.13 (t, 3H), 1.11 (t, 3H), 0.83 (t, 3H).

LC/MS (Method 1, ESIpos): $R_t$=0.96 min, m/z=476 [M+H]⁺.

Example 129

5-Methyl-6-[(3-oxopiperazin-1-yl)carbonyl]-3-(2-phenylethyl)-1-[2-(trifluoromethoxy)ethyl]thieno[2,3-d]pyrimidine-2,4(1H,3H)-dione

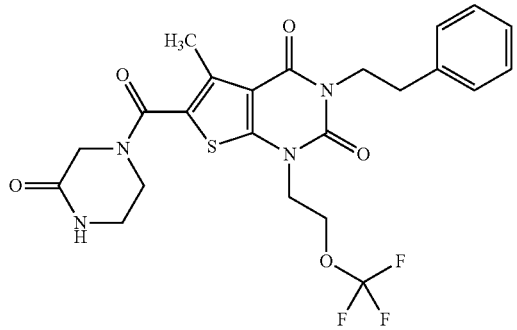 [SMILES: Cc1c(C(=O)N2CCNC(=O)C2)sc2c1c(=O)n(CCc1ccccc1)c(=O)n2CCOC(F)(F)F]

16 mg (0.162 mmol) of piperazin-2-one, 67 mg (0.176 mmol) of HATU and 64 μl (0.367 mmol) of N,N-diisopropylethylamine were added successively to a solution of 65 mg (0.147 mmol) of the compound from Ex. 118A in 2 ml of anhydrous DMF. After a reaction time of about 16 h at RT, the reaction mixture was separated directly by preparative HPLC (Method 5) into its components. The product fractions were combined and concentrated, and the residue was dried under high vacuum. 69 mg (77% of theory) of the title compound were obtained.

¹H-NMR (400 MHz, DMSO-d₆, δ/ppm): 8.14 (br. s, 1H), 7.32-7.28 (m, 2H), 7.25-7.20 (m, 3H), 4.39 (t, 2H), 4.23 (t, 2H), 4.08 (m, 2H), 4.04 (s, 2H), 3.67 (t, 2H), 3.26-3.22 (m, 2H), 2.84 (m, 2H), 2.39 (s, 3H).

LC/MS (Method 1, ESIpos): $R_t$=0.99 min, m/z=525 [M+H]⁺.

Example 130

3-Ethyl-5-methyl-6-[(3-oxopiperazin-1-yl)carbonyl]-1-[2-(trifluoromethoxy)ethyl]thieno[2,3-d]pyrimidine-2,4(1H,3H)-dione

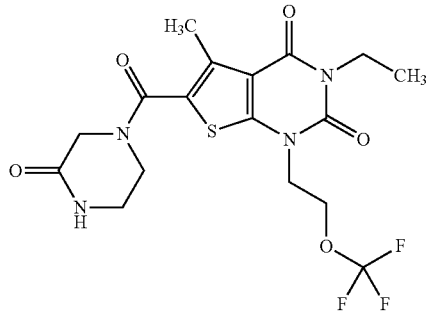 [SMILES: CCn1c(=O)c2c(C)c(C(=O)N3CCNC(=O)C3)sc2n(CCOC(F)(F)F)c1=O]

33 mg (0.328 mmol) of piperazin-2-one, 125 mg (0.328 mmol) of HATU and 62 μl (0.355 mmol) of N,N-diisopropylethylamine were added successively to a solution of 100 mg (0.273 mmol) of the compound from Ex. 104A in 3 ml of anhydrous DMF. After a reaction time of 1 h at RT, the reaction mixture was separated directly by preparative HPLC (Method 5) into its components. The product fractions were combined and concentrated, and the residue was dried under high vacuum. 95 mg (77% of theory) of the title compound were obtained.

$^1$H-NMR (400 MHz, DMSO-$d_6$, δ/ppm): 8.13 (br. s, 1H), 4.42 (t, 2H), 4.23 (t, 2H), 4.03 (s, 2H), 3.92 (quart, 2H), 3.67 (t, 2H), 3.25-3.21 (m, 2H), 2.40 (s, 3H), 1.13 (t, 3H).

LC/MS (Method 1, ESIpos): R$_t$=0.74 min, m/z=449 [M+H]$^+$.

Example 131

5-(Difluoromethyl)-3-ethyl-6-[(3-oxopiperazin-1-yl)carbonyl]-1-(3,3,3-trifluoropropyl)thieno[2,3-d]pyrimidine-2,4(1H,3H)-dione

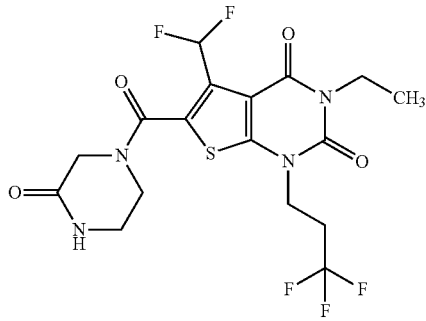 [SMILES: CCn1c(=O)c2c(C(F)F)c(C(=O)N3CCNC(=O)C3)sc2n(CCC(F)(F)F)c1=O]

Analogously to the process described in Ex. 122, 80 mg (0.207 mmol) of the compound from Ex. 119A and 23 mg (0.228 mmol) of piperazin-2-one gave 49 mg (50% of theory) of the title compound. Purification was carried out by preparative HPLC (twice) according to Method 5.

$^1$H-NMR (400 MHz, DMSO-$d_6$, δ/ppm): 8.15 (br. s, 1H), 7.35 (t, 1H), 4.16 (t, 2H), 4.05 (broad, 2H), 3.93 (quart, 2H), 3.75 (broad, 1H), 3.53 (broad, 1H), 3.21 (broad, 2H), 2.88-2.76 (m, 2H), 1.14 (t, 3H).

LC/MS (Method 1, ESIpos): R$_t$=0.77 min, m/z=469 [M+H]$^+$.

Example 132

3-(2-Hydroxy-2-phenylpropyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 1)

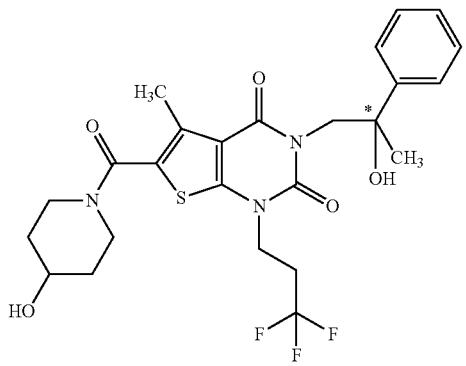 [SMILES: Cc1c(C(=O)N2CCC(O)CC2)sc2c1c(=O)n(CC(C)(O)c1ccccc1)c(=O)n2CCC(F)(F)F]

35 mg (0.065 mmol) of the racemic compound from Ex. 105 were dissolved in 6 ml of isohexane/ethanol (1:1) and, in 3 portions, separated into the enantiomers by preparative HPLC on a chiral phase [column: Daicel Chiralpak ID 5 μm 250 mm×20 mm; mobile phase: isohexane/ethanol 50:50; flow rate: 20 ml/min, temperature: 35° C.; detection: 220 nm]. This gave, after concentration of the product fractions and drying of the residue under high vacuum, 11 mg (62% of theory) of enantiomer 1.

$^1$H-NMR (400 MHz, DMSO-$d_6$, δ/ppm): 7.48 (d, 2H), 7.30 (t, 2H), 7.21 (t, 1H), 5.05 (s, 1H), 4.81 (d, 1H), 4.18 (quart, 2H), 4.12-4.03 (m, 2H), 3.81-3.72 (m, 3H), 3.28-3.21 (m, 2H), 2.76-2.63 (m, 2H), 2.34 (s, 3H), 1.80-1.73 (m, 2H), 1.42 (s, 3H), 1.41-1.32 (m, 2H).

Chiral analytical HPLC [column: Daicel Chiralpak IB-3, 3 μm 50 mm×4.6 mm; mobile phase: isohexane/ethanol 50:50; flow rate: 1 ml/min, temperature: 40° C.; detection: 220 nm]: R$_t$=1.23 min; >99% ee.

Example 133

3-(2-Hydroxy-2-phenylpropyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 2)

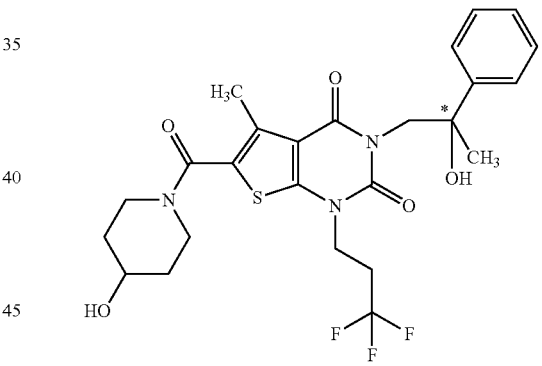

35 mg (0.065 mmol) of the racemic compound from Ex. 105 were dissolved in 6 ml of isohexane/ethanol (1:1) and, in 3 portions, separated into the enantiomers by preparative HPLC on a chiral phase [column: Daicel Chiralpak ID 5 μm 250 mm×20 mm; mobile phase: isohexane/ethanol 50:50; flow rate: 20 ml/min, temperature: 35° C.; detection: 220 nm]. This gave, after concentration of the product fractions and drying of the residue under high vacuum, 10 mg (57% of theory) of enantiomer 2.

$^1$H-NMR (400 MHz, DMSO-$d_6$, δ/ppm): 7.48 (d, 2H), 7.30 (t, 2H), 7.21 (t, 1H), 5.05 (s, 1H), 4.81 (d, 1H), 4.18 (quart, 2H), 4.12-4.03 (m, 2H), 3.82-3.72 (m, 3H), 3.28-3.21 (m, 2H), 2.76-2.63 (m, 2H), 2.34 (s, 3H), 1.81-1.73 (m, 2H), 1.42 (s, 3H), 1.41-1.32 (m, 2H).

Chiral analytical HPLC [column: Daicel Chiralpak IB-3, 3 μm 50 mm×4.6 mm; mobile phase: isohexane/ethanol 50:50; flow rate: 1 ml/min, temperature: 40° C.; detection: 220 nm]: R$_t$=1.10 min; >99% ee.

Example 134

3-Ethyl-6-[(4-hydroxypiperidin-1-yl)carbonyl]-5-methyl-1-(3-methylbutyl)thieno[2,3-d]pyrimidine-2,4(1H,3H)-dione

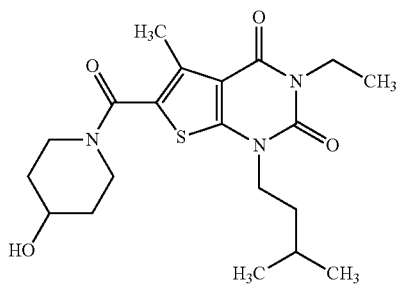 [SMILES: CCn1c(=O)c2c(C)c(C(=O)N3CCC(O)CC3)sc2n(CCC(C)C)c1=O]

135 mg (0.300 mmol) of the compound from Ex. 130A were dissolved in 5 ml of ethanol/THF (1:1), and 360 µl (0.360 mmol) of a 1 M solution of lithium hydroxide in water were added. After stirring at RT for about 16 h, 250 µl of glacial acetic acid were added and the reaction mixture was diluted with about 200 ml of ethyl acetate. The mixture was washed successively twice with water and once with saturated sodium chloride solution. After drying over anhydrous magnesium sulphate, the mixture was filtered and concentrated to dryness. 115 mg (94% of theory) of the title compound were obtained.

$^1$H-NMR (400 MHz, DMSO-d$_6$, δ/ppm): 4.79 (d, 1H), 3.92-3.88 (m, 2H), 3.91 (quart, 2H), 3.81-3.70 (m, 3H), 3.23 (m, 2H), 2.37 (s, 3H), 1.79-1.72 (m, 2H), 1.65 (sept, 1H), 1.59-1.54 (m, 2H), 1.39-1.31 (m, 2H), 1.12 (t, 3H), 0.94 (d, 6H).

LC/MS (Method 1, ESIpos): R$_t$=0.91 min, m/z=408 [M+H]$^+$.

Example 135

3-Ethyl-6-[(4-hydroxypiperidin-1-yl)carbonyl]-5-methyl-1-(4,4,4-trifluorobutyl)thieno[2,3-d]pyrimidine-2,4(1H,3H)-dione

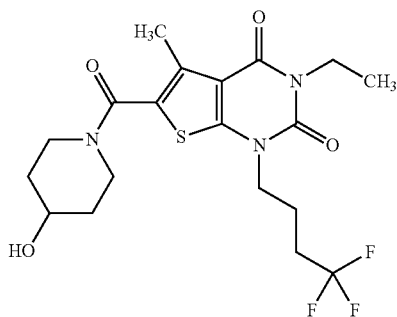 [SMILES: CCn1c(=O)c2c(C)c(C(=O)N3CCC(O)CC3)sc2n(CCCC(F)(F)F)c1=O]

Analogously to the process described in Ex. 134, 150 mg (0.306 mmol) of the compound from Ex. 131A gave 127 mg (92% of theory) of the title compound. Here, at RT the product was stirred with a mixture of 10 ml of pentane and 2 ml of diethyl ether for 10 min.

$^1$H-NMR (400 MHz, DMSO-d$_6$, δ/ppm): 4.79 (d, 1H), 3.97 (t, 2H), 3.90 (quart, 2H), 3.81-3.71 (m, 3H), 3.23 (m, 2H), 2.46-2.40 (m, 2H), 2.38 (s, 3H), 1.91 (quint, 2H), 1.79-1.72 (m, 2H), 1.39-1.31 (m, 2H), 1.12 (t, 3H).

LC/MS (Method 1, ESIpos): R$_t$=0.83 min, m/z=448 [M+H]$^+$.

Example 136

3-Ethyl-6-[(4-hydroxypiperidin-1-yl)carbonyl]-5-methyl-1-(3,4,4-trifluorobut-3-en-1-yl)thieno[2,3-d]pyrimidine-2,4(1H,3H)-dione

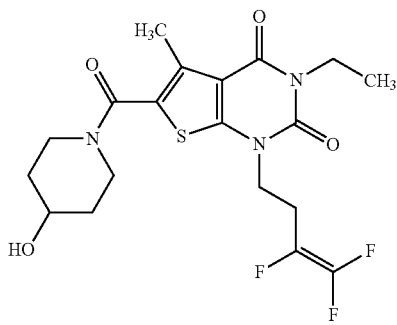 [SMILES: CCn1c(=O)c2c(C)c(C(=O)N3CCC(O)CC3)sc2n(CCC(F)=C(F)F)c1=O]

69 mg (0.143 mmol) of the compound from Ex. 132A were dissolved in 2.5 ml of ethanol/THF (1:1), and 158 µl (0.158 mmol) of a 1 M solution of lithium hydroxide in water were added. After stirring at RT for 2 h, the reaction mixture was concentrated to dryness. The residue was taken up in 3 ml of dichloromethane and 1 ml of water and stirred vigorously. The aqueous phase was then separated off via an Extrelut®-NT3 cartridge. Concentration of the organic phase and drying of the residue under high vacuum gave 57 mg (89% of theory, 98% pure) of the title compound.

$^1$H-NMR (400 MHz, DMSO-d$_6$, δ/ppm): 4.80 (d, 1H), 4.10 (t, 2H), 3.91 (quart, 2H), 3.80-3.71 (m, 3H), 3.23 (m, 2H), 2.81 (m, 2H), 2.38 (s, 3H), 1.79-1.72 (m, 2H), 1.39-1.31 (m, 2H), 1.12 (t, 3H).

LC/MS (Method 1, ESIpos): R$_t$=0.81 min, m/z=446 [M+H]$^+$.

Example 137

5-(Difluoromethyl)-6-[(4-hydroxypiperidin-1-yl)carbonyl]-3-isobutyl-1-[2-(trifluoromethoxy)ethyl]thieno[2,3-d]pyrimidine-2,4(1H,3H)-dione

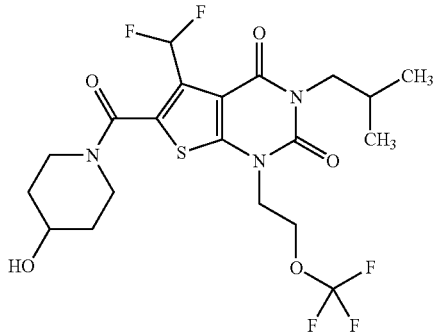 [SMILES: CC(C)Cn1c(=O)c2c(C(F)F)c(C(=O)N3CCC(O)CC3)sc2n(CCOC(F)(F)F)c1=O]

28 mg (0.279 mmol) of 4-hydroxypiperidine, 106 mg (0.279 mmol) of HATU and 53 μl (0.302 mmol) of N,N-diisopropylethylamine were added successively to a solution of 100 mg (0.232 mmol) of the compound from Ex. 138A in 3 ml of anhydrous DMF. After a reaction time of about 16 h at RT, the reaction mixture was separated directly by preparative HPLC (Method 5) into its components. The product fractions were combined and concentrated, and the residue was dried under high vacuum. 102 mg (85% of theory) of the title compound were obtained.

$^1$H-NMR (400 MHz, DMSO-$d_6$, δ/ppm): 7.32 (t, 1H), 4.81 (d, 1H), 4.42 (t, 2H), 4.26 (t, 2H), 3.95 (broad, 1H), 3.75 (m, 1H), 3.73 (d, 2H), 3.48 (broad, 1H), 3.20 (broad, 2H), 2.04 (m, 1H), 1.72 (broad, 2H), 1.35 (broad, 2H), 0.86 (d, 6H).

LC/MS (Method 1, ESIpos): $R_t$=0.96 min, m/z=514 [M+H]$^+$.

Example 138

5-(Difluoromethyl)-6-[(4-hydroxy-4-methylpiperidin-1-yl)carbonyl]-3-isobutyl-1-[2-(trifluoromethoxy)ethyl]thieno[2,3-d]pyrimidine-2,4(1H,3H)-dione

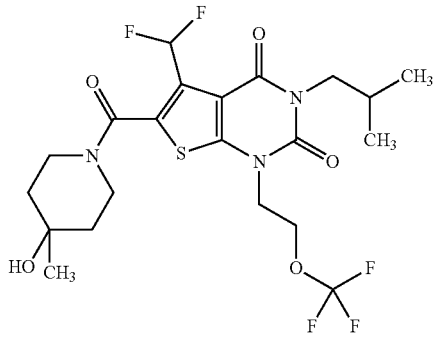 [SMILES: CC(C)Cn1c(=O)c2c(C(F)F)c(C(=O)N3CCC(C)(O)CC3)sc2n(CCOC(F)(F)F)c1=O]

Analogously to the process described in Ex. 137, 100 mg (0.232 mmol) of the compound from Ex.

138A and 32 mg (0.279 mmol) of 4-methylpiperidin-4-ol [commercially available; lit. e.g.: J. M. McManus et al., *J. Med. Chem.* 1965, 8 (6), 766-776] gave 55 mg (44% of theory) of the title compound. In deviation from the process described above, here the first preparative HPLC purification (according to Method 5) was followed by a second HPLC purification on [column: Kinetix C18, 5 μm, 100 mm×21.5 mm; mobile phase: 50% water, 45% acetonitrile, 5% formic acid (1% in water); flow rate: 25 ml/min, temperature: 25° C.; detection: 210 nm].

$^1$H-NMR (400 MHz, DMSO-$d_6$, δ/ppm): 7.31 (t, 1H), 4.47 (s, 1H), 4.42 (t, 2H), 4.25 (t, 2H), 4.06 (broad, 1H), 3.73 (d, 2H), 3.22 (broad, 3H), 2.04 (m, 1H), 1.52 (broad, 1H), 1.43 (broad, 3H), 1.14 (s, 3H), 0.86 (d, 6H).

LC/MS (Method 1, ESIpos): $R_t$=1.01 min, m/z=528 [M+H]$^+$.

Example 139

5-(Difluoromethyl)-6-[(4-hydroxypiperidin-1-yl)carbonyl]-3-isobutyl-1-(3,3,3-trifluoropropyl)thieno[2,3-d]pyrimidine-2,4(1H,3H)-dione

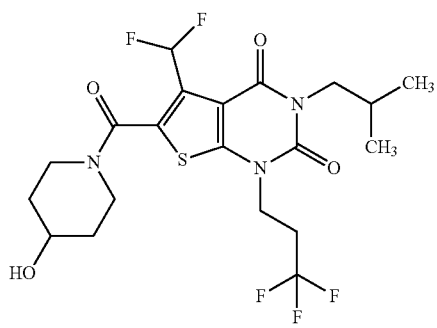 [SMILES: CC(C)Cn1c(=O)c2c(C(F)F)c(C(=O)N3CCC(O)CC3)sc2n(CCC(F)(F)F)c1=O]

Analogously to the process described in Ex. 137, 100 mg (0.241 mmol) of the compound from Ex. 139A and 29 mg (0.290 mmol) of 4-hydroxypiperidine gave 109 mg (90% of theory) of the title compound.

$^1$H-NMR (400 MHz, DMSO-$d_6$, δ/ppm): 7.32 (t, 1H), 4.81 (d, 1H), 4.15 (t, 2H), 3.96 (broad, 1H), 3.75 (m, 1H), 3.73 (d, 2H), 3.51 (broad, 1H), 3.21 (broad, 2H), 2.81 (m, 2H), 2.04 (m, 1H), 1.73 (broad, 2H), 1.36 (broad, 2H), 0.87 (d, 6H).

LC/MS (Method 1, ESIpos): $R_t$=0.94 min, m/z=498 [M+H]$^+$.

Example 140

5-(Difluoromethyl)-6-[(4-hydroxy-4-methylpiperidin-1-yl)carbonyl]-3-isobutyl-1-(3,3,3-trifluoropropyl)thieno[2,3-d]pyrimidine-2,4(1H,3H)-dione

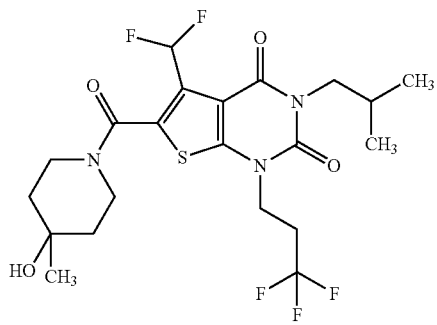 [SMILES: CC(C)Cn1c(=O)c2c(C(F)F)c(C(=O)N3CCC(C)(O)CC3)sc2n(CCC(F)(F)F)c1=O]

Analogously to the process described in Ex. 138, 100 mg (0.241 mmol) of the compound from Ex. 139A and 33 mg (0.279 mmol) of 4-methylpiperidin-4-ol [commercially available; lit. e.g.: J. M. McManus et al., *J. Med. Chem.* 1965, 8 (6), 766-776] gave 47 mg (38% of theory) of the title compound.

$^1$H-NMR (400 MHz, DMSO-$d_6$, δ/ppm): 7.31 (t, 1H), 4.47 (s, 1H), 4.15 (t, 2H), 4.06 (broad, 1H), 3.73 (d, 2H), 3.35 (broad, 2H), 3.22 (broad, 1H), 2.81 (m, 2H), 2.04 (m, 1H), 1.52 (broad, 1H), 1.44 (broad, 3H), 1.15 (s, 3H), 0.87 (d, 6H).

LC/MS (Method 1, ESIpos): $R_t$=1.00 min, m/z=512 [M+H]$^+$.

Example 141

5-(Difluoromethyl)-6-[(4-hydroxypiperidin-1-yl) carbonyl]-3-propyl-1-(3,3,3-trifluoropropyl)thieno[2,3-d]pyrimidine-2,4(1H,3H)-dione

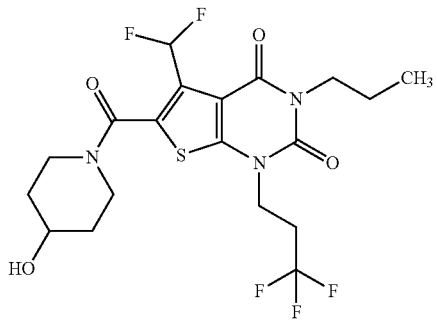 [SMILES: CCCn1c(=O)c2c(C(F)F)c(C(=O)N3CCC(O)CC3)sc2n(CCC(F)(F)F)c1=O]

Analogously to the process described in Ex. 137, 55 mg (0.137 mmol) of the compound from Ex. 148A and 17 mg (0.165 mmol) of 4-hydroxypiperidine gave 54 mg (81% of theory) of the title compound.

$^1$H-NMR (400 MHz, DMSO-d$_6$, δ/ppm): 7.32 (t, 1H), 4.81 (broad, 1H), 4.15 (t, 2H), 3.95 (broad, 1H), 3.84 (t, 2H), 3.75 (broad, 1H), 3.50 (broad, 1H), 3.21 (broad, 2H), 2.89-2.75 (m, 2H), 1.73 (broad, 2H), 1.58 (m, 2H), 1.36 (broad, 2H), 0.88 (t, 3H).

LC/MS (Method 1, ESIpos): $R_t$=0.88 min, m/z=484 [M+H]$^+$.

Example 142

5-(Difluoromethyl)-6-[(4-hydroxy-4-methylpiperidin-1-yl)carbonyl]-3-propyl-1-(3,3,3-trifluoropropyl)thieno[2,3-d]pyrimidine-2,4(1H,3H)-dione

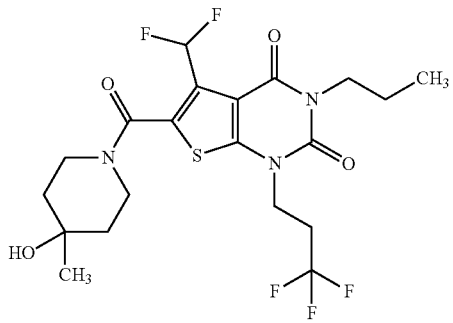 [SMILES: CCCn1c(=O)c2c(C(F)F)c(C(=O)N3CCC(C)(O)CC3)sc2n(CCC(F)(F)F)c1=O]

Analogously to the process described in Ex. 137, 55 mg (0.137 mmol) of the compound from Ex. 148A and 19 mg (0.165 mmol) of 4-methylpiperidin-4-ol [commercially available; lit. e.g.: J. M. McManus et al., J. Med. Chem. 1965, 8 (6), 766-776] gave 56 mg (78% of theory, purity 95%) of the title compound.

$^1$H-NMR (400 MHz, DMSO-d$_6$, δ/ppm): 7.32 (t, 1H), 4.47 (broad, 1H), 4.15 (t, 2H), 4.05 (broad, 1H), 3.84 (t, 2H), 3.25 (broad, 3H), 2.87-2.75 (m, 2H), 1.58 (m, 2H), 1.55 (broad, 2H), 1.44 (broad, 2H), 1.15 (s, 3H), 0.88 (t, 3H).

LC/MS (Method 1, ESIpos): $R_t$=0.94 min, m/z=498 [M+H]$^+$.

Example 143

3-Ethyl-5-(fluoromethyl)-6-[(4-hydroxypiperidin-1-yl)carbonyl]-1-(3,3,3-trifluoropropyl)thieno[2,3-d]pyrimidine-2,4(1H,3H)-dione

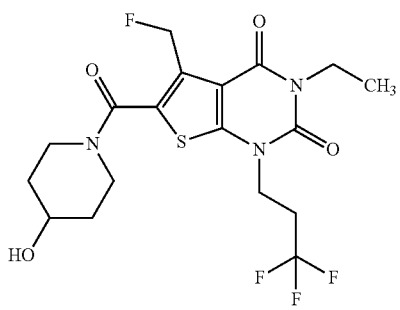 [SMILES: CCn1c(=O)c2c(CF)c(C(=O)N3CCC(O)CC3)sc2n(CCC(F)(F)F)c1=O]

Analogously to the process described in Ex. 137, 40 mg (0.109 mmol) of the compound from Ex. 149A and 13 mg (0.130 mmol) of 4-hydroxypiperidine gave 46 mg (93% of theory) of the title compound. In this case, the reaction time was 1 h, and purification by preparative HPLC was carried out according to Method 19.

$^1$H-NMR (400 MHz, DMSO-d$_6$, δ/ppm): 5.57 (d, 2H), 4.15 (t, 2H), 3.92 (quart, 2H), 3.87-3.58 (broad and m, together 4H), 3.28-3.20 (m, 2H), 2.87-2.75 (m, 2H), 1.78-1.71 (m, 2H), 1.41-1.31 (m, 2H), 1.14 (t, 3H).

LC/MS (Method 1, ESIpos): $R_t$=0.81 min, m/z=452 [M+H]$^+$.

Example 144

3-Ethyl-5-(fluoromethyl)-6-[(4-hydroxy-4-methylpiperidin-1-yl)carbonyl]-1-(3,3,3-trifluoropropyl)thieno[2,3-d]pyrimidine-2,4(1H,3H)-dione

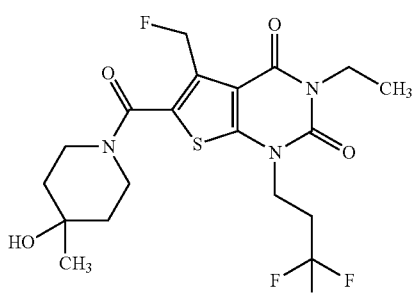

Analogously to the process described in Ex. 137, 60 mg (0.163 mmol) of the compound from Ex. 149A and 30 mg (0.195 mmol) of 4-methylpiperidin-4-ol [commercially available; lit. e.g.: J. M. McManus et al., J. Med. Chem. 1965, 8 (6), 766-776] gave 53 mg (69% of theory) of the title compound. In this case, the reaction time was 1 h, and purification by preparative HPLC was carried out according to Method 19.

¹H-NMR (400 MHz, DMSO-d₆, δ/ppm): 5.57 (d, 2H), 4.15 (t, 2H), 3.92 (quart, 2H), 3.36-3.27 (m, 2H), 2.87-2.75 (m, 2H), 1.52-1.40 (m, 4H), 1.15 (s, 3H), 1.14 (t, 3H).

LC/MS (Method 1, ESIpos): R$_t$=0.84 min, m/z=466 [M+H]⁺.

Example 145

3-Ethyl-5-(1-fluoroethyl)-6-[(4-hydroxypiperidin-1-yl)carbonyl]-1-(3,3,3-trifluoropropyl)thieno[2,3-d]pyrimidine-2,4(1H,3H)-dione (racemate)

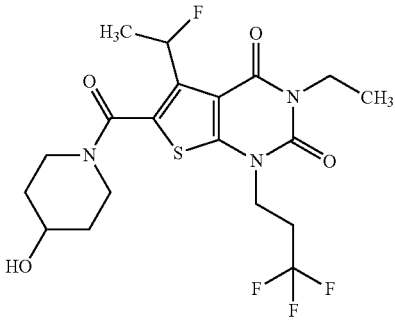

Analogously to the process described in Ex. 137, 11 mg (0.029 mmol) of the compound from Ex. 150A and 3.5 mg (0.035 mmol) of 4-hydroxypiperidine gave 13 mg (97% of theory) of the title compound. In this case, the reaction time was 1 h, and purification by preparative HPLC was carried out according to Method 19.

¹H-NMR (400 MHz, DMSO-d₆, δ/ppm): 6.20 (d of quart, 1H), 4.19-4.06 (m, 4H), 3.91 (quart, 2H), 3.76-3.70 (m, 1H), 3.25-3.11 (m, 2H), 2.86-2.74 (m, 2H), 1.76-1.66 (m, 2H), 1.61 (dd, 3H), 1.39-1.29 (m, 2H), 1.13 (t, 3H).

LC/MS (Method 1, ESIpos): R$_t$=0.81 min, m/z=466 [M+H]⁺.

Example 146

3-Ethyl-5-(1-fluoroethyl)-6-[(4-hydroxy-4-methylpiperidin-1-yl)carbonyl]-1-(3,3,3-trifluoropropyl)thieno[2,3-d]pyrimidine-2,4(1H,3H)-dione (racemate)

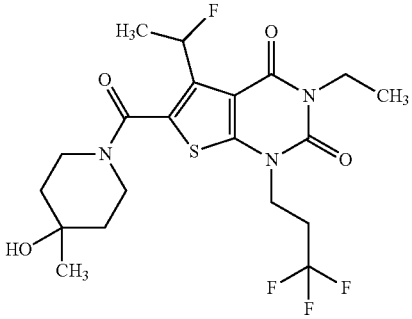 [SMILES: CCn1c(=O)c2c(C(C)F)c(C(=O)N3CCC(C)(O)CC3)sc2n(CCC(F)(F)F)c1=O]

Analogously to the process described in Ex. 137, 80 mg (0.178 mmol, purity 85%) of the compound from Ex. 150A and 32 mg (0.213 mmol) of 4-methylpiperidin-4-ol hydrochloride [commercially available; lit. e.g.: J. M. McManus et al., *J. Med. Chem.* 1965, 8 (6), 766-776] gave 46 mg (53% of theory) of the title compound. In this case, the reaction time was 1 h, and purification by preparative HPLC was carried out according to Method 19.

¹H-NMR (400 MHz, DMSO-d₆, δ/ppm): 6.20 (d of quart, 1H), 4.44 (broad, 1H), 4.19-4.05 (m, 2H), 3.91 (quart, 2H), 3.24 (broad, 2H), 2.86-2.74 (m, 2H), 1.61 (dd, 3H), 1.52-1.37 (m, 4H), 1.14 (s, 3H), 1.13 (t, 3H).

LC/MS (Method 1, ESIpos): R$_t$=0.89 min, m/z=480 [M+H]⁺.

Example 147

3-Ethyl-5-(1-fluoroethyl)-6-[(3-oxopiperazin-1-yl)carbonyl]-1-(3,3,3-trifluoropropyl)thieno[2,3-d]pyrimidine-2,4(1H,3H)-dione (racemate)

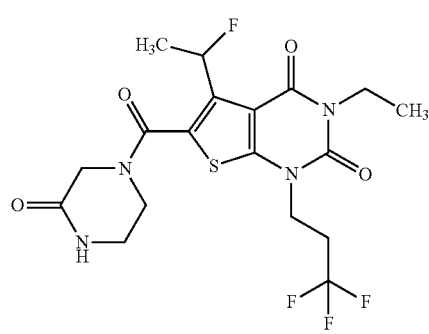 [SMILES: CCn1c(=O)c2c(C(C)F)c(C(=O)N3CCNC(=O)C3)sc2n(CCC(F)(F)F)c1=O]

Analogously to the process described in Ex. 137, 100 mg (0.222 mmol, purity 85%) of the compound from Ex. 150A and 27 mg (0.267 mmol) of 2-oxopiperazine gave 72 mg (66% of theory, purity 95%) of the title compound. In this case, the reaction time was 1 h, and purification by preparative HPLC was carried out according to Method 19.

¹H-NMR (400 MHz, DMSO-d₆, δ/ppm): 8.12 (s, 1H), 6.23 (d of quart, 1H), 4.19-4.07 (m, 2H), 3.91 (quart, 2H), 3.60-3.48 (broad, 4H), 3.22-3.18 (broad, 2H), 2.87-2.75 (m, 2H), 1.61 (dd, 3H), 1.13 (t, 3H).

LC/MS (Method 17, ESIpos): R$_t$=2.09 min, m/z=465 [M+H]⁺.

Example 148

3-Ethyl-5-(1-fluoroethyl)-6-[(3-oxopiperazin-1-yl)carbonyl]-1-(3,3,3-trifluoropropyl)thieno[2,3-d]pyrimidine-2,4(1H,3H)-dione (enantiomer 1)

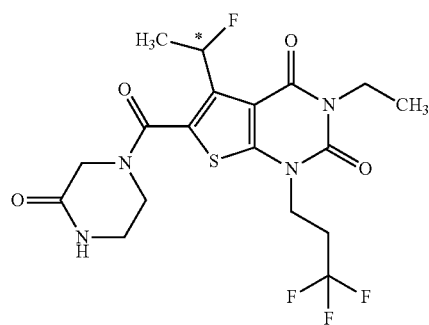 [SMILES: CCn1c(=O)c2c(C(C)F)c(C(=O)N3CCNC(=O)C3)sc2n(CCC(F)(F)F)c1=O]

60 mg (0.123 mmol) of the racemic compound from Ex. 147 were dissolved in 7 ml of methanol/ethanol/acetonitrile (1:1:1) and, in 4 portions, separated into the enantiomers by preparative SFC-HPLC on a chiral phase [column: Daicel Chiralpak IC 5 μm 250 mm×20 mm; mobile phase: carbon dioxide/ethanol 75:25; flow rate: 60 ml/min, temperature: 40° C.; detection: 210 nm]. This gave, after concentration of the product fractions and drying of the residue under high vacuum, 12 mg (42% of theory) of enantiomer 1.

$^1$H-NMR (400 MHz, DMSO-d$_6$, δ/ppm): 8.12 (s, 1H), 6.23 (d of quart, 1H), 4.19-4.08 (m, 2H), 3.97 (broad, 2H), 3.91 (quart, 2H), 3.56 (broad, 2H), 3.20 (broad, 2H), 2.86-2.76 (m, 2H), 1.61 (dd, 3H), 1.13 (t, 3H).

LC/MS (Method 1, ESIpos): R$_t$=0.78 min, m/z=465 [M+H]$^+$.

Chiral analytical SFC [column: Daicel Chiralpak IC 3 μm 250 mm×4.6 mm; mobile phase: carbon dioxide/methanol 95:5→50:50; flow rate: 3 ml/min, temperature: 40° C.; detection: 210 nm]: R$_t$=2.91 min; >99% ee.

Example 149

3-Ethyl-5-(1-fluoroethyl)-6-[(3-oxopiperazin-1-yl)carbonyl]-1-(3,3,3-trifluoropropyl)thieno[2,3-d]pyrimidine-2,4(1H,3H)-dione (enantiomer 2)

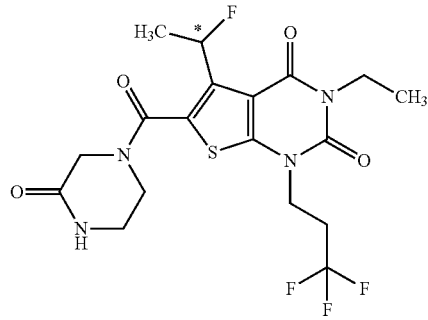 [SMILES: CCn1c(=O)c2c(C(C)F)c(C(=O)N3CCNC(=O)C3)sc2n(CCC(F)(F)F)c1=O]

60 mg (0.123 mmol) of the racemic compound from Ex. 147 were dissolved in 7 ml of methanol/ethanol/acetonitrile (1:1:1) and, in 4 portions, separated into the enantiomers by preparative SFC-HPLC on a chiral phase [column: Daicel Chiralpak IC 5 μm 250 mm×20 mm; mobile phase: carbon dioxide/ethanol 75:25; flow rate: 60 ml/min, temperature: 40° C.; detection: 210 nm]. This gave, after concentration of the product fractions and drying of the residue under high vacuum, 12 mg (42% of theory) of enantiomer 2.

$^1$H-NMR (400 MHz, DMSO-d$_6$, δ/ppm): 8.12 (s, 1H), 6.23 (d of quart, 1H), 4.18-4.08 (m, 2H), 3.96 (broad, 2H), 3.91 (quart, 2H), 3.57 (broad, 2H), 3.20 (broad, 2H), 2.86-2.76 (m, 2H), 1.61 (dd, 3H), 1.13 (t, 3H).

LC/MS (Method 1, ESIpos): R$_t$=0.78 min, m/z=465 [M+H]$^+$.

Chiral analytical SFC [column: Daicel Chiralpak IC 3 μm 250 mm×4.6 mm; mobile phase: carbon dioxide/methanol 95:5→50:50; flow rate: 3 ml/min, temperature: 40° C.; detection: 210 nm]: R$_t$=3.48 min; >99% ee.

Example 150

5-(Difluoromethyl)-6-[(4-hydroxypiperidin-1-yl)carbonyl]-3-propyl-1-[2-(trifluoromethoxy)ethyl]thieno[2,3-d]pyrimidine-2,4(1H,3H)-dione

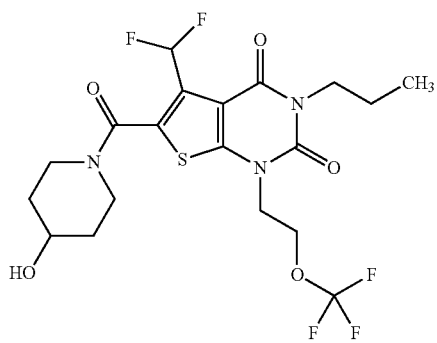 [SMILES: CCCn1c(=O)c2c(C(F)F)c(C(=O)N3CCC(O)CC3)sc2n(CCOC(F)(F)F)c1=O]

Analogously to the process described in Ex. 137, 100 mg (0.240 mmol) of the compound from Ex. 154A and 29 mg (0.288 mmol) of 4-hydroxypiperidine gave 93 mg (77% of theory) of the title compound.

$^1$H-NMR (400 MHz, DMSO-d$_6$, δ/ppm): 7.32 (t, 1H), 4.81 (d, 1H), 4.42 (t, 2H), 4.25 (t, 2H), 3.95 (broad, 1H), 3.85 (t, 2H), 3.74 (m, 1H), 3.47 (broad, 1H), 3.20 (broad, 2H), 1.72 (broad, 2H), 1.58 (m, 2H), 1.35 (broad, 2H), 0.87 (t, 3H).

LC/MS (Method 1, ESIpos): R$_t$=0.89 min, m/z=500 [M+H]$^+$.

Example 151

5-(Difluoromethyl)-6-[(4-hydroxy-4-methylpiperidin-1-yl)carbonyl]-3-propyl-1-[2-(trifluoromethoxy)ethyl]thieno[2,3-d]pyrimidine-2,4(1H,3H)-dione

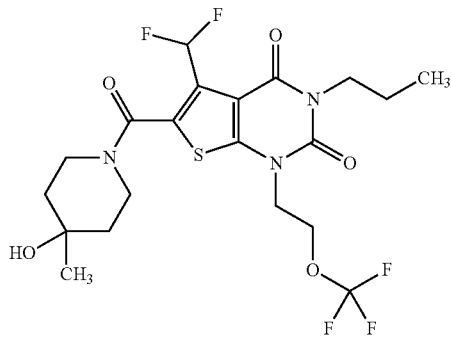 [SMILES: CCCn1c(=O)c2c(C(F)F)c(C(=O)N3CCC(C)(O)CC3)sc2n(CCOC(F)(F)F)c1=O]

Analogously to the process described in Ex. 137, 100 mg (0.240 mmol) of the compound from Ex. 154A and 33 mg (0.165 mmol) of 4-methylpiperidin-4-ol [commercially available; lit. e.g.: J. M. McManus et al., J. Med. Chem. 1965, 8 (6), 766-776] gave 65 mg (52% of theory) of the title compound. In deviation from the process described above, here the first preparative HPLC purification (according to Method 5) was followed by a second HPLC purification on [column: XBridge C18, 5 μm, 100 mm×30 mm; mobile phase: water/acetonitrile/1% aq. ammonia 55:40:5; flow rate: 75 ml/min, temperature: 40° C.; detection: 210 nm].

¹H-NMR (400 MHz, DMSO-d₆, δ/ppm): 7.31 (t, 1H), 4.48 (s, 1H), 4.42 (t, 2H), 4.25 (t, 2H), 4.05 (broad, 1H), 3.85 (t, 2H), 3.30 (broad, 1H), 3.21 (broad, 2H), 1.58 (m, 2H), 1.53 (broad, 2H), 1.43 (broad, 2H), 1.14 (s, 3H), 0.87 (t, 3H).

LC/MS (Method 1, ESIpos): $R_t$=0.94 min, m/z=514 [M+H]⁺.

Example 152

6-{[4-Hydroxy-4-(hydroxymethyl)piperidin-1-yl]carbonyl}-3-isobutyl-5-methyl-1-(3,3,3-trifluoropropyl)thieno[2,3-d]pyrimidine-2,4(1H,3H)-dione

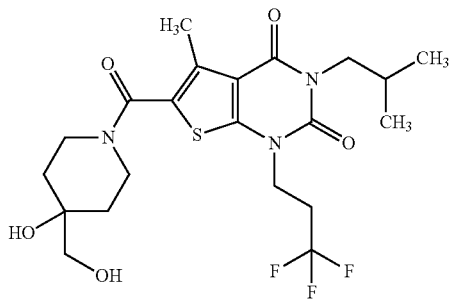 [SMILES: Cc1c(C(=O)N2CCC(O)(CO)CC2)sc2c1c(=O)n(CC(C)C)c(=O)n2CCC(F)(F)F]

Analogously to the process described in Ex. 122, 100 mg (0.264 mmol) of the compound from Ex. 160A and 53 mg (0.317 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 106 mg (81% of theory) of the title compound. In this case, the reaction time was 30 min.

¹H-NMR (400 MHz, DMSO-d₆, δ/ppm): 4.64 (t, 1H), 4.36 (s, 1H), 4.13 (t, 2H), 3.85 (broad, 2H), 3.72 (d, 2H), 3.28 (br. t, 2H), 3.21 (d, 2H), 2.85-2.73 (m, 2H), 2.37 (s, 3H), 2.04 (m, 1H), 1.55 (br. dt, 2H), 1.40 (br. d, 2H), 0.86 (d, 6H).

LC/MS (Method 1, ESIpos): $R_t$=0.82 min, m/z=492 [M+H]⁺.

Example 153

3-(Cyclopropylmethyl)-6-{[4-hydroxy-4-(hydroxymethyl)piperidin-1-yl]carbonyl}-5-methyl-1-(3,3,3-trifluoropropyl)thieno[2,3-d]pyrimidine-2,4(1H,3H)-dione

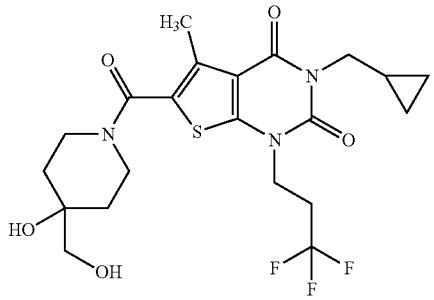 [SMILES: Cc1c(C(=O)N2CCC(O)(CO)CC2)sc2c1c(=O)n(CC1CC1)c(=O)n2CCC(F)(F)F]

Analogously to the process described in Ex. 122, 100 mg (0.266 mmol) of the compound from Ex. 161A and 53 mg (0.319 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 45 mg (34% of theory) of the title compound. In this case, the reaction time was 30 min.

¹H-NMR (400 MHz, DMSO-d₆, δ/ppm): 4.64 (broad, 1H), 4.36 (br. s, 1H), 4.14 (t, 2H), 3.85 (broad, 2H), 3.77 (d, 2H), 3.27 (br. t, 2H), 3.21 (broad, 2H), 2.86-2.74 (m, 2H), 2.38 (s, 3H), 1.55 (br. dt, 2H), 1.40 (br. d, 2H), 1.17 (m, 1H), 0.45-0.40 (m, 2H), 0.36-0.32 (m, 2H).

LC/MS (Method 1, ESIpos): $R_t$=0.78 min, m/z=490 [M+H]⁺.

Example 154

6-{[4-Hydroxy-4-(hydroxymethyl)piperidin-1-yl]carbonyl}-3-(2-methoxypropyl)-5-methyl-1-(3,3,3-trifluoropropyl)thieno[2,3-d]pyrimidine-2,4(1H,3H)-dione (racemate)

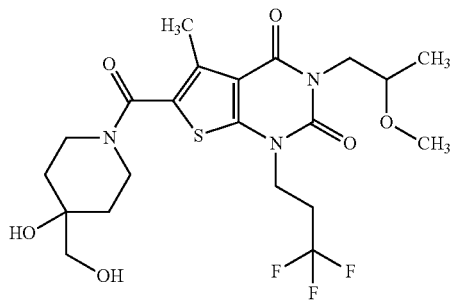 [SMILES: COC(C)Cn1c(=O)c2c(C)c(C(=O)N3CCC(O)(CO)CC3)sc2n(CCC(F)(F)F)c1=O]

Analogously to the process described in Ex. 122, 99 mg (0.166 mmol, purity 66%) of the compound from Ex. 162A and 33 mg (0.199 mmol) of 4-(hydroxymethyl)piperidin-4-ol hydrochloride [commercially available; lit. e.g.: WO 2005/103037-A2, Example A3b (free base); US 2011/288065-A1, Example 105/Step 1 (hydrochloride)] gave 37 mg (44% of theory) of the title compound. Here, the reaction time was 30 min.

¹H-NMR (400 MHz, DMSO-d₆, δ/ppm): 4.64 (t, 1H), 4.37 (s, 1H), 4.15-4.11 (m, 2H), 4.06 (dd, 1H), 3.85 (broad, 2H), 3.77 (dd, 1H), 3.68-3.60 (m, 1H), 3.28 (broad, 2H), 3.22 (s, 3H), 3.21 (d, 2H), 2.85-2.73 (m, 2H), 2.38 (s, 3H), 1.55 (br. dt, 2H), 1.40 (br. d, 2H), 1.06 (d, 3H).

LC/MS (Method 1, ESIpos): $R_t$=0.75 min, m/z=508 [M+H]⁺.

B. Assessment of Pharmacological Efficacy

The pharmacological activity of the compounds according to the invention can be demonstrated by in vitro and in vivo studies, as known to the person skilled in the art. The application examples which follow describe the biological action of the compounds according to the invention, without restricting the invention to these examples.

B-1. Cellular In Vitro Tests for Determining A2b Receptor Activity and Adenosine Receptor Selectivity The identification of selective antagonists of the human adenosine A2b receptor and the quantification of the efficacy and selectivity of the compounds according to the invention was carried out with the aid of recombinant cell lines for the human adenosine receptors A1, A2a, A2b and A3. These cell lines were originally derived from an ovarepithelial cell of the hamster (Chinese Hamster Ovary, CHO-K1, American Type Culture Collection, Manassas, Va. 20108, USA). In addition to the respective recombinantly expressed adenosine receptor for testing the efficacy at the A1, A2a and A2b receptors, the cell lines contain a reporter gene construct where expression of the firefly (*Photinus pyralis*) luciferase is under the control of a promoter which can be activated via intracellular signal cascades by stimulation of the receptors with the (not subtype-selective) adenosine receptor agonist NECA (5'-N-ethylcarboxamidoadenosine) [S. J. Hill, J. G. Baker, S. Rhees, *Curr. Opin. Pharmacol.* 1, 526-532 (2001)].

In the case of the A2a and A2b cell lines, this is a minimal promoter having a plurality of cAMP-responsive elements (CRE). Stimulation of the $G_s$ coupled A2b or A2a receptors by NECA ultimately leads, via formation of cAMP, to CRE-dependent induction of luciferase expression, which is detected 3 hours after the start of the incubation with NECA using a detection solution in a suitable luminometer. For testing the antagonists, initially, in a pre-experiment, the concentration of NECA which, at the test day in question, results in half-maximum stimulation of luciferase expression ($EC_{50}$ concentration) is determined By joint incubation of this $EC_{50}$ concentration of NECA with the substances to be tested, it is possible to determine their antagonistic activity.

The cell line for testing the $G_i$-coupled A1 receptor contains a different reporter gene construct where expression of the firefly luciferase is under the control of an NFAT (nuclear factor of activated T-cells) promoter. This cell line was, in addition to the A1 receptor and the NFAT reporter gene, also stably transfected with a further gene coding for the promiscuous $G\alpha_{16}$ protein [T. T. Amatruda, D. A. Steele, V. Z. Slepak, M. I. Simon, *Proc. Natl. Acad. Sci. USA* 88, 5587-5591 (1991)], either independently or as a fusion gene. The resulting test cells react to stimulation of the usually $G_i$-coupled A1 receptor with an increased intracellular calcium concentration which then leads to a NFAT-dependent luciferase expression. The procedure of the experiment for testing the antagonists at the A1 receptor corresponds to the procedure for testing with the A2a and A2b cell lines.

During generation of the A3 receptor cell line, co-transfection of the A3 receptor and the promiscuous $G\alpha_{16}$ protein were also carried out so that here, too, stimulation of the receptor leads to an increased intracellular calcium concentration. However, in the A3 receptor test, this increase in calcium is measured directly via the calcium-sensitive photoprotein Photina® [S. Bovolenta, M. Foti, S. Lohmer, S. Corazza, *J. Biomol. Screen.* 12, 694-704 (2007)]. After determination of the $EC_{50}$ concentration of NECA, the effects of the substance were measured after 5-10 minutes of pre-incubation with substance by addition of this $EC_{50}$ concentration in measuring position in a suitable luminometer capable of dispensing.

The $IC_{50}$ values from the A2b receptor assay for individual working examples are given in Table 1 below (in some cases as means of a plurality of independent individual determinations and rounded to two significant digits):

TABLE 1

| Example No. | A2b receptor $IC_{50}$ [nmol/l] |
| --- | --- |
| 1 | 37 |
| 2 | 44 |
| 3 | 290 |
| 4 | 25 |
| 5 | 52 |
| 6 | 13 |
| 7 | 110 |
| 8 | 20 |
| 9 | 52 |
| 10 | 310 |
| 11 | 510 |
| 12 | 65 |
| 13 | 100 |
| 14 | 190 |
| 15 | 32 |
| 16 | 38 |
| 17 | 350 |
| 18 | 57 |
| 19 | 92 |
| 20 | 340 |
| 21 | 25 |
| 22 | 67 |
| 23 | 43 |
| 24 | 13 |
| 25 | 49 |
| 26 | 17 |
| 27 | 41 |
| 28 | 150 |
| 29 | 21 |
| 30 | 53 |
| 31 | 16 |
| 32 | 110 |
| 33 | 67 |
| 34 | 120 |
| 35 | 120 |
| 36 | 200 |
| 37 | 340 |
| 38 | 140 |
| 39 | 220 |
| 40 | 230 |
| 41 | 26 |
| 42 | 88 |
| 43 | 6.3 |
| 44 | 4.6 |
| 45 | 150 |
| 46 | 7.9 |
| 47 | 4.4 |
| 48 | 59 |
| 49 | 68 |
| 50 | 150 |
| 51 | 16 |
| 52 | 210 |
| 53 | 170 |
| 54 | 76 |
| 55 | 250 |
| 56 | 19 |
| 57 | 130 |
| 58 | 380 |
| 59 | 370 |
| 60 | 12 |
| 61 | 17 |
| 62 | 120 |
| 63 | 210 |
| 64 | 45 |
| 65 | 96 |
| 66 | 280 |
| 67 | 13 |
| 68 | 20 |
| 69 | 60 |
| 70 | 28 |
| 71 | 420 |
| 72 | 17 |
| 73 | 53 |
| 74 | 110 |
| 75 | 33 |
| 76 | 27 |
| 77 | 75 |
| 78 | 350 |
| 79 | 8.0 |
| 80 | 27 |
| 81 | 170 |

TABLE 1-continued

| Example No. | A2b receptor IC$_{50}$ [nmol/l] |
|---|---|
| 82 | 23 |
| 83 | 56 |
| 84 | 19 |
| 85 | 9.5 |
| 86 | 12 |
| 87 | 26 |
| 88 | 8.7 |
| 89 | 35 |
| 90 | 440 |
| 91 | 260 |
| 92 | 370 |
| 93 | 36 |
| 94 | 490 |
| 95 | 140 |
| 96 | 65 |
| 97 | 7.0 |
| 98 | 100 |
| 99 | 10 |
| 100 | 29 |
| 101 | 1200 |
| 102 | 3.6 |
| 103 | 16 |
| 104 | 9.1 |
| 105 | 69 |
| 106 | 19 |
| 107 | 45 |
| 108 | 580 |
| 109 | 3.9 |
| 110 | 14 |
| 111 | 4.0 |
| 112 | 7.9 |
| 113 | 70 |
| 114 | 110 |
| 115 | 610 |
| 116 | 200 |
| 117 | 140 |
| 118 | 200 |
| 119 | 210 |
| 120 | 130 |
| 121 | 180 |
| 122 | 32 |
| 123 | 18 |
| 124 | 37 |
| 125 | 48 |
| 126 | 84 |
| 127 | 9.5 |
| 128 | 13 |
| 129 | 12 |
| 130 | 9.0 |
| 131 | 34 |
| 132 | 24 |
| 133 | 850 |
| 134 | 360 |
| 135 | 94 |
| 136 | 310 |
| 137 | 12 |
| 138 | 15 |
| 139 | 39 |
| 140 | 39 |
| 141 | 57 |
| 142 | 53 |
| 143 | 82 |
| 144 | 170 |
| 145 | 97 |
| 146 | 40 |
| 147 | 100 |
| 148 | 240 |
| 149 | 320 |
| 150 | 9.8 |
| 151 | 14 |

B-2. Measurement of NECA-Induced IL-6 Release by LL29 Fibroblasts

Stimulation of fibroblasts with adenosine or the adenosine analog 5'-N-ethylcarboxamidoadenosine (NECA) leads to release of the pro-inflammatory and pro-fibrotic cytokine IL-6 which can be prevented by inhibition of the A2b receptor.

Accordingly, confluent cells of the human fibroblast cell line LL29 were treated with the test substances and stimulated with NECA (10 μM). After an incubation time of 24 hours, the cell supernatant is removed and human IL-6 in the cell supernatant is determined by ELISA (Quantikine® IL6 ELISA, R&D Systems, Minneapolis, USA).

The IC$_{50}$ values from this assay for representative working examples are given in Table 2 below (in some cases as means of a plurality of independent individual determinations and rounded to two significant digits):

TABLE 2

| Example No. | IC$_{50}$ [nmol/l] |
|---|---|
| 1 | 59 |
| 2 | 53 |
| 4 | 39 |
| 6 | 27 |
| 8 | 34 |
| 16 | 89 |
| 18 | 170 |
| 21 | 69 |
| 24 | 10 |
| 26 | 53 |
| 29 | 23 |
| 31 | 16 |
| 32 | 230 |
| 33 | 140 |
| 35 | 250 |
| 41 | 29 |
| 54 | 330 |
| 74 | 250 |
| 88 | 9 |
| 89 | 48 |

B-3. Animal Model of Monocrotaline-induced Pulmonary Hypertension

Monocrotaline-induced pulmonary hypertension of the rat is a widely used animal model of pulmonary hypertension. The pyrrolizidine alkaloid monocrotaline is, after subcutaneous injection, metabolized in the liver to the toxic monocrotalinepyrrole, and within a few days endothelium injury in the pulmonary circulation results, followed by remodeling of the small pulmonary arteries (mediahypertrophy, de novo muscularization). A single subcutaneous injection suffices to induce pronounced pulmonary hypertension in rats within 4 weeks [Cowan et al., Nature Med. 6, 698-702 (2000)].

Male Sprague-Dawley rats are used for the model. On day 0, the animals receive a subcutaneous injection of 60 mg of monocrotaline/kg. Treatment of the animals with the test substance (by gavage, by addition to the feed or drinking water, using an osmotic minipump, by subcutaneous or intraperitoneal injection or by inhalation) starts 14 days after the monocrotaline injection at the earliest and extends over a period of at least 14 days. At the end of the study, the animals are examined haemodynamically. For the haemodynamic measurement, the rats are initially anaesthetized with pentobarbital (60 mg/kg). The animals are then tracheotomized and artificially ventilated (frequency: 60 breaths/min; ratio inspiration to expiration: 50:50; positive end-expiratory pressure: 1 cm H$_2$O; tidal volume: 10 ml/kg of body weight; FIO$_2$: 0.5). Anaesthesia is maintained by inhalative isofluran anaesthesia. The systemic blood pressure is determined in the left carotid artery using a Millar microtip catheter. A polyethylene catheter is advanced via the right jugular vein into the right ventricle to determine the right-ventricular pressure. Following the haemodynamic measurements, the heart is removed, the ratio of right to left ventricle including septum is determined and the tissue is deep-frozen for expression analyses. The lung is likewise removed, the left half of the lung is fixed in formalin for histopathological examination and the right half of the lung is deep-frozen for expression analyses. Furthermore, plasma samples are obtained to determine biomarkers (for example proBNP) and plasma substance concentrations.

B-4. Animal Model of SU5416/Hypoxia-Induced Pulmonary Hypertension

SU5416/hypoxia-induced pulmonary hypertension of the rat is a widely used animal model of pulmonary hypertension. By injection of the VEGF receptor antagonist SU5416 in combination with hypoxia, the effect of the reduced oxygen content may be enhanced, leading to changes in the endothelium in the form of plexiform lesions. A single subcutaneous injection, generally of 20 mg/kg, is, in combination with hypoxia, i.e. increased vascular shear forces by vasoconstriction, sufficient to induce severe pulmonary hypertension [Oka et al., *Circ. Res.* 100 (8), 923-929 (2007)].

Male Sprague-Dawley rats or Dahl-Salz rats are used for the model. On day 0, the animals receive a subcutaneous injection of SU5416 and are kept in a controlled hypoxic atmosphere (10% oxygen). Corresponding control rats receive an injection of vehicle and are kept under normoxic conditions. Chronic hypoxia of at least 14 days with subsequent normoxia of at least 28 days leads to the development of pulmonary hypertension which can be demonstrated both functionally and morphologically. Treatment of the animals with the test substance (by gavage, by addition to the feed or drinking water, using an osmotic minipump, by subcutaneous or intraperitoneal injection or by inhalation) starts 14 days after the SU5416 injection and at the beginning of the animals being kept in a controlled hypoxic atmosphere at the earliest and extends over a period of at least 14-28 days.

At the end of the study, the animals are examined haemodynamically. For the haemodynamic measurement, the rats are initially anaesthetized with pentobarbital (60 mg/kg). The animals are then tracheotomized and artificially ventilated (frequency: 60 breaths/min; ratio inspiration to expiration: 50:50; positive end-expiratory pressure: 1 cm $H_2O$; tidal volume: 10 ml/kg of body weight; $FIO_2$: 0.5). Anaesthesia is maintained by inhalative isofluran anaesthesia. The systemic blood pressure is determined in the left carotid artery using a Millar microtip catheter. A polyethylene catheter is advanced via the right jugular vein into the right ventricle to determine the right-ventricular pressure. Following the haemodynamic measurements, the heart is removed, the ratio of right to left ventricle including septum is determined and the tissue is deep-frozen for expression analyses. The lung is likewise removed, the left half of the lung is fixed in formalin for histopathological examination and the right half of the lung is deep-frozen for expression analyses. Furthermore, plasma samples are obtained to determine biomarkers (for example proBNP) and plasma substance concentrations.

B-5. Animal Model of Bleomycin-Induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumours and Hodgkin- and Non-Hodgkin tumours. It is eliminated renally, has a half-life of about 3 hours and, as cytostatic, influences various phases of the division cycle [Lazo et al., *Cancer Chemother. Biol. Response Modif.* 15, 44-50 (1994)]. Its anti-neoplastic effect is based on an oxidatively damaging action on DNA [Hay et al., *Arch. Toxicol.* 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, a bronchio-alveolar lavage to determine the cell content and the pro-inflammatory and pro-fibrotic markers and a histological assessment of pulmonary fibrosis are carried out.

B-6. Animal Model of DQ12 Quartz-Induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-12 weeks. At the end of the study, a bronchio-alveolar lavage to determine the cell content and the pro-inflammatory and pro-fibrotic markers and a histological assessment of pulmonary fibrosis are carried out.

B-7. Animal Model of DQ12 Quartz or FITC-Induced Pulmonary Inflammation

In the mouse and the rat, intratracheal administration of DQ12 quartz or fluorescein isothiocyanate (FITC) leads to an inflammation in the lung [Shimbori et al., *Exp. Lung Res.* 36, 292-301 (2010)]. At the day of the instillation of DQ12 quartz or FITC or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchio-alveolar lavage to determine the cell content and the pro-inflammatory and pro-fibrotic markers is carried out.

B-8. Animal Model of the Elastase-Induced Pulmonary Emphysema

The elastase-induced pulmonary emphysema in the mouse, rat or hamster is a widely used animal model of pulmonary emphysema [Sawada et al., *Exp. Lung Res.* 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, an alveolar morphometry is carried out.

B-9. Animal Model of Permanent Coronary Ligature in Mouse and Rat

Mice or rats are anaesthetized with 5% isoflurane in an anaesthetization cage, intubated, connected to a ventilation pump and ventilated with 2% of isoflurane/N₂O/O₂. The body temperature is maintained at 37-38° C. by a heating mat. Temgesic® is administered as painkiller. The chest is opened laterally between the third and fourth ribs, and the heart is exposed. The coronary artery of the left ventricle (LAD) is permanently ligated with an occlusion thread passed underneath shortly below its origin (below the left atrium). The thorax is closed again, and the muscle layers and the epidermis are sutured. From the day of the operation or up to a week later the animals are treated with the test substance over a period of 4-8 weeks (by gavage, by addition of the test substance to the feed or drinking water, using an osmotic minipump, by subcutaneous or intraperitoneal injection or by inhalation). A further control included is a sham group in which only the surgical procedure, but not the LAD occlusion, was performed.

At the end of the experiment, the animals are anaesthetized again [1.5% isoflurane (mouse), 2% isoflurane (rat)/N₂O/air], and a pressure catheter is introduced via the carotid artery into the left ventricle. The heart rate, left-ventricular pressure (LVP), left-ventricular end-diastolic pressure (LVEDP), contractility (dp/dt) and relaxation rate (tau) are measured there and analyzed with the aid of the Powerlab system (AD Instruments, ADI-PWLB-4SP) and the Chart5 software (SN 425-0586). A blood sample is then taken to determine the blood levels of the substance and plasma biomarkers, and the animals are sacrificed. The heart (heart chambers, left ventricle plus septum, right ventricle), liver, lung and kidney are removed and weighed.

C. Working Examples For Pharmaceutical Compositions

The compounds according to the invention can be converted to pharmaceutical formulations as follows:

Tablet:
Composition:
100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:
The mixture of compound according to the invention, lactose and starch is granulated with a 5% solution (w/w) of the PVP in water. The granules are dried and mixed with the magnesium stearate for 5 minutes. This mixture is compressed in a conventional tablet press (see above for format of the tablet). The guide value used for the pressing is a pressing force of 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol; the compound according to the invention is added to the suspension. The water is added while stirring. The mixture is stirred for about 6 h before swelling of the Rhodigel is complete.

Solution for Oral Administration:
Composition:
500 mg of the compound according to the invention, 2.5 g of polysorbate and 97 g of polyethylene glycol 400. 20 g of oral solution correspond to a single dose of 100 mg of the compound according to the invention.

Production:
The compound according to the invention is suspended in the mixture of polyethylene glycol and polysorbate with stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. A compound of the formula (I)

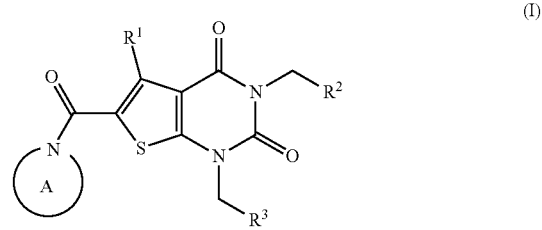

in which $R^1$ represents methyl, where methyl may be substituted up to three times by fluorine, $R^2$ represents methyl or represents a group of the formula

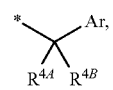

in which * denotes the point of attachment to the CH₂ group,

Ar represents phenyl or 5- or 6-membered heteroaryl having up to two ring nitrogen atoms, where phenyl and heteroaryl may be mono- or disubstituted by identical or different radicals selected from the group consisting of fluorine, chlorine, methyl, trifluoromethyl, methoxy and trifluoromethoxy, $R^{4A}$ represents hydrogen, fluorine or methyl, $R^{4B}$ represents hydrogen, fluorine, methyl, trifluoromethyl, hydroxy or methoxy, or $R^{4A}$ and $R^{4B}$ are attached to one another and together with the carbon atom to which they are attached form a cyclopropyl or cyclobutyl ring, $R^3$ represents $(C_1-C_6)$-alkyl, where alkyl may be substituted up to three times by fluorine and where in alkyl up to two CH₂ groups may be replaced by —O— or —S—, with the proviso that there are at least two carbon atoms between such heteroatoms including the uracil $N^1$-atom, and the ring A represents an aza heterocycle of the formula

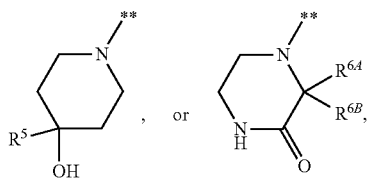

in which ** denotes the point of attachment to the carbonyl group,
$R^5$ represents hydrogen, methyl, trifluoromethyl, hydroxymethyl or ethyl,
$R^{6A}$ and $R^{6B}$ each independently of one another represent hydrogen, methyl or ethyl,
and their salts, solvates and solvates of the salts.

2. The compound of claim 1 of the formula (I) in which
$R^1$ represents methyl, difluoromethyl, or trifluoromethyl,
$R^2$ represents methyl or represents a group of the formula

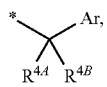

in which * denotes the point of attachment to the $CH^2$ group,
Ar represents phenyl or pyridyl,
where phenyl and pyridyl may be substituted by fluorine, chlorine, methyl or methoxy,
$R^{4A}$ represents hydrogen, fluorine or methyl,
$R^{4B}$ represents hydrogen, fluorine, methyl, hydroxy or methoxy,
or
$R^{4A}$ and $R^{4B}$ are attached to one another and together with the carbon atom to which they are attached form a cyclopropyl ring,
$R^3$ represents $(C_2-C_4)$-alkyl,
where alkyl may be substituted up to three times by fluorine,
where in alkyl one $CH_2$ group may be replaced by —O— or —S—, with the proviso that there are at least two carbon atoms between such a heteroatom and the uracil $N^1$-atom, and
the ring A represents an aza heterocycle of the formula

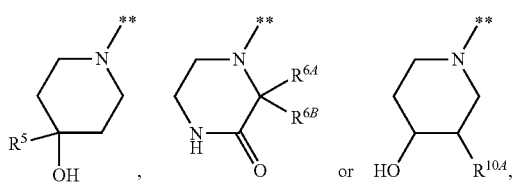

in which ** denotes the point of attachment to the carbonyl group,
$R^5$ represents hydrogen, methyl, trifluoromethyl, hydroxymethyl or ethyl,
$R^{6A}$ and $R^{6B}$ independently of one another represent hydrogen, methyl or ethyl, and
$R^{10A}$ represents methyl or ethyl, and their salts, solvates and solvates of the salts.

3. The compound of claim 1 of the formula (I) in which
$R^1$ represents methyl,
$R^2$ represents methyl or represents a group of the formula

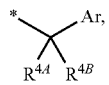

in which * denotes the point of attachment to the $CH_2$ group,
Ar represents phenyl, 3-pyridyl or 4-pyridyl,
where phenyl may be substituted in the meta- or para-position by fluorine or in the ortho-position by fluorine, chlorine or methyl,
$R^{4A}$ represents hydrogen, fluorine or methyl,
$R^{4B}$ represents hydrogen, fluorine, methyl, hydroxy or methoxy,
or
$R^{4A}$ and $R^{4B}$ are attached to one another and together with the carbon atom to which they are attached form a cyclopropyl ring,
$R^3$ represents 2,2,2-trifluoroethyl, 3,3-difluoroprop-2-en-1-yl, methoxymethyl, (trifluoromethoxy)methyl or [(trifluoromethyl)sulphanyl]methyl, and
the ring A represents an aza heterocycle of the formula

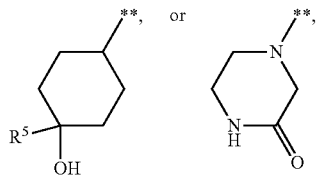

in which ** denotes the point of attachment to the carbonyl group, and
$R^5$ represents hydrogen, methyl, trifluoromethyl, hydroxymethyl or ethyl, and their salts, solvates and solvates of the salts.

4. The compound as defined in claim 1, which is 3-ethyl-6-[(4-hydroxypiperidin-1-yl)carbonyl]-5-methyl-1-(3,3,3-trifluoropropyl)thieno[2,3-d]pyrimidine-2,4(1H,3H)-dione of the formula

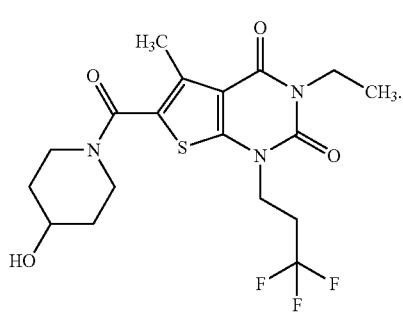 [SMILES: CCn1c(=O)c2c(C)c(C(=O)N3CCC(O)CC3)sc2n(CCC(F)(F)F)c1=O]

5. The compound as defined in claim 1, which is 5-(difluoromethyl)-6-{[4-hydroxy-4-(hydroxymethyl)piperidin-1-yl]carbonyl}-3-(2-phenylethyl)-1-(3,3,3-trifluoropropyl)thieno[2,3-d]pyrimidine-2,4(1H,3H)-dione of the formula

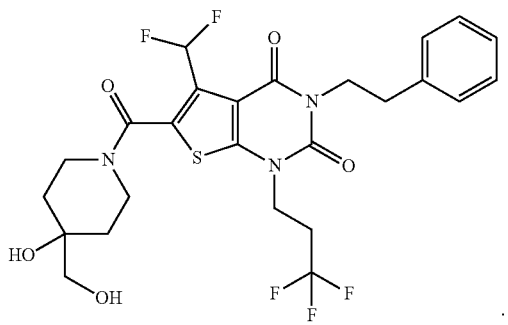 [SMILES: O=C(c1sc2c(c1C(F)F)c(=O)n(CCc1ccccc1)c(=O)n2CCC(F)(F)F)N1CCC(O)(CO)CC1]

6. The compound as defined in claim 1, which is 5-(difluoromethyl)-6-[(3-oxopiperazin-1-yl)carbonyl]-3-(2-phenylethyl)-1-(3,3,3-trifluoropropyl)thieno[2,3-d]pyrimidine-2,4(1H,3H)-dione of the formula

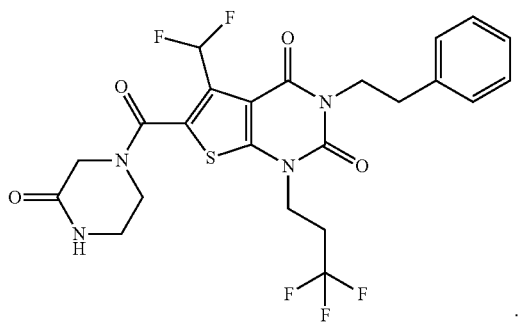 [SMILES: O=C1CN(C(=O)c2sc3c(c2C(F)F)c(=O)n(CCc2ccccc2)c(=O)n3CCC(F)(F)F)CCN1]

7. The compound as defined in claim 1, which is 3-(2-fluoro-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 1) of the formula

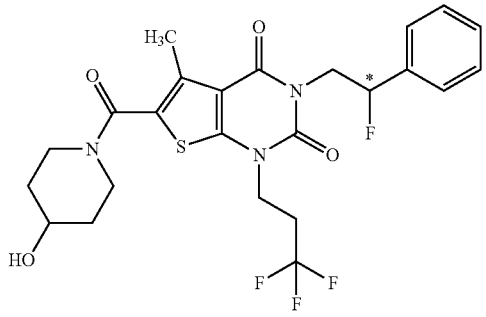

8. The compound as defined in claim 1, which is 3-ethyl-6-[(4-hydroxy-4-methylpiperidin-1-yl)carbonyl]-5-methyl-1-[2-(trifluoromethoxy)ethyl]thieno[2,3-d]pyrimidine-2,4(1H,3H)-dione of the formula

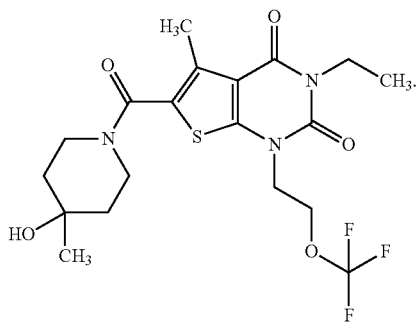 [SMILES: CCn1c(=O)c2c(C)c(C(=O)N3CCC(C)(O)CC3)sc2n(CCOC(F)(F)F)c1=O]

9. The compound as defined in claim 1, which is 3-(2-hydroxy-2-phenylethyl)-6-[(4-hydroxypiperidin-1-yl)carbonyl]-5-methyl-1-(3,3,3-trifluoropropyl)thieno[2,3-d]pyrimidine-2,4(1H,3H)-dione (enantiomer 1) of the formula

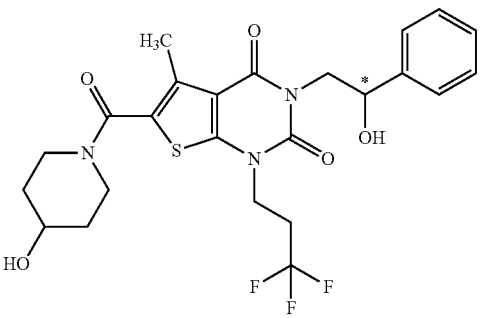

10. The compound as defined in claim 1, which is 5-(difluoromethyl)-3-ethyl-6-[(4-hydroxypiperidin-1-yl)carbonyl]-1-(3,3,3-trifluoropropyl)thieno[2,3-d]pyrimidine-2,4(1H,3H)-dione of the formula

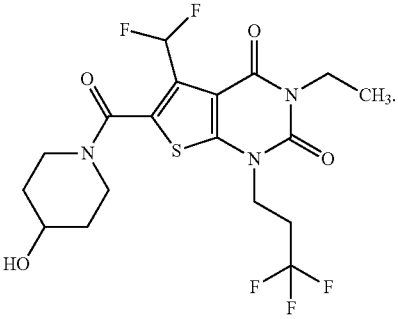 [SMILES: CCn1c(=O)c2c(C(F)F)c(C(=O)N3CCC(O)CC3)sc2n(CCC(F)(F)F)c1=O]

11. The compound as defined in claim 1, which is 5-methyl-6-[(3-oxopiperazin-1-yl)carbonyl]-3-(2-phenylethyl)-1-[2-(trifluoromethoxy)ethyl]thieno[2,3-d]pyrimidine-2,4(1H,3H)-dione of the formula

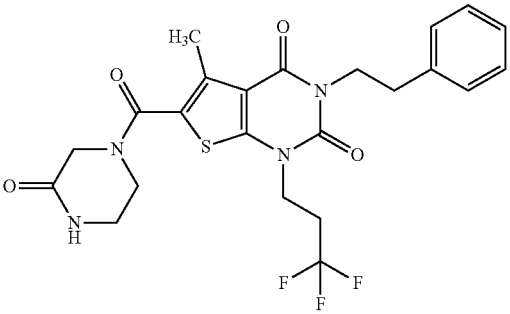

* * * * *

UNITED STATES PATENT AND TRADEMARK OFFICE
CERTIFICATE OF CORRECTION

PATENT NO. : 9,604,996 B2  
APPLICATION NO. : 15/027519  
DATED : March 28, 2017  
INVENTOR(S) : Härter et al.

It is certified that error appears in the above-identified patent and that said Letters Patent is hereby corrected as shown below:

In the Claims

Claim 2, Column 249, Line 29, change CH² to -- CH₂ --.

Claim 2, Column 249, Line 50, change

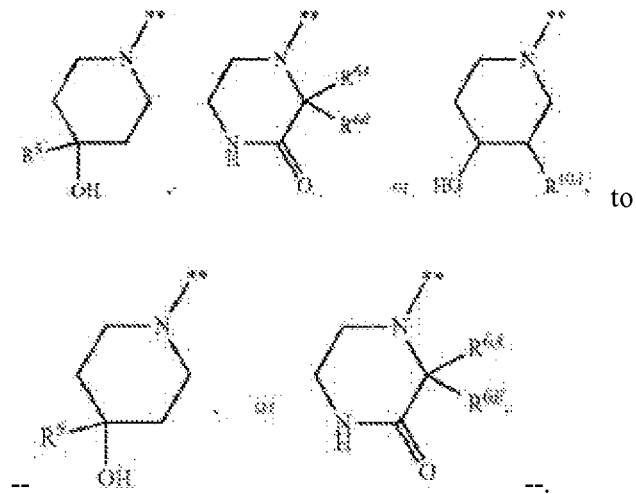

Claim 11, Column 252, Line 60, change

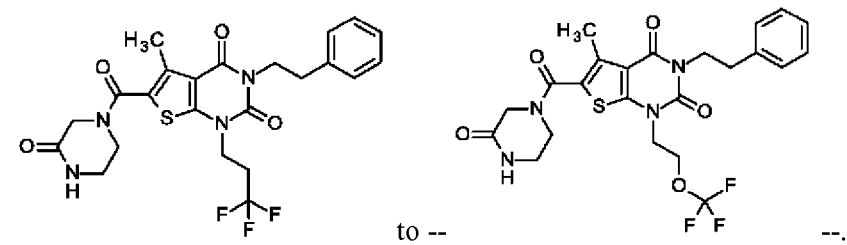

Signed and Sealed this  
Seventeenth Day of October, 2017

Joseph Matal  
*Performing the Functions and Duties of the*  
*Under Secretary of Commerce for Intellectual Property and*  
*Director of the United States Patent and Trademark Office*